(12) United States Patent
Cummings et al.

(10) Patent No.: US 12,129,290 B2
(45) Date of Patent: Oct. 29, 2024

(54) MONOCLONAL ANTIBODIES, COMPOSITIONS AND METHODS FOR DETECTING COMPLEMENT FACTOR D

(71) Applicant: Omeros Corporation, Seattle, WA (US)

(72) Inventors: William Jason Cummings, Bellevue, WA (US); Jeremy A. Freeman, Shoreline, WA (US); Yi Li, Seattle, WA (US); Kathleen A. Shaffer, Rosharon, TX (US); Munehisa Yabuki, Seattle, WA (US)

(73) Assignee: Omeros Corporation, Seattle, WA (US)

( * ) Notice: Subject to any disclaimer, the term of this patent is extended or adjusted under 35 U.S.C. 154(b) by 26 days.

(21) Appl. No.: 17/404,323

(22) Filed: Aug. 17, 2021

(65) Prior Publication Data
US 2022/0056117 A1    Feb. 24, 2022

Related U.S. Application Data

(60) Provisional application No. 63/197,833, filed on Jun. 7, 2021, provisional application No. 63/066,942, filed
(Continued)

(51) Int. Cl.
*C07K 16/18* (2006.01)
*G01N 33/573* (2006.01)

(52) U.S. Cl.
CPC ........... *C07K 16/18* (2013.01); *G01N 33/573* (2013.01); *C07K 2317/34* (2013.01); *C07K 2317/92* (2013.01); *G01N 2333/96433* (2013.01)

(58) Field of Classification Search
CPC ................ C07K 16/18; C07K 2317/34; C07K 2317/92; G01N 33/573; G01N 2333/96433
See application file for complete search history.

(56) References Cited

U.S. PATENT DOCUMENTS

| 4,816,567 A | 3/1989 | Cabilly et al. |
| 5,530,101 A | 6/1996 | Queen et al. |

(Continued)

FOREIGN PATENT DOCUMENTS

| WO | WO1998/45322 | 10/1998 |
| WO | WO2008068048 | * 6/2008 |

(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).*
(Continued)

*Primary Examiner* — Adam Weidner
*Assistant Examiner* — Laura Ann Essex
(74) *Attorney, Agent, or Firm* — Glenda A. Gertz

(57) ABSTRACT

Disclosed herein are monoclonal antibodies that specifically bind to human mature Factor D and that do not bind to human Pro-Factor D, monoclonal antibodies that specifically bind to human Pro-Factor D and do not bind to human mature Factor D, and monoclonal antibodies that bind to both human mature Factor D and human Pro-Factor D. Also disclosed are methods of using the monoclonal antibodies, and compositions comprising the same, for detection of the mature and/or the pro-form of Factor D in biological samples, to determine the status of the Alternative Pathway of Complement (APC) in a mammalian subject, or to determine the status of Factor D after treatment with a
(Continued)

Anti-human Pro-Factor D-specific antibodies: heavy chain variable region

```
VH
Kabat                              31   35           50                 65                                            95  102
18F5  EVKLEESGGG LVQPGGSMKL SCVASGFTFG -NYWMSWVRQ SPEKGLEWVA EIRLKSDNYA THYAESVKGK FTISRDDSKS RLYLQMNSLR GEDTGLYYCT N-AWFASWGQ GTLVTVSA (SIN:136)
1F9   EVKLEESGGG LVQPGGSMKL SCVASGFTFG -SYWMSWVRQ SPEKGLEWVA EIRLKSONYA AHYAESVKGK FTISRDDSKS RLYLQMNSLR GEDTGIYYCT N-AWFASWGQ GTLVTVSA (SIN:137)
2A4   EVKLEESGGG LVQPGGSMKL SCVASGFTFS -TYWMSWVRQ SPEKGLEWVA EIRLKSDNYA THYTESVKGK FTISRDDSKS RLYLQMNSLR VEDTGIYYCT N-AWFAYWGQ GTLVTVSA (SIN:138)
20A1  EVKLEESGGG LVQPGGSMKL SCIASGFTFS -TYWMSWVRQ SPEKGLEWVA EIRLKSENYA TYYAESVKGK FIISRDDSKS RLYLQMNSLR AEDTGIYYCT N-AWFANWGQ GTLVTVSA (SIN:139)
13A10 DVQLQESGPG LVKPSQSLSL TCTVTGYSIT SDYAWNWIRQ FPGNKLEWMG YI---SYIGG IGYNPSLKSR ISITRDTSKN QFFLHLNSVT TGDTATYYCA RNGAMDFWGQ GISVTVSS (SIN:140)
21H1  DVQLQESGPG LVKPSQSLSL TCTVTGYSIT SDYAWNWIRQ FPGNKLEWMG YI---SYSGS IGYSPSLKSR ISITRDTSKN QFFLHLNSVT TGDTATYYCA RNGAMDYWGQ GISVTVSS (SIN:141)
```

MASP-3 inhibitory agent which inhibits the conversion of Pro-Factor D to mature Factor D.

33 Claims, 30 Drawing Sheets

Specification includes a Sequence Listing.

Related U.S. Application Data on Aug. 18, 2020, provisional application No. 63/066,948, filed on Aug. 18, 2020.

(56) References Cited

U.S. PATENT DOCUMENTS

| | | | |
|---|---|---|---|
| 5,585,089 | A | 12/1996 | Queen et al. |
| 5,693,762 | A | 12/1997 | Queen et al. |
| 6,180,377 | B1 | 1/2001 | Morgan et al. |
| 6,407,213 | B1 | 6/2002 | Carter et al. |
| 2017/0355756 | A1* | 12/2017 | Julien ............... A61P 25/00 |
| 2018/0140697 | A1 | 5/2018 | Cummings et al. |
| 2019/0040137 | A1 | 2/2019 | Hu et al. |

FOREIGN PATENT DOCUMENTS

| | | |
|---|---|---|
| WO | WO2011/016238 A1 | 2/2011 |
| WO | WO2013/180834 | 12/2013 |
| WO | WO2013/192240 | 12/2013 |
| WO | WO2018/026722 | 2/2018 |
| WO | WO2020/010235 A1 | 1/2020 |

OTHER PUBLICATIONS

Kussie "A Single Engineered Amino Acid Substitution Changes Antibody Fine Specificity" J immunol 152(1):146-52 (Year: 1994).*
Oroszlan "MASP-1 and MASP-2 Do Not Activate Pro-Factor D in Resting Human Blood, whereas MASP-3 Is a Potential Activator: Kinetic Analysis Involving Specific MASP-1 and MASP-2 Inhibitors" J Immunol (2016) 196(2): 857-865 (Year: 2016).*
Clackson, T., et al., "Making antibody fragments using phage display libraries," *Nature* 352:624-628 (1991).
Riechmann et al., "Reshaping human antibodies for therapy," *Nature* 332:323 (1988).
Kohler, G., et al., "Continuous cultures of fused cells secreting antibody of predefined specificity," *Nature* 256:495 (1975).
Marks, J.D., et al., "By-passing Immunization: Human Antibodies from V-gene Libraries Displayed on Phage," *J. Mol. Biol.* 222:581-597 (1991).
Jones, P.T., et al., "Replacing the complementarity-determining regions in a human antibody with those from a mouse," *Nature* 321:522-525 (1986).

Yongqing T. et al., "Mannose-binding lectin serine proteases and associated proteins of the lectin pathway of complement: two genes, five proteins and many functions?" *Biochim Biophys Acta* 1824(1):253-62 (2012).
Logan & Shenk, "Adenovirus tripartite leader sequence enhances translation of mRNAs late after infection," *Proc. Natl. Acad. Sci. USA* 81:3655-3659 (1984).
Chothia and Lesk, "Canonical structures for the hypervariable regions of immunoglobulins," *J. Mol. Biol.* 196:901-917 (1987).
Ruiz, M., et al., "IMGT, the international ImMunoGeneTics database," *Nucleic Acids Res* 28(1):219-221 (2000).
Graham et al., "Characteristics of a human cell line transformed by DNA from human adenovirus type 5," *J. Gen Virol.* 36:59 (1977).
Urlaaub et al., "Isolation of Chinese hamster cell mutants deficient in dihydrofolate reductase activity," *Proc. Natl. Acad. Sci. (USA)* 77(7):4216 (1980).
Mather, J.P., "Establishment and characterization of two distinct mouse testicular epithelial cell lines," *Biol. Reprod.* 23(1):243-252 (1980).
Mather et al., "Culture of testicular cells in hormone-supplemented serum-free medium," *Annals N.Y. Acad. Sci* 383:44-68 (1982).
Coligan, J.E., et al. (Eds.). 1991. Production of Monoclonal Antibodies. *Current Protocols in Immunology*, pp. 25.1-26.7. vol. 1. John E. Wiley & Sons.
Ricklin et al., "Complement: a key system for immune surveillance and homeostasis," *Nat Immunol* 11(9):785-97 (2010).
Lefranc, M.P., et al., "IMGT, the international ImMunoGeneTics database," *Nucleic Acids Res* 27(1):209-212.
Lachmann P.J, "The Amplification Loop of the Complement Pathways," Adv Immunol 104:115-49, 2009.
Noris M., et al., "Overview of Complement Activation and Regulation," *Semin Nephrol* 33(6):479-92 (2013).
Winter, et al., "Man-made antibodies," *Nature* 349:293-299 (1991).
Field et al., "Elevated expression of the c-myc oncoprotein correlates with poor prognosis in head and neck squamous cell carcinoma," *Oncogene* 4:1463-1468 (1989).
Spandidos et al., "High levels of c-myc protein in human breast tumours determined by a sensitive ELISA technique," AntiCancer Res. 9(4): 821-826 (1989).
Deng R. et al., "Projecting human pharmacokinetics of therapeutic antibodies from nonclinical data," MAbs, 3:1, 61-66, 2011.
Verhoeyen et al., "Reshaping Human Antibodies: Grafting an Antilysozyme Activity," *Science* 239(4847):1534-36 (1988).
Bitter et al., "Expression and Secretion Vectors for Yeast," *Methods in Enzymol.* 153:516-544 (1987).
Gold et al., "New MUC1 Serum Immunoassay Differentiates Pancreatic Cancer From Pancreatitis," *J Clin Oncol.* 24(2):252-58, 2006.
Rycyzyn, Michael A., et al., "The Use of an Anti-CD40 Agonist Monoclonal Antibody During Immunizations Enhances Hybridoma Generation," *Hybridoma* 27(1):25-30, 2008.
Dong J. et al., "Quantitative prediction of human pharmacokinetics for monoclonal antibodies: retrospective analysis of monkey as a single species for first-in-human prediction," *Clin Pharmacokinel* 50(2): 131-42(2011).

* cited by examiner

Human full-length Factor D (SEQ ID NO:1)

MHSWERLAVLVLLGAAACAAPPRGRILGGREAEAHARPYMASVQLNGAHLCGGVLVAEQWVLSAAHCLED
AADGKVQVLLGAHSLSQPEPSKRLYDVLRAVPHPDSQPDTIDHDLLLLQLSEKATLGPAVRPLPWQRVDR
DVAPGTLCDVAGWGIVNHAGRRPDSLQHVLLPVLDRATCNRRTHHDGAITERLMCAESNRRDSCKGDSGG
PLVCGGVLEGVVTSGSRVCGNRKKPGIYTRVASYAAWIDSVLA

Human Pro-Factor D (SEQ ID NO:2)

APPRGRILGGREAEAHARPYMASVQLNGAHLCGGVLVAEQWVLSAAHCLED
AADGKVQVLLGAHSLSQPEPSKRLYDVLRAVPHPDSQPDTIDHDLLLLQLSEKATLGPAVRPLPWQRVDR
DVAPGTLCDVAGWGIVNHAGRRPDSLQHVLLPVLDRATCNRRTHHDGAITERLMCAESNRRDSCKGDSGG
PLVCGGVLEGVVTSGSRVCGNRKKPGIYTRVASYAAWIDSVLA

Human mature Factor D (SEQ ID NO:3)

ILGGREAEAHARPYMASVQLNGAHLCGGVLVAEQWVLSAAHCLED
AADGKVQVLLGAHSLSQPEPSKRLYDVLRAVPHPDSQPDTIDHDLLLLQLSEKATLGPAVRPLPWQRVDR
DVAPGTLCDVAGWGIVNHAGRRPDSLQHVLLPVLDRATCNRRTHHDGAITERLMCAESNRRDSCKGDSGG
PLVCGGVLEGVVTSGSRVCGNRKKPGIYTRVASYAAWIDSVLA

FIG. 2

|       | Signal Peptide | Activation Peptide | Mature Factor D | |
|-------|---|---|---|---|
| Homo    | ---MHSWERLAVLVLLGAAA | AAPPR | RILGGREAEAEAHARPYMASVQLNGAHLCGGVLVA... | (aa1-57 of SIN:1) |
| Macaca  | ---MHSWEHLAVLVLLGVAACAAQ | PRGR | RILGGREAEAEAHARPYMASVQVNGEHLCGGVLVA... | (aa1-57 of SIN:8) |
| Canis   | MAPRLGPVPLVPLVLLGAALCAAQ | PRGR | RILGGSEAESHARPYMASVQVDGKHVCGGFLVS... | (aa1-60 of SIN:9) |
| Rattus  | ---MHSSVYLVALVVLEAAVCVAQ | PRGR | RILGGQEAMAHARPYMASVQVNGTHVCGGTLVD... | (aa1-57 of SIN:10) |
| Mus     | ---MHSSVYFVALVILGAAVCAAQ | PRGR | RILGGQEAAAHARPYMASVQVNGTHVCGGTLLD... | (aa1-57 of SIN:11) |

FIG. 3

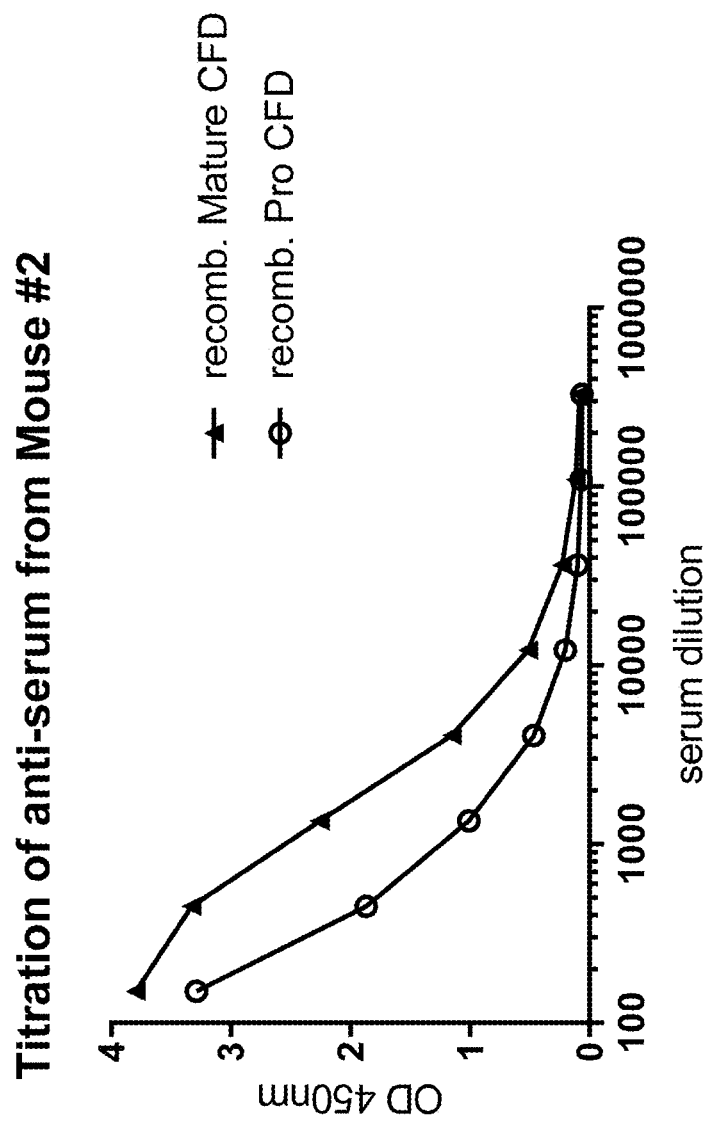

Anti-human mature-Factor D-specific antibodies: heavy chain variable region

```
VH
Kabat                                                      31         35                    50                    65                             95           102
6G6    QITLKESGPG ILQSSQTLSL TCSFSGISLT TSGMGVSWIR QPSGKGLEWL AHIYWDDEKH YHPSLKSRLT ISKDASRNQV FFRILSVDTA DTATYYCALR YYGYRSEMDY WGQGTSVTVS S (SIN:12)
14A11  QITLKESGPG ILQSSQTLSL TCSFSGVSLT ISGMGVSWIR QPSGKGLEWL AHIYWDDEKH YHPSLKSRLT ISKDASRNQV FFRILSVDTA DTATYYCALR YYGYRSEMDY WGQGTSVTVS S (SIN:13)
27B3   QVTLKESGPG ILQSSQTLSL TCSFSGISLN ISIMGVSWIR QPSGKGLEWL AHIYWDDEKH YNPSLKSRLT ISKDASRNQV FFRISSVDSA DTATYYCALR YYGYGSIMDY WGHGTSVTVS S (SIN:14)
58F5   QVTLKESGPG ILQSSQTLSL TCSFSGISLN ISIMGVSWIR QPSGKGLEWL AHIYWDDEKH YNPSLKSRLT ISKDASRNQI FLKIISVDTA DTATYYCALR YYGYNYVMHY WGQGTSVTVS S (SIN:15)
49G3   QVTLKESGPG ILQSSQTLSL TCSFSGISLS SSGMGVSWIR QPSGKGLEWL AHIYWDDEKH YNPSLKSRLT ISKGASRNQV FLKIISVDTA DTATYYCALR YYGYNYVMHY WGQGTSVTVS S (SIN:16)
10G1   QVTLKESGPG ILQSSQTLSL TCSFSGVSLS SSGMGVSWIR QPSGKGLEWL AHIYWDDEKH YNPSLKSRLT ISKGASRNQV FLKIISVDTA DTATYYCALR YYGYNSIMHY WGQGASVTVS S (SIN:17)
```

FIG. 7A

Anti-human mature-Factor D-specific antibodies: light chain variable region

```
Vκ
Kabat & Chothia
              24                    34                  50    56                          89      97
6G6   DVLMTQSPLS LPVSLGDQAS IFCRSNQSIV HSNGNTYFEW YLQKPGQSPK LLIYKVSNRF SGVPDRFSGS GSGTDFTLRI SRVEAEDLGV YYCFQGSHVP PTFGGGTKLE IKR (SIN:18)
14A11 DVLMTQSPLS LPVSLGDQAS IFCRSNQSIV HSNGNTYFEW YLQKPGQSPK LLIYKVSNRF SGVPDRFSGS GSGTDFTLRI SRVEAEDLGI YYCFQGSHVP PTFGGGTKLE IKR (SIN:19)
27B3  DVLMTQTPLS LPVSLGDQAS ISCRSSQSIV HSNGNTYFEW YLQKPGQSPK LLIYKVSNRF SGVPDRFSGS GSGTDFTLKI SRVEAEDLGV YYCFQGSHVP PTFGGGTKLE IKR (SIN:20)
58F5  DVLMTQTPLS LPVSLGDQAS ISCRSSQSIL HSNGNTYLEW YLQKPGQSPK LLIYKVSNRF SGVPDRFSGS GSGTDFTLKI SRVEADDLGV YYCFQGSHVP PTFGGGTKLE IKR (SIN:21)
49G3  DVLMTQTPLS LPVSLGDQAS ISCRSSQSIL HSNGNTYFEW YLQKPGQSPK LLIYKVSNRF SGVPDRFSGS GSGTDFTLKI SRVEAEDLGV YYCFQGSHVP PTFGGGTKLE IKR (SIN:22)
10G1  DVLMTQTPLS LPVSLGDQAS ISCRSSESIV HSNGNTYLEW YLQKPGQSPK LLIYKVYNRF SGVPDRFSGS GSGTDFTLKI SRVEAEDLGV YYCFQGSHVP PTFGGGTKLE IKR (SIN:23)
```

FIG. 7B

Anti-human Factor D antibodies: heavy chain variable region

```
VH                                                                                                                                     95          102
Kabat                      31    35                  50                           65                                                VGLYGNFFMD      YWGQGTSVTV SS (SIN:85)
3C5    EVKLVESGGG LVQPGGGSLKL SCATSGFTFS DYGMAWVRQA PGKGPEWVAF ISNLA--YSF YVVDIVMGRF TISRENAKNT LYLEMSSLRS EDTAMYYCAR VGLYGNFFMD YWGQGTSVTV SS (SIN:85)
30H2   EVKLVESGGG LVQPGGGSLKL SCATSGFTFS DYGMAWVRQA PGKGPEWVAF ISNLA--YSF YVVDIVMGRF TISRENAKNT LYLEMSSLRS EDTAMYYCAR VGLYGNFFMD YWGQGTSVTV SS (SIN:85)
11H1   EVQLVESGGG LVQPKGSLKL SCAASGFSFN IYAMNWVRQA PGKGLEWVAR IRSKSNNYAT HYADSVKDRF TISRDDSESM LYLQMNNLKT EDTAMYYCVR QGYY--WYFD VWGTGTTVTV SS (SIN:86)
12M10  EVQLVESGGG LVQPKGSLKL SCAASGFSFN IYAMNWVRQA PGKGLEWVAR IRSKSNNYAT YYADSVKDRF TISRDDSESM LYLQMNNLKT EDTAMYYCVR HGYY--WYFD VWGTGTTVTV SS (SIN:87)
7H2    EVQVVESGGG LVRPKGSLKL SCAASGFSFN IYAMNWVRQA PGKGLEWVAR IRSKSNNYAT YYADSVKDRF TISRDDSESM LSLQMNNLKT EDTAMYYCVR QGYY--WYFD VWGTGTTVTV SS (SIN:88)
```

FIG. 10A

Anti-human Factor D antibodies: light chain variable region

```
VK                                                                                                                             
Kabat & Chothia                24               34                    50      56                           89        97
3C5     DIQMNQSPSS LSASLGDTIT ITCHASQNI- ----NVWLSW YQQKPGNIPE LLIYKASNLH TGVPSRFSGN RSGTSFTLTI SSLQPEDIGT YFCQQGQSYP LTFGAGTKLE LRR    (SEQ ID NO: 89)
30H2    DIQMNQSPSS LSASLGDTIT ITCHASQNI- ----NVWLSW YQQKPGNIPE LLIYKASNLH TGVPSRFSGN RSGTSFTLTI SSLQPEDIGT YFCQQGQSYP LTFGAGTKLE IKR    (SEQ ID NO: 90)
11H1    DVLMTQTPLS LPVSLGDQAS ISCRSSQSIV HSNGNTYLEW YLQKPGQSPK LLIYTVSNRF SGVPDRFSGS GSGTDFTLKI SRVEAEDLGV YCFQGSHVP WTFGGGTKLE IKR    (SEQ ID NO: 91)
12H10   DVLMTQTPLS LPVSLGDQAS ISCRSSQSIV HSNGNTYLEW YLQKPGQSPK LLIYTVSNRF SGVPDRFSGS GSGTDFTLKI SRVEAEDLGV YCFQGSHVP YTFGGGTKLE IKR    (SEQ ID NO: 92)
7H2     DVLMTQTPLS LPVSLGDQAS ISCRSSQSIV HSNGNTYLEW YLQKPGQSPK LLIYTVSNRF SGVPDRFRGS GSGTDFTLKI SRVEAEDLGV YCFQGSHVP WTFGGGTKLE IKR    (SEQ ID NO: 93)
```

FIG. 10B

Anti-human Pro-Factor D-specific antibodies: heavy chain variable region

```
VH
Kabat                                              31   35                        50                    65                                       95  102
18F5  EVKLEESGGG LVQPGGSMKL SCVASGFTFG -NYWMSWVRQ SPEKGLEWVA EIRLKSDNYA THYAESVKGK FTISRDDSKS RLYLQMNSLR GEDTGLYYCT N-AWFASWGQ GTLVTVSA (SIN:136)
1F9   EVKLEESGGG LVQPGGSMKL SCVASGFTFG -SYWMSWVRQ SPEKGLEWVA EIRLKSDNYA AHYAESVKGK FTISRDDSKS RLYLQMNSLR GEDTGIYYCT N-AWFASWGQ GTLVTVSA (SIN:137)
2A4   EVKLEESGGG LVQPGGSMKL SCVASGFTFS -TYWMSWVRQ SPEKGLEWVA EIRLKSDNYA THYTESVKGK FTISRDDSKS RLYLQMNSLR VEDTGIYYCT N-AWFAYWGQ GTLVTVSA (SIN:138)
20A1  EVKLEESGGG LVQPGGSMKL SCIASGFTFS -TYWMSWVRQ SPEKGLEWVA EIRLKSENYA TYYAESVKGK FIISRDDSKS RLYLQMNSLR AEDTGIYYCT N-AWFANWGQ GTLVTVSA (SIN:139)
13A10 DVQLQESGPG LVKPSQSLSL TCTVTGYSIT SDYAWNWIRQ FPGNKLEWMG YI---SYIGG IGYNPSLKSR ISITRDTSKN QFFLHLNSVT TGDTATYYCA RNGAMDFWGQ GISVTVSS (SIN:140)
21H1  DVQLQESGPG LVKPSQSLSL TCTVTGYSIT SDYAWNWIRQ FPGNKLEWMG YI---SYSGS IGYSPSLKSR ISITRDTSKN QFFLHLNSVT TGDTATYYCA RNGAMDYWGQ GISVTVSS (SIN:141)
```

FIG. 16A

Anti-human Pro-Factor D-specific antibodies: light chain variable region

```
VK
Kabat & Chothia
                             24                    34                   50     56                       89          97
18F5  DIVMSQSPSS LAVSVGEKVT MSCMSSSQSLL YSKDQKNYLA WYQQKPGQSP KLLIYWASIR ESGVPDRFTG SGSGTDFTLT ISSVKAEDLA VYYCLQYYTY PYIFGGGTKL EIKR (SIN:142)
1F9   DIVMSQSPSS LTVSVGEKVT MSCMSSSQSLL YSKDQKNYLA WYQQKPGQSP TLLIYWASIR ESGVPDRFTG SGSGTDFTLT ISSVKAEDLA VYYCLQYYTY PYIFGGGTKL EIKR (SIN:143)
2A4   DIVMSQSPSS LAVSVGEKFT MSCKSSSQSLL YSRDQKNYLA WYQQQPGQSP KLLIYWASIR ESGVPDRFTG SGSGTDFTLT ISSVKTEDLA VYYCLQYYTY PYIFGGGTKL EIKR (SIN:144)
20A1  DIVMSQSPSS LVVSVGEKVT MSCKSSSONLL YSRDQKNYLA WYQQKPGQSP NLLIYWASIR ESGVPDRFTG SGSGTDFSLT ISSVKAEDLA VYYCLQYYSY PYIFGGGTKL EMKR (SIN:145)
13A10 DIVLTQSPAS LAVSLGQRAT ISCKASQSVD YDGD--SYMN WYQQKPGQPP KLLIYDASNL ESGIPARFSG SGSGTDFTLN IHPVEEEDAA TYYCQQSNEA PWIFGGGTKL EIRR (SIN:146)
21H1  DIVLTQSPAS LAVSLGQRAT ISCKASQSVD YDGD--SYMN WYQQKPGQPP KLLIYDASIL ESGIPARFSG SGSGTDFTLN IHPVEEEDAA TYYCQQNYEA PWIFGGGTKL EIKR (SIN:147)
```

FIG. 16B

MONOCLONAL ANTIBODIES, COMPOSITIONS AND METHODS FOR DETECTING COMPLEMENT FACTOR D

CROSS-REFERENCE TO RELATED APPLICATIONS

This application claims the benefit of U.S. Provisional Application No. 63/066,942 filed Aug. 18, 2020, U.S. Provisional Application No. 63/066,948, filed Aug. 18, 2020, and U.S. Provisional Application No. 63/197,833 filed Jun. 7, 2021, which are hereby incorporated by reference in their entirety.

FIELD OF THE INVENTION

The present invention relates to monoclonal antibodies and compositions comprising such antibodies for use in detecting the presence and amount of mature Factor D and Pro-Factor D.

STATEMENT REGARDING SEQUENCE LISTING

The sequence listing associated with this application is provided in text format in lieu of a paper copy and is hereby incorporated by reference into the specification. The name of the text file containing the sequence listing is: MP_1_0316_US_Sequence_Listing_20210816_ST25. The text file is 139 KB; was created on Aug. 16, 2021 and is being submitted via EFS-Web with the filing of the specification.

BACKGROUND

The complement system supports innate host defense against pathogens, dysregulated and unabated complement activity can also function as a major driver of autoimmune disease, causing unchecked propagation of inflammation and tissue destruction. However, dysregulated and unabated complement activity can also function as a major driver of disease, causing unchecked propagation of inflammation and tissue destruction. The alternative pathway of complement (APC) is typically described as a downstream amplifier of complement activity, increasing the host immune response following activation of complement via the classical and lectin pathways. However, the ability of the APC to create a positive feedback loop of protease complexes with activity that drives the formation of new complexes of the same type is unique within the complement pathways (Lachmann P. J, *Adv Immunol* 104:115-49, 2009).

Complement Factor D (CFD) is a serine protease that is essential for activation of the APC. Factor D cleaves factor B bound to C3b, generating the C3b/Bb enzyme which is the active component of the alternative pathway C3/C5 convertases. While CFD is expressed as an inactive zymogen (referred to herein as "Pro-Factor D"), it circulates in plasma predominantly as a cleaved, mature serine protease (referred to herein as "mature Factor D"). As described in WO2013/180834 and WO2013/192240, it has recently been determined that MASP-3 is responsible for the conversion of complement factor D (CFD) from the zymogen form of the protein (Pro-Factor D) to the active form (mature Factor D), thus placing the MASP-3 protein at a key upstream regulatory step for the APC. As further described in WO2018/026722, hereby incorporated herein by reference, numerous high affinity anti-MASP-3 inhibitory antibodies have been generated that bind the serine protease domain of MASP-3 and inhibit its catalytic activity.

A current problem in the area of complement research is that anti-Factor D antibodies in commercially available test kits do not differentiate between Pro-Factor D and the active form (mature Factor D). In a wild-type animal or human plasma, the large majority of systemic CFD has already been processed to the mature form by in vivo MASP-3 activity, making in vitro assessment of APC inhibition by MASP-3 inhibitors using traditional assays impossible. Therefore, a need exists for detection reagents and assays for measuring the presence and amount of Pro-Factor D and/or mature Factor D in a biological sample for use as a biomarker of APC status and thereby allowing for in vitro assessment of APC inhibition by MASP-3 inhibitors.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention addresses the need for detection reagents and assays for measuring the presence and amount of Pro-Factor D and/or mature Factor D in a biological sample.

In one aspect, the present disclosure provides an isolated antibody, or antigen binding fragment thereof, that specifically binds to an epitope in the amino-terminal region of human mature Factor D, wherein the epitope comprises or consists of the amino acid sequence ILGGREA (SEQ ID NO:5). In one embodiment, the isolated antibody or fragment thereof specifically binds human mature Factor D (SEQ ID NO:3) and does not bind to human Pro-Factor D (SEQ ID NO:2). In one embodiment, the antibody is a monoclonal antibody. In one embodiment, the present disclosure provides a nucleic acid molecule encoding the CDRs of a heavy chain variable region and/or the CDRS of a light chain variable region of an antibody, or fragment thereof, that specifically binds human mature Factor D.

In another aspect, the present disclosure provides an isolated antibody, or antigen binding fragment thereof, that specifically binds to an epitope on the activation ("Pro") peptide of human Factor D, wherein the epitope comprises or consists of "APPRGR" (SEQ ID NO:4). In one embodiment, the antibody specifically binds to human Pro-Factor D (SEQ ID NO:2) and does not bind to mature Factor D (SEQ ID NO:3). In one embodiment, the antibody is a monoclonal antibody. In one embodiment, the present disclosure provides a nucleic acid molecule encoding the CDRs of a heavy chain variable region and/or the CDRs of a light chain variable region of an antibody, or fragment thereof, that specifically binds human Pro-Factor D.

In another aspect, the present disclosure provides a kit for detecting the presence or amount of mature factor D and/or Pro-Factor D in a test sample, said kit comprising (a) at least one container, and (b) at least one antibody, or fragment thereof, that specifically binds human mature Factor D and/or Pro-Factor D.

In another aspect, the present disclosure provides an isolated antibody or antigen-binding fragment thereof that binds to an epitope shared by human mature Factor D and human Pro-Factor D, wherein the antibody comprises a binding domain comprising HC-CDR1, HC-CDR2 and HC-CDR3 in a heavy chain variable region selected from the group consisting of SEQ ID NO:s 85-88 and comprising LC-CDR1, LC-CDR2 and LC-CDR3 in a light chain variable region selected from the group consisting of SEQ ID NO:s 89-93, wherein the CDRs are numbered according to the Kabat numbering system.

In another aspect, the present disclosure provides a method of determining the presence or amount of mature Factor D in a test sample, the method comprising: (a) contacting a test sample with a mature Factor D-specific monoclonal antibody or antigen-binding fragment thereof, in an in vitro immunoassay; and (b) detecting the presence or absence or amount of the antibody or fragment thereof bound to mature Factor D, wherein the presence of binding indicates the presence or amount of mature Factor D in the sample; wherein the anti-human mature Factor D-specific antibody or antigen binding fragment thereof binds to an epitope in the N-terminal region of mature Factor D, set forth as amino acids ILGGREA (SEQ ID NO:5).

In another aspect, the present disclosure provides a method of determining the presence or amount of Pro-Factor D in a test sample, the method comprising: (a) contacting a test sample with an anti-human Pro-Factor D-specific monoclonal antibody or antigen-binding fragment thereof, in an in vitro immunoassay; and (b) detecting the presence or amount of the antibody or fragment thereof bound to Pro-Factor D, wherein the presence of binding indicates the presence or amount of Pro-Factor D in the sample; wherein the anti-human mature Pro-Factor D-specific antibody or antigen binding fragment thereof specifically binds to an epitope in the activation ("Pro") peptide of human Factor D, set forth as "APPRGR" (SEQ ID NO:4).

In another aspect, the present disclosure provides a method of assessing the extent of alternative pathway complement (APC) activation in a test sample comprising: (a) providing a test sample; (b) performing an immunoassay comprising at least one of: (i) capturing and detecting mature Factor D in the test sample, wherein mature Factor D is either captured or detected with a mature Factor D-specific monoclonal antibody or fragment thereof that specifically binds to an epitope in "ILGGREA" (SEQ ID NO:5) present in mature Factor D, but does not bind to Pro-Factor D; and/or (ii) capturing and detecting Pro-Factor D in the test sample, wherein Pro-Factor D is either captured or detected with a Pro-Factor D-specific monoclonal antibody or fragment thereof that specifically binds to an epitope on the activation ("Pro") peptide "APPRGR" (SEQ ID NO:4) present in Pro-Factor D, but does not bind to mature Factor D; and (c) comparing the level of mature Factor D detected in accordance with (b)(i) with a predetermined level or control sample and/or comparing the level of Pro-Factor D detected in accordance with (b(ii) with a predetermined level or control sample, wherein the level of mature Factor D and/or Pro-Factor D detected in the test sample is indicative of the extent of alternative pathway complement activation.

In another aspect, the present disclosure provides a method for monitoring the efficacy of treatment with a MASP-3 inhibitory antibody in a mammalian subject, the method comprising: (a) administering a dose of a MASP-3 inhibitory antibody to a mammalian subject at a first point in time; (b) assessing a first concentration of mature Factor D and/or Pro-Factor D in a biological sample obtained from the subject after step (a); (c) treating the subject with the MASP-3 inhibitory antibody at a second point in time; (d) assessing a second concentration of mature Factor D and/or Pro-Factor D in a biological sample obtained from the subject after step (c); and (e) comparing the level of mature Factor D and/or Pro-Factor D assessed in step (b) with the level of mature Factor D and/or Pro-Factor D assessed in step (d) to determine the efficacy of the MASP-3 inhibitory antibody in the mammalian subject.

In another aspect, the present disclosure provides a method of treating a mammalian subject suffering from, or at risk of developing an alternative-pathway disease or disorder, comprising administering a MASP-3 inhibitory antibody to the subject if the subject is determined to have: (i) a lower or decreased level of Pro-Factor D in one or more samples taken from the subject compared to a predetermined Pro-Factor D level or compared to the Pro-Factor D level in one or more control samples; and/or (ii) a higher or increased level of mature Factor D in one or more samples taken from the subject compared to a predetermined mature Factor D level or compared to the mature Factor D level in one or more control samples.

In another aspect, the present disclosure provides a pharmaceutical composition comprising a MASP-3 inhibitory antibody in an aqueous solution comprising a buffer system having a pH of 6.0±5%, 20±5% mM histidine, 100±5% mg/mL sucrose, and 0.035%±5%, polysorbate 80 wherein said MASP-3 inhibitory antibody is included at a concentration of 110 mg/mL±5%, and wherein said MASP-3 inhibitory antibody comprises a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT).

In another aspect, the present disclosure provides an article of manufacture containing a pharmaceutical composition comprising a MASP-3 inhibitory antibody, wherein the MASP-3 inhibitory antibody is in a unit dosage form of from 10 mg to 1000 mg suitable for therapeutic administration to a human subject.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 provides the amino acid sequences of (i) human full-length Factor D (SEQ ID NO:1), including the signal sequence aa 1-19 (shown in italic) and the activation (pro) peptide underlined; (ii) human Pro-Factor D (SEQ ID NO:2), with the pro-peptide underlined; and (iii) human mature Factor D (SEQ ID NO:3).

FIG. 3 provides an alignment of the amino acid sequences of pro-Factor D from various species.

FIG. 4 graphically illustrates the titration of anti-serum from representative mouse #2 after immunization with a peptide corresponding to the N-terminus of mature human factor D, as described in Example 1.

As shown in FIG. 6A, hybridoma supernatant 14A11 is capable of selectively detecting recombinant mature complement factor D and does not detect recombinant pro factor D, as described in Example 1.

As shown in FIG. 6B, hybridoma supernatant 6G6 is capable of selectively detecting recombinant mature complement factor D and does not detect recombinant pro factor D, as described in Example 1.

As shown in FIG. 6C, monoclonal antibody 1824 (R&D Systems) detects both recombinant mature CFD and recombinant active CFD and therefore is not capable of selectively detecting mature CFD as compared to pro CFD, as described in Example 1.

FIG. 7A shows an amino acid alignment of the heavy chain variable region (VH) sequences for the anti-human mature-Factor D-specific clones: 6G6_VH (SEQ ID NO:12), 14A11_VH (SEQ ID NO:13), 27B3_VH (SEQ ID NO:14), 58F5_VH (SEQ ID NO:15), 49G3_VH (SEQ ID NO:16), and 10G1_VH (SEQ ID NO:17), as described in Example 2.

FIG. 7B shows an amino acid alignment of the light chain variable region (VL) sequences for the anti-human mature-Factor D-specific clones: 6G6_VK (SEQ ID NO:18), 14A11_VK: (SEQ ID NO:19), 27B3_VK: (SEQ ID NO:20), 58F5_VK: (SEQ ID NO:21), 49G3_VK: (SEQ ID NO:22), and 10G1_VK: (SEQ ID NO:23), as described in Example 2.

As shown in FIG. 8, all the purified antibodies tested, namely 6G6, 14A11, 10G1, 49G3, 27B3 and 58F5, were found to be specific for the mature form of Factor D, as described in Example 3.

As shown in FIG. 9, the serum from representative mouse #1189 contains antibodies capable of binding to both mature Factor D and pro-Factor D, as described in Example 4.

FIG. 10A shows an amino acid alignment of the heavy chain variable region (VH) sequences for the anti-human Factor D clones: 3C5_VH (SEQ ID NO:85), 30H2_VH (SEQ ID NO:85), 11H1_VH (SEQ ID NO:86), 12H10_VH (SEQ ID NO:87), and 7H2_VH (SEQ ID NO:88), as described in Example 5.

FIG. 10B shows an amino acid alignment of the light chain variable region (VL) sequences for the anti-human Factor D clones: 3C5_VL (SEQ ID NO:89), 30H2_VL (SEQ ID NO:90), 11H1_VL (SEQ ID NO:91), 12H10_VL (SEQ ID NO:92) and 7H2_VL (SEQ ID NO:93), as described in Example 5.

As shown in FIG. 14, the serum from representative mouse #2 contains antibodies capable of selectively binding to mature Factor D as compared to pro-Factor D, as described in Example 7.

FIG. 16A shows an amino acid alignment of the heavy chain variable region (VH) sequences for the anti-human Pro-Factor D-specific clones: 18F5_VH (SEQ ID NO:136), 1F9_VH (SEQ ID NO:137), 2A4_VH (SEQ ID NO:138), 20A1_VH (SEQ ID NO:139), 13A10_VH (SEQ ID NO:140) and 21H1_VH (SEQ ID NO:141), as described in Example 8.

FIG. 16B shows an amino acid alignment of the light chain variable region (VL) sequences for the anti-human Pro-Factor D-specific clones: 18F5_VK (SEQ ID NO:142), 1F9_VK (SEQ ID NO:143), 2A4_VK (SEQ ID NO:144), 20A1_VK (SEQ ID NO:145), 13A10_VK (SEQ ID NO:146), and 21H1_VK (SEQ ID NO:147), as described in Example 8.

17A, all the purified antibodies tested, namely, 18F5, 1F9, 2A4, 20A1, 13A10, and 21H1, were capable of detecting the pro form of Factor D, as described in Example 9.

Figures 17A, 17B:
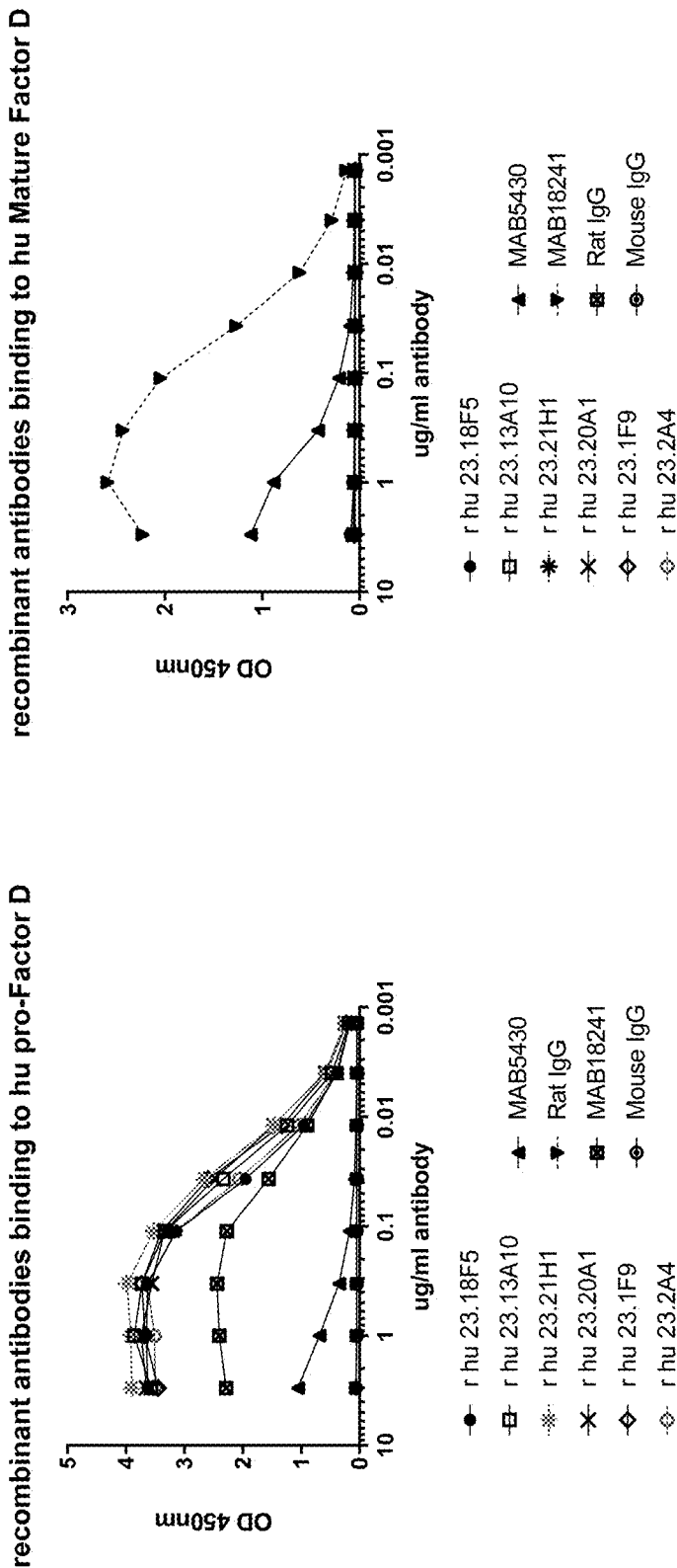
FIG. 17A graphically illustrates the detection of recombinant human Pro-Factor D with numerous candidate anti-human Pro Factor-D-specific antibodies. As shown in FIG.

FIG. 17B graphically illustrates the detection of recombinant human mature-Factor D with numerous candidate anti-human Pro Factor-D-specific antibodies. As shown in FIG. 17B, none of the purified antibodies tested, namely, 18F5, 1F9, 2A4, 20A1, 13A10, and 21H1, were capable of detecting the mature form of Factor D, as described in Example 9.

Figure 18:
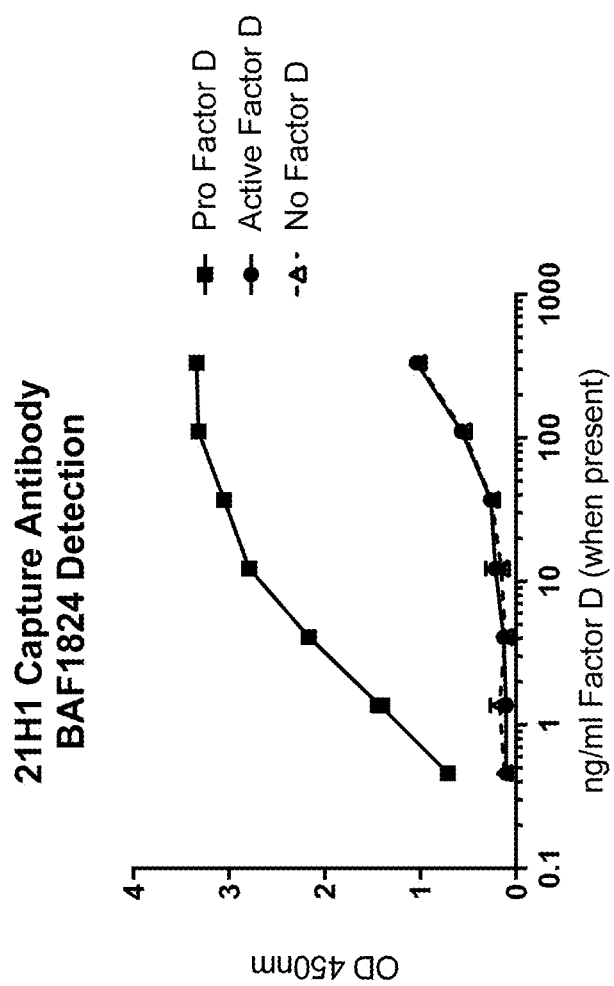

FIG. 18 graphically illustrates the detection of Pro-Factor D and mature Factor D in an ELISA assay with anti-Pro-Factor D antibody 21H1 as the coating antibody and goat polyclonal anti-Factor D antibody AF1824 (R&D Systems) as the detection antibody, as described in Example 9.

Figure 19:
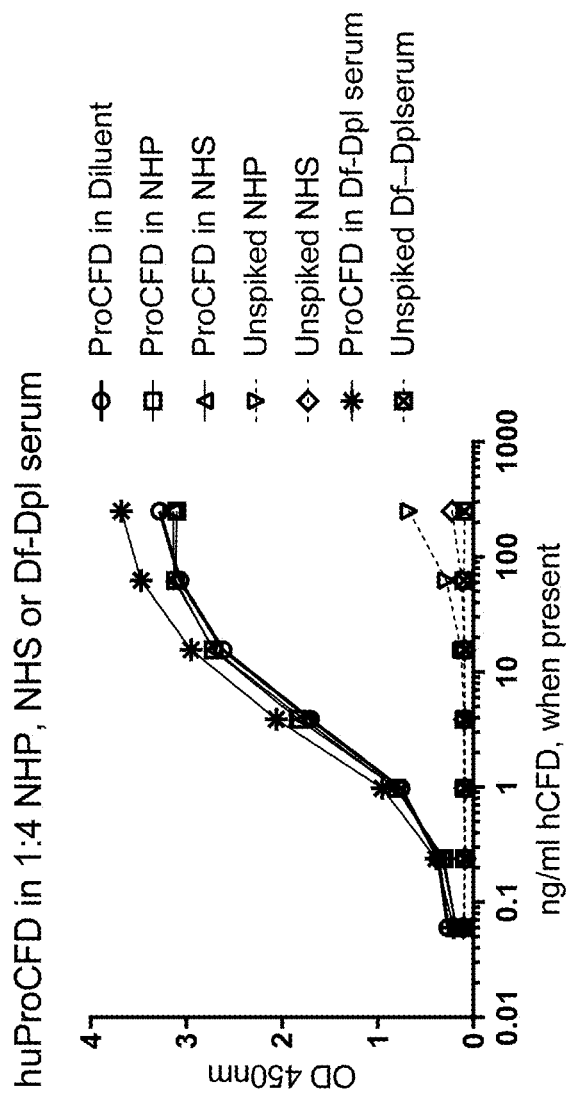

FIG. 19 graphically illustrates the detection of Pro-Factor D and mature Factor D in normal human plasma (NHP), normal human serum (NHS) or Factor-D-depleted serum (Df-Dpl serum) an ELISA assay with anti-Pro-Factor D antibody 21H1 as the coating antibody and goat polyclonal anti-Factor D antibody AF1824 (R&D Systems) as the detection antibody, as described in Example 9.

Figure 20:
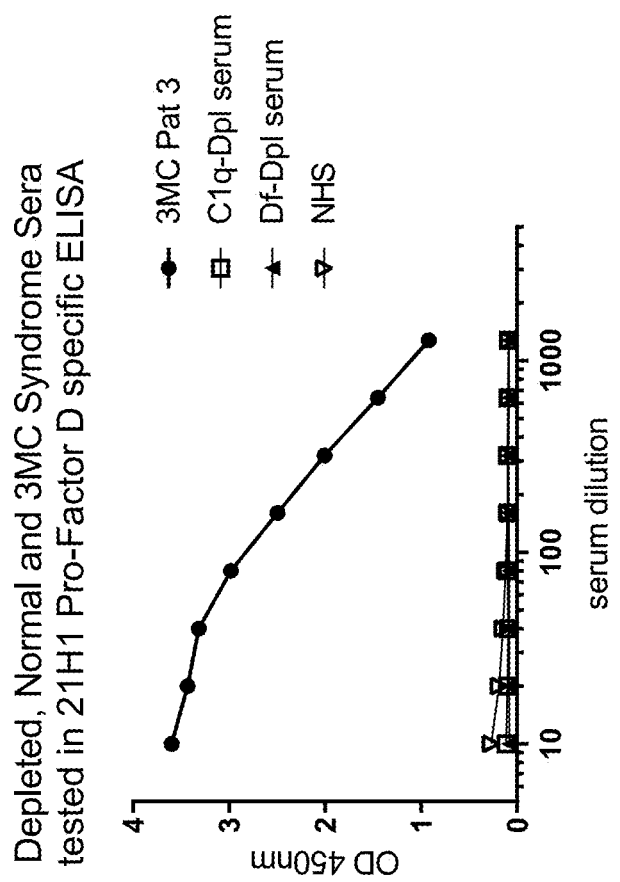

FIG. 20 graphically illustrates the amount of Pro-Factor D present in Normal Human Serum (NHS), C1q-Depleted Serum (C1q-Dpl), Factor D-Depleted Serum (Df-Dpl) and 3MC-syndrome patient serum_as determined in an ELISA assay with anti-Pro-Factor D antibody 21H1 as the coating antibody and goat polyclonal anti-Factor D antibody AF1824 (R&D Systems) as the detection antibody, as described in Example 9.

Figure 21B:
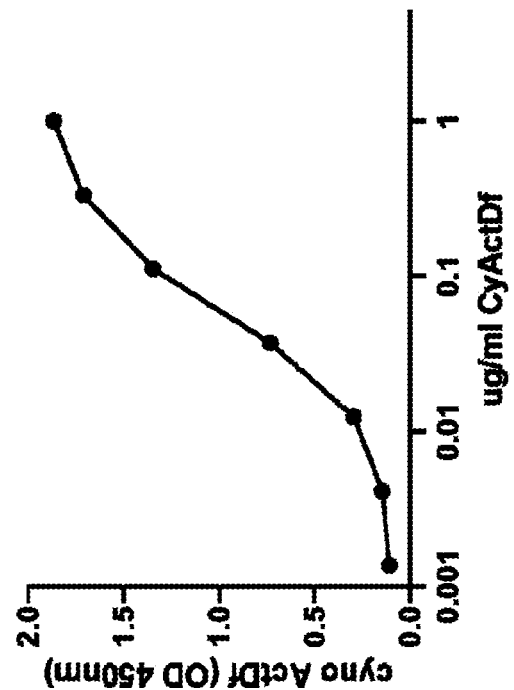
Figure 21A:
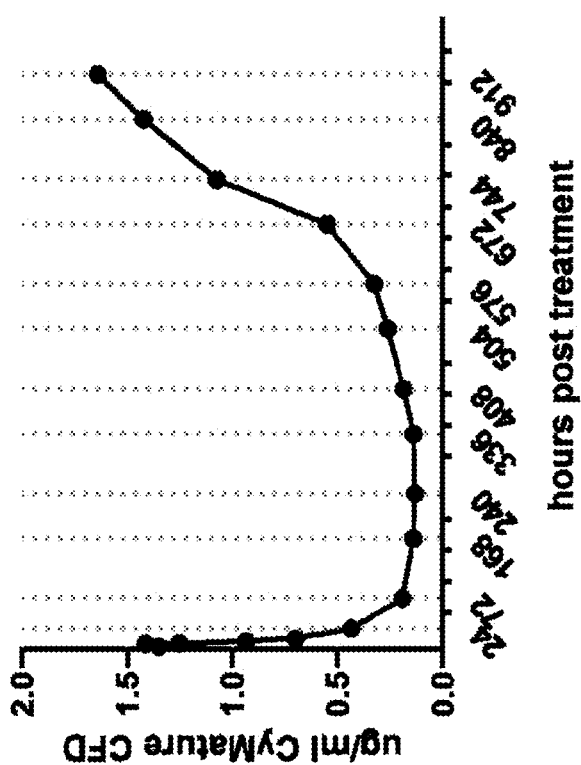

FIG. 21A graphically illustrates the amount of mature Factor D in a cynomolgus monkey over a time period of 912 hours post treatment with representative anti-MASP-3 mAb13B1, as described in Example 11.

FIG. 21B graphically illustrates the standard curve as determined from a 4-parameter logistics curve of cynomolgus recombinant mature Factor D dilutions, as described in Example 11.

Figures 22A, 22B:
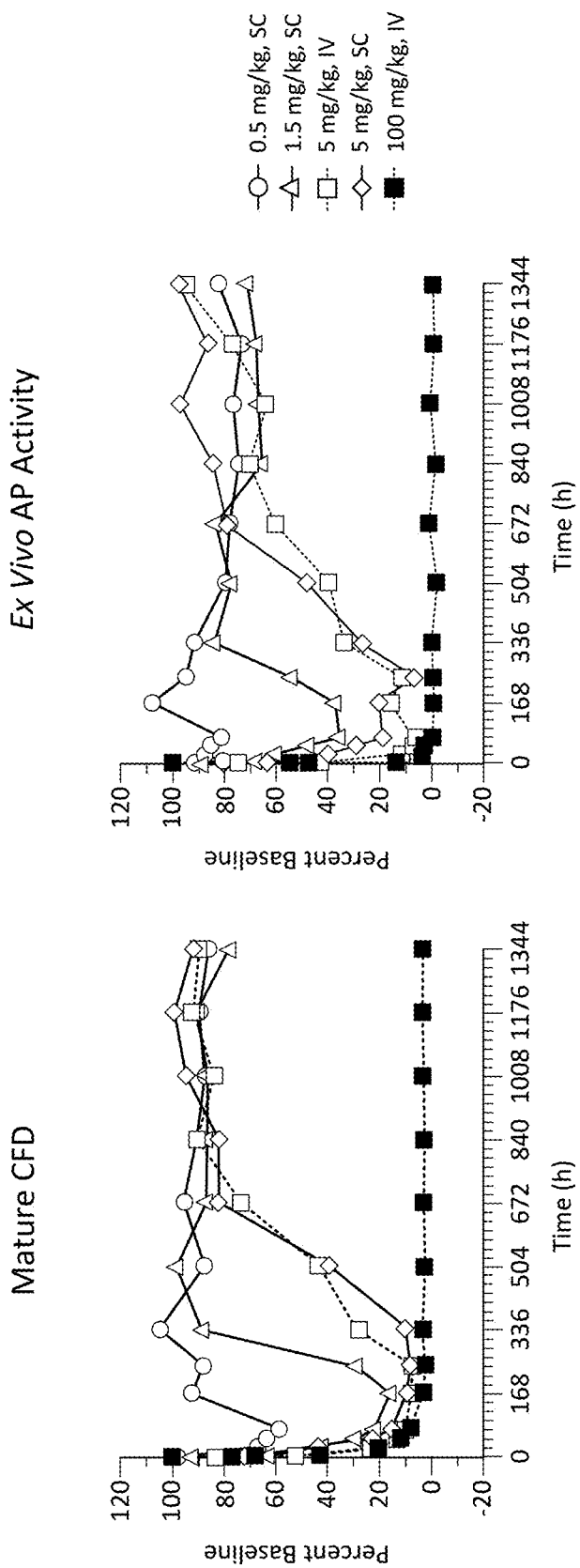

FIG. 22A graphically illustrates the concentration of mature Factor D in monkeys over a time period of 1344 hours after subcutaneous (SC) or intravenous (IV) administration of anti-MASP-3 mAb13B1, as measured in an ELISA assay with mature Factor D-specific antibody 14A11, as described in Example 12.

FIG. 22B graphically illustrates the ex vivo alternative pathway activity (% baseline) over a time period of 1344 hours after administration anti-MASP-3 mAb13B1, as determined in a Factor Ba assay, as described in Example 12.

Figure 23:
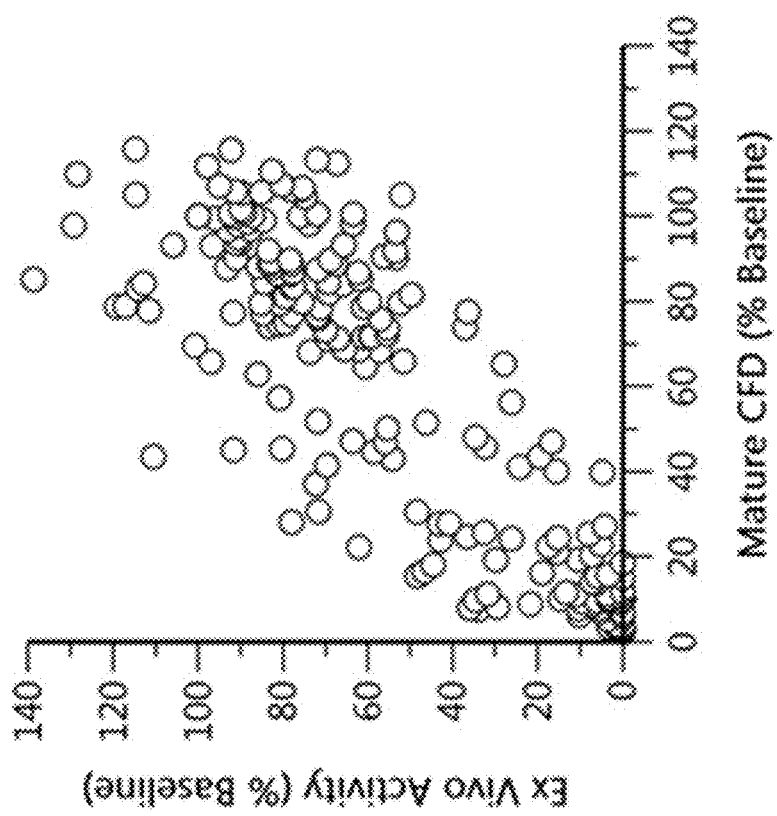

FIG. 23 graphically illustrates the PD-PD relationship of anti-MASP-3 mAb13B1 effects on ex vivo alternative pathway activity and mature Factor D concentration following a single intravenous bolus or subcutaneous administration in monkey, as described in Example 12.

Figure 24:
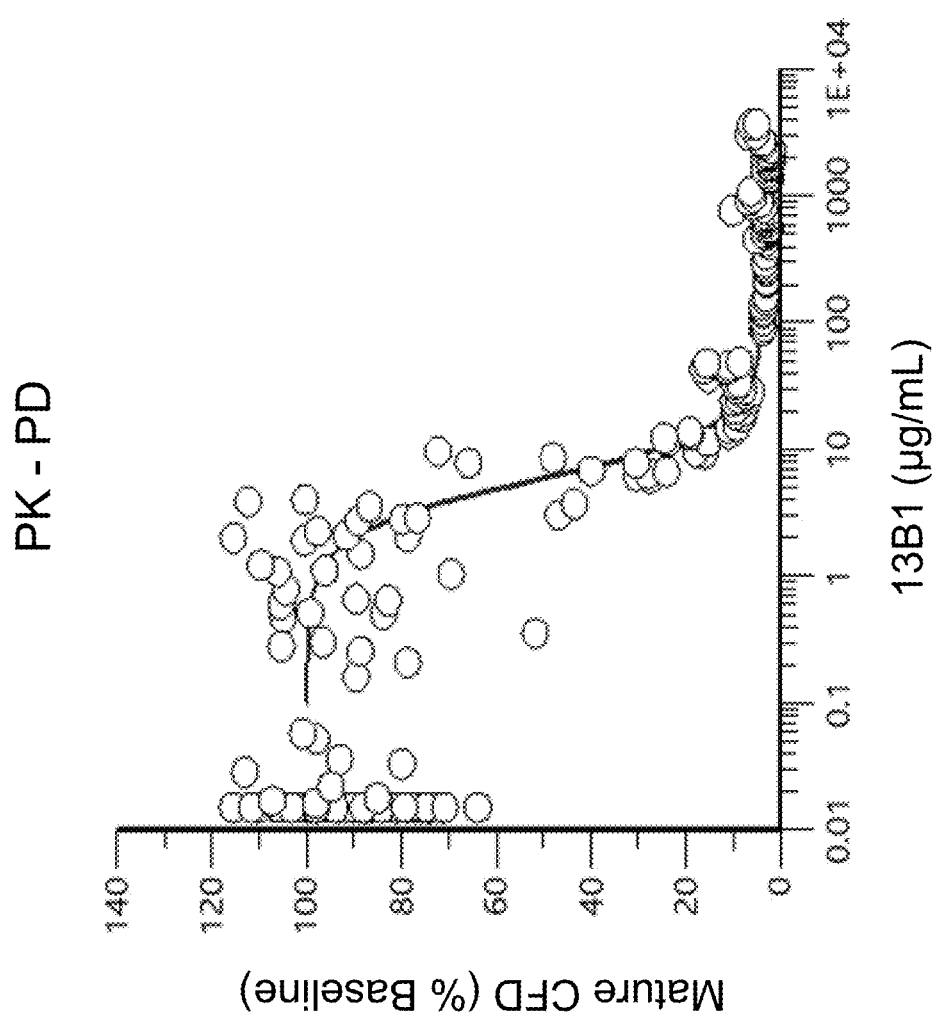

FIG. 24 graphically illustrates the PK-PD relationship of the dosage of anti-MASP-3 mAb13B1 and the effect on mature Factor D (% baseline), as described in Example 12.

Figure 25A:
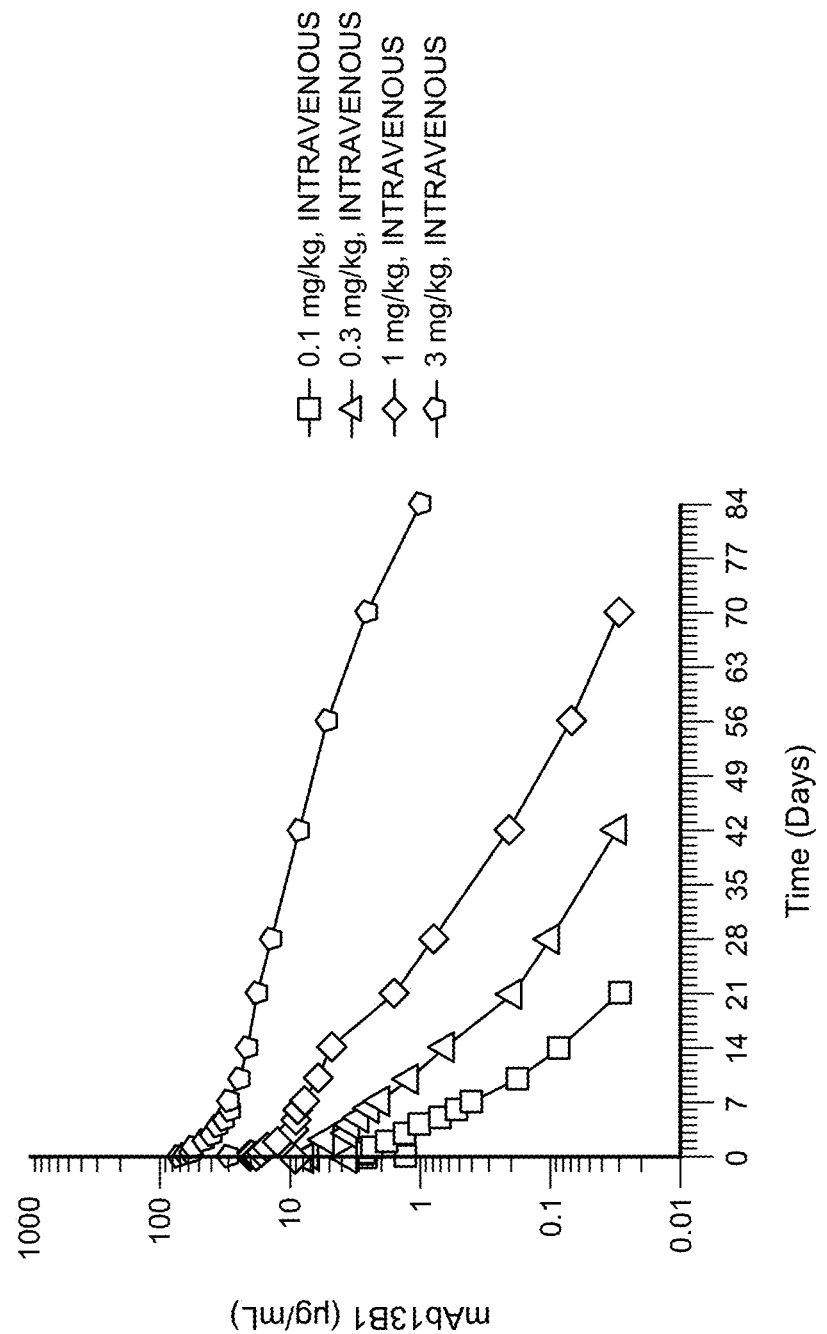

FIG. 25A graphically illustrates the concentration of mAb13B1 in serum of subjects over a time period of up to 84 days after intravenous (IV) administration of mAb13B1, as determined by ELISA, as described in Example 13.

Figure 25B:
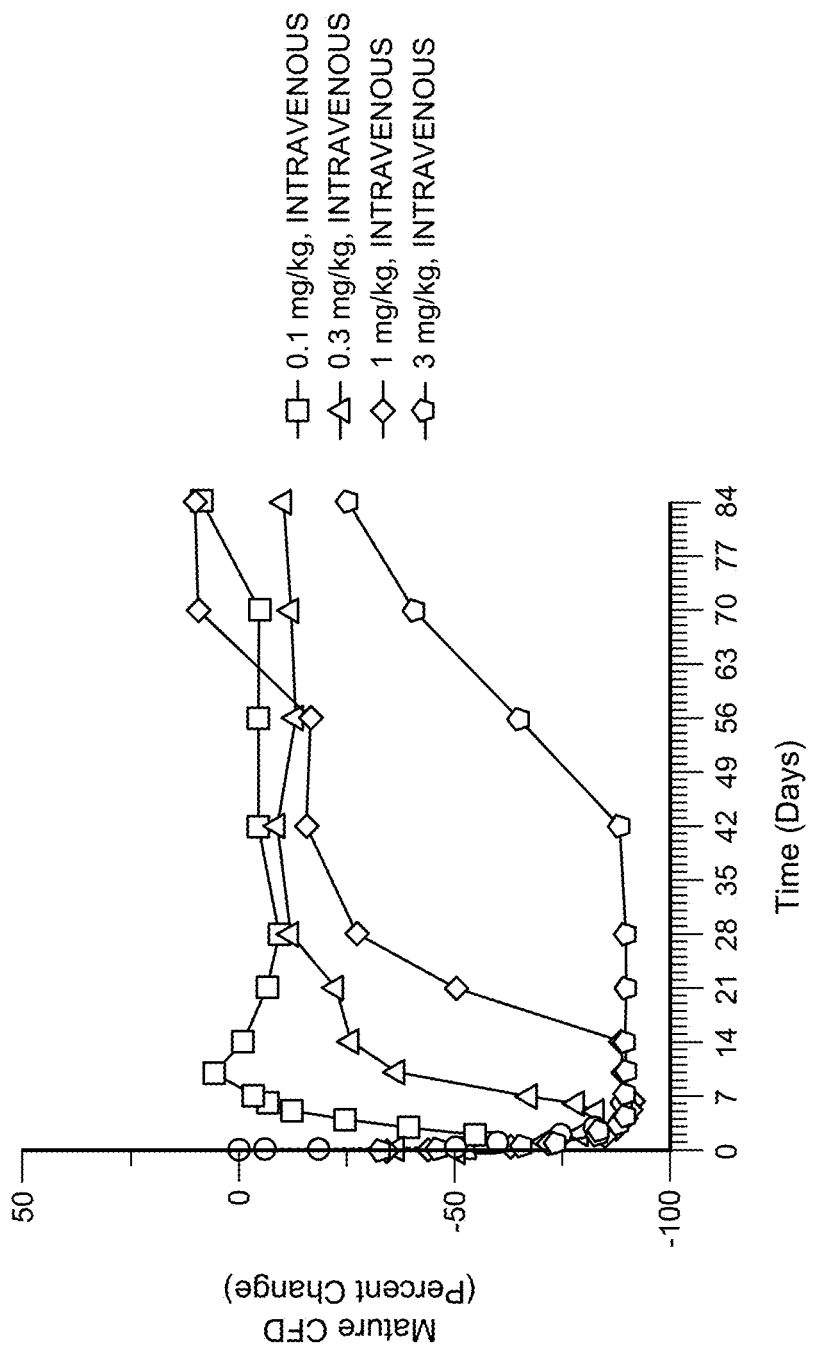

FIG. 25B graphically illustrates the levels of mature Factor D in subjects over a time period of 84 days after intravenous (IV) administration of anti-MASP-3 mAb 13B1, as determined in an ELISA assay with mature Factor D-specific antibody 14A11 used as a detection antibody, as described in Example 13.

DESCRIPTION OF THE SEQUENCE LISTING

SEQ ID NO:1 human full-length Factor D amino acid sequence (including the signal sequence)
SEQ ID NO:2 human pro-Factor D amino acid sequence (without signal sequence) SEQ ID NO:3: human mature Factor D amino acid sequence
SEQ ID NO:4 human pro peptide "APPRGR", corresponding to residues 20-25 of human full-length Factor D
SEQ ID NO:5 human Mature Factor D N-terminal peptide ("ILGGREA"), corresponding to residues 1-7 of human mature Factor D.
SEQ ID NO:6 synthetic ILGGREA peptide-KLH conjugate "ILGGREAGPGPGAKFVAAAWTLKAAAKKC"
SEQ ID NO:7: human MASP-3 protein
SEQ ID NO:8: *macaca* full length Factor D
SEQ ID NO:9: *canis* full-length Factor D
SEQ ID NO: 10: *rattus* full-length Factor D
SEQ ID NO:11: *mus* full-length Factor D
Anti-Human Mature Factor D-Specific mAbs: VH Chains
SEQ ID NO:12: mAb clone 6G6 VH amino acid sequence
SEQ ID NO:13: mAb clone 14A11 VH amino acid sequence
SEQ ID NO: 14: mAb clone 27B3 VH amino acid sequence
SEQ ID NO: 15: mAb clone 58F5 VH amino acid sequence
SEQ ID NO: 16: mAb clone 49G3 VH amino acid sequence
SEQ ID NO:17: mAb clone 10G1 VH amino acid sequence
Anti-Human Mature Factor D-Specific mAbs: VL Chains
SEQ ID NO:18: mAb clone 6G6 VL amino acid sequence
SEQ ID NO: 19: mAb clone 14A11 VL amino acid sequence
SEQ ID NO:20: mAb clone 27B3 VL amino acid sequence
SEQ ID NO:21: mAb clone 58F5 VL amino acid sequence
SEQ ID NO:22: mAb clone 49G3 VL amino acid sequence
SEQ ID NO:23: mAb clone 10G1 VL amino acid sequence
SEQ ID NOs:24-48: heavy chain FRs and CDRs from mouse anti-human mature Factor D-specific mAbs
SEQ ID NOs:49-64 light chain FRs and CDRs from mouse anti-human mature Factor D-specific mAbs
SEQ ID NOS:65-69: CDR consensus sequences from mouse anti-human mature Factor D-specific mAbs
SEQ ID NO:70: human IgG4 constant region
SEQ ID NO:71: human IgG4 constant region with S228P mutation
SEQ ID NO:72: human IgK constant region
SEQ ID NO:73: nucleic acid encoding 6G6 HC variable region
SEQ ID NO:74: nucleic acid encoding 14A11 HC variable region
SEQ ID NO:75: nucleic acid encoding 27B3 HC variable region
SEQ ID NO:76: nucleic acid encoding 58F5 HC variable region
SEQ ID NO:77: nucleic acid encoding 49G3 HC variable region
SEQ ID NO:78: nucleic acid encoding 10G1 HC variable region
SEQ ID NO:79: nucleic acid encoding 6G6 LC variable region SEQ ID NO:80: nucleic acid encoding 14A11 LC variable region
SEQ ID NO:81: nucleic acid encoding 27B3 LC variable region
SEQ ID NO:82: nucleic acid encoding 58F5 LC variable region
SEQ ID NO:83: nucleic acid encoding 49G3 LC variable region
SEQ ID NO:84: nucleic acid encoding 10G1 LC variable region Anti-human Factor D (c-term) mAbs: VH chains
SEQ ID NO:85: mAb clone 3C5 VH amino acid sequence
SEQ ID NO:86: mAb clone 11H1 VH amino acid sequence
SEQ ID NO:87: mAb clone 12H10 VH amino acid sequence
SEQ ID NO:88: mAb clone 7H2 VH amino acid sequence Anti-Human Factor D (c-Term) mAbs: VL Chains
SEQ ID NO:89: mAb clone 3C5 VL amino acid sequence
SEQ ID NO:90: mAb clone 30H2 VL amino acid sequence
SEQ ID NO:91: mAb clone 11H1 VL amino acid sequence
SEQ ID NO:92: mAb clone 12H10 VL amino acid sequence
SEQ ID NO:93: mAb clone 7H2 VL amino acid sequence
SEQ ID NOs:94-109: heavy chain FRs and CDRs from mouse anti-human Factor D mAbs that bind an epitope shared by mature Factor D and Pro-Factor D
SEQ ID NOs:110-126: light chain FRs and CDRs from mouse anti-human Factor D mAbs that bind an epitope shared by mature Factor D and Pro-Factor D
SEQ ID NO:127: nucleic acid encoding 3C5 HC and 30H2 variable region
SEQ ID NO: 128: nucleic acid encoding 11H1 VH variable region
SEQ ID NO: 129: nucleic acid encoding 12H10 VH variable region
SEQ ID NO:130: nucleic acid encoding 7H2 VH variable region
SEQ ID NO:131: nucleic acid encoding 3C5 VL variable region
SEQ ID NO:132: nucleic acid encoding 30H2 VL variable region
SEQ ID NO:133: nucleic acid encoding 11H1 VL variable region
SEQ ID NO: 134: nucleic acid encoding 12H10 VL variable region
SEQ ID NO: 135: nucleic acid encoding 7H2 VL variable region Anti-Human Pro-Factor D-Specific mAbs: VH Chains
SEQ ID NO:136: mAb clone 18F5 VH amino acid sequence
SEQ ID NO: 137: mAb clone 1F9 VH amino acid sequence
SEQ ID NO: 138: mAb clone 2A4 VH amino acid sequence
SEQ ID NO:139: mAb clone 20A1 VH amino acid sequence
SEQ ID NO:140: mAb clone 13A10 VH amino acid sequence
SEQ ID NO: 141: mAb clone 21H1VH amino acid sequence Anti-Human Pro-Factor D-Specific mAbs: VL Chains
SEQ ID NO:142: mAb clone 18F5 VL amino acid sequence
SEQ ID NO: 143: mAb clone 1F9 VL amino acid sequence
SEQ ID NO: 144: mAb clone 2A4 VL amino acid sequence
SEQ ID NO:145: mAb clone 20A1 VL amino acid sequence
SEQ ID NO:146: mAb clone 13A10 VL amino acid sequence
SEQ ID NO:147: mAb clone 21H1 VL amino acid sequence
SEQ ID NOs:148-174: heavy chain FRs and CDRs from mouse anti-human Pro-Factor D-specific mAbs
SEQ ID NOs: 175-200: light chain FRs and CDRs from mouse anti-human Pro-Factor D-specific mAbs
SEQ ID NO:201-205: CDR consensus sequences from mouse anti-human Pro-Factor D-specific mAbs
SEQ ID NO:206 nucleic acid encoding 18F5 HC variable region
SEQ ID NO:207 nucleic acid encoding 1F9 HC variable region
SEQ ID NO:208: nucleic acid encoding 2A4 HC variable region
SEQ ID NO:209: nucleic acid encoding 20A1 HC variable region
SEQ ID NO:210: nucleic acid encoding 13A10 HC variable region
SEQ ID NO:211: nucleic acid encoding 21H1 HC variable region
SEQ ID NO:212 nucleic acid encoding 18F5 LC variable region
SEQ ID NO:213 nucleic acid encoding 1F9 LC variable region
SEQ ID NO:214: nucleic acid encoding 2A4 LC variable region
SEQ ID NO:215: nucleic acid encoding 20A1 LC variable region
SEQ ID NO:216: nucleic acid encoding 13A10 LC variable region
SEQ ID NO:217: nucleic acid encoding 21H1 LC variable region
SEQ ID NO:218: mouse IgG2a constant region
SEQ ID NO:219: mouse kappa light chain constant region Anti-human MASP-3 inhibitory mAbs
SEQ ID NO:220: h4D5_VH-14 VH
SEQ ID NO:221: h4D5_VL-1-NA
SEQ ID NO:222: h4D5_VH-19
SEQ ID NO:223: h10D12 VH-45
SEQ ID NO:224: h10D12_VL-21-GA
SEQ ID NO:225: h10D12_VH-49
SEQ ID NO:226: h13B1 VH-9
SEQ ID NO:227: h13B1 VL-1-NA
SEQ ID NO:228: h13B1_VH-10
SEQ ID NO:229: h4D5: 14_1 NA HC-CDR1
SEQ ID NO:230: h10D12-45-21-GA HC-CDR1
SEQ ID NO:231: h13B1-9-1-NA HC-CDR1
SEQ ID NO:232: h4D5: 14_1 NA HC-CDR2
SEQ ID NO:233: h10D12-45-21-GA HC-CDR2
SEQ ID NO:234: h13B1-9-1-NA HC-CDR2
SEQ ID NO:235: h13B1-10-1-NA: HC-CDR2
SEQ ID NO:236: h4D5: 14_1 NA HC-CDR3
SEQ ID NO:237: h10D12-45-21-GA HC-CDR3
SEQ ID NO:238: h13B1-9-1-NA HC-CDR3
SEQ ID NO:239: h4D5: 14_1 NA LC-CDR1
SEQ ID NO:240: h10D12-45-21-GA LC-CDR1
SEQ ID NO:241: h10D12-45-21-GA LC-CDR2
SEQ ID NO:242: h4D5: 14_1 NA LC-CDR3
SEQ ID NO:243: h10D12-45-21-GA LC-CDR3

SEQ ID NO:244: h13B1-9-1-NA LC-CDR3

SEQ ID NO:245: human IgG4 constant region with S228P and X mutation

SEQ ID NO:246: mAb clone 7H2 HC FR3 amino acid sequence

SEQ ID NO:247: mAb clone 2A4 HC FR1 amino acid sequence

DETAILED DESCRIPTION

As described in Examples 1-3, monoclonal antibodies have been generated that specifically bind to the N-terminal region of human mature Factor D and that do not bind to Pro-Factor D. As further described in Examples 8-9, monoclonal antibodies have been generated that specifically bind to the Pro-peptide of Pro-Factor D and do not bind to mature Factor D. The mature-Factor D-specific monoclonal antibodies and the Pro-Factor D-specific antibodies are useful for detection of the mature and/or the pro-form of Factor D in biological samples and may be used to determine the status of the Alternative Pathway of Complement (APC) in a mammalian subject. As further described in Examples 10-12, the mature-Factor D specific monoclonal antibodies may also be used to determine the status of Factor D after treatment with a MASP-3 inhibitory agent which inhibits the conversion of Pro-Factor D to mature Factor D. Accordingly, in one embodiment, the present invention is directed to monoclonal antibodies that specifically bind to the N-terminal region of human mature Factor D and the use of these antibodies in methods of detecting the presence or amount of mature Factor D in a biological sample. In another embodiment, the present invention is directed to monoclonal antibodies that specifically bind to the activation (pro) peptide of Pro-Factor D and the use of these antibodies in methods of detecting the presence or amount of Pro-Factor D in a biological sample. In another embodiment, the present invention is directed to the use of mature-Factor-D specific monoclonal antibodies and/or the use of Pro-Factor-D-specific monoclonal antibodies to measure the presence or amount of mature-Factor D and/or Pro-Factor D in a mammalian subject before and after treatment with a MASP-3 inhibitory agent, such as a high affinity MASP-3 inhibitory antibody, wherein the MASP-3 inhibitory antibody is capable of inhibiting the conversion of Pro-Factor D to mature Factor D and thereby inhibit the APC.

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

The terms "antibody" and "immunoglobulin" are used interchangeably herein. These terms are well understood by those in the field and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

As used herein, the term "antibody" encompasses antibodies and antibody fragments thereof, derived from any antibody-producing mammal (e.g., mouse, rat, rabbit, and primate including human), or from a hybridoma, phage selection, recombinant expression or transgenic animals (or other methods of producing antibodies or antibody fragments), that specifically bind to an antigen, such as human Pro-Factor D set forth as SEQ ID NO:2 (e.g., an epitope in the Pro Peptide "APPRGR" set forth as SEQ ID NO:4), or human mature Factor D, set forth as SEQ ID NO:3 (e.g., an epitope at the N-terminus of mature Factor D comprising or consisting of "ILGGREA," set forth as SEQ ID NO:5), or that bind to an epitope shared by human Pro-Factor D and human mature Factor D (e.g., an epitope in the C-terminal region of Factor D (e.g., amino acids 8 to 228 of SEQ ID NO:3). It is not intended that the term "antibody" be limited as regards to the source of the antibody or manner in which it is made (e.g., by hybridoma, phage selection, recombinant expression, transgenic animal, peptide synthesis, etc). Exemplary antibodies include polyclonal, monoclonal and recombinant antibodies; multispecific antibodies (e.g., bispecific antibodies); humanized antibodies; fully human antibodies, murine antibodies; chimeric, mouse-human, mouse-primate, primate-human monoclonal antibodies; and anti-idiotype antibodies, and may be any intact molecule or fragment thereof. As used herein, the term "antibody" encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

As used herein, the term "antigen-binding fragment" refers to a polypeptide fragment that contains at least one CDR of an immunoglobulin heavy and/or light chains that specifically binds to an antigen such as human Pro-Factor D set forth as SEQ ID NO:2 (e.g., an epitope in the Pro Peptide "APPRGR" set forth as SEQ ID NO:4), or human mature Factor D, set forth as SEQ ID NO:3 (e.g., an epitope at the N-terminus of mature Factor D comprising or consisting of "ILGGREA," set forth as SEQ ID NO:5), or an epitope shared by human Pro-Factor D and human mature Factor D (e.g., an epitope in the C-terminal region of Factor D (e.g., amino acids 8 to 228 of SEQ ID NO:3). In this regard, an antigen-binding fragment of the herein described antibodies may comprise 1, 2, 3, 4, 5, or all 6 CDRs of a VH and VL sequence, such as 1, 2, 3, 4, 5, or 6 CRS of a VH and VL sequence from the disclosed anti-human Factor D antibodies set forth herein.

As used herein the term "anti-Factor D monoclonal antibodies" refers to a homogenous antibody population, wherein the monoclonal antibody is comprised of amino acids that are involved in the selective binding of an epitope on human Factor D, such as human Pro-Factor D set forth as SEQ ID NO:2 (e.g., an epitope in the Pro Peptide "APPRGR" set forth as SEQ ID NO:4), or that specifically bind to human mature Factor D, set forth as SEQ ID NO:3 (e.g., an epitope at the N-terminus of mature Factor D comprising or consisting of "ILGGREA," set forth as SEQ ID NO:5), or that bind to an epitope shared by human Pro-Factor D and human mature Factor D (e.g., an epitope in the C-terminal region of Factor D (e.g., amino acids 8 to 228 of SEQ ID NO:3). The term "monoclonal antibody" encompasses not only intact monoclonal antibodies and full-length monoclonal antibodies, but also fragments thereof (such as Fab, Fab', F(ab')2, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope.

As used herein, the modifier "monoclonal" indicates the character of the antibody as being obtained from a substantially homogenous population of antibodies, and is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody". Monoclonal antibodies can be obtained using any technique that provides for the production of antibody molecules by continuous cell lines in culture, such as the hybridoma method described by Kohler, G., et al., *Nature* 256:495, 1975, or they may be made by recombinant DNA methods (see, e.g., U.S. Pat. No. 4,816,567 to Cabilly). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991. Such antibodies can be of any immunoglobulin class including IgG, IgM, IgE, IgA, IgD and any subclass thereof.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids) similarly comprise a variable region (of about 116 amino acids) and one of the aforementioned heavy chain constant regions, e.g., gamma (of about 330 amino acids).

The basic four-chain antibody unit is a heterotetrameric glycoprotein composed of two identical light (L) chains and two identical heavy (H) chains. An IgM antibody consists of 5 of the basic heterotetramer units along with an additional polypeptide called the J chain, and therefore contains 10 antigen binding sites. Secreted IgA antibodies can polymerize to form polyvalent assemblages comprising 2-5 of the basic 4-chain units along with J chain. Each L chain is linked to an H chain by one covalent disulfide bond, while the two H chains are linked to each other by one or more by one or more disulfide bonds, depending on the H chain isotype. Each H and L chain also has regularly spaced intrachain disulfide bridges. The pairing of a VH and VL together forms a single antigen-binding site.

Each H chain has at the N-terminus, a variable domain (VH), followed by three constant domains (CH) for each of the α and γ chains, and four CH domains (CH) for u and & isotypes.

Each L chain has at the N-terminus, a variable domain (VL) followed by a constant domain (CL) at its other end. The VL is aligned with the VH and the CL is aligned with the first constant domain of the heavy chain (CH1). The L chain from any vertebrate species can be assigned to one of two clearly distinct types, called kappa (κ) and lambda (λ), based on the amino acid sequences of their constant domains (CL).

Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated alpha (α), delta (δ), epsilon (ε) gamma (γ) and mu (μ), respectively. The γ and α classes are further divided into subclasses on the basis of minor differences in CH sequence and function, for example, humans express the following subclasses: IgG1, IgG2, IgG3, IgG4, IgA1 and IgA2.

For the structure and properties of the different classes of antibodies, see, e.g., Basic and Clinical Immunology, 8th Edition, Daniel P. Stites, Abba I. Terr and Tristram G. Parslow (eds); Appleton and Lange, Norwalk, Conn., 1994, page 71 and Chapter 6.

The term "variable" refers to that fact that certain segments of the V domains differ extensively in sequence among antibodies. The V domain mediates antigen binding and defines specificity of a particular antibody for its particular antigen. However, the variability is not evenly distributed across the 110 amino acid span of the variable domains. Rather, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the n-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md (1991)). The constant domains are not involved directly in binding an antibody to an antigen, but exhibit various effector functions, such as participation of the antibody dependent cellular cytotoxicity (ADCC).

As used herein, the term "hypervariable region" refers to the amino acid residues of an antibody that are responsible for antigen binding. The hypervariable region generally comprises amino acid residues from a "complementary determining region" or "CDR" (i.e., from around about residues 24-34 (L1), 50-56 (L2) and 89-97 (L3) in the light chain variable domain, and around about 31-35 (H1), 50-66 (H2) and 95-102 (H3) in the heavy chain variable domain when numbering in accordance with the Kabat numbering system as described in Kabat, et al., *Sequences of Proteins of Immunological Interest,* 5th Ed. Public Health Service, National Institutes of Health, Bethesda, Md (1991)); and/or those residues from a "hypervariable loop" (i.e., residues 24-34 (L1), 50-56 (L2) and 89-97 (L3) in the light chain variable domain, and 26-32 (H1), 52-56 (H2) and 95-101 (H3) in the heavy chain variable domain when numbered in accordance with the Chothia numbering system, as described in Chothia and Lesk, *J. Mol. Biol.* 196:901-917 (1987)); and/or those residues from a "hypervariable loop"/ CDR (e.g., residues 27-38 (L1), 56-65 (L2) and 105-120 (L3) in the VL, and 27-38 (H1), 56-65 (H2), and 105-120 (H3) in the VH when numbered in accordance with the IMGT numbering system as described in Lefranc, J. P., et al., *Nucleic Acids Res* 27:209-212; Ruiz, M., et al., *Nucleic Acids Res* 28:219-221 (2000)).

As used herein, the term "antibody fragment" refers to a portion derived from or related to a full-length anti-Factor D antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules, bispecific and multispecific antibodies formed from antibody fragments.

As used herein, a "single-chain Fv" or "scFv" antibody fragment comprises the VH and VL domains of an antibody, wherein these domains are present in a single polypeptide chain. Generally, the Fv polypeptide further comprises a polypeptide linker between the VH and VL domains, which enables the scFv to form the desired structure for antigen binding. See Pluckthun in The Pharmacology of Monoclonal Antibodies, Vol. 113, Rosenburg and Moore eds., Springer-Verlag, New York, pp. 269-315 (1994). "Fv" is the minimum antibody fragment that contains a complete antigen-recognition and binding site. This fragment consists of a dimer of one heavy and one light chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

As used herein, a "humanized antibody" is a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable regions fused onto constant domains or only the CDRs grafted onto appropriate framework regions in the variable domains. Epitope binding sites may be wild type or may be modified by one or more amino acid substitutions. Another approach focuses not only on providing human-derived constant regions, but also on modifying the variable regions as well so as to reshape them as closely as possible to human form. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

As used herein, the term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the affinity between a capture agent and analyte when they are specifically bound in a capture agent/analyte complex is characterized by a K$_D$ (dissociation constant) of less than about 100 nM, or less than about 50 nM, or less than about 25 nM, or less than about 10 nM, or less than about 5 nM, or less than about 1 nM.

As used herein, the term "variant" antibody refers to a molecule, which differs in amino acid sequence from a "parent" or reference antibody amino acid sequence by virtue of addition, deletion, and/or substitution of one or more amino acid residue(s) in the parent antibody sequence. In one embodiment, a variant anti-Factor D antibody refers to a molecule which contains variable regions that are identical to the parent variable domains, except for a combined total of 1, 2, 3, 4, 5, 6, 7, 8 9 or 10 amino acid substitutions within the CDR regions of the heavy chain variable region, and/or up to a combined total of 1, 2, 3, 4, 5, 6, 7, 8, 9, or 10 amino acid substitutions with said CDR regions of the light chain variable region. In some embodiments, the amino acid substitutions are conservative sequence modifications.

As used herein, the term "parent antibody" refers to an antibody, which is encoded by an amino acid sequence used for the preparation of the variant. Preferably, the parent antibody has a human framework region and, if present, has human antibody constant region(s). For example, the parent antibody may be a humanized or fully human antibody.

As used herein, the term "isolated antibody" refers to an antibody that has been identified and separated and/or recovered from a component of its natural environment. Contaminant components of its natural environment are materials, which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "epitope" refers to the portion of an antigen to which a monoclonal antibody specifically binds. Epitopic determinants usually consist of chemically active surface groupings of molecules such as amino acids or sugar side chains and usually have specific three-dimensional structural characteristics, as well as specific charge characteristics. More specifically, the term "Pro-Factor D epitope" as used herein refers to a portion of the corresponding polypeptide (SEQ ID NO:4) to which an antibody immunospecifically binds as determined by any method well known in the art, for example, by immunoassays. The term "mature Factor D epitope" as used herein refers to an epitope encompassing the amino-terminal portion of the corresponding polypeptide (SEQ ID NO:3), e.g., an epitope at the N-terminus of mature Factor D comprising or consisting of "ILGGREA," set forth as SEQ ID NO:5, to which an antibody immunospecifically binds as determined by any method well known in the art, for example, by immunoassays. The term "epitope shared by Pro-Factor D and mature Factor D" as used herein refers to an epitope in the C-terminal region shared by Pro-Factor D and mature Factor D (e.g., amino acids 8 to 228 of SEQ ID NO:3) to which an antibody immunospecifically binds as determined by any method well known in the art, for example, by immunoassays. Antigenic epitopes need not necessarily be immunogenic. Such epitopes can be linear in nature or can be a discontinuous epitope. Thus, as used herein, the term "conformational epitope" refers to a discontinuous epitope formed by a spatial relationship between amino acids of an antigen other than an unbroken series of amino acids.

As used herein, "a mammalian subject" includes, without limitation, humans, non-human primates, dogs, cats, horses, sheep, goats, cows, rabbits, pigs, and rodents.

As used herein, the term "biological sample" includes, without limitation, blood, plasma, serum, sputum, amniotic fluid, cerebrospinal fluid, cell lysate, ascites, urine, saliva, and tissue.

As used herein, the term "contacting" refers to a combining action that brings an antibody of the invention into contact with the biological sample in a manner that a binding interaction will occur between the antibody and the target protein (e.g., Pro-Factor D or mature Factor D) in the biological sample.

As used herein, the term "detecting antibody" or "detection antibody" refers to antibodies that are capable of being discovered. The detecting antibody may be directly or indirectly (e.g. through another antibody) conjugated to a detectable label or signal or to a signal-generating moiety. The signal may be can be radioactive (e.g., radioactive iodine, tritium, carbon, sulfur, or the like), colorimetric, fluorescent signal and the like. Signal-generating moieties that act on signal-generating substrates include, but are not limited to, horseradish peroxidase (HRP) [suitable substrates include 3,3',5,5'-tetramethylbenzidine (TMB); OPD; 2,2'-azinobis(3-ethylbenzothiazoline)-6-sulfonic acid diammonium salt]; alkaline phosphatase [suitable substrates include p-nitrophenyl phosphate disodium salt]; and beta-galactosidase [suitable substrates include O-nitrophenyl-beta-D-galactopyranoside]. The signal may be amplified by using an Avidin-Biotin conjugation system. A detectable label or signal-generating moiety may be coupled either directly and/or indirectly to the anti-Factor D antibodies and antigen binding fragments thereof of the present invention. For example, the immunoconjugate may comprise an anti-Factor D antibody that is labeled with a radioactive isotope or enzymatic activity which permits detection in an immunoassay.

As used herein, the term "MASP-3 inhibitory agent" refers to any agent that binds to MASP-3 and inhibits the conversion of Pro-Factor D to mature Factor D, thereby inhibiting the alternative pathway of complement activation (APC), including anti-MASP-3 antibodies and MASP-3 binding fragments thereof, natural and synthetic peptides, competitive substrates, small molecules, and expression inhibitors. Exemplary MASP-3 inhibitory antibodies are disclosed in WO2018/026722, hereby incorporated herein by reference. In some embodiments, the MASP-3 inhibitory agent is a MASP-3 inhibitory antibody, such as a MASP-3 inhibitory monoclonal antibody selected from the group consisting of 4D5, 10D12 and 13B1.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

As used herein, an "isolated nucleic acid molecule" is a nucleic acid molecule (e.g., a polynucleotide) that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

As used herein, a "nucleic acid molecule construct" is a nucleic acid molecule, either single- or double-stranded, that has been modified through human intervention to contain segments of nucleic acid combined and juxtaposed in an arrangement not existing in nature.

As used herein, an "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

As used herein, the terms "approximately" or "about" in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

As used herein the singular forms "a", "an" and "the" include plural aspects unless the context clearly dictates otherwise. Thus, for example, reference to "a cell" includes a single cell, as well as two or more cells; reference to "an agent" includes one agent, as well as two or more agents; reference to "an antibody" includes a plurality of such antibodies and reference to "a framework region" includes reference to one or more framework regions and equivalents thereof known to those skilled in the art, and so forth.

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y.; Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or other relevant Current Protocol publications and other like references. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

It is contemplated that any embodiment discussed in this specification can be implemented with respect to any method, kit, reagent, or composition of the invention, and vice versa. Furthermore, compositions of the invention can be used to achieve methods of the invention.

II. Overview

As described in Examples 1-3 herein, the present invention provides monoclonal anti-Factor D antibodies that specifically bind to human mature Factor D (also referred to as mature Factor-D specific antibodies) and do not bind to Pro-Factor D. As described in Examples 8-9, the present invention also provides monoclonal anti-Factor D antibodies that specifically bind to Pro-Factor D (also referred to as Pro-Factor-D-specific antibodies) and do not bind to mature Factor D. As described in Examples 4-5 herein, the present invention also provides monoclonal anti-Factor D antibodies that bind to both Pro- and mature-Factor D. As described in Examples 6 and 7, the mature-Factor D-specific monoclonal antibodies and the Pro-Factor D-specific monoclonal antibodies are useful for detection of the mature and/or the pro-form of Factor D in biological samples and may also be used to determine the status of the Alternative Pathway of Complement (APC) in a mammalian subject. As further described in Examples 10-12, the mature-Factor D specific monoclonal antibodies and/or the Pro-Factor D-specific antibodies may also be used to determine the status of Factor D after treatment with a MASP-3 inhibitory agent, such as a MASP-3 inhibitory antibody which inhibits the conversion of Pro-Factor D to mature Factor D.

Accordingly, in one embodiment, the present invention is directed to monoclonal antibodies that specifically bind to the N-terminal region of human mature Factor D and the use of these antibodies in methods of detecting the presence or amount of mature Factor D in a biological sample. In another embodiment, the present invention is directed to monoclonal antibodies that specifically bind to the activation (pro) peptide of Pro-Factor D and the use of these antibodies in methods of detecting the presence or amount of Pro-Factor D in a biological sample. In another embodiment, the present invention is directed to the use of mature-Factor-D specific monoclonal antibodies and/or the use of Pro-Factor-D-specific monoclonal antibodies to measure the presence or amount of mature-Factor D and/or Pro-Factor D in a mammalian subject before and after treatment with a MASP-3 inhibitory agent, such as a high affinity MASP-3 inhibitory antibody, wherein the MASP-3 inhibitory antibody is capable of inhibiting the conversion of Pro-Factor D to mature Factor D and thereby inhibit the APC.

Therefore, the subject antibodies can be used in diagnostic methods to detect the presence or amount of mature Factor D and/or Pro-Factor D in a biological sample obtained from a subject. In one embodiment, the presence or amount of mature Factor D and/or Pro-Factor D is useful as a biomarker for the determination of efficacy of a MASP-3 inhibitory agent for inhibiting the APC and/or monitoring the dosing in a subject undergoing treatment with a MASP-3 inhibitory agent, such as a MASP-3 inhibitory antibody (e.g., MASP-3 inhibitory antibodies 4D5, 10D12 or 13B1) in the subject.

III. Overview of the Complement System

Figure 1:
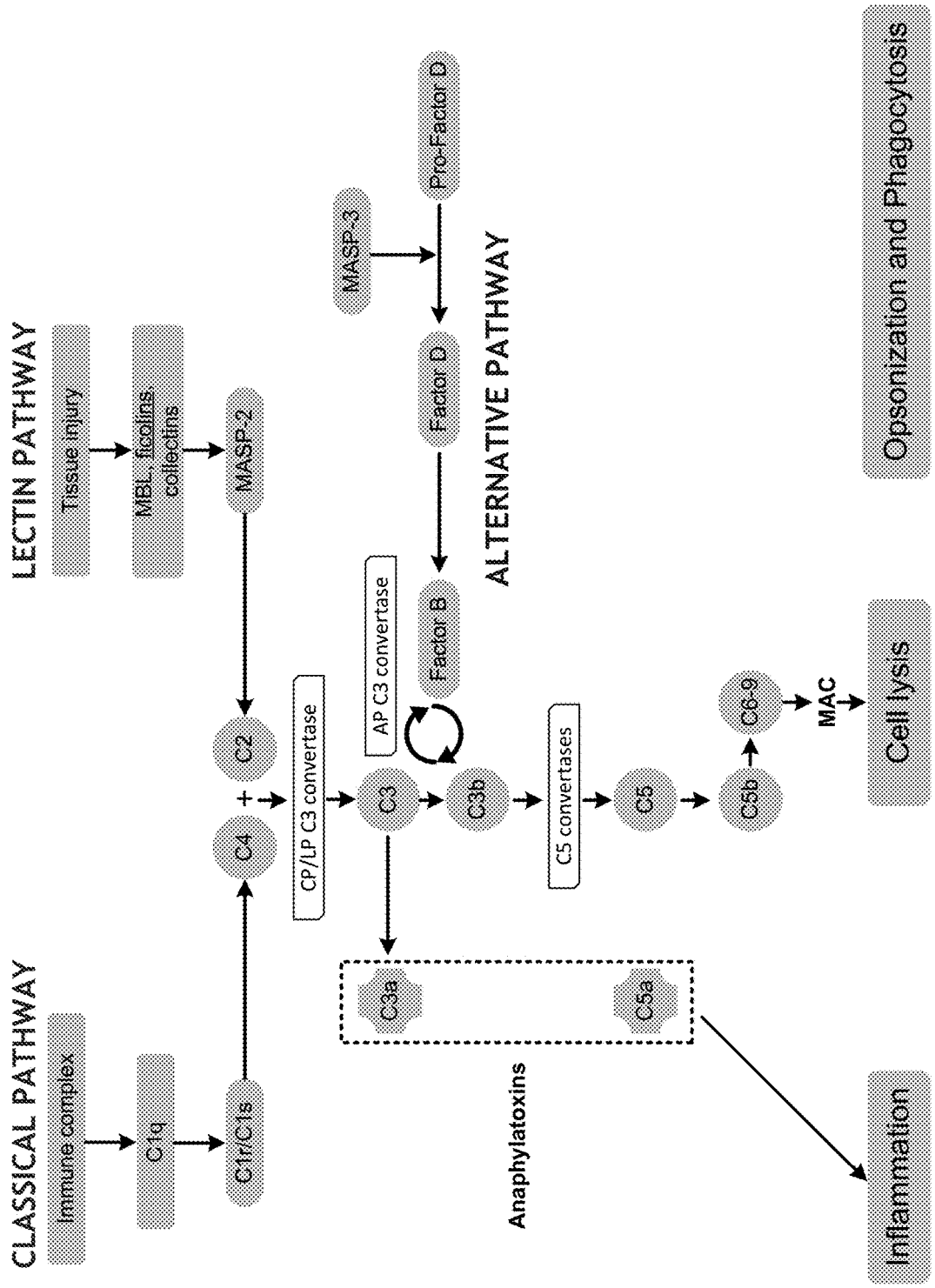
FIG. 1 is a diagram illustrating the classical, lectin and alternative complement pathways.

FIG. 1 illustrates the three pathways that drive complement activity in response to distinct initiating events: the classical, lectin, and alternative pathways (Noris M., *Semin Nephrol* 33(6):479-92, 2013). The classical pathway is triggered by immune complexes and mediates important immune effector functions through the early activity of two proteases, C1r and C1s. The lectin pathway can be activated by specific types of cell-surface carbohydrate patterns that are usually found on microbes or on injured host tissue, but not on healthy host cell surfaces. Lectin pathway activation is initiated by a group of enzymes known as mannan-binding lectin-associated serine protease-1 and 2 (MASP-1 and MASP-2) (Yongqing T. et al., *Biochim Biophys Acta* 1824 (1):253-62, 2012). These proteases form complexes with lectins, such as the mannan-binding lectin (MBL), ficolins, and collectins 10 and 11. The lectins bind carbohydrate patterns on foreign or injured host cells, thus targeting the proteolytic activity of the MASPs to specific surfaces. Complement Factor D (CFD) is a serine protease that is essential for activation of the alternative pathway. As shown in FIG. 1, Factor D (CFD) is expressed as an inactive zymogen (referred to herein as "Pro-Factor D) and it circulates in plasma predominantly as a cleaved, mature serine protease (referred to herein as "mature Factor D"). As described in WO2013/180834 and WO2013/192240, it has recently been determined that MASP-3 is responsible for the conversion of complement factor D (CFD) from the zymogen form of the protein (Pro-Factor D) to the mature form (mature Factor D), thus placing the MASP-3 protein at a key upstream regulatory step for the alternative pathway. As further described in WO2018/026722, hereby incorporated herein by reference, numerous high affinity anti-MASP-3 inhibitory antibodies have been generated that bind the serine protease domain of MASP-3 and inhibit its catalytic activity, thereby inhibiting the conversion of Pro-Factor D to mature Factor D and blocking activation of the alternative pathway.

The primary function of the complement system, a part of the innate immune response, is to protect the host against infectious agents (Ricklin et al., *Nat Immunol* 11(9):785-97, 2010). Through the coordinated action of protein complex assembly and proteolytic cascades, this intricate physiological system targets immune and inflammatory responses to surfaces that display molecular patterns not usually present on healthy host cells. Complement system activation culminates in targeted cell destruction by the formation of the membrane attack complex (MAC), which directly disrupts the membranes of the pathogen causing cell lysis, or by opsonization, which facilitates the uptake of the infectious agent by phagocytic cells as shown in FIG. 1. In addition, substrate cleavage by complement proteases releases cytokine-like peptides, called anaphylatoxins, that trigger several important biological activities such as leukocyte recruitment and immune cell activation.

The alternative pathway of complement (APC) is typically described as a downstream amplifier of complement activity, increasing the host immune response following activation of complement via the classical and lectin pathways. However, the ability of the APC to create a positive feedback loop of protease complexes with activity that drives the formation of new complexes of the same type is unique within the complement pathways (Lachmann et al., *Adv Immunol* 104:115-49, 2009). The self-propagating complex, the APC C3 convertase, is composed of 2 proteins: C3b and Bb. Newly formed C3b can covalently attach to local surfaces via a thioester bond and function as a potent opsonin, targeting the engulfment and destruction of marked cells. In addition, C3b provides the scaffold for binding and activation of complement factor B (CFB) (Lachmann et al., *Adv Immunol* 104:115-49, 2009; Noris et al., *Semin Nephrol* 33(6):479-92, 2013). In complex with C3b, CFB, adopts an appropriate configuration for cleavage by complement factor D (CFD). This cleavage event converts the single chain polypeptide into noncatalytic (Ba) and catalytic fragments (Bb). The Ba fragment is released from the complex; however, the Bb fragment remains associated with C3b, producing the active APC C3 convertase, C3bBb Lachmann et al., *Adv Immunol* 104:115-49, 2009; Noris et al., *Semin Nephrol* 33(6):479-92, 2013). It is the ability of C3bBb to cleave additional C3 and produce multiple new convertases that provides the mechanism for rampant signal amplification.

While the complement system supports innate host defense against pathogens, dysregulated and unabated complement activity can also function as a major driver of disease, causing unchecked propagation of inflammation and tissue destruction. In many contexts, the APC and the C3b amplification loop play an important role in determining the magnitude of the complement response and its downstream consequences. Thus, the therapeutic modulation of APC by inhibiting Bb activity or blocking the activation of the CFB through cleavage by CFD are well characterized potential control points for treating many autoimmune and inflammatory diseases mediated by the APC.

As noted above, it has been demonstrated that MASP-3 is responsible for the conversion of CFD from the zymogen form of the protein to the mature form, thus placing the MASP-3 protein at a key upstream regulatory step for the alternative pathway. In a wild-type animal or human plasma, the large majority of systemic CFD has already been processed to the mature form by in vivo MASP-3 activity, making in vitro assessment of APC inhibition by MASP-3 inhibitors using traditional assays impossible. Therefore, a need exists for detection reagents and assays for measuring the presence and amount of Pro-Factor D and/or mature Factor D in a biological sample, which can be used as a biomarker of APC status and also can be used for in vitro and/or in vivo assessment of APC inhibition by MASP-3 inhibitors.

IV. Anti-Factor D Antibodies

As described above, Complement Factor D (CFD) is a serine protease that is essential for activation of the APC. As shown in FIG. 1, Factor D (CFD) is expressed as an inactive zymogen (referred to herein as "Pro-Factor D") and it circulates in plasma predominantly as a cleaved, mature serine protease (referred to herein as "mature Factor D").

FIG. 2 provides the amino acid sequences of (i) human full-length Factor D (SEQ ID NO:1), including the signal sequence aa 1-19 (shown in italics) with the activation (pro) peptide underlined; (ii) human Pro-Factor D (SEQ ID NO:2), with the pro-peptide underlined; and (iii) human mature Factor D (SEQ ID NO:3). As shown in FIG. 2, the pro-peptide of human Pro-Factor D is ("APPRGR" (SEQ ID NO:4).

FIG. 3 provides an alignment of the amino acid sequences of complement Factor D (full-length) from various species including *Homo sapiens* (SEQ ID NO:1); *Macaca* (SEQ ID NO:8); *Canis* (SEQ ID NO:9); *Rattus* (SEQ ID NO:10); and *Mus musculus* (SEQ ID NO:11). The italicized portion of each sequence depicts the signal sequence and the underlined portion depicts the activation "pro" peptide sequence.

As shown in FIGS. 2 and 3, the Factor D protein comprises an N-terminal Pro region, an activation peptide region, and the remaining C-terminal region. Mature Factor D has a unique amino-terminus as compared to pro-Factor D in each species (e.g., an N-terminus starting at residue 26 of human full-length Factor D (SEQ ID NO:1)). Mature and Pro-Factor D have a shared sequence in the C-terminal portion of the respective proteins (e.g., from amino acids 27 to 253 of SEQ ID NO:1).

A. Anti-Human Mature Factor D-Specific Monoclonal Antibodies

As described in Examples 1 and 2 herein, the inventors have used a peptide "ILGGREA" (SEQ ID NO:5), corresponding to amino acid residues 1 to 7 of the amino-terminal region of human mature Factor D (SEQ ID NO:3) as an antigen to generate anti-mature Factor D-specific antibodies suitable for use in the detection assays and methods described herein. As shown in FIG. 3, the N-terminal sequence "ILLGGREA" (SEQ ID NO:5) is conserved between human (*Homo sapiens*) and macaque (*macaca*) mature Factor D proteins.

As described in Example 2, the variable heavy and light chain fragments of several representative anti-mature Factor D-specific monoclonal antibodies have been cloned and sequenced.

FIG. 7A is an amino acid sequence alignment of the variable heavy chain regions of six anti-mature Factor D-specific clones that were identified as having high binding affinity to the N-terminal peptide "ILGGREA" (SEQ ID NO:5) of mature Factor D.

FIG. 7B is an amino acid sequence alignment of the variable light chain regions of six anti-mature Factor D-specific clones that were identified as having high binding affinity to the N-terminal peptide "ILGGREA," SEQ ID NO:5, of mature Factor D.

The heavy chain and light chain variable regions and CDRs therein of the six mature Factor D-specific antibodies are provided below in TABLES 1 and 2.

TABLE 1 anti-human mature-Factor D-specific Antibody Sequences: mouse parental

| Anti-human active-Factor D Antibody Reference No | Heavy Chain Variable Region (amino acid) | Light Chain Variable Region (amino acid) | Heavy chain variable region (DNA) | Light chain variable region (DNA) |
|---|---|---|---|---|
| 6G6 | SEQ ID NO: 12 | SEQ ID NO: 18 | SEQ ID NO: 73 | SEQ ID NO: 79 |
| 14A11 | SEQ ID NO: 13 | SEQ ID NO: 19 | SEQ ID NO: 74 | SEQ ID NO: 80 |
| 27B3 | SEQ ID NO: 14 | SEQ ID NO: 20 | SEQ ID NO: 75 | SEQ ID NO: 81 |
| 58F5 | SEQ ID NO: 15 | SEQ ID NO: 21 | SEQ ID NO: 76 | SEQ ID NO: 82 |
| 49G3 | SEQ ID NO: 16 | SEQ ID NO: 22 | SEQ ID NO: 77 | SEQ ID NO: 83 |
| 10G1 | SEQ ID NO: 17 | SEQ ID NO: 23 | SEQ ID NO: 78 | SEQ ID NO: 84 |

TABLE 2 anti-human mature-Factor D-specific antibodies: CDRs

| Anti-human active-Factor D Antibody Reference No. | Heavy Chain: CDR1; CDR2; CDR3 (SEQ ID NOs) | Light Chain: CDR1; CDR2; CDR3 (SEQ ID NOs) | Heavy Chain: consensus CDR1; CDR2; CDR3 (SEQ ID NOs) | Light Chain consensus CDR1; CDR2; CDR3 (SEQ ID NOs) |
|---|---|---|---|---|
| 6G6 | 25; 27; 29 | 50; 52; 54 | 65; 66; 67 | 68; 69; 54 |
| 14A11 | 25; 27; 29 | 50; 52; 54 | 65; 66; 67 | 68; 69; 54 |
| 27B3 | 33, 34, 36 | 58, 52, 54 | 65; 66; 67 | 68; 69; 54 |
| 58F5 | 38, 39, 41 | 60, 52, 54 | 65; 66; 67 | 68; 69; 54 |
| 49G3 | 43, 39, 41 | 62, 52, 54 | 65; 66; 67 | 68; 69; 54 |
| 10G1 | 43, 39, 47 | 63, 64, 54 | 65; 66; 67 | 68; 69; 54 |

Accordingly, in one aspect, the present invention provides an isolated antibody, or antigen-binding fragment thereof, that specifically binds to an epitope in the amino-terminal (N-terminal) region of human mature Factor D, wherein the epitope comprises or consists of the amino acid sequence "ILGGREA" (SEQ ID NO:5). In one embodiment, the mature Factor D-specific antibody or fragment thereof specifically binds to human mature Factor D (SEQ ID NO:3) and does not bind to human Pro-Factor D (SEQ ID NO:2). In one embodiment, the mature Factor D-specific antibody is a monoclonal antibody. In one embodiment the mature Factor D-specific antibody is a humanized, chimeric, or fully human antibody. In one embodiment the mature Factor D-specific antibody fragment is selected from the group consisting of Fv, Fab, Fab', F(ab)$_2$ and F(ab')$_2$. In one embodiment, the mature Factor D-specific antibody is a single-chain molecule. In one embodiment, the mature Factor D-specific antibody is an IgG molecule selected from the group consisting of IgG1, IgG2 and IgG4. In one embodiment, the mature Factor D-specific antibody or antigen-binding fragment thereof binds to human mature Factor D with a $K_D$ of less than 10 nM. In one embodiment, the mature Factor D-specific antibody or antigen-binding fragment thereof is labeled with a detectable moiety, for example a detectable moiety suitable for use in an immunoassay as further described herein. In one embodiment, the mature Factor D-specific antibody or fragment thereof is immobilized on a substrate, such as a substrate suitable for use in an immunoassay, as further described herein.

In one embodiment, the mature Factor D-specific antibody or fragment thereof (i.e., an antibody or fragment thereof that specifically binds to human mature Factor D) comprises a binding domain comprising HC-CDR1, HC-CDR2 and HC-CDR3 in a heavy chain variable region selected from the group consisting of SEQ ID NO:s 12-17 and comprising LC-CDR1, LC-CDR2 and LC-CDR3 in a light chain variable region selected from the group consisting of SEQ ID NO:s 18-23, wherein the CDRs are numbered according to the Kabat numbering system. In one embodiment, the mature Factor D-specific antibody or fragment thereof comprises a binding domain comprising the following six CDRs: (a) an HC-CDR1 comprising the amino acid sequence XSXMGVS (SEQ ID NO:65), wherein X at position 1 is T, I or S and X at position 3 is G or I; (b) an HC-CDR2 comprising the amino acid sequence HIYWD-DEKHYXPSLKX (SEQ ID NO:66), wherein X at position 11 is H or N and X at position 16 is S or R; (c) an HC-CDR3 comprising the amino acid sequence RYYGYXXXMXY (SEQ ID NO:67), wherein X at position 6 is R, G or N, X at position 7 is S or Y, X at position 8 is F, I or V, and X at position 10 is D or H; (d) a LC-CDR1 comprising the amino acid sequence RSXXSIXHSNGNTYXE (SEQ ID NO:68), wherein: X at position 3 is N or S, X at position 4 is Q or E, X at position 7 is V or L, and X at position 15 is F or L; (e) a LC-CDR2 comprising the amino acid sequence KVXNRFS (SEQ ID NO:69), wherein: X at position 3 is S or Y; and (f) a LC-CDR3 comprising the amino acid sequence FQGSHVPPT (SEQ ID NO:54).

In one embodiment, the mature Factor D-specific antibody or fragment thereof comprises a binding domain comprising the following six CDRs: (a) an HC-CDR1 comprising SEQ ID NO:25, (b) an HC-CDR2 comprising SEQ ID NO:27; (c) an HC-CDR3 comprising SEQ ID NO:29; (d) a LC-CDR-1 comprising SEQ ID NO:50, (e) a LC-CDR2 comprising SEQ ID NO:52 and (f) a LC-CDR3 comprising SEQ ID NO:54. In one embodiment the mature Factor D-specific antibody or fragment thereof comprises a VH domain having at least 95% sequence identity (such as at least 96%, at least 97%, at least 98%, or at least 99% identity) to the amino acid sequence of SEQ ID NO:12 or SEQ ID NO:13. In one embodiment, the mature Factor D-specific antibody or fragment thereof comprises a VL domain having at least 95% sequence identity (such as at least 96%, at least 97%, at least 98%, or at least 99% identity) to the amino acid sequence of SEQ ID NO:18 or SEQ ID NO:19. In one embodiment, the mature Factor D-specific antibody or fragment thereof comprises a VH comprising SEQ ID NO:12 and a VL comprising SEQ ID NO:18. In one embodiment, the mature Factor D-specific antibody or fragment thereof comprises a VH comprising SEQ ID NO:13 and a VL comprising SEQ ID NO:19.

In one embodiment, the mature Factor D-specific antibody or fragment thereof comprises a binding domain comprising the following six CDRs: (a) an HC-CDR1 comprising SEQ ID NO:33, (b) an HC-CDR2 comprising SEQ ID NO:34; (c) an HC-CDR3 comprising SEQ ID NO: 36; (d) a LC-CDR1 comprising SEQ ID NO:58, (e) a LC-CDR2 comprising SEQ ID NO:52 and (f) a LC-CDR3 comprising SEQ ID NO:54. In one embodiment, the mature Factor D-specific antibody or fragment thereof comprises a VH domain having at least 95% sequence identity (such as at least 96%, at least 97%, at least 98%, or at least 99% identity) to the amino acid sequence of SEQ ID NO:14. In one embodiment, the mature Factor D-specific antibody or fragment thereof comprises a VL domain having at least 95% sequence identity (such as at least 96%, at least 97%, at least 98%, or at least 99% identity) to the amino acid sequence of SEQ ID NO:20. In one embodiment, the mature Factor D-specific antibody or fragment thereof comprises a VH comprising SEQ ID NO: 14 and a VL comprising SEQ ID NO:20.

In one embodiment, the mature Factor D-specific antibody or fragment thereof comprises a binding domain comprising the following six CDRs: (a) an HC-CDR1 comprising SEQ ID NO:38, (b) an HC-CDR2 comprising SEQ ID NO:39; (c) an HC-CDR3 comprising SEQ ID NO: 41; (d) a LC-CDR1 comprising SEQ ID NO:60, (e) a LC-CDR2 comprising SEQ ID NO:52 and (f) a LC-CDR3 comprising SEQ ID NO:54. In one embodiment the mature Factor D-specific antibody or fragment thereof comprises a VH domain having at least 95% sequence identity (such as at least 96%, at least 97%, at least 98%, or at least 99% identity) to the amino acid sequence of SEQ ID NO:15. In one embodiment, the mature Factor D-specific antibody or fragment thereof comprises a VL domain having at least 95% sequence identity (such as at least 96%, at least 97%, at least 98%, or at least 99% identity) to the amino acid sequence of SEQ ID NO:21. In one embodiment, the mature Factor D-specific antibody or fragment thereof comprises a VH comprising SEQ ID NO:15 and a VL comprising SEQ ID NO:21.

In one embodiment, the mature Factor D-specific antibody or fragment thereof comprises a binding domain comprising the following six CDRs: (a) an HC-CDR1 comprising SEQ ID NO:43, (b) an HC-CDR2 comprising SEQ ID NO:39; (c) an HC-CDR3 comprising SEQ ID NO: 41; (d) a LC-CDR1 comprising SEQ ID NO:62, (e) a LC-CDR2 comprising SEQ ID NO:52 and (f) a LC-CDR3 comprising SEQ ID NO:54. In one embodiment the mature Factor D-specific antibody or fragment thereof comprises a VH domain having at least 95% sequence identity (such as at least 96%, at least 97%, at least 98%, or at least 99% identity) to the amino acid sequence of SEQ ID NO:16. In one embodiment, the mature Factor D-specific antibody or fragment thereof comprises a VL domain having at least 95% sequence identity (such as at least 96%, at least 97%, at least 98%, or at least 99% identity) to the amino acid sequence of SEQ ID NO:22. In one embodiment, the mature Factor D-specific antibody or fragment thereof comprises a VH comprising SEQ ID NO: 16 and a VL comprising SEQ ID NO:22.

In one embodiment, the mature Factor D-specific antibody or fragment thereof comprises a binding domain comprising the following six CDRs: (a) an HC-CDR1 comprising SEQ ID NO:43, (b) an HC-CDR2 comprising SEQ ID NO:39; (c) an HC-CDR3 comprising SEQ ID NO: 47; (d) a LC-CDR1 comprising SEQ ID NO:63, (e) a LC-CDR2 comprising SEQ ID NO:64 and (f) a LC-CDR3 comprising SEQ ID NO:54. In one embodiment the mature Factor D-specific antibody or fragment thereof comprises a VH domain having at least 95% sequence identity (such as at least 96%, at least 97%, at least 98%, or at least 99% identity) to the amino acid sequence of SEQ ID NO:17. In one embodiment, the mature Factor D-specific antibody or fragment thereof comprises a VL domain having at least 95% sequence identity (such as at least 96%, at least 97%, at least 98%, or at least 99% identity) to the amino acid sequence of SEQ ID NO:23. In one embodiment, the mature Factor D-specific antibody or fragment thereof comprises a VH comprising SEQ ID NO:17 and a VL comprising SEQ ID NO:23.

In certain embodiments, the mature Factor D-specific antibody or fragment thereof that specifically binds to human mature Factor D has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the heavy chain variable domain sequences set forth in TABLE 1. In certain embodiments, the mature Factor D-specific antibody or fragment thereof that specifically binds to human mature Factor D has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the light chain variable domain sequences set forth in TABLE 1.

In another embodiment, the present disclosure provides a nucleic acid encoding the complementarity determining regions (CDRs) of a heavy chain variable region of a mature Factor D-specific antibody, or antigen-binding fragment thereof, that specifically binds to human mature Factor D, wherein the heavy chain variable region comprises an amino acid sequence set forth in SEQ ID NOs: 12-17, and wherein the CDRs are numbered according to the Kabat numbering system. In another embodiment, the present disclosure provides a nucleic acid encoding the complementarity determining regions (CDRs) of a light chain variable region of a mature Factor D-specific antibody, or antigen-binding fragment thereof that specifically binds to human mature Factor D, wherein the light chain variable region comprises an amino acid sequence set forth in SEQ ID NOs: 18-23, and wherein the CDRs are numbered according to the Kabat numbering system.

In another embodiment, the present disclosure provides a cloning or expression vector comprising a nucleic acid encoding complementarity determining regions (CDRs) of heavy and/or light chain variable regions of an antibody, or antigen-binding fragment thereof, that specifically binds to human mature Factor D, wherein the heavy chain variable region comprises the amino acid sequence set forth as any of SEQ ID NOs: 12-17 and the light chain variable region comprises the amino acid sequence set forth as any of SEQ ID NOs: 18-23, wherein the CDRs are numbered according to the Kabat numbering system.

In another embodiment, the present disclosure provides a cell containing a cloning or expression vector comprising a nucleic acid encoding complementarity determining regions (CDRs) of heavy and/or light chain variable regions of an antibody, or antigen-binding fragment thereof, that specifically binds to human mature Factor D, wherein the heavy chain variable region comprises the amino acid sequence set forth as any of SEQ ID NOs: 12-17 and the light chain variable region comprises the amino acid sequence set forth as any of SEQ ID NOs: 18-23, wherein the CDRs are numbered according to the Kabat numbering system.

In another embodiment, the present disclosure provides a method for producing a human mature Factor-D-specific antibody comprising culturing a cell containing an expression vector which contains a nucleic acid that encodes one or both of the heavy and light chain polypeptides of any of the mature Factor-D specific antibodies or antigen-binding fragments disclosed herein. The cell or culture of cells is cultured under conditions and for a time sufficient to allow expression by the cell (or culture of cells) of the antibody or antigen-binding fragment thereof encoded by the nucleic acid. The method can also include isolating the antibody or antigen binding fragment thereof from the cell (or culture of cells) or from the media in which the cell or cells were cultured.

In one embodiment, the present disclosure provides a composition comprising any of the mature Factor-D-specific antibodies, or antigen-binding fragments disclosed herein.

In one embodiment, the present disclosure provides a substrate for use in an immunoassay comprising at least one or more of any of the mature Factor-D-specific antibodies, or antigen-binding fragments disclosed herein.

In one embodiment, the present disclosure provides a kit for detecting the presence or amount of mature Factor D in a test sample, such as a biological sample, said kit comprising (a) at least one container, and (b) at least one or more of any of the mature Factor-D-specific antibodies, or antigen-binding fragments disclosed herein.

B. Anti-Human Pro-Factor D-Specific Monoclonal Antibodies

As described in Examples 8 and 9 herein, the inventors have used the human pro peptide "APPRGR" (SEQ ID NO:4), corresponding to residues 20-25 of human full-length Factor D, as an antigen to generate anti-Pro-Factor D-specific antibodies suitable for use in the detection assays and methods described herein.

As described in Example 9, the variable heavy and light chain fragments of several representative anti-Pro-Factor D-specific monoclonal antibodies have been cloned and sequenced.

FIG. 16A is an amino acid sequence alignment of the variable heavy chain regions of six anti-Pro-Factor D clones that were identified as having high binding affinity to the human Factor D pro peptide "APPRGR" (SEQ ID NO:4).

FIG. 16B is an amino acid sequence alignment of the variable light chain regions of six anti-Pro-Factor D clones that were identified as having high binding affinity to the human Factor D pro peptide "APPRGR" (SEQ ID NO:4).

The heavy chain and light chain variable regions and CDRs therein of the six pro-Factor D-specific monoclonal antibodies are provided below in TABLES 3 and 4.

TABLE 3

| anti-human Pro-Factor D-specific Antibody Sequences: mouse parental | | | | |
|---|---|---|---|---|
| Anti-human pro-Factor D Antibody Reference No | Heavy Chain Variable Region (amino acid) | Light Chain Variable Region (amino acid) | Heavy chain variable region (DNA) | Light chain variable region (DNA) |
| 18F5 | SEQ ID NO: 136 | SEQ ID NO: 142 | SEQ ID NO: 206 | SEQ ID NO: 212 |
| 1F9 | SEQ ID NO: 137 | SEQ ID NO: 143 | SEQ ID NO: 207 | SEQ ID NO: 213 |
| 2A4 | SEQ ID NO: 138 | SEQ ID NO: 144 | SEQ ID NO: 208 | SEQ ID NO: 214 |
| 20A1 | SEQ ID NO: 139 | SEQ ID NO: 145 | SEQ ID NO: 209 | SEQ ID NO: 215 |
| 13A10 | SEQ ID NO: 140 | SEQ ID NO: 146 | SEQ ID NO: 210 | SEQ ID NO: 216 |
| 21H1 | SEQ ID NO: 141 | SEQ ID NO: 147 | SEQ ID NO: 211 | SEQ ID NO: 217 |

TABLE 4

| anti-human Pro-Factor D-specific antibodies: CDRs | | | | |
|---|---|---|---|---|
| Anti-human pro-Factor D Antibody Reference No. | Heavy Chain: CDR1; CDR2; CDR3 (SEQ ID NOs) | Light Chain: CDR1; CDR2; CDR3 (SEQ ID NOs) | Heavy Chain: consensus CDR1; CDR2; CDR3 (SEQ ID NOS) | Light Chain consensus CDR1; CDR2; CDR3 (SEQ ID NOS) |
| 18F5 | 149, 151, 153 | 176, 178, 180 | 201, 202, 203 | 204, 178, 205 |
| 1F9 | 155, 156, 153 | 176, 178, 180 | 201, 202, 203 | 204, 178, 205 |
| 2A4 | 158, 159, 161 | 184, 178, 187 | 201, 202, 203 | 204, 178, 205 |

TABLE 4-continued anti-human Pro-Factor D-specific antibodies: CDRs

| Anti-human pro-Factor D Antibody Reference No. | Heavy Chain: CDR1; CDR2; CDR3 (SEQ ID NOs) | Light Chain: CDR1; CDR2; CDR3 (SEQ ID NOs) | Heavy Chain: consensus CDR1; CDR2; CDR3 (SEQ ID NOS) | Light Chain consensus CDR1; CDR2; CDR3 (SEQ ID NOS) |
|---|---|---|---|---|
| 20A1 | 158, 163, 165 | 189, 178, 187 | 201, 202, 203 | 204, 178, 205 |
| 13A10 | 167, 169, 171 | 194, 196, 198 | 167, 169, 171 | 194, 196, 198 |
| 21H1 | 167, 173, 174 | 194, 199, 200 | 167, 173, 174 | 194, 199, 200 |

According, in one aspect, the present invention provides an isolated antibody or fragment thereof that specifically binds to an epitope in the activation ("Pro") peptide of human Factor D set forth as "APPRGR" (SEQ ID NO:4), wherein the antibody or fragment specifically binds to human Pro-Factor D (SEQ ID NO:2) and does not bind to mature-Factor D (SEQ ID NO:3). In one embodiment, the Pro-Factor D-specific antibody is a monoclonal antibody. In one embodiment the Pro-Factor D-specific antibody is a humanized, chimeric, or fully human antibody. In one embodiment the Pro-Factor D-specific antibody fragment is selected from the group consisting of Fv, Fab, Fab', F(ab)$_2$ and F(ab')$_2$. In one embodiment, the Pro-Factor D-specific antibody is a single-chain molecule. In one embodiment, the Pro-Factor D-specific antibody is an IgG molecule selected from the group consisting of IgG1, IgG2 and IgG4. In one embodiment, the Pro-Factor D-specific antibody or antigen-binding fragment thereof binds to human Pro-Factor D with a K$_D$ of less than 10 nM. In one embodiment, the Pro-Factor D-specific antibody or antigen-binding fragment thereof is labeled with a detectable moiety, for example a detectable moiety suitable for use in an immunoassay as further described herein. In one embodiment, the Pro-Factor D-specific antibody or fragment thereof is immobilized on a substrate, such as a substrate suitable for use in an immunoassay, as further described herein.

In one embodiment, the Pro-Factor D-specific antibody or fragment thereof (i.e., an antibody or fragment thereof that specifically binds to human Pro-Factor D) comprises a binding domain comprising HC-CDR1, HC-CDR-2 and HC-CDR-3 of a heavy chain variable region selected from the group consisting of SEQ ID NO:s 136-141 and comprising LC-CDR-1, LC-CDR2 and LC-CDR3 in a light chain variable region selected from the group consisting of SEQ ID NO:s 142-147, wherein the CDRs are numbered according to the Kabat numbering system.

In one embodiment, the Pro-Factor D-specific antibody or fragment thereof that specifically binds to human Pro-Factor D comprises a binding domain comprising HC-CDR1, HC-CDR-2 and HC-CDR-3 in a heavy chain variable region selected from the group consisting of SEQ ID NO:s 136-139 and comprising LC-CDR1, LC-CDR2 and LC-CDR3 in a light chain variable region selected from the group consisting of SEQ ID NO:s 142-145, wherein the CDRs are numbered according to the Kabat numbering system. In one embodiment the Pro-Factor D-specific antibody or fragment thereof comprises a binding domain comprising the following six CDRs: (a) an HC-CDR1 comprising the amino acid sequence XYWMS (SEQ ID NO:201), wherein X at position 1 is N, S or T; (b) an HC-CDR2 comprising the amino acid sequence EIRLKSXNYAXXYXESVKG (SEQ ID NO:202), wherein: X at position 7 is D or E, X at position 11 is T or A, X at position 12 is H or Y and X at position 14 is A or T; (c) an HC-CDR3 comprising the amino acid sequence AWFAX (SEQ ID NO:203), wherein X at position 5 is S, Y or N; (d) a LC-CDR1 comprising the amino acid sequence XSSQXLLYSXDQKNYLA (SEQ ID NO:204), wherein X at position 1 is M or K, X at position 5 is S or N, and X at position 10 is K or R; (e) a LC-CDR2 comprising the amino acid sequence WASTRES (SEQ ID NO:178); and (f) a LC-CDR3 comprising the amino acid sequence LQYYXYPYT (SEQ ID NO:205), wherein X at position 5 is T or S. In one embodiment, the Pro-Factor D-specific antibody or fragment thereof comprises a binding domain comprising the following six CDRs: (a) an HC-CDR1 comprising SEQ ID NO:149 or SEQ ID NO:155, (b) an HC-CDR2 comprising SEQ ID NO:151 or SEQ ID NO:156; (c) an HC-CDR3 comprising SEQ ID NO:153; (d) a LC-CDR1 comprising SEQ ID NO:176, (e) a LC-CDR2 comprising SEQ ID NO:178 and (f) a LC-CDR3 comprising SEQ ID NO:180. In one embodiment, Pro-Factor D-specific antibody or fragment thereof comprises a VH domain having at least 95% sequence identity (such as at least 96%, at least 97%, at least 98%, or at least 99% identity) to the amino acid sequence of SEQ ID NO:136. In one embodiment, the Pro-Factor D-specific antibody or fragment thereof comprises a VH domain having at least 95% sequence identity (such as at least 96%, at least 97%, at least 98%, or at least 99% identity) to the amino acid sequence of SEQ ID NO:137. In one embodiment, the Pro-Factor D-specific antibody or fragment thereof comprises a VL domain having at least 95% sequence identity (such as at least 96%, at least 97%, at least 98%, or at least 99% identity) to the amino acid sequence of SEQ ID NO:142. In one embodiment, the Pro-Factor D-specific antibody or fragment thereof comprises a VL domain having at least 95% sequence identity (such as at least 96%, at least 97%, at least 98%, or at least 99% identity) to the amino acid sequence of SEQ ID NO: 143. In one embodiment, the Pro-Factor D-specific antibody or fragment thereof comprises a VH comprising SEQ ID NO: 136 and a VL comprising SEQ ID NO:142. In one embodiment, the Pro-Factor D-specific antibody or fragment thereof comprises a VH comprising SEQ ID NO:137 and a VL comprising SEQ ID NO: 143.

In one embodiment, the Pro-Factor D-specific antibody or fragment thereof that specifically binds to human Pro-Factor D comprises a binding domain comprising the following six CDRs: (a) an HC-CDR1 comprising SEQ ID NO:158, (b) an HC-CDR2 comprising SEQ ID NO:159 or SEQ ID NO: 163; (c) an HC-CDR3 comprising SEQ ID NO:161 or SEQ ID NO:165; (d) a LC-CDR1 comprising SEQ ID NO:184 or SEQ ID NO:189, (e) a LC-CDR2 comprising SEQ ID NO:178 and (f) a LC-CDR3 comprising SEQ ID NO:187. In one embodiment the Pro-Factor D-specific antibody or fragment thereof comprises a VH domain having at least 95% sequence identity (such as at least 96%, at least 97%, at least 98%, or at least 99% identity) to the amino acid sequence of SEQ ID NO:138. In one embodiment the Pro-Factor D-specific antibody or fragment thereof comprises a VH domain having at least 95% sequence identity (such as at least 96%, at least 97%, at least 98%, or at least 99% identity) to the amino acid sequence of SEQ ID NO:139. In one embodiment, the Pro-Factor D-specific antibody or fragment thereof comprises a VL domain having at least 95% sequence identity (such as at least 96%, at least 97%, at least 98%, or at least 99% identity) to the amino acid sequence of SEQ ID NO:144. In one embodiment, the Pro-Factor D-specific antibody or fragment thereof comprises a VL domain having at least 95% sequence identity (such as at least 96%, at least 97%, at least 98%, or at least 99% identity) to the amino acid sequence of SEQ ID NO:145. In one embodiment, the Pro-Factor D-specific antibody or fragment thereof comprises a VH comprising SEQ ID NO:138 and a VL comprising SEQ ID NO:144. In one embodiment, the Pro-Factor D-specific antibody or fragment thereof comprises a VH comprising SEQ ID NO: 139 and a VL comprising SEQ ID NO:145.

In one embodiment, the Pro-Factor D-specific antibody or fragment thereof that specifically binds to human Pro-Factor D comprises a binding domain comprising HC-CDR1, HC-CDR2 and HC-CDR3 in a heavy chain variable region selected from the group consisting of SEQ ID NO: 140 and SEQ ID NO:141 and comprising LC-CDR1, LC-CDR2 and LC-CDR3 in a light chain variable region selected from the group consisting of SEQ ID NO:146 and SEQ ID NO:147. In one embodiment, the Pro-Factor D-specific antibody or fragment thereof comprises a binding domain comprising the following six CDRs: (a) an HC-CDR1 comprising SEQ ID NO:167, (b) an HC-CDR2 comprising SEQ ID NO:169 or SEQ ID NO:173; (c) an HC-CDR3 comprising SEQ ID NO:171 or SEQ ID NO:174; (d) a LC-CDR1 comprising SEQ ID NO:194, (e) a LC-CDR2 comprising SEQ ID NO:196 or SEQ ID NO:199 and (f) a LC-CDR3 comprising SEQ ID NO:198 or SEQ ID NO:200. In one embodiment, the Pro-Factor D-specific antibody or fragment thereof comprises a VH domain having at least 95% sequence identity (such as at least 96%, at least 97%, at least 98%, or at least 99% identity) to the amino acid sequence of SEQ ID NO:140. In one embodiment, the Pro-Factor D-specific antibody or fragment thereof comprises a VH domain having at least 95% sequence identity (such as at least 96%, at least 97%, at least 98%, or at least 99% identity) to the amino acid sequence of SEQ ID NO:141. In one embodiment, the Pro-Factor D-specific antibody or fragment thereof comprises a VL domain having at least 95% sequence identity (such as at least 96%, at least 97%, at least 98%, or at least 99% identity) to the amino acid sequence of SEQ ID NO:146. In one embodiment, the Pro-Factor D-specific antibody or fragment thereof comprises a VL domain having at least 95% sequence identity (such as at least 96%, at least 97%, at least 98%, or at least 99% identity) to the amino acid sequence of SEQ ID NO:147. In one embodiment, the Pro-Factor D-specific antibody or fragment thereof comprises a VH comprising SEQ ID NO: 140 and a VL comprising SEQ ID NO:146. In one embodiment, the Pro-Factor D-specific antibody or fragment thereof comprises a VH comprising SEQ ID NO: 141 and a VL comprising SEQ ID NO:147.

In certain embodiments, the Pro-Factor D-specific antibody or fragment thereof has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the heavy chain variable domain sequences set forth in TABLE 3. In certain embodiments, the Pro-Factor D-specific antibody or fragment thereof has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the light chain variable domain sequences set forth in TABLE 3.

In another embodiment, the present disclosure provides a nucleic acid encoding the complementarity determining regions (CDRs) of a heavy chain variable region of a Pro-Factor D-specific antibody, or antigen-binding fragment thereof, that specifically binds to human Pro-Factor D, wherein the heavy chain variable region comprises an amino acid sequence set forth in SEQ ID NOs: 136-141 and wherein the CDRs are numbered according to the Kabat numbering system. In another embodiment, the present disclosure provides a nucleic acid encoding complementarity determining regions (CDRs) of a light chain variable region of a Pro-Factor D-specific antibody, or antigen-binding fragment thereof, that specifically binds to human Pro-Factor D, wherein the light chain variable region comprises an amino acid sequence set forth in SEQ ID NOs: 142-147 and wherein the CDRs are numbered according to the Kabat numbering system.

In another embodiment, the present disclosure provides a cloning or expression vector comprising a nucleic acid encoding complementarity determining regions (CDRs) of heavy and/or light chain variable regions of an antibody, or antigen-binding fragment thereof, that specifically binds to human Pro-Factor D, wherein the heavy chain variable region comprises the amino acid sequence set forth as any of SEQ ID NOs: 136-141 and the light chain variable region comprises the amino acid sequence set forth as any of SEQ ID NOs: 142-147 wherein the CDRs are numbered according to the Kabat numbering system.

In another embodiment, the present disclosure provides a cell containing a cloning or expression vector comprising a nucleic acid encoding complementarity determining regions (CDRs) of heavy and/or light chain variable regions of a Pro-Factor D-specific antibody, or antigen-binding fragment thereof that specifically binds to human Pro-Factor D, wherein the heavy chain variable region comprises the amino acid sequence set forth as any of SEQ ID NOs: 136-141 and the light chain variable region comprises the amino acid sequence set forth as any of SEQ ID NOs: 142-147 wherein the CDRs are numbered according to the Kabat numbering system.

In another embodiment, the present disclosure provides a method for producing a human Pro-Factor-D-specific antibody comprising culturing a cell containing an expression vector which contains a nucleic acid that encodes one or both of the heavy and light chain polypeptides of any of the Pro-Factor-D specific antibodies or antigen-binding fragments disclosed herein. The cell or culture of cells is cultured under conditions and for a time sufficient to allow expression by the cell (or culture of cells) of the antibody or antigen-binding fragment thereof encoded by the nucleic acid. The method can also include isolating the antibody or antigen binding fragment thereof from the cell (or culture of cells) or from the media in which the cell or cells were cultured.

In one embodiment, the present disclosure provides a composition comprising any of the Pro-Factor-D-specific antibodies, or antigen-binding fragments disclosed herein.

In one embodiment, the present disclosure provides a substrate for use in an immunoassay comprising at least one or more of any of the Pro-Factor-D-specific antibodies, or antigen-binding fragments disclosed herein.

In one embodiment, the present disclosure provides a kit for detecting the presence or amount of Pro-Factor D in a test sample, such as a biological sample, said kit comprising (a) at least one container, and (b) at least one or more of any of the Pro-Factor-D-specific antibodies, or antigen-binding fragments disclosed herein.

C. Anti-Human Factor D Monoclonal Antibodies that Bind to Both Pro and Mature Forms of Factor D As described in Examples 4-5 herein, the present invention also provides anti-Factor D antibodies that bind to an epitope that is present in both human Pro- and human mature-Factor D. As described in Example 4, the inventors have used the human mature Factor D (SEQ ID NO:3) as an antigen to generate anti-Factor D antibodies which were screened and selected for the ability to detect both the Pro- and mature forms of Factor D and are suitable for use in combination with the mature-Factor D-specific antibodies and the Pro-Factor D-specific antibodies disclosed herein in the detection assays and methods described herein.

As described in Example 5, the variable heavy and light chain fragments of several representative anti-Factor D monoclonal antibodies that bind to both Pro- and mature-Factor D have been cloned and sequenced.

FIG. 10A is an amino acid sequence alignment of the variable heavy chain regions of five anti-Factor D clones that were identified as having high binding affinity to both mature and pro-Factor D.

FIG. 10B is an amino acid sequence alignment of the variable light chain regions of five anti-Factor D clones that were identified as having high binding affinity to both mature and pro-Factor D.

The heavy chain and light chain variable regions and CDRs therein of the five anti-Factor D monoclonal antibodies that bind to both mature and pro-Factor D are provided below in TABLES 5 and 6.

TABLE 6 anti-human Factor D antibodies: CDRs

| Anti-human Factor D Antibody Reference No. | Heavy Chain: CDR1; CDR2; CDR3 (SEQ ID NOs) | Light Chain: CDR1; CDR2; CDR3 (SEQ ID NOs) |
|---|---|---|
| 3C5 | 95; 97; 99 | 111; 113; 115 |
| 30H2 | 95; 97; 99 | 111; 113; 115 |
| 11H1 | 101; 103; 105 | 60; 119; 121 |
| 12H10 | 101; 107; 108 | 123; 124; 125 |
| 7H2 | 101; 107; 105 | 60; 126; 121 |

According, in one aspect, the present invention provides an isolated antibody or fragment thereof that specifically binds to an epitope present in both human Pro-Factor D (SEQ ID NO:2), and human mature Factor D (SEQ ID NO:3), wherein the antibody comprises a binding domain comprising HC-CDR1, HC-CDR2 and HC-CDR3 in a heavy chain variable region selected from the group consisting of SEQ ID NO:s 85-88 and comprising LC-CDR1, LC-CDR2 and LC-CDR3 in a light chain variable region selected from the group consisting of SEQ ID NO:s 89-93, wherein the CDRs are numbered according to the Kabat numbering system.

In one embodiment, the anti-Factor D antibody that binds to an epitope present in both Pro-Factor D and mature Factor D is a monoclonal antibody. In one embodiment the anti-Factor D antibody is a humanized, chimeric, or fully human antibody. In one embodiment the anti-Factor D antibody fragment is selected from the group consisting of Fv, Fab, Fab', F(ab)$_2$ and F(ab')$_2$. In one embodiment, the anti-Factor D antibody is a single-chain molecule. In one embodiment, the anti-Factor D antibody is an IgG molecule selected from the group consisting of IgG1, IgG2 and IgG4. In one embodiment, the anti-Factor D antibody or antigen-binding fragment thereof binds to both human Pro-Factor D and human mature Factor D with a $K_D$ of less than 10 nM. In one embodiment, the anti-Factor D antibody or antigen-binding fragment thereof that binds to an epitope present in both Pro-Factor D and mature Factor D is labeled with a detectable moiety, for example a detectable moiety suitable for use in an immunoassay as further described herein. In one embodiment, the anti-Factor D antibody or fragment thereof that binds to an epitope present in both Pro-Factor D and mature Factor D is immobilized on a substrate, such as a substrate suitable for use in an immunoassay, as further described herein.

TABLE 5 anti-human Factor D Antibody Sequences: mouse parental

| Anti-human Factor D Antibody Reference No | Heavy Chain Variable Region (amino acid) | Light Chain Variable Region (amino acid) | Heavy chain variable region (DNA) | Light chain variable region (DNA) |
|---|---|---|---|---|
| 3C5 | SEQ ID NO: 85 | SEQ ID NO: 89 | SEQ ID NO: 127 | SEQ ID NO: 131 |
| 30H2 | SEQ ID NO: 85 | SEQ ID NO: 90 | SEQ ID NO: 127 | SEQ ID NO: 132 |
| 11H1 | SEQ ID NO: 86 | SEQ ID NO: 91 | SEQ ID NO: 128 | SEQ ID NO: 133 |
| 12H10 | SEQ ID NO: 87 | SEQ ID NO: 92 | SEQ ID NO: 129 | SEQ ID NO: 134 |
| 7H2 | SEQ ID NO: 88 | SEQ ID NO: 93 | SEQ ID NO: 130 | SEQ ID NO: 135 |

In one embodiment, the anti-Factor D antibody or fragment thereof that binds to an epitope shared by both human mature Factor D and human Pro-Factor D comprises a binding domain comprising HC-CDR1, HC-CDR2 and HC-CDR3 of a heavy chain variable region selected from the group consisting of SEQ ID NO:s 136-141 and comprising LC-CDR1, LC-CDR2 and LC-CDR3 in a light chain variable region selected from the group consisting of SEQ ID NO:s 142-147, wherein the CDRs are numbered according to the Kabat numbering system.

In one embodiment, the anti-Factor D antibody or fragment thereof that binds to an epitope shared by both human mature Factor D and human Pro-Factor D comprises a binding domain comprising the following six CDRs: (a) an HC-CDR1 comprising the amino acid sequence SEQ ID NO:95 (b) an HC-CDR2 comprising the amino acid sequence SEQ ID NO:97 (c) an HC-CDR3 comprising the amino acid sequence SEQ ID NO:99 (d) a LC-CDR1 comprising the amino acid sequence SEQ ID NO:111; (e) a LC-CDR2 comprising the amino acid sequence SEQ ID NO:113); and (f) a LC-CDR3 comprising the amino acid sequence SEQ ID NO:115.

In one embodiment, the anti-Factor D antibody or fragment thereof that binds to an epitope shared by both human mature Factor D and human Pro-Factor D comprises a binding domain comprising the following six CDRs: (a) an HC-CDR1 comprising the amino acid sequence SEQ ID NO:101 (b) an HC-CDR2 comprising the amino acid sequence SEQ ID NO:103 or 107 (c) an HC-CDR3 comprising the amino acid sequence SEQ ID NO:105 or 108, (d) a LC-CDR1 comprising the amino acid sequence SEQ ID NO:60 or 123; (e) a LC-CDR2 comprising the amino acid sequence SEQ ID NO: 119, 124 or 126 and (f) a LC-CDR3 comprising the amino acid sequence SEQ ID NO:121 or 125.

In one embodiment, the anti-Factor D antibody or fragment thereof that binds to an epitope shared by both human mature Factor D and human Pro-Factor D comprises a VH domain having at least 95% sequence identity (such as at least 96%, at least 97%, at least 98%, or at least 99% identity) to the amino acid sequence of SEQ ID NO:85. In one embodiment, the anti-Factor D antibody or fragment thereof comprises a VL domain having at least 95% sequence identity (such as at least 96%, at least 97%, at least 98%, or at least 99% identity) to the amino acid sequence of SEQ ID NO:89. In one embodiment, the anti-Factor D antibody or fragment thereof comprises a VL domain having at least 95% sequence identity (such as at least 96%, at least 97%, at least 98%, or at least 99% identity) to the amino acid sequence of SEQ ID NO:90. In one embodiment, the anti-Factor D antibody or fragment thereof comprises a VH comprising SEQ ID NO:85 and a VL comprising SEQ ID NO:89. In one embodiment, the anti-Factor D antibody or fragment thereof comprises a VH comprising SEQ ID NO:85 and a VL comprising SEQ ID NO:90.

In one embodiment the anti-Factor D antibody or fragment thereof that binds to an epitope shared by both human mature Factor D and human Pro-Factor D comprises a VH domain having at least 95% sequence identity (such as at least 96%, at least 97%, at least 98%, or at least 99% identity) to the amino acid sequence of SEQ ID NO:86. In one embodiment the anti-Factor D antibody or fragment thereof comprises a VH domain having at least 95% sequence identity (such as at least 96%, at least 97%, at least 98%, or at least 99% identity) to the amino acid sequence of SEQ ID NO:87. In one embodiment the anti-Factor D antibody or fragment thereof comprises a VH domain having at least 95% sequence identity (such as at least 96%, at least 97%, at least 98%, or at least 99% identity) to the amino acid sequence of SEQ ID NO:88.

In one embodiment, the anti-Factor D antibody or fragment thereof that binds to an epitope shared by both human mature Factor D and human Pro-Factor D comprises a VL domain having at least 95% sequence identity (such as at least 96%, at least 97%, at least 98%, or at least 99% identity) to the amino acid sequence of SEQ ID NO:91. In one embodiment, the anti-Factor D antibody or fragment thereof comprises a VL domain having at least 95% sequence identity (such as at least 96%, at least 97%, at least 98%, or at least 99% identity) to the amino acid sequence of SEQ ID NO:92. In one embodiment, the anti-Factor D antibody or fragment thereof comprises a VL domain having at least 95% sequence identity (such as at least 96%, at least 97%, at least 98%, or at least 99% identity) to the amino acid sequence of SEQ ID NO:93. In one embodiment, the anti-Factor D antibody or fragment thereof comprises a VH comprising SEQ ID NO:86 and a VL comprising SEQ ID NO:91. In one embodiment, the anti-Factor D antibody or fragment thereof comprises a VH comprising SEQ ID NO:87 and a VL comprising SEQ ID NO:92. In one embodiment, the anti-Factor D antibody or fragment thereof comprises a VH comprising SEQ ID NO:88 and a VL comprising SEQ ID NO:93.

In certain embodiments, the anti-Factor D antibody or fragment thereof that binds to an epitope shared by both human mature Factor D and human Pro-Factor D has a heavy chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the heavy chain variable domain sequences set forth in TABLE 5.

In certain embodiments, the anti-Factor D antibody or fragment thereof that binds to an epitope shared by both human mature Factor D and human Pro-Factor D has a light chain variable domain that is substantially identical (e.g., at least about 70%, at least 75%, at least about 80%, at least about 85%, at least about 90%, at least about 95%, or at least about 96% identical, or at least about 97% identical, or at least about 98% identical, or at least 99% identical), to that of any of the light chain variable domain sequences set forth in TABLE 5.

In another embodiment, the present disclosure provides a nucleic acid encoding the complementarity determining regions (CDRs) of a heavy chain variable region of an anti-Factor D antibody, or antigen-binding fragment thereof, that binds to an epitope shared by both human mature Factor D and human Pro-Factor D, wherein the heavy chain variable region comprises an amino acid sequence set forth in SEQ ID NOs:85-88 and wherein the CDRs are numbered according to the Kabat numbering system. In another embodiment, the present disclosure provides a nucleic acid encoding complementarity determining regions (CDRs) of a light chain variable region of an antibody, or antigen-binding fragment thereof, that binds to an epitope shared by both human mature Factor D and human Pro-Factor D, wherein the light chain variable region comprises an amino acid sequence set forth in SEQ ID NOs:89-93 and wherein the CDRs are numbered according to the Kabat numbering system.

In another embodiment, the present disclosure provides a cloning or expression vector comprising a nucleic acid encoding complementarity determining regions (CDRs) of heavy and/or light chain variable regions of an anti-Factor D antibody, or antigen-binding fragment thereof, that binds to an epitope shared by both human mature Factor D and human Pro-Factor D, wherein the heavy chain variable region comprises the amino acid sequence set forth as any of SEQ ID NOs:85-88 and the light chain variable region comprises the amino acid sequence set forth as any of SEQ ID NOs:89-93 wherein the CDRs are numbered according to the Kabat numbering system.

In another embodiment, the present disclosure provides a cell containing a cloning or expression vector comprising a nucleic acid encoding complementarity determining regions (CDRs) of heavy and/or light chain variable regions of an anti-Factor D antibody, or antigen-binding fragment thereof, that binds to an epitope shared by both human mature Factor D and human Pro-Factor D, wherein the heavy chain variable region comprises the amino acid sequence set forth as any of SEQ ID NOs: 85-88 and the light chain variable region comprises the amino acid sequence set forth as any of SEQ ID NOs: 89-93 wherein the CDRs are numbered according to the Kabat numbering system.

In another embodiment, the present disclosure provides a method for producing an anti-Factor D antibody that binds to an epitope shared by both human mature Factor D and human Pro-Factor D comprising culturing a cell containing an expression vector which contains a nucleic acid that encodes one or both of the heavy and light chain polypeptides of any of the antibodies or antigen-binding fragments disclosed herein. The cell or culture of cells is cultured under conditions and for a time sufficient to allow expression by the cell (or culture of cells) of the anti-Factor D antibody or antigen-binding fragment thereof encoded by the nucleic acid. The method can also include isolating the antibody or antigen binding fragment thereof from the cell (or culture of cells) or from the media in which the cell or cells were cultured.

In one embodiment, the present disclosure provides a composition comprising any of the anti-Factor D antibodies, or antigen-binding fragments thereof, that bind to an epitope shared by both human mature Factor D and human Pro-Factor D disclosed herein.

In one embodiment, the present disclosure provides a substrate for use in an immunoassay comprising at least one or more of any of the anti-Factor D antibodies, or antigen-binding fragments thereof, that bind to an epitope shared by both human mature Factor D and human Pro-Factor D disclosed herein.

In one embodiment, the present disclosure provides a kit for detecting the presence of Factor D in a test sample, such as a biological sample, said kit comprising (a) at least one container, and (b) at least one or more of any of the anti-Factor D antibodies, or antigen-binding fragments thereof, that bind to an epitope shared by both human mature Factor D and human Pro-Factor D disclosed herein.

Single-Chain Anti-Factor D Antibodies

In one embodiment of the present invention, the anti-Factor D antibodies (i.e., any of the mature Factor-D specific antibodies, the Pro-Factor-D-specific antibodies or the anti-Factor-D antibodies that bind both the mature and Pro-forms of Factor D) are single-chain antibodies, defined as a genetically engineered molecule containing the variable region of the light chain, the variable region of the heavy chain, linked by a suitable polypeptide linker as a genetically fused single-chain molecule. Such single-chain antibodies are also referred to as "single-chain Fv" or "scFv" antibody fragments. Generally, the Fv polypeptide further comprises a polypeptide linker between the VH and VL domains that enables the scFv to form the desired structure for antigen binding. The scFv antibodies that bind Factor D can be oriented with the variable light region either amino terminal to the variable heavy region or carboxyl terminal to it.

Humanized Anti-Factor D Antibodies

The anti-Factor D antibodies disclosed herein (i.e., any of the mature Factor-D specific antibodies, the Pro-Factor-D-specific antibodies or the anti-Factor-D antibodies that bind both the mature and Pro-forms of Factor D) can be modified without changing their ability to be used for the purposes described herein. As an initial matter, it is noted that the antibodies described herein originated from immunized mice. The antibodies thus have framework regions (regions outside the complementarity determining regions, or "CDRs") which contain the amino acid residues usually found in the framework regions in murine antibodies, and which may be immunogenic when administered to a human patient. To reduce immunogenicity of murine antibodies when used in humans, it is common in the art to engineer the framework regions by replacing residues found at particular positions in the antibodies of mice with the residues more typically found at the same position in human antibodies. Antibodies engineered in these ways are referred to as "humanized antibodies" and are typically preferred for in vivo use, since they have a lower risk of inducing side effects and typically can remain in the circulation longer. Methods of humanizing antibodies are known in the art and are set forth in detail in, for example, U.S. Pat. Nos. 6,180,377; 6,407,213; 5,693,762; 5,585,089; and 5,530,101.

Further, since the CDRs of the variable regions determine antibody specificity, the anti-Factor D antibody CDRs set forth in TABLES 2, 4, 6-10 and 12-17 can be grafted or engineered into an antibody of choice to confer specificity for binding to Factor D upon that antibody. For example, the CDRs from mature Factor-D-specific clones 6G6, 14A11, 27B3, 58F5, 49G3 and 10G1 as set forth in TABLE 2 and/or from Pro-Factor D-specific clones 18F5, 1F9, 2A4, 20A1, 13A10 and 21H1 as set forth in TABLE 4 can be grafted onto a human antibody framework of known three dimensional structure (see e.g., WO98/45322; Jones et al., *Nature* 321:522 (1986); Verhoeyen et al., *Science* 239:1534 (1988); Riechmann et al., *Nature* 332:323 (1988) and Winter & Milstein, *Nature* 349:293 (1991) to generate an anti-mature Factor D-specific or anti-Pro-Factor D specific antibody with reduced or no immunogenic responses when administered to humans.

Methods for Producing Anti-Factor D Antibodies

In another aspect, the present invention provides a method of producing an antibody specifically recognizing and binding human Factor D, such as mature Factor-D specific antibodies, the Pro-Factor-D-specific antibodies or anti-Factor-D antibodies that bind both the mature and Pro-forms of Factor D comprising culturing a cell containing an expression vector which contains a nucleic acid that encodes one or both of the heavy and light chain polypeptides of any of the antibodies or antigen-binding fragments disclosed herein. The cell or culture of cells is cultured under conditions and for a time sufficient to allow expression by the cell (or culture of cells) of the antibody or antigen-binding fragment thereof encoded by the nucleic acid. The method can also include isolating the antibody or antigen binding fragment thereof from the cell (or culture of cells) or from the media in which the cell or cells were cultured.

In one embodiment, the present disclosure features a cell containing a cloning or expression vector comprising a nucleic acid encoding complementarity determining regions (CDRs) of heavy and/or light chain variable regions of an antibody, or antigen-binding fragment thereof, that specifically binds to human mature Factor D, wherein the heavy chain variable region comprises the amino acid sequence set forth as any of SEQ ID NOs: 12-17 and the light chain variable region comprises the amino acid sequence set forth as any of SEQ ID NOs: 18-23.

In another embodiment, the present disclosure features a cell containing a cloning or expression vector comprising a nucleic acid encoding complementarity determining regions (CDRs) of heavy and/or light chain variable regions of an antibody, or antigen-binding fragment thereof, that specifically binds to human Pro-Factor D, wherein the heavy chain variable region comprises the amino acid sequence set forth as any of SEQ ID NOs: 136-141 and the light chain variable region comprises the amino acid sequence set forth as any of SEQ ID NOs: 142-147.

In some embodiments, the invention provides a nucleic acid molecule encoding an anti-Factor D antibody, or fragment thereof, of the invention, such as an antibody or antigen-binding fragment thereof that specifically binds to human mature Factor D (e.g., as set forth in TABLE 1), an antibody or antigen-binding fragment thereof that specifically binds to human Pro-Factor D (e.g., as set forth in TABLE 3) or an antibody or antigen-binding fragment thereof that binds to an epitope shared by both human mature Factor D and human Pro-Factor D (e.g., as set forth in TABLE 5). In some embodiments the invention provides a nucleic acid molecule comprising a nucleic acid sequence encoding an anti-Factor D antibody, such as encoding an antibody or antigen-binding fragment thereof that specifically binds to human mature Factor D (e.g., SEQ ID NOs: 73-84), or encoding an antibody or antigen-binding fragment thereof that specifically binds to human Pro-Factor D (e.g., SEQ ID NOs: 206-217) or encoding an antibody or antigen-binding fragment thereof that binds to an epitope shared by both human mature Factor D and human Pro-Factor D (e.g., SEQ ID NOs: 127-135).

In some embodiments, the invention provides a cell comprising a nucleic acid molecule encoding a Factor D-specific monoclonal antibody of the invention (including mature Factor-D specific antibodies, the Pro-Factor-D-specific antibodies and anti-Factor-D antibodies that bind both the mature and Pro-forms of Factor D).

In some embodiments, the invention provides an expression cassette comprising a nucleic acid molecule encoding a Factor D-specific monoclonal antibody of the invention (including mature Factor-D specific antibodies, the Pro-Factor-D-specific antibodies and anti-Factor-D antibodies that bind both the mature and Pro-forms of Factor D).

In some embodiments, the invention provides a method of producing Factor D-specific monoclonal antibodies comprising culturing a cell comprising a nucleic acid molecule encoding a Factor D-specific antibody of the invention (including mature Factor-D specific antibodies, the Pro-Factor-D-specific antibodies and anti-Factor-D antibodies that bind both the mature and Pro-forms of Factor D).

In many embodiments, the nucleic acids encoding a subject monoclonal antibody are introduced directly into a host cell, and the cell incubated under conditions sufficient to induce expression of the encoded antibody.

In one embodiment, the method of producing a Factor D-specific monoclonal antibody (including mature Factor-D specific antibodies, the Pro-Factor-D-specific antibodies or the anti-Factor-D antibodies that bind both the mature and Pro-forms of Factor D) comprises culturing a cell comprising a nucleic acid molecule encoding a Factor D-specific antibody of the invention.

According to certain related embodiments there is provided a recombinant host cell which comprises one or more constructs as described herein; a nucleic acid encoding any anti-Factor D antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

For example, any cell suitable for expression of expression cassettes may be used as a host cell, for example, yeast, insect, plant, etc., cells. In many embodiments, a mammalian host cell line that does not ordinarily produce antibodies is used, examples of which are as follows: monkey kidney cells (COS cells), monkey kidney CVI cells transformed by SV40 (COS-7, ATCC CRL 165 1); human embryonic kidney cells (HEK-293, Graham et al., *J. Gen Virol.* 36:59 (1977)); baby hamster kidney cells (BHK, ATCC CCL 10); Chinese hamster ovary-cells (CHO, Urlaub and Chasin, *Proc. Natl. Acad. Sci.* (USA) 77:4216, (1980); mouse sertoli cells (TM4, Mather, *Biol. Reprod.* 23:243-251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., *Annals N.Y. Acad. Sci* 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e., in vitro, ex vivo, or in vivo). A general discussion of these methods can be found in Ausubel, et al., Short Protocols in Molecular Biology, 3d ed., Wiley & Sons, 1995. In some embodiments, lipofectamine and calcium mediated gene transfer technologies are used.

After the subject nucleic acids have been introduced into a cell, the cell is typically incubated, normally at 37° C., sometimes under selection, for a suitable time to allow for the expression of the antibody. In most embodiments, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). The efficiency of expression may be enhanced by the inclusion of appropriate transcription enhancer elements, transcription terminators, etc. (see Bittner et al., *Methods in Enzymol.* 153:51-544 (1987)).

For long-term, high-yield production of recombinant antibodies, stable expression may be used. For example, cell lines, which stably express the antibody molecule, may be engineered. Rather than using expression vectors, which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci, which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium. For example, a nucleic acid sequence encoding a signal peptide may be included adjacent the coding region of the antibody or fragment. Such a signal peptide may be incorporated adjacent to the 5' end of the amino acid sequences set forth herein for the subject antibodies in order to facilitate production of the subject antibodies.

Anti-Factor D Antibodies Labeled with a Detectable Moiety

In another aspect, the invention provides anti-Factor D antibodies (including mature Factor-D-specific antibodies, Pro-Factor-D-specific antibodies and anti-Factor-D antibodies that bind both the mature and Pro-forms of Factor D) that are labeled with a detectable moiety (i.e., a moiety that permits detection and/or quantitation). In various embodiments, the antibodies described herein are conjugated to a detectable label that may be detected directly or indirectly. In this regard, an antibody "conjugate" refers to an anti-Factor D antibody that is covalently linked to a detectable label. In the present invention, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically, or otherwise) signal that indicates the presence and/or concentration of the label in a sample. When conjugated to an antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific antibodies can be used in combination to detect one or more targets.

Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

Examples of detectable labels which may be conjugated to antibodies of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes, or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, ß-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.-NP), o-dianisidine (OD), 5-bromo-4-chloro-3-indolylphosphate (BCIP), Nitro blue tetrazolium (NBT), 2-(p-iodophenyl)-3-p-nitropheny-1-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/- fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein (i.e., any of the mature Factor-D specific antibodies, the Pro-Factor-D-specific antibodies or the anti-Factor-D antibodies that bind both the mature and Pro-forms of Factor D) or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.). In another embodiment, the anti-Factor D antibody is not labeled (i.e., is naked), and the presence thereof can be detected using a labeled antibody which binds to the anti-Factor D antibody (i.e., any of the mature Factor-D specific antibodies, the Pro-Factor-D-specific antibodies or the anti-Factor-D antibodies that bind both the mature and Pro-forms of Factor D)

V. Compositions and Kits Comprising Anti-Factor D Antibodies

Compositions

In another aspect, the present disclosure provides a substrate, such as a solid support (e.g., an insoluble substrate, such as non-aqueous matrix, such as a plate or slide made of glass, polysaccharides (e.g., agarose), polyacrylamides, polystyrene, plastic or metal, a polymer-coated bead, a tube, or a ceramic or metal chip) that comprises immobilized (or otherwise deposited) monoclonal anti-Factor D antibodies disclosed herein (such as mature Factor-D specific antibodies, Pro-Factor-D-specific antibodies and anti-Factor-D antibodies that bind both the mature and Pro-forms of Factor D). In some embodiments, the anti-Factor D antibodies are immobilized (or deposited) at discrete locations (e.g., in the wells of a multiwall plate, or deposited in an array on a biochip). In some embodiments, the substrate comprising the anti-Factor D antibodies may be part of a kit for detecting Factor D (such as mature Factor D, Pro-Factor D, or total Factor D (mature and Pro-Factor D) in a biological sample obtained from a mammalian subject.

Kits

In another aspect, the present disclosure provides kits for use in performing one or more assays disclosed herein.

In one embodiment, the present disclosure provides a kit (i.e., a packaged combination of reagents in predetermined amounts) with reagents and instructions for detecting the presence of Factor D (such as mature Factor D, Pro-Factor D, or total Factor D (mature and Pro-Factor D)) in a test sample, such as a biological sample. Exemplary kits may contain at least one anti-Factor D monoclonal antibody or antigen binding fragment thereof as described herein (i.e., any of the mature Factor-D specific antibodies, the Pro-Factor-D-specific antibodies or the anti-Factor-D antibodies that bind both the mature and Pro-forms of Factor D). Where the anti-Factor D antibody is labeled with a detectable moiety, such as an enzyme, the kit will include substrates and cofactors required by the enzyme (e.g., a substrate precursor which provides the detectable chromophore or fluorophore). In addition, other additives may be included such as stabilizers, buffers (e.g., a blocking buffer or lysis buffer) and the like. The relative amounts of the various reagents may be varied widely to provide for concentrations in solution of the reagents, which substantially optimize the sensitivity of the assay. Particularly, the reagents may be provided as dry powders, usually lyophilized, including excipients which on dissolution will provide a reagent solution having the appropriate concentration.

In addition, kits may include instructional materials disclosing means of use of an antibody of the present invention (e.g., for detection of mature Factor D or Pro-Factor D as a biomarker for the level of Alternative Pathway Complement (APC) activation, or absence thereof). The kits may also include additional components to facilitate the particular application for which the kit is designed. For example, the kit may additionally contain means of detecting a label (e.g., enzyme substrates for enzymatic labels, filter sets to detect fluorescent labels, appropriate secondary labels such as a sheep anti-mouse-HRP or the like). The kits may additionally include buffers and other reagents routinely used for the practice of a particular immunoassay, as is well known in the art.

Certain embodiments provide kits for detecting the presence or amount of mature Factor D in a sample, wherein the kits contain at least one mature Factor D-specific antibody as described herein, such as an antibody or fragment comprising the CDRs from mature Factor-D-specific clones 6G6, 14A11, 27B3, 58F5, 49G3 and 10G1 as set forth in TABLE 2. In certain embodiments, a kit may comprise buffers, enzymes, labels, substrates, beads, or other surfaces to which the antibodies of the invention are attached, and the like, and instructions for use.

Certain embodiments provide kits for detecting the presence or amount of Pro-Factor D in a sample, wherein the kits contain at least one Pro-Factor D-specific antibody as described herein, such an antibody or fragment comprising the CDRs from Pro-Factor D-specific clones 18F5, 1F9, 2A4, 20A1, 13A10 and 21H1 as set forth in TABLE 4. The subject anti-Factor D antibodies and antigen-binding fragments thereof can be labeled with any appropriate detectable moiety as described herein. In certain embodiments, a kit may comprise buffers, enzymes, labels, substrates, beads, or other surfaces to which the antibodies of the invention are attached, and the like, and instructions for use.

Items in a kit may be individually wrapped or packaged in individual receptacles, which are provided together in a larger container (e.g., a cardboard or styrofoam box).

In accordance with the foregoing, in one embodiment, the present disclosure provides a kit comprising at least one monoclonal antibody that specifically detects or quantitates human mature Factor D (SEQ ID NO:3) and/or Pro-Factor D (SEQ ID NO:2) in an immunoassay, wherein the at least one monoclonal antibody comprises: (i) a mature Factor D-specific monoclonal antibody, or antigen-binding fragment thereof, that specifically binds to an epitope encompassing the amino-terminus of human mature Factor D, wherein the epitope comprises or consists of the amino acids ILGGREA (SEQ ID NO:5) and wherein said antibody does not bind to human Pro-Factor D (SEQ ID NO:2); and/or (ii) a Pro-Factor D-specific monoclonal antibody, or antigen-binding fragment thereof, that specifically binds to an epitope on the activation ("Pro") peptide of human Factor D, wherein the epitope comprises or consists of "APPRGR" (SEQ ID NO:4) and wherein said antibody does not bind to mature Factor D (SEQ ID NO:3). In one embodiment, the mature Factor D-specific antibody or fragment thereof comprises a binding domain comprising HC-CDR-1, HC-CDR-2 and HC-CDR-3 in a heavy chain variable region selected from the group consisting of SEQ ID NO:s 12-17 and comprising LC-CDR-1, LC-CDR2 and LC-CDR3 in a light chain variable region selected from the group consisting of SEQ ID NO:s 18-23, wherein the CDRs are numbered according to the Kabat numbering system. In one embodiment the Pro-Factor D-specific antibody or fragment thereof comprises a binding domain comprising HC-CDR1, HC-CDR2 and HC-CDR3 of a heavy chain variable region selected from the group consisting of SEQ ID NO:s 136-141 and comprising LC-CDR1, LC-CDR2 and LC-CDR3 in a light chain variable region selected from the group consisting of SEQ ID NO:s 142-147, wherein the CDRs are numbered according to the Kabat numbering system.

In some embodiments, the kit further comprises an anti-Factor D antibody, or fragment thereof, that binds to an epitope shared by both human mature Factor D (SEQ ID NO:3) and human Pro-Factor D (SEQ ID NO:2). In some embodiments, the anti-Factor D antibody or fragment thereof comprises a binding domain comprising HC-CDR1, HC-CDR2 and HC-CDR3 in a heavy chain variable region selected from the group consisting of SEQ ID NO:s 85-88 and comprising LC-CDR1, LC-CDR2 and LC-CDR3 in a light chain variable region selected from the group consisting of SEQ ID NO:s 89-93, wherein the CDRs are numbered according to the Kabat numbering system.

In some embodiments, the kit further comprises at least one container.

In some embodiments, the kit is for carrying out an enzyme-linked immunosorbent assay (ELISA). In one embodiment, the mature Factor D-specific antibody or fragment thereof is a coating antibody. In one embodiment, the mature Factor D-specific antibody or fragment thereof is a detecting antibody. In one embodiment, the Pro-Factor D-specific antibody or fragment thereof is a coating antibody. In one embodiment, the Pro-Factor D-specific antibody or fragment thereof is a detecting antibody.

In various embodiments of the kits of the invention, the subject anti-Factor D antibodies and antigen-binding fragments thereof (i.e., mature Factor D-specific antibodies, Pro-Factor D-specific antibodies and/or anti-Factor D antibodies) can be labeled with any appropriate detectable moiety as described herein. In certain embodiments, the kit further comprises buffers, enzymes, labels, substrates, beads, or other surfaces to which the antibodies of the invention are attached, and the like, and instructions for use.

VI. Methods of Detecting Factor D Using Anti-Factor D Antibodies

As described herein, the inventors have generated anti-Factor D antibodies that are suitable for use in an immunoassay for detecting the presence and/or amount of Factor D (such as mature Factor D, Pro-Factor D and total Factor D (both mature and pro forms of Factor D) in a test sample, such as a biological sample obtained from a mammalian subject.

In one aspect, the anti-Factor D antibodies (including mature Factor-D specific antibodies, the Pro-Factor-D-specific antibodies and the anti-Factor-D antibodies that bind both the mature and Pro-forms of Factor D) of the present invention are used in an in vitro immunoassay for analyzing a test sample, such as a biological sample obtained from a test subject, for the presence or amount of Pro-Factor D, mature Factor D, and/or total Factor D. In such in vitro immunoassays, the anti-Factor D antibody, or antigen-binding fragment thereof, may be naked or may be labeled with a detectable moiety, as described herein, and may be utilized in liquid phase or bound to a substrate, as described below. For purposes of in vitro assays, any type of antibody such as murine, chimeric, humanized or human may be utilized, since there is no host immune response to consider.

The antibodies of the present disclosure may be employed in any known immunoassay method, such as competitive binding assays, direct and indirect sandwich assays, lateral flow assays (e.g., dipstick format) and immunoprecipitation assays (see e.g., Zola, Monoclonal Antibodies: A Manual of Techniques, pp. 147-158 (CRC Press. Inc., 1987).

Sandwich assays involve the use of two antibodies, each capable of binding to a different immunogenic portion, or epitope, of the protein to be detected (e.g., Factor D). In a sandwich assay, the test sample analyte is bound by a first antibody (e.g., an anti-Factor D antibody, such as a mature Factor D-specific antibody, a Pro-Factor D-specific antibody and/or an antibody that binds to both mature and pro Factor D), which is immobilized on a solid support (e.g., substrate), and thereafter a second antibody binds to the analyte, thus forming an insoluble three-part complex. The second antibody may itself be labeled with a detectable moiety (direct sandwich assays) or may be measured using an anti-immunoglobulin antibody that is labeled with a detectable moiety (indirect sandwich assay).

For example, one preferable type of sandwich assay is an ELISA assay, in which case the detectable moiety is an enzyme. ELISA assays, regardless of the detection system employed, generally include the immobilization of an antigen or antibody to a substrate (e.g., a solid support), as well as the use of an appropriate detecting reagent. In an ELISA assay, the protein antigen-antibody reaction takes place on a substrate (e.g., a solid support), typically in wells on microtiter plates. Antigen and this first antibody, also called the coating or capture antibody, react and produce a stable complex, which can be visualized by addition of a second antibody, called the detection antibody, which may be directly or indirectly linked to an enzyme. Addition of a substrate for that enzyme results in a color formation, which can be measured photometrically.

In one embodiment, the anti-Factor D antibodies (including mature Factor-D specific antibodies, the Pro-Factor-D-specific antibodies and the anti-Factor-D antibodies that bind both the mature and Pro-forms of Factor D) of the invention are used to detect the presence of the mature or Pro-forms of the Factor D antigen in a biological sample using an enzyme-linked immunosorbent assay (ELISA) (see e.g., Gold et al. *J Clin Oncol.* 24:252-58, 2006).

In the direct competitive ELISA, a pure or semipure antigen preparation is bound to a substrate that is insoluble in the fluid or cellular extract being tested and a quantity of detectably labeled soluble antibody is added to permit detection and/or quantitation of the binary complex formed between substrate-bound antigen and labeled antibody.

In contrast, a "double-determinant" ELISA, also known as a "two-site ELISA" or "sandwich assay," requires small amounts of antigen and the assay does not require extensive purification of the antigen. Thus, the double-determinant ELISA is preferred to the direct competitive ELISA for the detection of an antigen in a clinical sample. See, for example, the use of the double-determinant ELISA for quantitation of the c-myc oncoprotein in biopsy specimens. Field et al., *Oncogene* 4: 1463 (1989); Spandidos et al., AntiCancer Res. 9: 821 (1989). In a double-determinant ELISA, a quantity of unlabeled monoclonal antibody or antibody fragment (the "capture antibody") is bound to a substrate (e.g., a solid support), the test sample is brought into contact with the capture antibody, and a quantity of detectably labeled soluble antibody (or antibody fragment) is added to permit detection and/or quantitation of the ternary complex formed between the capture antibody, antigen, and labeled antibody.

In one embodiment, the capture antibody bound to a substrate (e.g., solid support) is an anti-Factor D antibody or antigen-binding fragment thereof as disclosed herein that binds to an epitope that is shared by both the Pro- and mature-Factor D (i.e., in the C-terminal portion of Factor D). In one embodiment, the capture antibody bound to a substrate (e.g., solid support) is a mature Factor D-specific antibody or antigen-binding fragment thereof as disclosed herein. In one embodiment, the capture antibody bound to a substrate (e.g., solid support) a Pro-Factor D-specific antibody or antigen-binding fragment thereof as disclosed herein.

Methods of performing a double-determinant ELISA are well-known by those of skill in the art. See, for example, Field et al., *Oncogene* 4: 1463 (1989); Spandidos et al., *AntiCancer Res.* 9: 821 (1989); and Moore et al., *Methods in Molecular Biology* Vol 10:273-281 (The Humana Press, Inc. 1992).

In the double-determinant ELISA, the soluble antibody or antibody fragment must bind to a Factor D epitope that is distinct from the epitope recognized by the capture antibody. The double-determinant ELISA can be performed to ascertain whether the Factor D antigen (i.e., mature Factor D or Pro-Factor D) is present in a test biological sample, such as a body fluid (e.g., blood, plasma or serum) or a biopsy sample. Alternatively, the assay can be performed to quantitate the amount of Factor D antigen that is present in a clinical sample of body fluid. The quantitative assay can be performed by including dilutions of purified Factor D antigen.

In vitro immunoassays can be performed in which at least one anti-Factor D antibody or antigen-binding fragment thereof (e.g., a mature Factor-D specific antibody, a Pro-Factor-D-specific antibody and/or an anti-Factor-D antibody that binds both the mature and Pro-forms of Factor D) is bound to a substrate (e.g., a solid-phase carrier). For example, anti-Factor D monoclonal antibodies or fragments thereof can be attached to a polymer, such as aminodextran, in order to link the monoclonal antibody to an insoluble substrate such as a polymer-coated bead, a plate, a tube, or a ceramic or metal chip. In one embodiment, the substrate is suitable for use in an ELISA method (e.g., a multiwell microtitre plate). Accordingly, the determination of the level of Factor D (such as mature Factor D, pro-Factor D, or both mature and pro-Factor D) in the sample may be determined by commercially available methods such as an ELISA based assay, chemical or enzymatic protein determination.

Other suitable in vitro assays will be readily apparent to those of skill in the art. The specific concentrations of detectably labeled anti-anti-Factor D antibody, the temperature and time of incubation, as well as other assay conditions may be varied, depending on various factors including the concentration of the Factor D antigen in the sample, the nature of the sample, and the like. The binding activity of a sample of anti-Factor D antibody may be determined according to well-known methods. Those skilled in the art will be able to determine operative and optimal assay conditions for each determination by employing routine experimentation.

In another embodiment, the subject antibodies and antigen-binding fragments thereof can be used to detect the presence of the Factor D antigen in tissue sections prepared from a histological specimen (e.g., a biopsy sample). Such in situ detection can be used to determine the presence of the Factor D antigen and to determine the distribution of the Factor D antigen in the examined tissue. In situ detection can be accomplished by applying a detectably labeled anti-Factor D antibody to tissue sections. General techniques of in situ detection are well-known to those of ordinary skill. See, for example, Ponder, "Cell Marking Techniques and Their Application," in *Mammalian Development: A Practical Approach* 113-38 Monk (ed.) (IRL Press 1987).

A. Assays to Detect Mature Factor D

In accordance with the foregoing, in one aspect, the present invention provides a method of determining the presence or amount of mature Factor D in a test sample, such as a biological sample, the method comprising (a) contacting a test sample with a mature Factor D-specific monoclonal antibody or antigen-binding fragment thereof in an in vitro immunoassay and (b) detecting the presence or absence of binding of said antibody, wherein the presence of binding indicates the presence or amount of mature Factor D in the sample. In one embodiment, the mature Factor D-specific antibody or fragment thereof binds to an epitope in the amino-terminal region of human mature Factor D, wherein said epitope comprises or consists of the amino acids ILGGREA (SEQ ID NO:5) and wherein the antibody does not bind to Pro-Factor D.

In one embodiment, the anti-human mature Factor D-specific antibody or antigen-binding fragment thereof comprises a binding domain comprising HC-CDR1, HC-CDR2 and HC-CDR3 in a heavy chain variable region selected from the group consisting of SEQ ID NO:s 12-17 and comprising LC-CDR1, LC-CDR2 and LC-CDR3 in a light chain variable region selected from the group consisting of SEQ ID NO:s 18-23. In one embodiment, the anti-human mature Factor D-specific antibody or antigen-binding fragment thereof comprises a binding domain comprising the following six CDRs: a) an HC-CDR1 comprising the amino acid sequence XSXMGVS (SEQ ID NO:65), wherein X at position 1 is T, I or S and X at position 3 is G or I; (b) an HC-CDR2 comprising the amino acid sequence HIYWD-DEKHYXPSLKX (SEQ ID NO:66), wherein X at position 11 is H or N and X at position 16 is S or R; (c) an HC-CDR3 comprising the amino acid sequence RYYGYXXXMXY (SEQ ID NO:67), wherein X at position 6 is R, G or N, X at position 7 is S or Y, X at position 8 is F, I or V, and X at position 10 is D or H; (d) a LC-CDR1 comprising the amino acid sequence RSXXSIXHSNGNTYXE (SEQ ID NO:68), wherein: X at position 3 is N or S, X at position 4 is Q or E, X at position 7 is V or L, and X at position 15 is F or L; (e) a LC-CDR2 comprising the amino acid sequence KVXNRFS (SEQ ID NO:69), wherein: X at position 3 is S or Y; and (f) a LC-CDR3 comprising the amino acid sequence FQGSHVPPT (SEQ ID NO:54). In one embodiment, the anti-human mature Factor D-specific antibody or antigen-binding fragment thereof comprises a binding domain comprising the following six CDRs: (a) an HC-CDR1 comprising SEQ ID NO:25, (b) an HC-CDR2 comprising SEQ ID NO:27; (c) an HC-CDR3 comprising SEQ ID NO: 29; (d) a LC-CDR1 comprising SEQ ID NO:50, (e) a LC-CDR2 comprising SEQ ID NO:52 and (f) a LC-CDR3 comprising SEQ ID NO:54.

In some embodiments, the anti-human mature Factor D-specific antibody or fragment thereof is a monoclonal antibody comprising the CDRs from mature Factor-D-specific clones 6G6, 14A11, 27B3, 58F5, 49G3 and 10G1 as set forth in TABLE 2.

In one embodiment, the method further comprises comparing the amount of mature-Factor D detected in accordance with step (b) with a reference standard or control sample to determine the level of mature-Factor D in the test sample.

In one embodiment, the control sample is an individual or pooled sample of subjects suffering from an alternative pathway disease or disorder (e.g., paroxysmal nocturnal hemoglobinuria (PNH), C3 glomerulopathy, or other alternative pathway disease or disorder). In one embodiment, the control sample is an individual or pooled sample of normal healthy volunteers. In one embodiment, the control sample is a baseline sample of a subject prior to treatment with a complement inhibitor (e.g., a MASP-3 inhibitory agent or other complement inhibitor). In one embodiment, the reference standard is a ratio of at least one of: Pro-Factor D versus mature Factor D or mature Factor D versus total Factor D, wherein the ratio is obtained from a test sample or a control sample (e.g., an individual or pooled sample of normal healthy volunteers, or a baseline sample of a subject prior to treatment with a complement inhibitor, or an individual or pooled sample of subject(s) suffering from an alternative pathway disease or disorder). In one embodiment, the anti-human mature Factor D-specific antibody or antigen-binding fragment thereof is immobilized on a substrate. In one embodiment, the immunoassay is an ELISA assay.

In one embodiment, the anti-human mature Factor D-specific antibody is labeled with a detectable moiety and step (b) comprises detecting the presence of said detectable moiety. In one embodiment, said anti-human mature Factor D-specific antibody or antigen-binding fragment thereof is naked (i.e., not labeled), and the presence or amount of the antibody or fragment thereof bound to mature Factor D is detected using a labeled antibody which binds to the anti-mature Factor D antibody. In one embodiment, said anti-human mature Factor D-specific antibody or antigen-binding fragment thereof is immobilized on a substrate (i.e., capture/coating) and the bound mature Factor D is detected with a second antibody that binds to a different epitope of Factor D (e.g., an anti-Factor D antibody that binds to an epitope shared by mature Factor D and Pro-Factor D as described herein).

In one embodiment, the test sample is a biological sample obtained from a mammalian subject. In various embodiments, the biological sample is selected from the group consisting of whole blood, serum, plasma, sputum, amniotic fluid, cerebrospinal fluid, cell lysate, ascites, urine, saliva, and tissue. In one embodiment, the biological sample is selected from the group consisting of blood, serum, plasma, urine, and cerebrospinal fluid.

In one embodiment, the mammalian subject (e.g., human) is suffering from, or at risk for developing an alternative pathway disease or disorder. In one embodiment, the mammalian subject is suffering from, or for developing, a renal disease in which complement Factor D removal is impaired due to a decrease in kidney function.

In one embodiment, the mammalian subject (e.g., human) has been treated with a complement inhibitor, such an alternative pathway complement inhibitor, such as a MASP-3 inhibitory agent (e.g. a MASP-3 inhibitory antibody), as further described herein.

As described herein, the methods of detecting mature Factor D according to various embodiments of the present disclosure may be used to define a pharmacodynamic endpoint or therapeutic threshold of a complement inhibitor, such as an alternative pathway complement inhibitor, such as a MASP-3 inhibitory agent, (e.g., a MASP-3 inhibitory antibody).

Although the details of an immunoassay may vary with the particular format employed, the method of detecting mature Factor D in a test sample comprises the steps of contacting the test sample with an antibody that specifically binds to mature Factor D. The antibody is allowed to bind to mature Factor D in the sample under immunologically reactive conditions, and the presence of the bound antibody is detected directly or indirectly. The mature Factor D-specific antibodies may be used, for example, as the capture antibody of an ELISA, or as a second antibody to bind to mature Factor D captured by the capture antibody. As is known in the art, the presence of the second antibody is typically then detected. In some embodiments, the immunoassay is performed on a solid support. In some embodiments, the immunoassay is an ELISA assay.

B. Pro-Factor D Assays

In accordance with the foregoing, in another aspect, the present invention provides a method of detecting the presence or amount of Pro-Factor D in a test sample, the method comprising (a) contacting a test sample with a Pro-Factor D-specific antibody or antigen-binding fragment thereof in an in vitro immunoassay and (b) detecting the presence or absence of binding of said antibody, wherein the presence of binding indicates the presence of Pro-Factor D in the sample. In one embodiment, the Pro-Factor D-specific antibody or fragment thereof specifically binds to an epitope in the activation ("Pro") peptide of human Factor D "APPRGR" (SEQ ID NO:4), wherein the antibody or fragment thereof specifically binds human Pro-Factor D (SEQ ID NO:2) and does not bind to human mature-Factor D (SEQ ID NO:3).

In one embodiment, the Pro-Factor D-specific antibody or fragment thereof that specifically binds to human Pro-Factor D comprises a binding domain comprising HC-CDR1, HC-CDR2 and HC-CDR3 of a heavy chain variable region selected from the group consisting of SEQ ID NO:s 136-141 and comprising LC-CDR1, LC-CDR2 and LC-CDR3 in a light chain variable region selected from the group consisting of SEQ ID NO:s 142-147 wherein the CDRs are numbered according to the Kabat numbering system. In one embodiment, the Pro-Factor D-specific antibody or antigen-binding fragment thereof comprises a binding domain comprising HC-CDR1, HC-CDR2 and HC-CDR3 in a heavy chain variable region selected from the group consisting of SEQ ID NO:s 136-139 and comprising LC-CDR1, LC-CDR2 and LC-CDR3 in a light chain variable region selected from the group consisting of SEQ ID NO:s 142-145, wherein the CDRs are numbered according to the Kabat numbering system. In one embodiment, the Pro-Factor D-specific antibody or fragment thereof comprises a binding domain comprising HC-CDR1, HC-CDR2 and HC-CDR3 in a heavy chain variable region selected from the group consisting of SEQ ID NO: 140 and SEQ ID NO:141 and comprising LC-CDR-1, LC-CDR2 and LC-CDR3 in a light chain variable region selected from the group consisting of SEQ ID NO: 146 and SEQ ID NO:147 wherein the CDRs are numbered according to the Kabat numbering system.

In one embodiment, the Pro-Factor D-specific antibody or antigen-binding fragment thereof comprises a binding domain comprising the following six CDRs: (a) a CDR-H1 comprising SEQ ID NO:167, (b) a CDR-H2 comprising SEQ ID NO:169 or SEQ ID NO:173; (c) a CDR-H3 comprising SEQ ID NO:171 or SEQ ID NO:174; (d) a CDR-L1 comprising SEQ ID NO: 194, (e) a CDR-L2 comprising SEQ ID NO: 196 or SEQ ID NO: 199 and (f) a CDR-L3 comprising SEQ ID NO: 198 or SEQ ID NO:200.

In some embodiments, the Pro-Factor D-specific antibody or fragment thereof is a monoclonal antibody comprising the CDRs from Pro-Factor D-specific clones 18F5, 1F9, 2A4, 20A1, 13A10 and 21H1 as set forth in TABLE 4.

In one embodiment, the method further comprises comparing the amount of Pro-Factor D detected in accordance with step (b) with a reference standard or control sample to determine the level of Pro-Factor D in the test sample.

In one embodiment, the control sample is an individual or pooled sample of subjects suffering from an alternative pathway disease or disorder (e.g., paroxysmal nocturnal hemoglobinuria (PNH), C3 glomerulopathy, or other alternative pathway disease or disorder). In one embodiment, the control sample is an individual or pooled sample of normal healthy volunteers. In one embodiment, the control sample is a baseline sample of a subject prior to treatment with a complement inhibitor (e.g., a MASP-3 inhibitory agent or other complement inhibitor). In one embodiment, the reference standard is a ratio of at least one of: Pro-Factor D versus mature Factor D or Pro-Factor D versus total Factor D, wherein the ratio is obtained from a test sample or a control sample (e.g., an individual or pooled sample of normal healthy volunteers, or a baseline sample of a subject prior to treatment with a complement inhibitor, or an individual or pooled sample of subject(s) suffering from an alternative pathway disease or disorder).

In one embodiment, the anti-human Pro-Factor D-specific antibody or antigen-binding fragment thereof is immobilized on a substrate. In one embodiment, the immunoassay is an ELISA assay.

In one embodiment, the anti-human Pro-Factor D-specific antibody is labeled with a detectable moiety and step (b) comprises detecting the presence of said detectable moiety. In one embodiment, the anti-human Pro-Factor D-specific antibody or antigen-binding fragment thereof is naked (i.e., not labeled), and the presence or amount of the antibody or fragment thereof bound to Pro-Factor D is detected using a labeled antibody which binds to the anti-human Pro-Factor D antibody. In one embodiment, said anti-human Pro-Factor D-specific antibody or antigen-binding fragment thereof is immobilized on a substrate (i.e., capture/coating) and the bound Pro-Factor D is detected with a second antibody that binds to a different epitope of Factor D (e.g., an anti-Factor D antibody that binds to an epitope shared by mature Factor D and Pro-Factor D as described herein).

In one embodiment, the test sample is a biological sample obtained from a mammalian subject. In various embodiments, the biological sample is selected from the group consisting of whole blood, serum, plasma, sputum, amniotic fluid, cerebrospinal fluid, cell lysate, ascites, urine, saliva, and tissue. In one embodiment, the biological sample is selected from the group consisting of blood, serum, plasma, urine, and cerebrospinal fluid.

In one embodiment, the mammalian subject (e.g., human) is suffering from, or at risk for developing an alternative pathway disease or disorder. In one embodiment, the mammalian subject is suffering from, or for developing, a renal disease in which complement Factor D removal is impaired due to a decrease in kidney function.

In one embodiment, the mammalian subject (e.g., human) has been treated with a complement inhibitor, such an alternative pathway complement inhibitor, such as a MASP-3 inhibitory agent (e.g. a MASP-3 inhibitory antibody), as further described herein.

As described herein, the methods of detecting Pro-Factor D according to various embodiments of the present disclosure may be used to define a pharmacodynamic endpoint or therapeutic threshold of a complement inhibitor, such as an alternative pathway complement inhibitor, such as a MASP-3 inhibitory agent, (e.g., a MASP-3 inhibitory antibody). In one embodiment, the mammalian subject (e.g., human) has been treated with a MASP-3 inhibitory agent such as a MASP-3 inhibitory antibody as further described herein.

Although the details of an immunoassay may vary with the particular format employed, the method of detecting Pro-Factor D in a test sample comprises the steps of contacting the test sample with an antibody that specifically binds to Pro-Factor D. The antibody is allowed to bind to Pro-Factor D in the sample under immunologically reactive conditions, and the presence of the bound antibody is detected directly or indirectly. The Pro-Factor D-specific antibodies may be used, for example, as the capture antibody of an ELISA, or as a second antibody to bind to Pro-Factor D captured by the capture antibody. As is known in the art, the presence of the second antibody is typically then detected. In some embodiments, the immunoassay is performed on a solid support. In some embodiments, the immunoassay is an ELISA assay.

VII. Methods of Diagnosis, Monitoring and Treatment a Subject Suffering from, or at Risk for Developing an Alternative Pathway Disease or Disorder The inventive anti-Factor D antibodies, methods, reagents, and kits may be used in a number of applications. For example, in certain embodiments, an assay of this invention may be used to assess the level of mature Factor D and/or Pro-Factor D in a subject and/or to assess the extent to which a complement pathway inhibitor, such as an alternative pathway complement inhibitor, such as a MASP-3 inhibitory agent (e.g., a MASP-3 inhibitory antibody) affects the level of mature Factor D and/or Pro-Factor D in a biological sample obtained from the subject and thereby assess the extent of APC activation in said subject. In some embodiments, an assay of this invention may be used to assess the extent to which a complement pathway inhibitor (e.g., a MASP-3 inhibitory agent) decreases alternative complement pathway activation in vivo or in vitro. In some embodiments, an inventive method is performed on a biological sample obtained from a subject. In some embodiments, the level of mature Factor D and/or Pro-Factor D detected in an assay of this invention is compared with a suitable reference value. The reference value may be, e.g., a value measured from a sample obtained from a healthy patient (or a pool of healthy patients), or a value measured from a sample obtained from a patient undergoing treatment with a MASP-3 inhibitory agent (e.g., obtained prior to treatment or at a time point in a sequence of treatments), or the reference value may be a predetermined threshold. In one embodiment, the control sample is an individual or pooled sample of subjects suffering from an alternative pathway disease or disorder (e.g., paroxysmal nocturnal hemoglobinuria (PNH), C3 glomerulopathy, or other alternative pathway disease or disorder). In one embodiment, the control sample is an individual or pooled sample of normal healthy volunteers. In one embodiment, the control sample is a baseline sample of a subject prior to treatment with a complement inhibitor (e.g., a MASP-3 inhibitory agent or other complement inhibitor). In one embodiment, the reference standard is a ratio of at least one of: Pro-Factor D versus mature Factor D, mature Factor D versus total Factor D, or Pro-Factor D versus total Factor D, wherein the ratio is obtained from a test sample or a control sample (e.g., an individual or pooled sample of normal healthy volunteers, or a baseline sample of a subject prior to treatment with a complement inhibitor, or an individual or pooled sample of subject(s) suffering from an alternative pathway disease or disorder).

As described herein, the methods of detecting mature Factor D and/or Pro-Factor D according to various embodiments of the present disclosure may be used assess the extent of alternative pathway complement activation and thereby used to define a pharmacodynamic endpoint or therapeutic threshold of a complement inhibitor, such as an alternative pathway complement inhibitor, such as a MASP-3 inhibitory agent, (e.g., a MASP-3 inhibitory antibody).

A. Methods of Assessing the Extent of Alternative Pathway Complement Activation in a Mammalian Subject In one aspect, the present disclosure provides methods of assessing the extent of alternative pathway complement (APC) activation in a test sample and performing an immunoassay comprising capturing and detecting mature Factor D in the test sample and/or capturing and detecting pro-Factor D in the test sample, wherein the level of mature Factor D and/or the level of Pro-Factor D detected in the test sample is indicative of the extent of alternative pathway complement activation in the test sample. In one embodiment, the test sample is a biological sample obtained from a mammalian subject and the method comprises the steps of: (a) providing a biological sample obtained from the mammalian subject; and (b) assessing the extent of APC activation in the subject by performing an immunoassay comprising at least one of capturing and detecting mature Factor D in the biological sample; and/or capturing and detecting Pro-Factor D in the biological sample according to an inventive methods described herein. For example, in one embodiment, the immunoassay comprises capturing and detecting mature Factor D in the test sample, wherein mature Factor D is either captured or detected with a mature Factor D-specific monoclonal antibody or fragment thereof that specifically binds to an epitope in "ILGGREA" (SEQ ID NO:5) present in mature Factor D, but does not bind to Pro-Factor D. In one embodiment, the immunoassay comprises capturing and detecting Pro-Factor D in the test sample, wherein Pro-Factor D is either captured or detected with a Pro-Factor D-specific monoclonal antibody or fragment thereof that specifically binds to an epitope on the activation ("Pro") peptide "APPRGR" (SEQ ID NO:4) present in Pro-Factor D, but does not bind to mature Factor D. In various embodiments, the method comprises comparing the level of mature Factor D detected in the test sample (e.g., biological sample) with a predetermined level or control sample and/or comparing the level of Pro-Factor D detected in the test sample with a predetermined level or control sample, wherein the level of mature Factor D and/or Pro-Factor D detected in the test sample is indicative of the extent of alternative pathway complement activation in the test sample (e.g., biological sample). In some embodiments, the method further comprises using the result of the comparative analysis to provide diagnostic, prognostic or treatment-related information regarding the mammalian subject from which the biological sample was obtained. In some embodiments, the present disclosure provides a method of assessing the effect on alternative pathway complement activation in vivo of an inhibitor of human complement. Any compound which binds to or otherwise blocks the generation and/or activity of any of the human complement components may be utilized in accordance with the present disclosure. For example, an inhibitor of complement can be, e.g., a small molecule, a nucleic acid or nucleic acid analog, a peptidomimetic, or a macromolecule that is not a nucleic acid or a protein, such as an antibody, or fragment thereof. In some embodiments, the present disclosure provides a method of assessing the effect on alternative complement pathway activation in vivo of an inhibitor (e.g., an antibody or small molecule) specific to a human complement component, such as, for example an inhibitor of a complement component selected from the group consisting of C1 (C1q, C1r, C1s), C2, C3, C4, C5, C6, C7, C8, C9, Factor D, Factor B. Factor P, MBL, MASP-1, MASP-2, and MASP-3. In some embodiments, the present disclosure provides a method of assessing the effect of an alternative complement pathway inhibitor on alternative pathway complement activation. In some embodiments, the present disclosure provides a method of assessing the effect of an inhibitor of Pro-Factor D maturation on alternative pathway complement activation.

In some embodiments, the present disclosure provides a method of assessing the effect on alternative pathway complement activation in vivo of a MASP-3 inhibitory agent that has been administered to a mammalian subject. In various embodiments, a MASP-3 inhibitory agent (e.g., a MASP-3 inhibitory antibody) is administered to a mammalian subject, and a biological sample is subsequently obtained. The extent of alternative pathway complement (APC) activation in the biological sample is then assessed by performing an immunoassay comprising at least one of capturing and detecting mature Factor D in the biological sample; and/or capturing and detecting Pro-Factor D in the biological sample according to an inventive methods described herein.

B. Methods of Monitoring the Efficacy of a MASP-3 Inhibitory Antibody in a Mammalian Subject In one embodiment, the present disclosure provides a method for monitoring the efficacy of treatment with a MASP-3 inhibitory antibody in a mammalian subject, the method comprising the steps of (a) administering a dose of a MASP-3 inhibitory antibody to a mammalian subject at a first point in time; (b) assessing a first concentration of mature Factor D and/or Pro-Factor D in a biological sample obtained from the subject after step (a); (c) treating the subject with the MASP-3 inhibitory antibody at a second point in time; (d) assessing a second concentration of mature Factor D and/or Pro-Factor D in a biological sample obtained from the subject after step (c); and (e) comparing the level of mature Factor D and/or Pro-Factor D assessed in step (b) with the level of mature Factor D and/or Pro-Factor D assessed in step (d) to determine the efficacy of the MASP-3 inhibitory antibody in the mammalian subject. In one embodiment, the extent of APC activation in the subject is assessed in an immunoassay, wherein the immunoassay comprises capturing and detecting the level of mature Factor D in the biological sample. Optionally the level of mature Factor D detected in the biological sample is compared with a suitable reference value. The reference value may be, e.g., a value of mature Factor D measured from a biological sample obtained from the subject prior to administration of the MASP-3 inhibitory antibody, an average value measured from samples obtained from a group of healthy control subjects, a value that represents a desired extent of APC activation (e.g., a level of mature Factor D corresponding to 90% inhibition of APC, or 80% inhibition, or 70% inhibition, or 60% inhibition, or 50% inhibition of APC). For example, a first biological sample is obtained from a subject before administration of a MASP-3 inhibitory antibody and a second biological sample is obtained after administration of the MASP-3 inhibitory antibody and the level of mature Factor D is measured in the samples. If the level of mature Factor D in the second biological sample is less than the level of mature Factor D in the first biological sample, or is lower than a control value (e.g. a threshold value corresponding to a percent inhibition of APC), it can be concluded that the MASP-3 inhibitory antibody inhibited APC activation to a desired extent. Alternatively, if the level of mature Factor D in the second biological sample is higher than the level of mature Factor D in the first biological sample, or is higher than a control value (e.g., a threshold value corresponding to a percent inhibition of APC), it can be concluded that the dosage of the MASP-3 inhibitory antibody should be increased, and optionally, the method further comprises administering an increased dosage of the MASP-3 inhibitory antibody to the subject. In some embodiments, if the subject is administered an increased dose of the MASP-3 inhibitory antibody, steps (b) to (e) are repeated to determine whether the increased dose of the MASP-3 inhibitory antibody is sufficient to adjust the level of mature Factor D to the desired level as compared to the respective control or reference standard.

In another embodiment, the extent of APC activation in the mammalian subject is assessed in an immunoassay, wherein the immunoassay comprises capturing and detecting the level of Pro-Factor D in the biological sample. Optionally, the level of Pro-Factor D detected in the biological sample is compared with a suitable reference value. The reference value may be, e.g., a value of Pro-Factor D measured from a biological sample obtained from the subject prior to administration of the MASP-3 inhibitory antibody, an average value measured from samples obtained from a group of healthy control subjects, a value that represents a desired extent of APC activation (e.g., a level of Pro-Factor D corresponding to 90% inhibition of APC, or 80% inhibition, or 70% inhibition, or 60% inhibition, or 50% inhibition of APC). For example, a first biological sample is obtained from a subject before administration of a MASP-3 inhibitory antibody and a second biological sample is obtained after administration of the MASP-3 inhibitory antibody and the level of Pro-Factor D are measured in the samples. If the level of Pro-Factor D in the second biological sample is greater than the level of Pro-Factor D in the first biological sample, or is higher than a control value (e.g., a threshold value corresponding to a percent inhibition of APC), it can be concluded that the MASP-3 inhibitory antibody inhibited APC activation to a desired extent. Alternatively, if the level of Pro-Factor D in the second biological sample is lower than the level of Pro-Factor D in the first biological sample, or is lower than a control value (e.g., a threshold value corresponding to a percent inhibition of APC), it can be concluded that the dosage of the MASP-3 inhibitory antibody should be increased, and optionally, the method further comprises administering an increased dosage of the MASP-3 inhibitory antibody to the subject. In some embodiments, if the subject is administered an increased dose of the MASP-3 inhibitory antibody, steps (b) to (e) are repeated to determine whether the increased dose of the MASP-3 inhibitory antibody is sufficient to adjust the level of Pro-Factor D to the desired level as compared to the respective control or reference standard.

In some embodiments, the methods are used to monitor the efficacy of a MASP-3 inhibitory antibody that is administered to a human subject suffering from or at risk of developing an alternative pathway disease or disorder, such as wherein the alternative pathway disease or disorder is selected from the group consisting of paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenia purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

C. Methods of Treating a Mammalian Subject Suffering from, or at Risk of Developing an Alternative Pathway Disease or Disorder In another aspect, the present disclosure provides a method of treating a mammalian subject suffering from, or at risk of developing an alternative-pathway disease or disorder, comprising administering a MASP-3 inhibitory antibody to the subject if the subject is determined to have: (i) a lower or decreased level of Pro-Factor D in one or more samples taken from the subject compared to a predetermined Pro-Factor D level or compared to the Pro-Factor D level in one or more control samples; and/or (ii) a higher or increased level of mature Factor D in one or more samples taken from the subject compared to a predetermined mature Factor D level or compared to the mature Factor D level in one or more control samples. In one embodiment, the level of mature Factor D in one or more samples taken from the subject is determined by performing an immunoassay comprising the use of a mature Factor D-specific monoclonal antibody. In one embodiment, the level of mature Pro-Factor D in one or more samples taken from the subject is determined by performing an immunoassay comprising the use of a Pro-Factor D-specific monoclonal antibody.

In some embodiments, the methods are used to treat a human subject suffering from or at risk of developing an alternative pathway disease or disorder, such as wherein the alternative pathway disease or disorder is selected from the group consisting of paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopeniarpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

VIII. MASP-3 Inhibitory Agents

The human MASP-3 polypeptide (SEQ ID NO:7, from Genbank AAK84071.1) has 728 amino acid residues, which includes a leader peptide of 19 residues. As noted above, it has been demonstrated that MASP-3 is responsible for the conversion of complement Factor D from the zymogen form of the protein (i.e., Pro-Factor D) to the mature form (i.e., mature Factor D), thus placing the MASP-3 protein at a key upstream regulatory step for the alternative pathway. Accordingly, in the practice of various aspects and embodiments of the present disclosure, representative MASP-3 inhibitory agents include an agent that binds to or directly interacts with MASP-3 set forth as SEQ ID NO:7, including anti-MASP-3 antibodies and MASP-3 binding fragments thereof, small-molecules and expression inhibitors that inhibit alternative pathway complement activation. In preferred embodiments, the MASP-3 inhibitory agent is specific to MASP-3, and does not bind to MASP-1 or MASP-2. An example of a MASP-3 inhibitory agent is a MASP-3 specific inhibitory agent, such as a MASP-3 inhibitory agent that specifically binds to a portion of human MASP-3 (SEQ ID NO:7) with a binding affinity of at least 10 times greater than to other components in the complement system. In one embodiment, the MASP-3 inhibitory agent is a high affinity MASP-3 antibody that specifically binds to the serine protease domain of human MASP-3 (SEQ ID NO:7), with an affinity of less than 500 pM. In a preferred embodiment, a MASP-3 inhibitory agent, such as an antibody or antigen-binding fragment thereof or antigen binding peptide inhibits MASP-3-mediated maturation of factor D. MASP-3 inhibitory agents useful in the method of the invention may reduce MASP-3-dependent alternative pathway complement activation by greater than 10%, such as greater than 20%, greater than 50%, or greater than 90%. In one embodiment, the MASP-3 inhibitory agent reduces MASP-3-dependent alternative pathway complement activation by greater than 90% (i.e., resulting in MASP-3 complement activation of only 10% or less).

In one embodiment, the MASP-3 inhibitory agent useful in the methods of the invention is an isolated monoclonal antibody or antigen-binding fragment thereof that specifically binds to the serine protease domain of human MASP-3 (amino acid residues 450 to 728 of SEQ ID NO:7) with high affinity (having a $K_D$ of less than 500 pM), wherein the antibody or antigen-binding fragment thereof inhibits alternative pathway complement activation. For example, as described in WO2018/026722, hereby incorporated herein by reference, and as further described in Example 10 and TABLES 18-20 herein, numerous high affinity anti-MASP-3 inhibitory antibodies have been generated that bind the serine protease domain of MASP-3 and inhibit its catalytic activity. As further described in WO2018/026722, several representative MASP-3 inhibitory antibodies (e.g., 4D5, 10D12 and 13B1) were humanized. Representative humanized MASP-3 inhibitory antibodies are described below.

Accordingly, in one embodiment, a MASP-3 inhibitory agent for use in the compositions and methods of the claimed invention comprises a monoclonal antibody that binds a polypeptide consisting of human MASP-3 (SEQ ID NO:7), wherein the monoclonal antibody, or antigen-binding fragment thereof binds to MASP-3 and comprises: at least one of:

(i) a heavy chain variable region comprising a HC-CDR1 comprising SEQ ID NO:229 (TDDIN), a HC-CDR2 comprising SEQ ID NO:232 (WIYPRDDRTKYNDKFKD), a HC-CDR3 comprising SEQ ID NO:236 (LEDTY); and a light chain variable region comprising a LC-CDR1 comprising SEQ ID NO:239 (KSSQSLLASRTRKNYLA), a LC-CDR2 comprising SEQ ID NO:178 (WASTRES) and a LC-CDR3 comprising SEQ ID NO:242 (KQSYNLYT);

(ii) a heavy chain variable region comprising a HC-CDR1 comprising SEQ ID NO:230 (SYGMS), a HC-CDR2 comprising SEQ ID NO:233 (WINTYSGVPTYADDFKG) and a HC-CDR3 comprising SEQ ID NO:237 (GGEAMDY); and a light chain variable region comprising a LC-CDR1 comprising SEQ ID NO:240 (KSSQSLLDSDAKTYLN), a LC-CDR2 comprising SEQ ID NO:241 (LVSKLDS) and a LC-CDR3 comprising SEQ ID NO:243 (WQGTHFPWT); or (iii) a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT);

In one embodiment, the MASP-3 monoclonal antibody comprises a heavy chain variable region comprising at least 80%, 85%, 90%, 95%, 98%, 99% or 100% identical to at least one of SEQ ID NO:220, SEQ ID NO:222, SEQ ID NO:223, SEQ ID NO:225, SEQ ID NO:226, or SEQ ID NO:228 and a light chain variable region comprising at least 80%, 85%, 90%, 95%, 98%, 99% or 100% identical to at least one of SEQ ID NO:221, SEQ ID NO:224 or SEQ ID NO:227. In one embodiment, the MASP-3 monoclonal antibody comprises a heavy chain comprising at least 95% identical to SEQ ID NO:220 or SEQ ID NO:222 and a light chain comprising at least 95% identical to SEQ ID NO:221. In one embodiment, the MASP-3 monoclonal antibody comprises a heavy chain comprising at least 95% identical to SEQ ID NO:223 or SEQ ID NO:225 and a light chain comprising at least 95% identical to SEQ ID NO:224. In one embodiment, the MASP-3 monoclonal antibody comprises a heavy chain comprising at least 95% identical to SEQ ID NO:226 or SEQ ID NO:228 and a light chain comprising at least 95% identical to SEQ ID NO:227.

XIV. Pharmaceutical Compositions and Articles of Manufacture

In another aspect, the present disclosure provides a pharmaceutical composition comprising a MASP-3 inhibitory antibody in an aqueous solution comprising a buffer system having a pH of 6.0±5%, 20±5% mM histidine, 100±5% mg/mL sucrose, and 0.035%±5%, polysorbate 80, wherein said MASP-3 inhibitory antibody is included at a concentration of 110 mg/mL±5%, and wherein said MASP-3 inhibitory antibody comprises a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT). In one embodiment, the pharmaceutical composition is sterile. In one embodiment, the MASP-3 inhibitory antibody or antigen-binding fragment thereof comprises a heavy chain variable region comprising at least 80%, 85%, 90%, 95%, 98%, 99% or 100% identical to SEQ ID NO:226 or SEQ ID NO:227 and a light chain variable region comprising at least 80%, 85%, 90%, 95%, 98%, 99% or 100% identical to SEQ ID NO:227. In one embodiment, the MASP-3 inhibitory antibody or antigen binding fragment thereof is selected from the group consisting of a human antibody, a humanized antibody, a chimeric antibody, a murine antibody, and an antigen-binding fragment of any of the foregoing. In one embodiment, the MASP-3 inhibitory antibody or antigen-binding fragment thereof is selected from the group consisting of a single chain antibody, an ScFv, a Fab fragment, an Fab' fragment, an F(ab')2 fragment, a univalent antibody lacking a hinge region and a whole antibody. In one embodiment, the MASP-3 inhibitory antibody further comprises an immunoglobulin constant region. In one embodiment, the MASP-3 inhibitory antibody comprises a human IgG4 constant region. In one embodiment, the MASP-3 inhibitory antibody comprises a human IgG4 constant region with an S228P mutation. In one embodiment, the MASP-3 inhibitory antibody comprises a mutation that promotes FcRn interations at low pH, such as, for example, wherein the MASP-3 inhibitory antibody comprises human IgG4 constant region set forth as SEQ ID NO:245.

In one aspect, the present disclosure provides an article of manufacture containing a pharmaceutical composition comprising a MASP-3 inhibitory antibody in a unit dosage form suitable for therapeutic administration to a human subject, such as a unit dosage in the range of from 10 mg to 1000 mg (such as from 50 mg to 800 mg, or from 75 mg to 500, such as from 100 mg to 300 mg, such as 125 to 275 mg, such as 150 to 200 mg, such as 150±5% mg, 155±5% mg, 160±5% mg, 165±5% mg, 170±5% mg, 175±5% mg, 180±5% mg, 185±5% mg or 190±5% mg) of MASP-3 inhibitory antibody, wherein said MASP-3 inhibitory antibody comprises a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT).

In some embodiments, the article of manufacture comprises a container and a label or package insert on or associated with the container. Suitable containers include, for example, bottles, ampoules, pouches (e.g. an intravenous infusion bag), vials, syringes, cartridges, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is the MASP-3 inhibitory antibody or antigen binding fragment thereof of the invention. The label or package insert indicates that the composition is used for treating the particular condition. The label or package insert will further comprise instructions for administering the antibody composition to the patient.

In some embodiments, the pharmaceutical compositions and the articles of manufacture described herein are for use in the treatment of a subject suffering from, or at risk of developing an alternative pathway disease or disorder. In some embodiments, the alternative pathway disease or disorder is from the group consisting of paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenia purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

EXEMPLARY EMBODIMENTS

A. Mature Factor D-Specific mAbs:

1. An isolated antibody, or antigen-binding fragment thereof, that specifically binds to an epitope in the N-terminal region of human mature Factor D, wherein the epitope comprises or consists of the amino acids ILGGREA (SEQ ID NO:5).

2. The isolated antibody or antigen-binding fragment thereof of paragraph 1, wherein the antibody specifically binds human mature Factor D (SEQ ID NO:3) and does not bind to human Pro-Factor D (SEQ ID NO:2).

3. The isolated antibody or antigen-binding fragment thereof of paragraph 1 or paragraph 2, wherein the antibody is a monoclonal antibody.

4. The isolated antibody or antigen-binding fragment thereof of any of paragraphs 1 to 3, wherein said antibody is a humanized, chimeric, or fully human antibody.

5. The isolated antibody or antigen-binding fragment thereof of any of paragraphs 1 to 4, wherein said antigen-binding fragment selected from the group consisting of Fv, Fab, Fab', F(ab)2 and F(ab')2.

6. The isolated antibody or antigen-binding fragment thereof of any of paragraphs 1 to 4, wherein said antibody is a single chain molecule.

7. The isolated antibody or antigen-binding fragment thereof of any of paragraphs 1 to 4, wherein said antibody is an IgG molecule selected from the group consisting of IgG1, IgG2 and IgG4.

8. The isolated antibody or antigen-binding fragment thereof of any of paragraphs 1 to 7, wherein said antibody or antigen-binding fragment thereof binds to human mature Factor D with a $K_D$ of less than 10 nM.

9. The isolated antibody or antigen-binding fragment thereof of any of paragraphs 1 to 8, wherein, said antibody or antigen-binding fragment thereof is labeled with a detectable moiety.

10. The isolated antibody or antigen-binding fragment thereof of any of paragraphs 1 to 9, wherein said antibody or antigen-binding fragment thereof is immobilized on a substrate.

11. The isolated antibody or antigen-binding fragment thereof of any of paragraphs 1 to 10, wherein the isolated antibody or antigen-binding fragment thereof that specifically binds to human mature Factor D comprises a binding domain comprising HC-CDR1, HC-CDR2 and HC-CDR3 in a heavy chain variable region selected from the group consisting of SEQ ID NO:s 12-17 and comprising LC-CDR1, LC-CDR2 and LC-CDR3 in a light chain variable region selected from the group consisting of SEQ ID NO:s 18-23, wherein the CDRs are numbered according to the Kabat numbering system.

12. The isolated antibody or antigen-binding fragment thereof of any of paragraphs 1 to 10, wherein the antibody or antigen-binding fragment thereof that specifically binds to human mature Factor D comprises a binding domain comprising the following six CDRs: a) an HC-CDR1 comprising the amino acid sequence XSXMGVS (SEQ ID NO:65), wherein X at position 1 is T, I or S and X at position 3 is G or I; (b) an HC-CDR2 comprising the amino acid sequence HIYWDDEKHYXPSLKX (SEQ ID NO:66), wherein X at position 11 is H or N and X at position 16 is S or R; (c) an HC-CDR3 comprising the amino acid sequence RYYGYXXXMXY (SEQ ID NO:67), wherein X at position 6 is R, G or N, X at position 7 is S or Y, X at position 8 is F, I or V, and X at position 10 is D or H; (d) a LC-CDR1 comprising the amino acid sequence RSXXSIXHSNGN-TYXE (SEQ ID NO:68), wherein: X at position 3 is N or S, X at position 4 is Q or E, X at position 7 is V or L, and X at position 15 is F or L; (e) a LC-CDR2 comprising the amino acid sequence KVXNRFS (SEQ ID NO:69), wherein: X at position 3 is S or Y; and (f) a LC-CDR3 comprising the amino acid sequence FQGSHVPPT (SEQ ID NO:54).

13. The isolated antibody or antigen-binding fragment thereof of paragraph 12, wherein the binding domain comprises the following six CDRs: (a) an HC-CDR-1 comprising SEQ ID NO:25, (b) an HC-CDR2 comprising SEQ ID NO:27; (c) an HC-CDR3 comprising SEQ ID NO: 29; (d) a LC-CDR1 comprising SEQ ID NO:50, (e) a LC-CDR2 comprising SEQ ID NO:52 and (f) a LC-CDR3 comprising SEQ ID NO:54.

14. The isolated antibody or antigen-binding fragment thereof of paragraph 13, wherein the isolated antibody or fragment thereof comprises at least one of:
(a) a VH domain having at least 95% sequence identity to the amino acid sequence of SEQ ID NO: 12 or SEQ ID NO:13;
(b) a VL domain having at least 95% sequence identity to the amino acid sequence of SEQ ID NO:18 or SEQ ID NO:19;
(c). a VH comprising SEQ ID NO: 12 and a VL comprising SEQ ID NO:18; and/or
(d) a VH domain comprising SEQ ID NO:13 and a VL domain comprising SEQ ID NO:19.

15. The isolated antibody or antigen-binding fragment thereof of paragraph 12, wherein the binding domain comprises the following six CDRs: (a) an HC-CDR1 comprising SEQ ID NO:33, (b) an HC-CDR2 comprising SEQ ID NO:34; (c) an HC-CDR3 comprising SEQ ID NO: 36; (d) a LC-CDR1 comprising SEQ ID NO:58, (e) a LC-CDR2 comprising SEQ ID NO:52 and (f) a LC-CDR3 comprising SEQ ID NO:54.

16. The isolated antibody or antigen-binding fragment thereof of paragraph 15, wherein the isolated antibody or antigen-binding fragment thereof comprises at least one of:
(a) a VH domain having at least 95% sequence identity to the amino acid sequence of SEQ ID NO:14;
(b) a VL domain having at least 95% sequence identity to the amino acid sequence of SEQ ID NO:20; and/or
(c) a VH domain comprising SEQ ID NO:14 and a VL domain comprising SEQ ID NO:20.

17. The isolated antibody or antigen-binding fragment thereof of paragraph 12, wherein the binding domain comprises the following six CDRs: (a) aHC-CDR1 comprising SEQ ID NO:38, (b) an HC-CDR2 comprising SEQ ID NO:39; (c) an HC-CDR3 comprising SEQ ID NO: 41; (d) a LC-CDR1 comprising SEQ ID NO:60, (e) a LC-CDR2 comprising SEQ ID NO:52 and (f) a LC-CDR3 comprising SEQ ID NO:54.

18. The isolated antibody or antigen-binding fragment thereof of paragraph 17, wherein the isolated antibody or antigen-binding fragment thereof comprises at least one of:
(a) a VH domain having at least 95% sequence identity to the amino acid sequence of SEQ ID NO:15;
(b) a VL domain having at least 95% sequence identity to the amino acid sequence of SEQ ID NO:21; and/or
(c) a VH domain comprising SEQ ID NO:15 and a VL domain comprising SEQ ID NO:21.

19. The isolated antibody or antigen-binding fragment thereof of paragraph 12, wherein the binding domain comprises the following six CDRs: (a) an HC-CDR1 comprising SEQ ID NO:43, (b) an HC-CDR2 comprising SEQ ID NO:39; (c) an HC-CDR3 comprising SEQ ID NO: 41; (d) a LC-CDR1 comprising SEQ ID NO:62, (e) a LC-CDR22 comprising SEQ ID NO:52 and (f) a LC-CDR3 comprising SEQ ID NO:54.

20. The isolated antibody or antigen-binding fragment thereof of paragraph 19, wherein the isolated antibody or antigen-binding fragment thereof comprises at least one of:
(a) a VH domain having at least 95% sequence identity to the amino acid sequence of SEQ ID NO:16;
(b) a VL domain having at least 95% sequence identity to the amino acid sequence of SEQ ID NO:22; and/or
(c) a VH domain comprising SEQ ID NO:16 and a VL comprising SEQ ID NO:22.

21. The isolated antibody or antigen-binding fragment thereof of paragraph 12, wherein the binding domain comprises the following six CDRs: (a) an HC-CDR1 comprising SEQ ID NO:43, (b) an HC-CDR2 comprising SEQ ID NO:39; (c) an HC-CDR3 comprising SEQ ID NO: 47; (d) a LC-CDR1 comprising SEQ ID NO:63, (e) a LC-CDR2 comprising SEQ ID NO:64 and (f) a LC-CDR3 comprising SEQ ID NO:54.

22. The isolated antibody or antigen-binding fragment thereof of paragraph 21, wherein the isolated antibody or antigen-binding fragment thereof comprises at least one of:
(a) a VH domain having at least 95% sequence identity to the amino acid sequence of SEQ ID NO:17;
(b) a VL domain having at least 95% sequence identity to the amino acid sequence of SEQ ID NO:23; and/or
(c) a VH domain comprising SEQ ID NO:17 and a VL domain comprising SEQ ID NO:23.

23. A nucleic acid molecule encoding the amino acid sequence of an antibody, or antigen-binding fragment thereof, that specifically binds human mature Factor D as set forth in any of paragraphs 11 to 22.

24. An expression cassette comprising a nucleic acid molecule encoding an antibody, or antigen-binding fragment thereof, that specifically binds human mature Factor D of the invention according to paragraph 23.

25. A cell comprising at least one of the nucleic acid molecules encoding an antibody, or antigen-binding fragment thereof, that specifically binds human mature Factor D of the invention according to paragraph 23 or paragraph 24.

26. A method of generating an isolated antibody, or antigen-binding fragment thereof, that specifically binds human mature Factor D comprising culturing the cell of paragraph 25 under conditions allowing for expression of the nucleic acid molecules encoding the antibody, or antigen-binding fragment thereof, that specifically binds human mature Factor D and isolating said anti-mature-Factor-D specific antibody, or antigen-binding fragment thereof.

27. A composition comprising an antibody, or antigen-binding fragment thereof, that specifically binds human mature Factor D as set forth in any of paragraphs 1 to 22.

28. A substrate for use in an immunoassay comprising at least one antibody, or antigen-binding fragment thereof, that specifically binds human mature Factor D as set forth in any of paragraphs 1 to 22

29. A kit for detecting the presence or amount of mature Factor D in a test sample, said kit comprising (a) at least one container, and (b) at least one antibody, or antigen-binding fragment thereof, that specifically binds human mature Factor D as set forth in any of paragraphs 1 to 22.

B. Pro-Factor D-Specific mAbs:

1. An isolated antibody, or antigen-binding fragment thereof, that specifically binds to an epitope on the activation ("Pro") peptide of human Factor D, wherein the epitope comprises or consists of "APPRGR" (SEQ ID NO:4).

2. The antibody or antigen-binding fragment of paragraph 1, wherein the antibody or antigen-binding fragment thereof specifically binds to human Pro-Factor D (SEQ ID NO:2) and does not bind to mature Factor D (SEQ ID NO:3).

3. The isolated antibody or antigen-binding fragment thereof of paragraph 1 or paragraph 2, wherein the antibody is a monoclonal antibody.

4. The isolated antibody or antigen-binding fragment thereof of any of paragraphs 1 to 3, wherein said antibody is a humanized, chimeric, or fully human antibody.

5. The isolated antibody or antigen-binding fragment thereof of any of paragraphs 1 to 4, wherein said antigen-binding fragment is selected from the group consisting of Fv, Fab, Fab', F(ab)$_2$ and F(ab')$_2$.

6. The isolated antibody or antigen-binding fragment thereof of any of paragraphs 1 to 4, wherein said antibody is a single chain molecule.

7. The isolated antibody or antigen-binding fragment thereof of any of paragraphs 1 to 4, wherein said antibody is an IgG molecule selected from the group consisting of IgG1, IgG2 and IgG4.

8. The isolated antibody or antigen-binding fragment thereof of any of paragraphs 1 to 7, wherein said antibody or antigen-binding fragment thereof binds to human Pro-Factor D with a K$_D$ of less than 10 nM.

9. The isolated antibody or antigen-binding fragment thereof of any of paragraphs 1 to 8, wherein said antibody or antigen-binding fragment thereof is labeled with a detectable moiety.

10. The isolated antibody or antigen-binding fragment thereof of any of paragraphs 1 to 9, wherein said antibody or antigen-binding fragment thereof is immobilized on a substrate.

11. The isolated antibody or antigen-binding fragment thereof that specifically binds to human Pro-Factor D of any of paragraphs 1 to 10, wherein the antibody or antigen-binding fragment thereof comprises a binding domain comprising HC-CDR1, HC-CDR2 and HC-CDR3 of a heavy chain variable region selected from the group consisting of SEQ ID NO:s 136-141 and comprising LC-CDR1, LC-CDR2 and LC-CDR3 in a light chain variable region selected from the group consisting of SEQ ID NO:s 142-147, wherein the CDRs are numbered according to the Kabat numbering system.

12. The isolated antibody or antigen-binding fragment thereof of paragraph 11, wherein the isolated antibody or antigen-binding fragment thereof comprises a binding domain comprising HC-CDR1, HC-CDR2 and HC-CDR3 in a heavy chain variable region selected from the group consisting of SEQ ID NO:s 136-139 and comprising LC-CDR1, LC-CDR2 and LC-CDR3 in a light chain variable region selected from the group consisting of SEQ ID NO:s 142-145.

13. The isolated antibody or antigen-binding fragment thereof of paragraph 12, wherein the isolated antibody or antigen-binding fragment thereof comprises a binding domain comprising the following six CDRs: (a) an HC-CDR1 comprising the amino acid sequence XYWMS (SEQ ID NO:201), wherein X at position 1 is N, S or T; (b) an HC-CDR2 comprising the amino acid sequence EIRLKSXNYAXXYXESVKG (SEQ ID NO:202), wherein: X at position 7 is D or E, X at position 11 is T or A, X at position 12 is H or Y and X at position 14 is A or T; (c) an HC-CDR3 comprising the amino acid sequence AWFAX (SEQ ID NO:203), wherein X at position 5 is S, Y or N; (d) a LC-CDR1 comprising the amino acid sequence XSSQXL-LYSXDQKNYLA (SEQ ID NO:204), wherein X at position 1 is M or K, X at position 5 is S or N, and X at position 10 is K or R; (e) a LC-CDR2 comprising the amino acid sequence WASTRES (SEQ ID NO:178); and (f) a LC-CDR3 comprising the amino acid sequence LQYYXYPYT (SEQ ID NO:205), wherein X at position 5 is T or S.

14. The isolated antibody or antigen-binding fragment thereof of paragraph 13, wherein the isolated antibody or antigen-binding fragment thereof comprises a binding domain comprising the following six CDRs: (a) an HC-CDR1 comprising SEQ ID NO:149 or SEQ ID NO:155, (b) a HC-CDR2 comprising SEQ ID NO:151 or SEQ ID NO:156; (c) an HC-CDR3 comprising SEQ ID NO:153; (d) a LC-CDR1 comprising SEQ ID NO:176, (e) a LC-CDR2 comprising SEQ ID NO:178 and (f) a LC-CDR3 comprising SEQ ID NO:180.

15. The isolated antibody or antigen-binding fragment thereof of paragraph 14, wherein the isolated antibody or antigen-binding fragment thereof comprises at least one of:
(a) a VH domain having at least 95% sequence identity to the amino acid sequence of SEQ ID NO:136;
(b) a VH domain having at least 95% sequence identity to the amino acid sequence of SEQ ID NO:137;
(c) a VL domain having at least 95% sequence identity to the amino acid sequence of SEQ ID NO:142;
(d) a VL domain having at least 95% sequence identity to the amino acid sequence of SEQ ID NO:143;
(e) a VH domain comprising SEQ ID NO:136 and a VL domain comprising SEQ ID NO:142; and/or (f) a VH domain comprising SEQ ID NO:137 and a VL domain comprising SEQ ID NO:143.

16. The isolated antibody or antigen-binding fragment thereof of paragraph 13, wherein the isolated antibody or antigen-binding fragment thereof comprises a binding domain comprising the following six CDRs: (a) an HC-CDR1 comprising SEQ ID NO:158, (b) an HC-CDR2 comprising SEQ ID NO:159 or SEQ ID NO:163; (c) an HC-CDR3 comprising SEQ ID NO:161 or SEQ ID NO:165; (d) a LC-CDR-1 comprising SEQ ID NO:184 or SEQ ID NO:189, (e) a LC-CDR2 comprising SEQ ID NO:178 and (f) a LC-CDR3 comprising SEQ ID NO: 187.

17. The isolated antibody or antigen-binding fragment thereof of paragraph 16, wherein the isolated antibody or antigen-binding fragment thereof comprises at least one of:
(a) a VH domain having at least 95% sequence identity to the amino acid sequence of SEQ ID NO:138; (b) a VH domain having at least 95% sequence identity to the amino acid sequence of SEQ ID NO:139;
(c) a VL domain having at least 95% sequence identity to the amino acid sequence of SEQ ID NO:144;
(d) a VL domain having at least 95% sequence identity to the amino acid sequence of SEQ ID NO:145;
(e) a VH domain comprising SEQ ID NO:138 and a VL domain comprising SEQ ID NO:144; and/or
(f) a VH domain comprising SEQ ID NO:139 and a VL domain comprising SEQ ID NO:145.

18. The isolated antibody or antigen-binding fragment thereof of paragraph 11, wherein the isolated antibody or antigen-binding fragment thereof comprises a binding domain comprising HC-CDR1, HC-CDR2 and HC-CDR3 in a heavy chain variable region selected from the group consisting of SEQ ID NO: 140 and SEQ ID NO:141 and comprising LC-CDR1, LC-CDR2 and LC-CDR3 in a light chain variable region selected from the group consisting of SEQ ID NO: 146 and SEQ ID NO:147.

19. The isolated antibody or antigen-binding fragment thereof of paragraph 18, wherein the isolated antibody or antigen-binding fragment thereof comprises a binding domain comprising the following six CDRs: (a) a CDR-H1 comprising SEQ ID NO:167, (b) a CDR-H2 comprising SEQ ID NO:169 or SEQ ID NO:173; (c) a CDR-H3 comprising SEQ ID NO:171 or SEQ ID NO:174; (d) a CDR-L1 comprising SEQ ID NO:194, (e) a CDR-L2 comprising SEQ ID NO:196 or SEQ ID NO:199 and (f) a CDR-L3 comprising SEQ ID NO:198 or SEQ ID NO:200.

20. The isolated antibody or antigen-binding fragment thereof of paragraph 19, wherein the isolated antibody or antigen-binding fragment thereof comprises at least one of:
(a) a VH domain having at least 95% sequence identity to the amino acid sequence of SEQ ID NO:140;
(b) a VH domain having at least 95% sequence identity to the amino acid sequence of SEQ ID NO:141;
(c) a VL domain having at least 95% sequence identity to the amino acid sequence of SEQ ID NO:146;
(d) a VL domain having at least 95% sequence identity to the amino acid sequence of SEQ ID NO:147;
(e) a VH domain comprising SEQ ID NO:140 and a VL domain comprising SEQ ID NO:146; and/or
(f) a VH domain comprising SEQ ID NO:141 and a VL domain comprising SEQ ID NO:147.

21. A nucleic acid molecule encoding the amino acid sequence of an antibody, or antigen-binding fragment thereof, that specifically binds human Pro-Factor D as set forth in any of paragraphs 11 to 20.

22. An expression cassette comprising a nucleic acid molecule encoding an antibody, or antigen-binding fragment thereof, that specifically binds human Pro-Factor D according to paragraph 21.

23. A cell comprising at least one of the nucleic acid molecules encoding an antibody, or antigen-binding fragment thereof, that specifically binds human Pro-Factor D according to paragraph 21 or paragraph 22.

24. A method of generating an isolated antibody, or antigen-binding fragment thereof, that specifically binds human Pro-Factor D comprising culturing the cell of paragraph 23 under conditions allowing for expression of the nucleic acid molecules encoding the antibody, or antigen-binding fragment thereof, that specifically binds human Pro-Factor D and isolating said anti-Pro-Factor-D specific antibody, or antigen-binding fragment thereof.

25. A composition comprising an antibody, or antigen-binding fragment thereof, that specifically binds human Pro-Factor D as set forth in any of paragraphs 1 to 20.

26. A substrate for use in an immunoassay comprising at least one antibody, or antigen-binding fragment thereof, that specifically binds human Pro-Factor D as set forth in any of paragraphs 1 to 20.

27. A kit for detecting the presence or amount of Pro-Factor D in a test sample, said kit comprising (a) at least one container, and (b) at least one antibody, or antigen-binding fragment thereof, that specifically binds human mature Factor D as set forth in any of paragraphs 1 to 20.

C. Anti-Factor D mAbs (Detect Pro and Mature Factor D Via Binding to a Shared Epitope)

1. An isolated antibody or antigen-binding fragment thereof that binds to an epitope shared by both human mature Factor D and human Pro-Factor D, wherein the antibody or antigen-binding fragment thereof comprises a binding domain comprising HC-CDR1, HC-CDR2 and HC-CDR3 in a heavy chain variable region selected from the group consisting of SEQ ID NO:s 85-88 and comprising LC-CDR1, LC-CDR2 and LC-CDR3 in a light chain variable region selected from the group consisting of SEQ ID NO:s 89-93, wherein the CDRs are numbered according to the Kabat numbering system.

2. The isolated antibody or antigen-binding fragment thereof of paragraph 1, wherein the antibody is a monoclonal antibody.

3. The isolated antibody or antigen-binding fragment thereof of any of paragraphs 1 to 2, wherein said antibody is a humanized, chimeric, or fully human antibody.

4. The isolated antibody or antigen-binding fragment thereof of any of paragraphs 1 to 3, wherein said antigen-binding fragment is selected from the group consisting of Fv, Fab, Fab', F(ab)2 and F(ab')2.

5. The isolated antibody or antigen-binding fragment thereof of any of paragraphs 1 to 4, wherein said antibody or antigen-binding fragment is a single chain molecule.

6. The isolated antibody or antigen-binding fragment thereof of any of paragraphs 1 to 4, wherein said antibody is an IgG molecule selected from the group consisting of IgG1, IgG2 and IgG4.

7. The isolated antibody or antigen-binding fragment thereof of any of paragraphs 1 to 7, wherein said antibody or antigen-binding fragment thereof binds to human Factor D with a $K_D$ of less than 10 nM.

8. The isolated antibody or antigen-binding fragment thereof of any of paragraphs 1 to 7, wherein, said antibody or antigen-binding fragment thereof is labeled with a detectable moiety.

9. The isolated antibody or antigen-binding fragment thereof of any of paragraphs 1 to 8, wherein said antibody or antigen-binding fragment thereof is immobilized on a substrate.

10. The isolated antibody or antigen-binding fragment thereof that specifically binds to human Pro Factor D of any of paragraphs 1 to 9, wherein the antibody or antigen-binding fragment thereof comprises a binding domain comprising HC-CDR1, HC-CDR2 and HC-CDR3 of a heavy chain variable region selected from the group consisting of SEQ ID NO:s 136-141 and comprising LC-CDR1, LC-CDR2 and LC-CDR3 in a light chain variable region selected from the group consisting of SEQ ID NO:s 142-147, wherein the CDRs are numbered according to the Kabat numbering system.

11. The isolated antibody or antigen-binding fragment thereof of any of paragraphs 1 to 10, wherein the antibody or antigen-binding fragment thereof comprises a binding domain comprising the following six CDRs: (a) an HC-CDR1 comprising the amino acid sequence SEQ ID NO:95, (b) a HC-CDR2 comprising the amino acid sequence SEQ ID NO:97 (c) an HC-CDR3 comprising the amino acid sequence SEQ ID NO:99 (d) a LC-CDR1 comprising the amino acid sequence SEQ ID NO:111; (e) a LC-CDR2 comprising the amino acid sequence SEQ ID NO:113); and (f) a LC-CDR3 comprising the amino acid sequence SEQ ID NO:115.

12. The isolated antibody or antigen-binding fragment thereof of any of paragraphs 1 to 10, wherein the antibody or antigen-binding fragment thereof comprises a binding domain comprising the following six CDRs: (a) an HC-CDR1 comprising the amino acid sequence SEQ ID NO:101 (b) an HC-CDR2 comprising the amino acid sequence SEQ ID NO:103 or 107 (c) an HC-CDR3 comprising the amino acid sequence SEQ ID NO:105 or 108, (d) a LC-CDR1 comprising the amino acid sequence SEQ ID NO:60 or 123; (e) a LC-CDR2 comprising the amino acid sequence SEQ ID NO:119, 124 or 126 and (f) a LC-CDR3 comprising the amino acid sequence SEQ ID NO:121 or 125.

13. The isolated antibody or antigen-binding fragment thereof of paragraph 10, wherein the isolated antibody or antigen-binding fragment thereof comprises at least one of:
(a) a VH domain having at least 95% sequence identity to the amino acid sequence of SEQ ID NO:85;
(b) a VH domain having at least 95% sequence identity to the amino acid sequence of SEQ ID NO:86;
(c) a VH domain having at least 95% sequence identity to the amino acid sequence of SEQ ID NO:87;
(d) a VH domain having at least 95% sequence identity to the amino acid sequence of SEQ ID NO:88;
(e) a VL domain having at least 95% sequence identity to the amino acid sequence of SEQ ID NO:89;
(f) a VL domain having at least 95% sequence identity to the amino acid sequence of SEQ ID NO:90;
(g) a VL domain having at least 95% sequence identity to the amino acid sequence of SEQ ID NO:91;
(h) a VL domain having at least 95% sequence identity to the amino acid sequence of SEQ ID NO:92;
(i) a VL domain having at least 95% sequence identity to the amino acid sequence of SEQ ID NO:93;
(j) a VH domain comprising SEQ ID NO:85 and a VL domain comprising SEQ ID NO:89 or SEQ ID NO:90;
(k) a VH domain comprising SEQ ID NO:86 and a VL domain comprising SEQ ID NO:91;
(l) a VH domain comprising SEQ ID NO:87 and a VL domain comprising SEQ ID NO:92; and/or
(m) a VH domain comprising SEQ ID NO:88 and a VL domain comprising SEQ ID NO:93.

14. A nucleic acid molecule encoding the amino acid sequence of an antibody, or antigen-binding fragment thereof, that binds an epitope shared by both human mature Factor D and human Pro-Factor D as set forth in any of paragraphs 10 to 13.

15. An expression cassette comprising a nucleic acid molecule encoding an antibody, or antigen-binding fragment thereof, that binds an epitope shared by both human mature Factor D and human Pro-Factor D according to paragraph 14.

16. A cell comprising at least one of the nucleic acid molecules encoding an antibody, or antigen-binding fragment thereof, that binds an epitope shared by both human mature Factor D and human Pro-Factor D according to paragraph 14 or paragraph 15.

17. A method of generating an isolated antibody, or antigen-binding fragment thereof, that binds an epitope shared by both human mature Factor D and human Pro-Factor D comprising culturing the cell of paragraph 16 under conditions allowing for expression of the nucleic acid molecules encoding the antibody, or antigen-binding fragment thereof, that binds human Factor D and isolating said anti-Factor-D antibody, or antigen-binding fragment thereof.

18. A composition comprising an antibody, or antigen-binding fragment thereof, that specifically binds an epitope shared by both human mature Factor D and human Pro-Factor D as set forth in any of paragraphs 1 to 13.

19. A substrate for use in an immunoassay comprising at least one antibody, or antigen-binding fragment thereof, that binds an epitope shared by both human mature Factor D and human Pro-Factor D as set forth in any of paragraphs 1 to 13.

20. A kit for detecting the presence of Factor D in a biological sample, said kit comprising (a) at least one container, and (b) at least one antibody, or antigen-binding fragment thereof, that binds an epitope shared by both human mature Factor D and human Pro-Factor D as set forth in any of paragraphs 1 to 13.

D. Kits for Detecting Mature Factor D and/or Pro-Factor D in an Immunoassay

1. A kit comprising at least one monoclonal antibody or antigen-binding fragment thereof that specifically detects or quantitates human mature Factor D (SEQ ID NO:3) and/or Pro-Factor D (SEQ ID NO:2) in an immunoassay, wherein the at least one monoclonal antibody or antigen-binding fragment thereof comprises:
(i) a monoclonal antibody, or antigen-binding fragment thereof, that specifically binds to an epitope encompassing the amino-terminus of human mature Factor D, wherein the epitope comprises or consists of the amino acids ILGGREA (SEQ ID NO:5) and wherein said antibody does not bind to human Pro-Factor D (SEQ ID NO:2); or
(ii) a monoclonal antibody, or antigen-binding fragment thereof, that specifically binds to an epitope on the activation ("Pro") peptide of human Factor D, wherein the epitope comprises or consists of "APPRGR" (SEQ ID NO:4) and wherein said antibody does not bind to mature Factor D (SEQ ID NO:3).

2. The kit of paragraph 1, wherein the kit further comprises an antibody, or fragment thereof, that binds to an epitope shared by both human mature Factor D (SEQ ID NO:3) and human Pro-Factor D (SEQ ID NO:2).

3. The kit of paragraph 1 or 2, wherein the kit further comprises at least one container.

4. The kit of any of paragraphs 1-3, wherein the antibody or antigen-binding fragment thereof of paragraph 1 subpart (i) that specifically binds to human mature Factor D comprises a binding domain comprising HC-CDR-1, HC-CDR-2 and HC-CDR-3 in a heavy chain variable region selected from the group consisting of SEQ ID NO:s 12-17 and comprising LC-CDR-1, LC-CDR2 and LC-CDR3 in a light chain variable region selected from the group consisting of SEQ ID NO:s 18-23, wherein the CDRs are numbered according to the Kabat numbering system.

5. The kit of any of paragraphs 1-3, wherein the antibody or antigen-binding fragment thereof of paragraph 1 subpart (ii) that specifically binds to an epitope on the activation ("Pro") peptide of human Factor D comprises a binding domain comprising HC-CDR1, HC-CDR2 and HC-CDR3 of a heavy chain variable region selected from the group consisting of SEQ ID NO:s 136-141 and comprising LC-CDR1, LC-CDR2 and LC-CDR3 in a light chain variable region selected from the group consisting of SEQ ID NO:s 142-147, wherein the CDRs are numbered according to the Kabat numbering system.

6. The kit of any of paragraphs 1-5, wherein the immunoassay is an enzyme-linked immunosorbent assay (ELISA).

7. The kit of any of paragraphs 1-6, wherein the antibody or antigen-binding fragment thereof of paragraph 1 subpart (i) is a coating antibody.

8. The kit of any of paragraphs 1-6, wherein the antibody or antigen-binding fragment thereof of paragraph 1 subpart (i) is a detecting antibody.

9. The kit of any of paragraphs 1-6, wherein the antibody or antigen-binding fragment thereof of paragraph 1 subpart (ii) is a coating antibody.

10. The kit of any of paragraphs 1-6, wherein the antibody or antigen-binding fragment thereof of paragraph 1 subpart (ii) is a detecting antibody.

11. The kit of any of paragraphs 1-10, wherein the kit further comprises an anti-Factor D antibody, or antigen-binding fragment thereof, that binds to an epitope shared by both human mature Factor D (SEQ ID NO:3) and human Pro-Factor D (SEQ ID NO:2).

12. The kit of paragraph 11, wherein the anti-Factor D antibody or antigen-binding fragment thereof comprises a binding domain comprising HC-CDR1, HC-CDR2 and HC-CDR3 in a heavy chain variable region selected from the group consisting of SEQ ID NO:s 85-88 and comprising LC-CDR1, LC-CDR2 and LC-CDR3 in a light chain variable region selected from the group consisting of SEQ ID NO:s 89-93, wherein the CDRs are numbered according to the Kabat numbering system.

E. Assays for Detecting Mature Factor D

1. A method of determining the presence or amount of mature Factor D in a test sample, the method comprising:
   (a) contacting a test sample with an anti-human mature Factor D-specific monoclonal antibody or antigen-binding fragment thereof, in an in vitro immunoassay; and
   (b) detecting the presence or absence or amount of the antibody or antigen-binding fragment thereof bound to mature Factor D, wherein the presence of binding indicates the presence or amount of mature Factor D in the sample;
   wherein the anti-human mature Factor D-specific antibody or antigen-binding fragment thereof binds to an epitope in the N-terminal region of mature Factor D, set forth as amino acids ILGGREA (SEQ ID NO:5).

2. The method of paragraph 1, wherein the antibody or antigen-binding fragment thereof specifically binds human mature Factor D (SEQ ID NO:3) and does not bind to human Pro-Factor D (SEQ ID NO:2).

3. The method of any of paragraphs 1 or 2, wherein the anti-human mature Factor D-specific antibody or antigen-binding fragment thereof is immobilized on a substrate.

4. The method of any of paragraphs 1 to 3, wherein the immunoassay is an ELISA assay.

5. The method of any of paragraphs 1 to 4, wherein said anti-human mature Factor D-specific antibody or antigen-binding fragment thereof is labeled with a detectable moiety and step (b) comprises detecting the presence or amount of said detectable moiety.

6. The method of any of paragraphs 1 to 4, wherein said anti-human mature Factor D-specific antibody or antigen-binding fragment thereof is naked (i.e., not labeled), and the presence or amount of the antibody or antigen-binding fragment thereof bound to mature Factor D is detected using a labeled antibody which binds to the anti-mature Factor D antibody.

7. The method of any of paragraphs 1 to 4, wherein said anti-human mature Factor D-specific antibody or antigen-binding fragment thereof is immobilized on a substrate (i.e., capture/coating) and the bound mature Factor D is detected with a second antibody that binds to a different epitope of Factor D.

8. The method of any of paragraphs 1 to 7, wherein the test sample is a biological sample obtained from a mammalian subject, such as wherein the biological sample is selected from the group consisting of blood, serum, plasma, urine and cerebrospinal fluid.

9. The method of any of paragraphs 1 to 8, wherein the sample is obtained from a mammalian subject that is suffering from, or at risk for developing an Alternative Pathway related disease.

10. The method of any of paragraphs 1 to 9, wherein the sample is obtained from a mammalian subject after treatment with a complement inhibitory agent, such as an alternative complement pathway inhibitory agent, such as an inhibitor of pro-Factor D maturation, such as a MASP-3 inhibitory antibody.

11. The method of any of paragraphs 1 to 10, wherein the anti-human mature Factor D-specific antibody or antigen-binding fragment thereof comprises a binding domain comprising HC-CDR1, HC-CDR2 and HC-CDR3 in a heavy chain variable region selected from the group consisting of SEQ ID NO:s 12-17 and comprising LC-CDR1, LC-CDR2 and LC-CDR3 in a light chain variable region selected from the group consisting of SEQ ID NO:s 18-23.

12. The method of any of paragraphs 1 to 11, wherein the anti-human mature Factor D-specific antibody or antigen-binding fragment thereof comprises a binding domain comprising the following six CDRs: a) an HC-CDR1 comprising the amino acid sequence XSXMGVS (SEQ ID NO:65), wherein X at position 1 is T, I or S and X at position 3 is G or I; (b) an HC-CDR2 comprising the amino acid sequence HIYWDDEKHYXPSLKX (SEQ ID NO:66), wherein X at position 11 is H or N and X at position 16 is S or R; (c) an HC-CDR3 comprising the amino acid sequence RYYGYXXXMXY (SEQ ID NO:67), wherein X at position 6 is R, G or N, X at position 7 is S or Y, X at position 8 is F, I or V, and X at position 10 is D or H; (d) a LC-CDR1 comprising the amino acid sequence RSXXSIXHSNGN-TYXE (SEQ ID NO:68), wherein: X at position 3 is N or S, X at position 4 is Q or E, X at position 7 is V or L, and X at position 15 is F or L; (e) a LC-CDR2 comprising the amino acid sequence KVXNRFS (SEQ ID NO:69), wherein: X at position 3 is S or Y; and (f) a LC-CDR3 comprising the amino acid sequence FQGSHVPPT (SEQ ID NO:54).

13. The method of any of paragraphs 1 to 11, wherein the anti-human mature Factor D-specific antibody or antigen-binding fragment thereof comprises a binding domain comprising the following six CDRs: (a) an HC-CDR1 comprising SEQ ID NO:25, (b) an HC-CDR2 comprising SEQ ID NO:27; (c) an HC-CDR3 comprising SEQ ID NO: 29; (d) a LC-CDR1 comprising SEQ ID NO:50, (e) a LC-CDR2 comprising SEQ ID NO:52 and (f) a LC-CDR3 comprising SEQ ID NO:54.

F. Assays for Detecting Pro-Factor D

1. A method of determining the presence or amount of Pro-Factor D in a test sample, the method comprising:
   (a) contacting a test sample with an anti-human Pro-Factor D-specific monoclonal antibody or antigen-binding fragment thereof, in an in vitro immunoassay; and
   (b) detecting the presence or absence or amount of the antibody or antigen-binding fragment thereof bound to Pro-Factor D, wherein the presence of binding indicates the presence or amount of Pro-Factor D in the sample;
   wherein the anti-human mature Pro-Factor D-specific antibody or antigen-binding fragment thereof specifically binds to an epitope in the activation ("Pro") peptide of human Factor D, set forth as "APPRGR" (SEQ ID NO:4).

2. The method of paragraph 1, wherein the antibody or antigen-binding fragment thereof specifically binds human Pro-Factor D (SEQ ID NO:2) and does not bind to human mature Factor D (SEQ ID NO:3).

3. The method of any of paragraphs 1 or 2, wherein the anti-human Pro-Factor D-specific antibody or antigen-binding fragment thereof is immobilized on a substrate.

4. The method of any of paragraphs 1 to 3, wherein the immunoassay is an ELISA assay.

5. The method of any of paragraphs 1 to 4, wherein said anti-human Pro-Factor D-specific antibody or antigen-binding fragment thereof is labeled with a detectable moiety and step (b) comprises detecting the presence or amount of said detectable moiety.

6. The method of any of paragraphs 1 to 4, wherein said anti-human Pro-Factor D-specific antibody or antigen-binding fragment thereof is naked (i.e., not labeled), and the presence or amount of the antibody or antigen-binding fragment thereof bound to mature Factor D is detected using a labeled antibody which binds to the anti-Pro-Factor D antibody.

7. The method of any of paragraphs 1 to 4, wherein said anti-human Pro-Factor D-specific antibody or antigen-binding fragment thereof is immobilized on a substrate (i.e., capture/coating) and the bound Pro-Factor D is detected with a second antibody or antigen-binding fragment thereof that binds to a different epitope of Factor D.

8. The method of any of paragraphs 1 to 7, wherein the test sample is a biological sample obtained from a mammalian subject, such as wherein the biological sample is selected from the group consisting of blood, serum, plasma, urine and cerebrospinal fluid.

9. The method of any of paragraphs 1 to 8, wherein the sample is obtained from a mammalian subject that is suffering from, or at risk for developing an Alternative Pathway related disease.

10. The method of any of paragraphs 1 to 9, wherein the sample is obtained from a mammalian subject after treatment with a complement inhibitory agent, such as an alternative complement pathway inhibitory agent, such as an inhibitor of pro-Factor D maturation, such as a MASP-3 inhibitory antibody.

11. The method of any of paragraphs 1 to 10, wherein the anti-human Pro-Factor D-specific antibody or antigen-binding fragment thereof comprises a binding domain comprising HC-CDR-1, HC-CDR-2 and HC-CDR-3 of a heavy chain variable region selected from the group consisting of SEQ ID NO:s 136-141 and comprising LC-CDR-1, LC-CDR2 and LC-CDR3 in a light chain variable region selected from the group consisting of SEQ ID NO:s 142-147.

12. The method of any of paragraphs 1 to 11, wherein the anti-human Pro-Factor D-specific antibody or antigen-binding fragment thereof comprises a binding domain comprising HC-CDR-1, HC-CDR-2 and HC-CDR-3 in a heavy chain variable region selected from the group consisting of SEQ ID NO:s 136-139 and comprising LC-CDR-1, LC-CDR2 and LC-CDR3 in a light chain variable region selected from the group consisting of SEQ ID NO:s 142-145.

13. The method of any of paragraphs 1 to 11, wherein the anti-human Pro-Factor D-specific antibody or antigen-binding fragment thereof comprises a binding domain comprising HC-CDR-1, HC-CDR-2 and HC-CDR-3 in a heavy chain variable region selected from the group consisting of SEQ ID NO:140 and SEQ ID NO:141 and comprising LC-CDR-1, LC-CDR2 and LC-CDR3 in a light chain variable region selected from the group consisting of SEQ ID NO: 146 and SEQ ID NO: 147.

14. The method of any of paragraphs 1 to 11, wherein the anti-human Pro-Factor D-specific antibody or antigen-binding fragment thereof comprises a binding domain comprising the following six CDRs: (a) a CDR-H1 comprising SEQ ID NO:167, (b) a CDR-H2 comprising SEQ ID NO:169 or SEQ ID NO:173; (c) a CDR-H3 comprising SEQ ID NO:171 or SEQ ID NO:174; (d) a CDR-L1 comprising SEQ ID NO:194, (e) a CDR-L2 comprising SEQ ID NO:196 or SEQ ID NO:199 and (f) a CDR-L3 comprising SEQ ID NO:198 or SEQ ID NO:200.

G. Method of Assessing the Extent of Alternative Pathway Activation in a Test Sample 1. A method of assessing the extent of alternative pathway complement (APC) activation in a test sample comprising:
   (a) providing a test sample;
   (b) performing an immunoassay comprising at least one of:
      (i) capturing and detecting mature Factor D in the test sample, wherein mature Factor D is either captured or detected with a monoclonal antibody or antigen-binding fragment thereof that specifically binds to an epitope in "ILGGREA" (SEQ ID NO:5) present in mature Factor D, but does not bind to Pro-Factor D; and/or
      (ii) capturing and detecting Pro-Factor D in the test sample, wherein Pro-Factor D is either captured or detected with a monoclonal antibody or antigen-binding fragment thereof that specifically binds to an epitope on the activation ("Pro") peptide "APPRGR" (SEQ ID NO:4) present in Pro-Factor D, but does not bind to mature Factor D; and
   (c) comparing the level of mature Factor D detected in accordance with (b)(i) with a predetermined level or control sample and/or comparing the level of Pro-Factor D detected in accordance with (b(ii) with a predetermined level or control sample, wherein the level of mature Factor D and/or Pro-Factor D detected in the test sample is indicative of the extent of Alternative Pathway Complement activation.

2. The method of paragraph 1, wherein step (b)(i) comprises capturing mature Factor D with a monoclonal antibody or antigen-binding fragment thereof that specifically binds to an epitope in "ILGGREA" (SEQ ID NO:5) present in mature Factor D, but does not bind to Pro-Factor D and detecting with an antibody or antigen-binding fragment thereof that binds to an epitope shared by both human mature Factor D and human Pro-Factor D.

3. The method of paragraph 1, wherein step (b)(i) comprises capturing mature Factor D with an antibody or antigen-binding fragment thereof that binds to an epitope shared by both human mature Factor D and human Pro-Factor D and detecting with a monoclonal antibody or antigen-binding fragment thereof that specifically binds to an epitope in "ILGGREA" (SEQ ID NO:5) present in mature Factor D, but does not bind to Pro-Factor D.

4. The method of paragraph 1, wherein step (b)(ii) comprises capturing Pro-Factor D with a monoclonal antibody or antigen-binding fragment thereof that specifically binds to an epitope on the activation ("Pro") peptide "APPRGR" (SEQ ID NO:4) present in Pro-Factor D, but does not bind to mature Factor D and detecting with an antibody or antigen-binding fragment thereof that binds to an epitope shared by both human mature Factor D and human Pro-Factor D.

5. The method of paragraph 1, wherein step (b)(ii) comprises capturing Pro-Factor D with an antibody or antigen-binding fragment thereof that binds to an epitope shared by both human mature Factor D and human Pro-Factor D and detecting with a monoclonal antibody or antigen-binding fragment thereof that specifically binds to an epitope on the activation ("Pro") peptide "APPRGR" (SEQ ID NO:4) present in Pro-Factor D, but does not bind to mature Factor D.

6. The method of paragraph 1, wherein the monoclonal antibody or antigen-binding fragment thereof that specifically binds to an epitope in "ILGGREA" (SEQ ID NO:5) present in mature Factor D, but does not bind to Pro-Factor D comprises a binding domain comprising HC-CDR1, HC-CDR2 and HC-CDR3 in a heavy chain variable region selected from the group consisting of SEQ ID NO:s 12-17 and comprising LC-CDR1, LC-CDR2 and LC-CDR3 in a light chain variable region selected from the group consisting of SEQ ID NO:s 18-23.

7. The method of paragraph 1, wherein the monoclonal antibody or antigen-binding fragment thereof that specifically binds to an epitope on the activation ("Pro") peptide "APPRGR" (SEQ ID NO:4) present in Pro-Factor D, but does not bind to mature Factor D comprises a binding domain comprising HC-CDR1, HC-CDR2 and HC-CDR3 of a heavy chain variable region selected from the group consisting of SEQ ID NO:s 136-141 and comprising LC-CDR1, LC-CDR2 and LC-CDR3 in a light chain variable region selected from the group consisting of SEQ ID NO:s 142-147, wherein the CDRs are numbered according to the Kabat numbering system.

8. The method of any of paragraphs 1-7, wherein the test sample is a biological sample obtained from a mammalian subject.

9. The method of paragraph 8, wherein the biological sample comprises whole blood, serum, plasma, urine, or cerebrospinal fluid.

10. The method of any of paragraphs 1-9, wherein the test sample comprises a complement inhibitory agent, such as an alternative complement pathway inhibitory agent, such as an inhibitor of pro-Factor D maturation, such as a MASP-3 inhibitory agent (e.g., a MASP-3 inhibitory antibody or an antigen-binding fragment thereof).

11. The method of paragraph 8, wherein the mammalian subject has been treated with a complement inhibitory agent, such as an alternative complement pathway inhibitory agent, such as an inhibitor of pro-Factor D maturation, such as a MASP-3 inhibitory agent (e.g., a MASP-3 inhibitory antibody or an antigen-binding fragment thereof).

12. The method of paragraph 8, wherein the mammalian subject is a human subject.

13 The method of paragraph 12, wherein the human subject is suffering from, or at risk of developing, or suspected of having an alternative-pathway disease or disorder.

14. The method of paragraph 13, wherein the alternative-pathway disease or disorder is selected from the group consisting of: paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenia purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

15. The method of any of paragraphs 11-14, wherein the control sample is a sample taken from the subject prior to treatment with the MASP-3 inhibitory agent, or a sample taken at an earlier point in time during a course of treatment with the MASP-3 inhibitory agent.

16. The method of any of paragraphs 11-15, wherein the MASP-3 inhibitory agent is a MASP-3 inhibitory antibody or antigen-binding fragment thereof.

17. The method of paragraph 16, wherein the MASP-3 inhibitory antibody or antigen-binding fragment thereof is a monoclonal antibody, or antigen-binding fragment thereof, that binds to MASP-3 and comprises at least one of:
(i) a binding domain comprising HC-CDR1, HC-CDR2 and HC-CDR3 of a heavy chain variable region selected from the group consisting of SEQ ID NO:s 220, 222, 223, 225, 226 and 228 and comprising LC-CDR1, LC-CDR2 and LC-CDR3 of a light chain variable region selected from the group consisting of SEQ ID NO:s 221, 224 and 227, wherein the CDRs are numbered according to the Kabat numbering system;
(ii) a heavy chain variable region comprising a HC-CDR1 comprising SEQ ID NO:229 (TDDIN), a HC-CDR2 comprising SEQ ID NO:232 (WIYPRDDRT-KYNDKFKD), a HC-CDR3 comprising SEQ ID NO:236 (LEDTY); and a light chain variable region comprising a LC-CDR1 comprising SEQ ID NO:239 (KSSQSLLASRTRKNYLA), a LC-CDR2 comprising SEQ ID NO:178 (WASTRES) and a LC-CDR3 comprising SEQ ID NO:242 (KQSYNLYT);

(iii) a heavy chain variable region comprising a HC-CDR1 comprising SEQ ID NO:230 (SYGMS), a HC-CDR2 comprising SEQ ID NO:233 (WINTYSGVP-TYADDFKG) and a HC-CDR3 comprising SEQ ID NO:237 (GGEAMDY); and a light chain variable region comprising a LC-CDR1 comprising SEQ ID NO:240 (KSSQSLLDSDAKTYLN), a LC-CDR2 comprising SEQ ID NO:241 (LVSKLDS) and a LC-CDR3 comprising SEQ ID NO:243 (WQGTHFPWT); or (iv) a heavy chain variable region comprising a HC-CDR1 comprising SEQ ID NO:231 (GKWIE); a HC-CDR2 comprising SEQ ID NO:234 (EILPGTG-STNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT).

H. Methods of Monitoring the Efficacy of Treatment with a MASP-3 Inhibitory Agent 1. A method for monitoring the efficacy of treatment with a MASP-3 inhibitory antibody in a mammalian subject, the method comprising:
   (a) administering a dose of a MASP-3 inhibitory antibody or antigen-binding fragment thereof to a mammalian subject at a first point in time;
   (b) assessing a first concentration of mature Factor D and/or Pro-Factor D in a biological sample obtained from the subject after step (a);
   (c) treating the subject with the MASP-3 inhibitory antibody or antigen-binding fragment thereof at a second point in time;
   (d) assessing a second concentration of mature Factor D and/or Pro-Factor D in a biological sample obtained from the subject after step (c); and
   (e) comparing the level of mature Factor D and/or Pro-Factor D assessed in step (b) with the level of mature Factor D and/or Pro-Factor D assessed in step (d) to determine the efficacy of the MASP-3 inhibitory antibody in the mammalian subject.

2. The method of paragraph 1, wherein the method further comprises adjusting the dose of the MASP-3 inhibitory antibody or antigen-binding fragment thereof.

3. The method of paragraph 2, wherein the dose of MASP-3 inhibitory antibody or antigen-binding fragment thereof administered to the subject is increased if the level of mature Factor D is higher than the control or reference standard.

4. The method of paragraph 2, wherein the dose of MASP-3 inhibitory antibody or antigen-binding fragment administered to the subject is increased if the level of Pro-Factor D is lower than the control or reference standard.

5. The method of paragraph 3 or 4, wherein if the subject is administered an increased dose of the MASP-3 inhibitory antibody or antigen-binding fragment thereof, steps (b) to (e) are repeated to determine whether the increased dose is sufficient to adjust the level of mature Factor D and/or Pro-Factor D to the desired level as compared to the respective control or reference standard.

6. The method of any of paragraphs 1-5, wherein steps (b) and (d) comprise assessing the concentration of mature Factor D in the biological samples in an immunoassay.

7. The method of paragraph 6, wherein the immunoassay comprises (i) a first monoclonal antibody or antigen-binding fragment thereof that specifically binds to an epitope in the N-terminal region of human mature Factor D, wherein the epitope comprises or consists of the amino acids ILGGREA (SEQ ID NO:5) and does not bind to human Pro-Factor D; and (ii) a second antibody or antigen-binding fragment thereof that binds to an epitope shared by both human mature Factor D and human Pro-Factor D, wherein the first and second antibody or antigen-binding fragments thereof function together in the immunoassay to specifically detect or quantitate the amount of mature Factor D protein (SEQ ID NO:3) and not Pro-Factor D protein (SEQ ID NO:2) that may be present in the biological sample.

8. The method of any of paragraphs 1-5, wherein steps (b) and (d) comprise assessing the concentration of Pro-Factor D in the biological samples in an immunoassay.

9. The method of paragraph 8, wherein the immunoassay comprises (i) a first monoclonal antibody or antigen-binding fragment thereof that specifically binds to an epitope in the pro peptide of human Factor D, wherein the epitope comprises or consists of the amino acids APPRGR (SEQ ID NO:4) and does not bind to human mature Factor D; and (ii) a second antibody or antigen-binding fragment thereof that binds to an epitope shared by both human mature Factor D and human Pro-Factor D, wherein the first and second antibody function together in the immunoassay to specifically detect or quantitate the amount of Pro-Factor D protein (SEQ ID NO:2) and not mature-Factor D protein (SEQ ID NO:3) that may be present in the biological sample.

10. The method of any of paragraphs 1-9, wherein the mammalian subject is a human subject.

11. The method of paragraph 10, wherein the human subject is suffering from, or at risk of developing an alternative pathway disease or disorder.

12. The method of paragraph 11, wherein the alternative pathway disease or disorder is selected from the group consisting of paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenia purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

13. The method of any of paragraphs 1-12 wherein the MASP-3 inhibitory antibody or antigen-binding fragment thereof is a monoclonal antibody or antigen-binding fragment thereof.

14. The method of paragraph 13, wherein the MASP-3 inhibitory antibody or antigen-binding fragment thereof is a monoclonal antibody, or antigen-binding fragment thereof binds to MASP-3 and comprises at least one of:
   (i) a binding domain comprising HC-CDR1, HC-CDR2 and HC-CDR3 of a heavy chain variable region selected from the group consisting of SEQ ID NO:s 220, 222, 223, 225, 226 and 228 and comprising LC-CDR1, LC-CDR2 and LC-CDR3 of a light chain variable region selected from the group consisting of SEQ ID NO:s 221, 224 and 227, wherein the CDRs are numbered according to the Kabat numbering system;
(ii) a heavy chain variable region comprising a HC-CDR1 comprising SEQ ID NO:229 (TDDIN), a HC-CDR2 comprising SEQ ID NO:232 (WIYPRDDRT-KYNDKFKD), a HC-CDR3 comprising SEQ ID NO:236 (LEDTY); and a light chain variable region comprising a LC-CDR1 comprising SEQ ID NO:239 (KSSQSLLASRTRKNYLA), a LC-CDR2 comprising SEQ ID NO:178 (WASTRES) and a LC-CDR3 comprising SEQ ID NO:242 (KQSYNLYT);
(iii) a heavy chain variable region comprising a HC-CDR1 comprising SEQ ID NO:230 (SYGMS), a HC-CDR2 comprising SEQ ID NO:233 (WINTYSGVP-TYADDFKG) and a HC-CDR3 comprising SEQ ID NO:237 (GGEAMDY); and a light chain variable region comprising a LC-CDR1 comprising SEQ ID NO:240 (KSSQSLLDSDAKTYLN), a LC-CDR2 comprising SEQ ID NO:241 (LVSKLDS) and a LC-CDR3 comprising SEQ ID NO:243 (WQGTHFPWT); or
(iv) a heavy chain variable region comprising a HC-CDR1 comprising SEQ ID NO:231 (GKWIE); a HC-CDR2 comprising SEQ ID NO:234 (EILPGTG-STNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT).

I. Methods of Treating a Mammalian Subject Suffering from or at Risk of Developing an Alternative Pathway Disease or Disorder 1. A method of treating a mammalian subject suffering from, or at risk of developing an alternative-pathway disease or disorder, comprising administering a MASP-3 inhibitory antibody or antigen-binding fragment thereof to the subject if the subject is determined to have:
(i) a lower or decreased level of Pro-Factor D in one or more samples taken from the subject compared to a predetermined Pro-Factor D level or compared to the Pro-Factor D level in one or more control samples; and/or
(ii) a higher or increased level of mature Factor D in one or more samples taken from the subject compared to a predetermined mature Factor D level or compared to the mature Factor D level in one or more control samples.

2. The method of paragraph 1, wherein the level of Pro-Factor D in one or more samples taken from the subject is determined by performing an immunoassay comprising the use of a Pro-Factor D-specific monoclonal antibody or antigen-binding fragment thereof.

3. The method of paragraph 2, wherein the immunoassay comprises (i) a first monoclonal antibody or antigen-binding fragment thereof that specifically binds to an epitope in the pro peptide of human Factor D, wherein the epitope comprises or consists of the amino acids APPRGR (SEQ ID NO:4) and does not bind to human mature Factor D; and (ii) a second antibody or antigen-binding fragment thereof that binds to an epitope shared by both human mature Factor D and human Pro-Factor D, wherein the first and second antibody or antigen-binding fragments thereof function together in the immunoassay to specifically detect or quantitate the amount of Pro-Factor D protein (SEQ ID NO:2) and not mature-Factor D protein (SEQ ID NO:3) that may be present in the sample.

4. The method of paragraph 1, wherein the level of mature Factor D in one or more samples taken from the subject is determined by performing an immunoassay comprising the use of a mature Factor D-specific monoclonal antibody or antigen-binding fragment thereof.

5. The method of paragraph 4, wherein the immunoassay comprises (i) a first monoclonal antibody or antigen-binding fragment thereof that specifically binds to an epitope in the N-terminal region of human mature Factor D, wherein the epitope comprises or consists of the amino acids ILGGREA (SEQ ID NO:5) and does not bind to human Pro-Factor D; and (ii) a second antibody or antigen-binding fragment thereof that binds to an epitope shared by both human mature Factor D and human Pro-Factor D, wherein the first and second antibody or antigen-binding fragments thereof function together in the immunoassay to specifically detect or quantitate the amount of mature Factor D protein (SEQ ID NO:3) and not Pro-Factor D protein (SEQ ID NO:2) that may be present in the sample.

6. The method of any of paragraphs 1-5, wherein the mammalian subject is a human subject.

7. The method of any of paragraphs 1-6, wherein the mammalian subject is suffering from, or at risk of developing an alternative pathway disease or disorder selected from the group consisting of paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenia purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

8. The method of any of paragraphs 1-7 wherein the MASP-3 inhibitory antibody or antigen-binding fragment thereof is a monoclonal antibody or antigen-binding fragment thereof.

9. The method of paragraph 8, wherein the MASP-3 inhibitory antibody or antigen-binding fragment thereof is a monoclonal antibody, or antigen-binding fragment thereof binds to MASP-3 and comprises at least one of:
(i) a binding domain comprising HC-CDR1, HC-CDR2 and HC-CDR3 of a heavy chain variable region selected from the group consisting of SEQ ID NO:s 220, 222, 223, 225, 226 and 228 and comprising LC-CDR1, LC-CDR2 and LC-CDR3 of a light chain variable region selected from the group consisting of SEQ ID NO:s 221, 224 and 227, wherein the CDRs are numbered according to the Kabat numbering system;
(ii) a heavy chain variable region comprising a HC-CDR1 comprising SEQ ID NO:229 (TDDIN), a HC-CDR2 comprising SEQ ID NO:232 (WIYPRDDRT- KYNDKFKD), a HC-CDR3 comprising SEQ ID NO:236 (LEDTY); and a light chain variable region comprising a LC-CDR1 comprising SEQ ID NO:239 (KSSQSLLASRTRKNYLA), a LC-CDR2 comprising SEQ ID NO:178 (WASTRES) and a LC-CDR3 comprising SEQ ID NO:242 (KQSYNLYT);

(iii) a heavy chain variable region comprising a HC-CDR1 comprising SEQ ID NO:230 (SYGMS), a HC-CDR2 comprising SEQ ID NO:233 (WINTYSGVPTYADDFKG) and a HC-CDR3 comprising SEQ ID NO:237 (GGEAMDY); and a light chain variable region comprising a LC-CDR1 comprising SEQ ID NO:240 (KSSQSLLDSDAKTYLN), a LC-CDR2 comprising SEQ ID NO:241 (LVSKLDS) and a LC-CDR3 comprising SEQ ID NO:243 (WQGTHFPWT); or (iv) a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT).

J. Pharmaceutical Compositions and Articles of Manufacture

1. A pharmaceutical composition comprising a MASP-3 inhibitory antibody or an antigen-binding fragment thereof in an aqueous solution comprising a buffer system having a pH of 6.0±5%, 20±5% mM histidine, 100±5% mg/mL sucrose, and 0.035%±5%, polysorbate 80 wherein said MASP-3 inhibitory antibody is included at a concentration of 110 mg/mL±5%, and wherein said MASP-3 inhibitory antibody or antigen-binding fragment thereof comprises a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT).

2. The pharmaceutical composition of paragraph 1, wherein the pharmaceutical composition is sterile.

3. The pharmaceutical composition of paragraph 1 or 2, wherein the MASP-3 inhibitory antibody or antigen-binding fragment thereof comprises a heavy chain variable region comprising at least 80%, 85%, 90%, 95%, 98%, 99% or 100% identical to SEQ ID NO:226 or SEQ ID NO:227 and a light chain variable region comprising at least 80%, 85%, 90%, 95%, 98%, 99% or 100% identical to SEQ ID NO:227.

4. The pharmaceutical composition of any of paragraphs 1 to 3, wherein the MASP-3 inhibitory antibody or antigen-binding fragment thereof is selected from the group consisting of a human antibody, a humanized antibody, a chimeric antibody, a murine antibody, and an antigen-binding fragment of any of the foregoing.

5. The pharmaceutical composition of any of paragraphs 1 to 3, wherein the MASP-3 inhibitory antibody or antigen-binding fragment thereof is selected from the group consisting of a single chain antibody, an ScFv, a Fab fragment, an Fab' fragment, an F(ab')2 fragment, a univalent antibody lacking a hinge region and a whole antibody.

6. The pharmaceutical composition of any of paragraphs 1 to 3, wherein the MASP-3 inhibitory antibody or antigen-binding fragment thereof further comprises an immunoglobulin constant region.

7. The pharmaceutical composition of paragraph 6, wherein the MASP-3 inhibitory antibody or antigen-binding fragment thereof comprises a human IgG4 constant region.

8. The pharmaceutical composition of paragraph 7, wherein the MASP-3 inhibitory antibody or antigen-binding fragment thereof comprises a human IgG4 constant region with an S228P mutation.

9. The pharmaceutical composition of paragraph 7 or 8, wherein the MASP-3 inhibitory antibody or antigen-binding fragment thereof comprises a mutation that promotes FcRn interactions at low pH.

10. The pharmaceutical composition of any of paragraphs 7-9, wherein the MASP-3 inhibitory antibody or antigen-binding fragment thereof comprises human IgG4 constant region set forth as SEQ ID NO:245.

11. An article of manufacture containing a pharmaceutical composition according to any of paragraphs 1-10.

12. The article of manufacture of paragraph 11, wherein the MASP-3 inhibitory antibody or antigen-binding fragment thereof is in a unit dosage form of from 10 mg to 1000 mg suitable for therapeutic administration to a human subject.

13. The article of manufacture of paragraph 10 or 11, wherein the article of manufacture comprises a container and a label or package insert on or associated with the container.

14. The article of manufacture of paragraph 13, wherein the container is selected from the group consisting of a bottle, an ampoule, a pouch (e.g. an intravenous infusion bag), a vial, a syringe, and a cartridge.

15. The pharmaceutical composition of any of paragraphs 1 to 10 or the article of manufacture of any of paragraphs 11 to 14, wherein the composition and/or article of manufacture is for use in the treatment of a subject suffering from, or at risk of developing an alternative pathway disease or disorder.

16. The pharmaceutical composition or article of manufacture of paragraph 15, wherein the alternative pathway disease or disorder is selected from the group consisting of paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenia purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis. The following examples merely illustrate the best mode now contemplated for practicing the invention, but should not be construed to limit the invention.

Example 1

This Example describes the generation of monoclonal antibodies that specifically bind to human mature Factor D.

BACKGROUND

This Example describes the generation of anti-human mature Factor D-specific antibodies suitable for use as detection reagents for use in assays to measuring the presence and/or amount of mature Factor D in a biological sample for use as a biomarker of APC status. The antibodies described in this Example specifically bind to human mature Factor D (SEQ ID NO: 3) and do not bind to human pro Factor D (SEQ ID NO:2).

Methods:

1. Expression of a Synthetic Mature Factor D Peptide Antigen

The amino acid sequences of human full-length Factor D (SEQ ID NO:1), human pro-Factor D (SEQ ID NO:2) and human mature Factor D (SEQ ID NO:3) are shown in FIG. 2. As shown in FIG. 2, the pro-peptide of human Pro-Factor D is "APPRGR" (SEQ ID NO:4). FIG. 3 provides an alignment of the amino acid sequences of complement Factor D (full-length) from various species including *Homo sapiens* (SEQ ID NO:1); *Macaca* (SEQ ID NO:8); *Canis* (SEQ ID NO:9); *Rattus* (SEQ ID NO:10); and Mus (SEQ ID NO:11). The italicized portion of each sequence depicts the signal sequence and the underlined portion depicts the activation "pro" peptide sequence. As shown in FIGS. 2 and 3, the Factor D protein comprises an activation peptide (Pro peptide, underlined). Once the pro peptide is cleaved, mature Factor D has a unique amino-terminus as compared to pro-Factor D in each species (e.g., having an N-terminus starting at residue 26 of human full-length Factor D (SEQ ID NO:1)).

In order to generate anti-human mature Factor D-specific antibodies, a synthetic peptide was generated corresponding to amino acid residues 26-32 of human complement factor D: "ILGGREA" (SEQ ID NO:5) as follows. A synthetic mature factor D peptide-KLH conjugate construct was generated by inserting the nucleic acid sequence encoding "ILGGREA" (SEQ ID NO:5) separated by a spacer amino acid sequence from the PADRE sequence, a spacer amino acid sequence and a C-terminal cysteine: "ILGGREAGPGPGAKFVAAAWTLKAAAKKC" (SEQ ID NO:6), allowing for conjugation to KLH by Sulfo-SMCC linkage chemistry.

2. Immunization with the mature Factor D antigen

C57BL6 mice were immunized with the synthetic mature factor D peptide-KLH conjugate (SEQ ID NO:6) described above. The mice were immunized three times, subcutaneously, with 50 µL of adjuvant-emulsions of peptide conjugate (50-100 µg total protein per injection).

Serum samples from the immunized mice were prepared from retro-orbital sinus bleeds and tested by ELISA for the presence of antigen-specific antibodies capable of binding to plate-immobilized recombinant human pro-factor D (hPro-CFD) (SEQ ID NO:2) and recombinant human mature Factor D (hCFD) (SEQ ID NO:3) as follows:

Recombinant human Pro-CFD-His or recombinant human mature CFD-His were immobilized on Maxisorp™ ELISA plates at 1 µg/mL in PBS, 100 µL/well and incubated overnight at 4° C. Plate wells were then washed three times with 300 µL PBS containing 0.05% Tween 20 (PBST), blocked for 1 hour at room temperature with 250 µL PBS containing 1% bovine serum albumen (BSA) and washed again. Serum from each mouse was diluted in PBST and allowed to bind for 1 hour at room temperature, then washed three times in PBST. A horseradish peroxidase (HRP)-labeled goat anti-mouse IgG Fc antibody (Jackson ImmunoResearch) was then applied (100 µL/well), allowed to bind for 1 hour at room temperature, and then washed three times with PBST. TMB substrate (ThermoFischer) (100 µL/well) was then applied and incubated for 5 minutes at room temperature. The reaction was then stopped with 1N $H_2SO_4$ (50 µL/well). The plate was read for optical density at 450 nM with a Biotek™ ELISA plate reader.

Results:

FIG. 4 graphically illustrates a titration of the serum of a representative mouse #2 after immunization with a synthetic peptide corresponding to amino acid residues 26-32 of human complement factor D "ILGGREA" (SEQ ID NO:5) in the presence of recombinant mature Factor D or recombinant pro-Factor D. As shown in FIG. 4, the serum from representative mouse #2 contains antibodies capable of selectively binding to mature Factor D as compared to pro-Factor D.

The mice showing the most favorable binding to mature Factor D and the least favorable binding to pro-Factor D (i.e., mouse #2) were selected for hybridoma fusion. Three days prior to the fusion, mice were treated subcutaneously with 50 µg of an anti-CD40 agonist mAb in PBS (R&D Systems, Minneapolis, MN) to increase B cells numbers (see Rycyzyn et al., *Hybridoma* 27:25-30, 2008). The mice were sacrificed, and the spleen cells were harvested and fused to a selected murine myeloma cell line P3/NSI/1-AG4-1 (NS-1) (ATCC No. TIB18) using 50% polyethylene glycol or 50% polyethylene glycol plus 10% DMSO. The fusions generated hybridoma cells which were plated in 96 well Nunc tissue culture treated plates containing HAT (hypoxanthine, aminopterin and thymidine) medium to inhibit proliferation of non-fused cells, myeloma hybrids and spleen hybrids. Hybridoma wells were fed by replacement of 80% of media with fresh medium containing HAT supplement. After hybridoma selection, the culture supernatants were assayed for binding to recombinant human mature factor D as described below.

3. Hybridoma Screening

Hybridoma supernatants were first screened for binding to immobilized recombinant human mature Factor D-His. 10 hybridomas were identified (n=10) which were then tested for their ability to detect recombinant human mature Factor D or recombinant human pro-Factor D when captured by a polyclonal goat anti-human factor D antibody AF1824 (R&D Systems) as follows. ELISA plates were coated with polyclonal anti-human factor D antibody AF1824 (R&D Systems). Hybridoma supernatants were diluted two-fold in PBS, 0.05% Tween 20 (PBST). Supernatant from NS-1 myeloma cell line (NS-1 sup) was included as a matrix control to determine the level of assay background.

Figure 5:
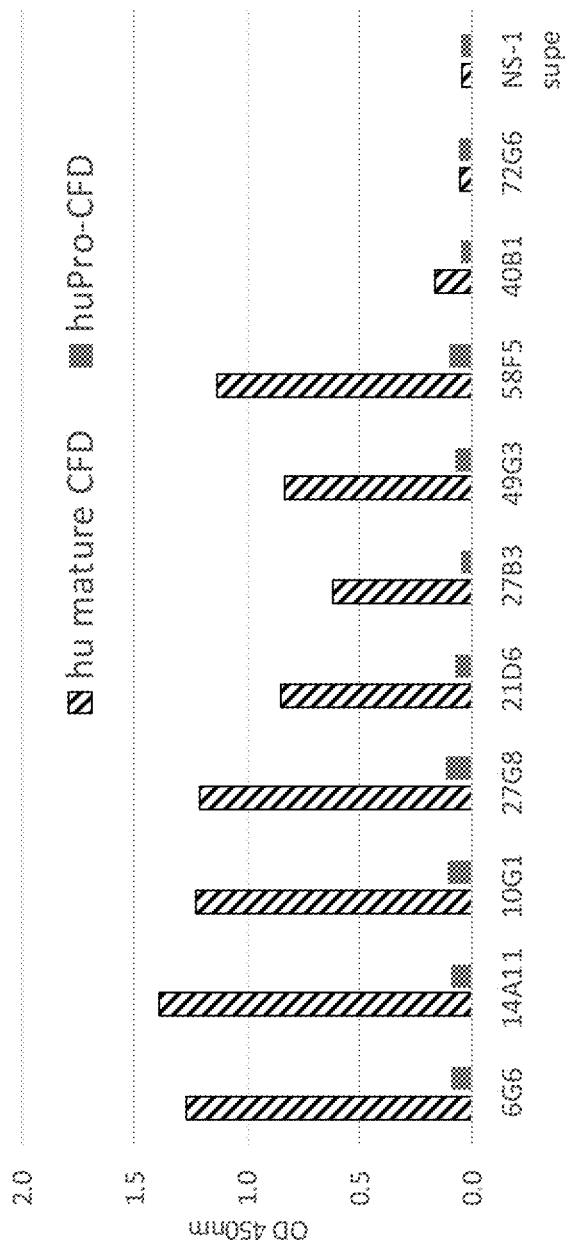
FIG. 5 graphically illustrates the results of a capture ELISA assay in which hybridoma supernatants were screened for binding to human mature-Factor D or human Pro-Factor D when captured by a polyclonal anti-Factor D antibody AF1824 (R&D Systems), as described in Example 1.

FIG. 5 graphically illustrates the results of a capture ELISA assay in which hybridoma supernatants were screened for binding to human mature-Factor D or human Pro-Factor D when captured by a polyclonal anti-Factor D antibody AF1824 (R&D Systems). As shown in FIG. 5, out of 10 hybridomas tested, the supernatants from 8 hybridomas (6G6, 14A11, 10G1, 27G8, 21D6, 27B3, 49G3, 58F5) showed preferential binding to recombinant human mature factor D as compared to recombinant human pro-Factor D. Hybridomas 6G6, 14A11, 10G1, 27B3, 49G3 and 58GF5 were selected for DNA cloning and recombinant antibody production.

Hybridoma Supernatant Specificity

The specificity of the supernatants of hybridomas 14A11 and 6G6 were further analyzed by measuring detection of captured or endogenous proteins in human serum or plasma matrix as follows. ELISA plates were coated overnight at 4° C. with polyclonal goat anti-human CFD AF1824 (R&D Systems). Plate wells were washed, blocked, and washed again. Normal human serum pool, normal human plasma pool or Factor D-depleted human serum were diluted 10-fold in assay buffer (PBS with 1% BSA and 0.05% Tween 20, PBST-BSA), either un-spiked or spiked with 2 µg/mL recombinant pro- (pro CFD) or mature-factor D (mature CFD). These matrices, including a buffer control with or without recombinant protein spiked in, were incubated for 60 minutes at room temperature, and then washed. Anti-human Factor D detection antibodies were diluted as follows then applied to the plate: subclones of 6G6 and 14A11 hybridoma supernatants were diluted in half with PBST-BSA. Purified mAb1824 mouse monoclonal antibody was diluted to 0.5 µg/mL in PBST-BSA buffer. The detection antibodies were incubated for one hour at room temperature and washed, then developed with a horseradish peroxidase (HRP)-labeled goat polyclonal to mouse IgG Fc (Jackson ImmunoResearch).

Figure 6B:
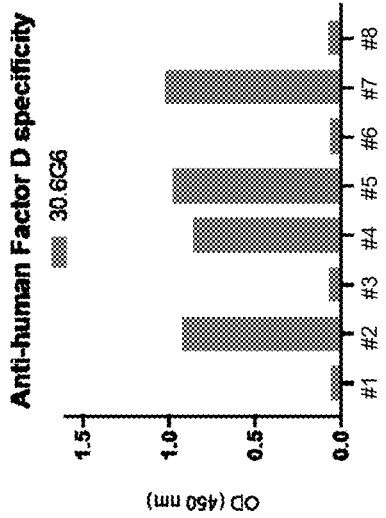
FIG. 6B graphically illustrates the results of an ELISA assay with coated polyclonal goat anti-human CFD 1824 and detected with hybridoma supernatant 6G6 present in each condition described in Example 1.
Figure 6A:
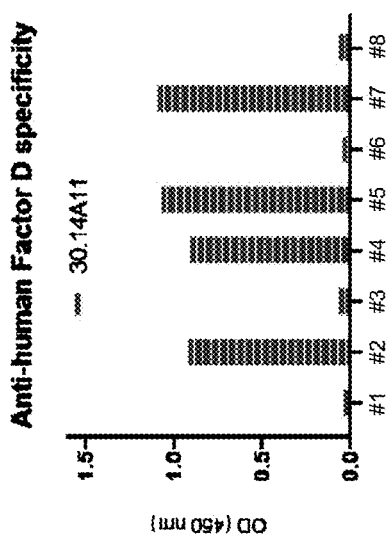
FIG. 6A graphically illustrates the results of an ELISA assay with coated polyclonal goat anti-human CFD 1824 and detected with hybridoma supernatant 14A11 present in each condition described in Example 1.
Figure 6C:
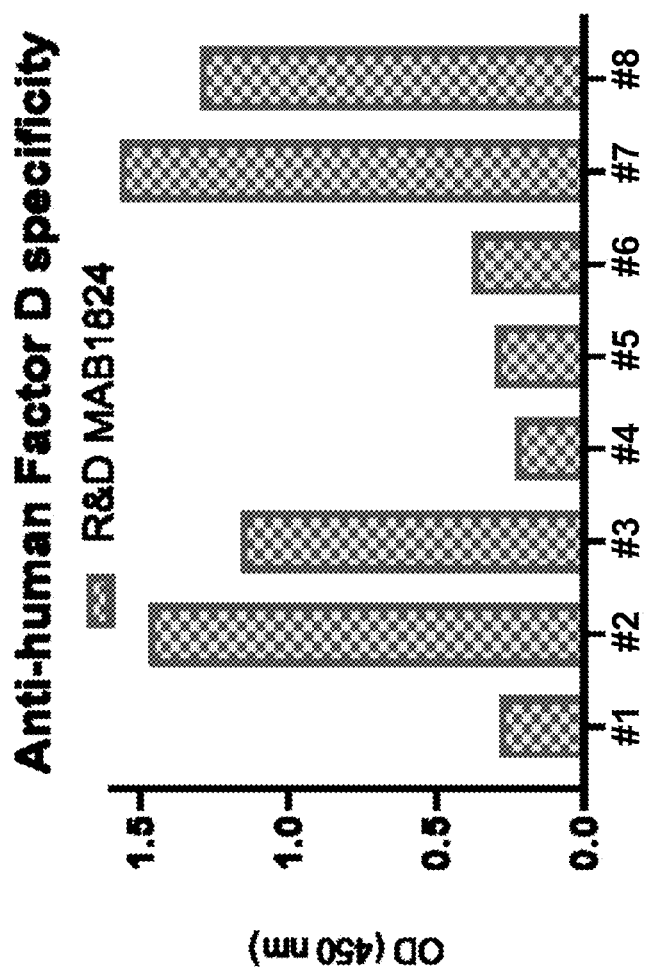
FIG. 6C graphically illustrates the results of an ELISA assay with coated polyclonal goat anti-human CFD 1824 and detected with monoclonal antibody mAb1824 (R&D Systems) present in each condition described in Example 1.

Results:

The results are shown in FIG. 6A-C. The following samples #1 to #8 are shown in each of FIGS. 6A-C:

1: Factor D-depleted serum control
2: Factor D-depleted serum spiked with recombinant human mature-CFD
3: Factor D-depleted serum spiked with recombinant human pro-CFD
4: Normal human serum control
5: Normal human plasma control
6: Buffer control
7: Buffer, spiked with recombinant human mature-CFD
8: Buffer, spiked with recombinant human pro-CFD FIG. 6A graphically illustrates the results with samples #1 to #8 described above in an ELISA assay with coated polyclonal goat anti-human CFD 1824 and detected with hybridoma supernatant 14A11 present in each condition. As shown in FIG. 6A, hybridoma supernatant 14A11 is capable of selectively detecting recombinant mature complement factor D and does not detect recombinant pro factor D. It is noted that the signal obtained when Df-Dpl serum is spiked with recombinant mature CFD (#2) is similar to the signal obtained when 10% normal human serum (#4) or normal human plasma (#5) are added, both of which should contain normal levels of mature Factor D.

FIG. 6B graphically illustrates the results with samples #1 to #8 described above in an ELISA assay with coated polyclonal goat anti-human CFD 1824 and detected with hybridoma supernatant 6G6 present in each condition. As shown in FIG. 6B, hybridoma supernatant 6G6 is capable of selectively detecting recombinant mature complement factor D and does not detect recombinant pro factor D. It is noted that the signal obtained when Df-Dpl serum is spiked with recombinant mature CFD (#2) is similar to the signal obtained when 10% normal human serum (#4) or normal human plasma (#5) are added, both of which should contain normal levels of mature CFD.

FIG. 6C graphically illustrates the results with samples #1 to #8 described above in an ELISA assay with coated polyclonal goat anti-human CFD 1824 and detected with mAb 1824 present in each condition. As shown in FIG. 6C, monoclonal antibody MAB1824 (R&D Systems) detects both recombinant mature CFD and recombinant active CFD and therefore is not capable of selectively detecting mature CFD as compared to pro CFD.

Those supernatants showing preferential binding to the mature version of Factor D (i.e., 6G6, 14A11, 10G1, 27B3, 49G3 and 58GF5) were expanded and cloned by limiting dilution until monoclonal.

Example 2

This Example describes the cloning and sequence analysis of anti-human mature factor D-specific monoclonal antibodies.

Background/Rationale:

This Example describes the cloning and sequence analysis of antibodies produced by the hybridomas showing preferential binding to the mature version of Factor D (i.e., clones 6G6, 14A11, 10G1, 27B3, 49G3 and 58F5) that were generated as described in Example 1.

Methods:

Cloning and Purification of Recombinant Antibodies:

Positive hybridomas 6G6, 14A11, 10G1, 27B3, 49G3, 58F5 were generated and identified as described in Example 1. These hybridomas were subcloned by serial dilution methods. The heavy chain and light chain variable regions were cloned from the hybridomas described in Example 1 using RT-PCR and were sequenced. Antibody-encoding sequences were amplified from total RNA with isotype-specific reverse primers using the SMARTer™ RACE 5'/3' kit (Takara Bio). After verifying the sequences, the variable (V) regions were re-amplified with designed cloning primers and cloned into expression vectors carrying either the human IgG4 heavy chain (SEQ ID NO:71) and kappa light chain (SEQ ID NO:72) constant regions or the mouse IgG2a (SEQ ID NO:218) and kappa light chain (SEQ ID NO:219) constant regions using the In-Fusion HD™ cloning kit (Clontech). The expression constructs were co-transfected transiently into Expi293 cells (Life Technologies) and after 5 days of culture, secreted recombinant antibodies were purified from supernatants by protein A chromatography.

The sequences of the heavy chain variable regions and light chain variable regions are shown in FIGS. 7A and 7B, respectively ("SIN"="SEQ ID NO:" in FIG. 7A and FIG. 7B), and are included below. The complementarity determining regions (CDRs) and framework regions (FRs) of each are provided in TABLES 7-10 below.

Anti-Human Mature-Factor D-Specific Antibody Heavy Chain Variable Region (VH) Sequences FIG. 7A shows an amino acid alignment of the heavy chain variable region (VH) sequences for the anti-human mature-Factor D-specific clones:6G6_VH (SEQ ID NO:12), 14A11_VH (SEQ ID NO:13), 27B3_VH (SEQ ID NO:14), 58F5_VH (SEQ ID NO:15), 49G3_VH (SEQ ID NO:16), and 10G1_VH (SEQ ID NO:17).

Presented below is the heavy chain variable region (VH) sequence for each anti-human mature-factor-D-specific antibody. The Kabat CDRs are underlined.

6G6_VH:

SEQ ID NO: 12

QITLKESGPGILQSSQTLSLTCSFSGISLTTSGMGVSWIRQPSGKGLEW
LAHIYWDDEKHYHPSLKSRLTISKDASRNQVFFRILSVDTADTATYYCA
LRYYGYRSFMDYWGQGTSVTVSS

-continued

14A11_VH:
SEQ ID NO: 13
QITLKESGPGILQSSQTLSLTCSFSGVSLTTSGMGVSWIRQPSGKGLEW
LAHIYWDDEKHYHPSLKSRLTISKDASRNQVFFRILSVDTADTATYYCA
LRYYGYRSFMDYWGQGTSVTVSS

27B3_VH:
SEQ ID NO: 14
QVTLKESGPGILQSSQTLSLTCSFSGISLNISGMGVSWIRQPSGKGLEW
LAHIYWDDEKHYNPSLKRRLTISKDASRNQVFFRISSVDSADTATYYCA
LRYYGYGSIMDYWGHGTSVTVSS

58F5_VH:
SEQ ID NO: 15
QVTLKESGPGILQSSQTLSLTCSFSGISLNTSIMGVSWIRQPSGKGLEW
LAHIYWDDEKHYNPSLKSRLTISKDASRNQVFLKIISVDTADTATYYCA
LRYYGYNYVMHYWGQGTSVTVSS

49G3_VH:
SEQ ID NO: 16
QVTLKESGPGILQSSQTLSLTCSFSGISLSSSGMGVSWIRQPSGKGLEW
LAHIYWDDEKHYNPSLKSRLTISKDASRNQIFLKIISVDTADTATYYCA
LRYYGYNYVMHYWGQGTSVTVSS

10G1_VH:
SEQ ID NO: 17
QVTLKESGPGILQSSQTLSLTCSFSGVSLSSSGMGVSWIRQPSGKGLEW
LAHIYWDDEKHYNPSLKSRLTISKGASRNQVFLKIISVDTADTATYYCA
LRYYGYNSIMHYWGQGASVTVSS

TABLE 7 anti-human mature-Factor D-specific Antibody VH Sequences (CDRs and FR regions, Kabat)

| Antibody | HC FR1 | HC CDR1 |
|---|---|---|
| 6G6 | QITLKESGPGILQSS QTLSLTCSFSGISLT (SEQ ID NO: 24) | TSGMGVS (SEQ ID NO: 25) |
| 14A11 | QITLKESGPGILQSS QTLSLTCSFSGVSLT (SEQ ID NO: 31) | TSGMGVS (SEQ ID NO: 25) |
| 27B3 | QVTLKESGPGILQSS QTLSLTCSFSGISLN (SEQ ID NO: 32) | ISGMGVS (SEQ ID NO: 33) |
| 58F5 | QVTLKESGPGILQSS QTLSLTCSFSGISLN (SEQ ID NO: 32) | TSIMGVS (SEQ ID NO: 38) |
| 49G3 | QVTLKESGPGILQSS QTLSLTCSFSGISLS (SEQ ID NO: 42) | SSGMGVS (SEQ ID NO: 43) |
| 10G1 | QVTLKESGPGILQSS QTLSLTCSFSGVSLS (SEQ ID NO: 45) | SSGMGVS (SEQ ID NO: 43) |
| Antibody | HC FR2 | HC CDR2 |
| 6G6 | WIRQPSGKGLEWLA (SEQ ID NO: 26) | HIYWDDEKHYHPSLKS (SEQ ID NO: 27) |
| 14A11 | WIRQPSGKGLEWLA (SEQ ID NO: 26) | HIYWDDEKHYHPSLKS (SEQ ID NO: 27) |
| 27B3 | WIRQPSGKGLEWLA (SEQ ID NO: 26) | HIYWDDEKHYNPSLKR (SEQ ID NO: 34) |
| 58F5 | WIRQPSGKGLEWLA (SEQ ID NO: 26) | HIYWDDEKHYNPSLKS (SEQ ID NO: 39) |
| 49G3 | WIRQPSGKGLEWLA (SEQ ID NO: 26) | HIYWDDEKHYNPSLKS (SEQ ID NO: 39) |
| 10G1 | WIRQPSGKGLEWLA (SEQ ID NO: 26) | HIYWDDEKHYNPSLKS (SEQ ID NO: 39) |
| Antibody | HC FR3 | HC CDR3 |
| 6G6 | RLTISKDASRNQVFFR ILSVDTADTATYYCAL (SEQ ID NO: 28) | RYYGYRSFMDY (SEQ ID NO: 29) |
| 14A11 | RLTISKDASRNQVFFR ILSVDTADTATYYCAL (SEQ ID NO: 28) | RYYGYRSFMDY (SEQ ID NO: 29) |
| 27B3 | RLTISKDASRNQVFFR ISSVDSADTATYYCAL SEQ ID NO: 35) | RYYGYGSIMDY (SEQ ID NO: 36) |
| 58F5 | RLTISKDASRNQVFLK IISVDTADTATYYCAL (SEQ ID NO: 40) | RYYGYNYVMHY (SEQ ID NO: 41) |
| 49G3 | RLTISKDASRNQIFLK IISVDTADTATYYCAL (SEQ ID NO: 44) | RYYGYNYVMHY (SEQ ID NO: 41) |
| 10G1 | RLTISKGASRNQVFLK IISVDTADTATYYCAL (SEQ ID NO: 46) | RYYGYNSIMHY (SEQ ID NO: 47) |
| Antibody | HC FR4 | |
| 6G6 | WGQGTSVTVSS (SEQ ID NO: 30) | |
| 14A11 | WGQGTSVTVSS (SEQ ID NO: 30) | |
| 27B3 | WGHGTSVTVSS (SEQ ID NO: 37) | |
| 58F5 | WGQGTSVTVSS (SEQ ID NO: 30) | |
| 49G3 | WGQGTSVTVSS (SEQ ID NO: 30) | |
| 10G1 | WGQGASVTVSS (SEQ ID NO: 48) | |

Anti-Human Mature-Factor D-Specific Antibody Light Chain Variable Region (VL) Sequences FIG. 7B shows an amino acid alignment of the light chain variable region (VL) sequences for the anti-human mature-Factor D-specific clones: 6G6_VK (SEQ ID NO:18), 14A11_VK: (SEQ ID NO:19), 27B3_VK: (SEQ ID NO:20), 58F5_VK: (SEQ ID NO:21), 49G3_VK: (SEQ ID NO:22), 10G1_VK: (SEQ ID NO:23).

Presented below is the light chain variable region (VL) sequence for each anti-human mature-factor-D-specific antibody. The Kabat CDRs are underlined. These regions are the same whether numbered by the Kabat or Chothia system.

6G6_VK:
SEQ ID NO: 18
DVLMTQSPLSLPVSLGDQASIFCRSNQSIVHSNGNTYFEWYLQKPGQSP
KLLIYKVSNRFSGVPDRFSGSGSGTDFTLRISRVEAEDLGVYYCFQGSH
VPPTFGGGTKLEIKR

-continued

14A11_VK:
SEQ ID NO: 19
DVLMTQSPLSLPVSLGDQASIFCRSNQSIVHSNGNTYFEWYLQKPGQSP
KLLIYKVSNRFSGVPDRFSGSGSGTDFTLRISRVEAEDLGIYYCFQGSH
VPPTFGGGTKLEIKR

27B3_VK:
SEQ ID NO: 20
DVLMTQTPLSLPVSLGDQASISCRSSQSIVHSNGNTYFEWYLQKPGQSP
KLLIYKVSNRFSGVPDRFSGSGSGTDFTLKISRVEAEDLGVYYCFQGSH
VPPTFGGGTKLEIKR

58F5_VK:
SEQ ID NO: 21
DVLMTQTPLSLPVSLGDQASISCRSSQSIVHSNGNTYLEWYLQKPGQSP
KLLIYKVSNRFSGVPDRFSGSGSGTDFTLKISRVEADDLGVYYCFQGSH
VPPTFGGGTKLEIKR

49G3_VK:
SEQ ID NO: 22
DVLMTQTPLSLPVSLGDQASISCRSSQSILHSNGNTYFEWYLQKPGQSP
KLLIYKVSNRFSGVPDRFSGSGSGTDFTLKISRVEAEDLGVYYCFQGSH
VPPTFGGGTKLEIKR

10G1_VK:
SEQ ID NO: 23
DVLMTQTPLSLPVSLGDQASISCRSSESIVHSNGNTYLEWYLQKPGQSP
KLLIYKVYNRFSGVPDRFSGSGSGTDFTLKISRVEAEDLGVYYCFQGSH
VPPTFGGGTKLEIKR

TABLE 8 anti-human mature-Factor D-specific Antibody VL Sequences (CDRs and FR regions, Kabat and Chothia)

| Antibody | LC FR1 | LC CDR1 |
|---|---|---|
| 6G6 | DVLMTQSPLSLPVSLGDQASIFC (SEQ ID NO: 49) | RSNQSIVHSNGNTYFE (SEQ ID NO: 50) |
| 14A11 | DVLMTQSPLSLPVSLGDQASIFC (SEQ ID NO: 49) | RSNQSIVHSNGNTYFE (SEQ ID NO: 50) |
| 27B3 | DVLMTQTPLSLPVSLGDQASISC (SEQ ID NO: 57) | RSSQSIVHSNGNTYFE (SEQ ID NO: 58) |
| 58F5 | DVLMTQTPLSLPVSLGDQASISC (SEQ ID NO: 57) | RSSQSIVHSNGNTYLE (SEQ ID NO: 60) |
| 49G3 | DVLMTQTPLSLPVSLGDQASISC (SEQ ID NO: 57) | RSSQSILHSNGNTYFE (SEQ ID NO: 62) |
| 10G1 | DVLMTQTPLSLPVSLGDQASISC (SEQ ID NO: 57) | RSSESIVHSNGNTYLE (SEQ ID NO: 63) |

| Antibody | LC FR2 | LC CDR2 |
|---|---|---|
| 6G6 | WYLQKPGQSPKLLIY (SEQ ID NO: 51) | KVSNRFS (SEQ ID NO: 52) |
| 14A11 | WYLQKPGQSPKLLIY (SEQ ID NO: 51) | KVSNRFS (SEQ ID NO: 52) |
| 27B3 | WYLQKPGQSPKLLIY (SEQ ID NO: 51) | KVSNRFS (SEQ ID NO: 52) |
| 58F5 | WYLQKPGQSPKLLIY (SEQ ID NO: 51) | KVSNRFS (SEQ ID NO: 52) |
| 49G3 | WYLQKPGQSPKLLIY (SEQ ID NO: 51) | KVSNRFS (SEQ ID NO: 52) |
| 10G1 | WYLQKPGQSPKLLIY (SEQ ID NO: 51) | KVYNRFS (SEQ ID NO: 64) |

TABLE 8-continued anti-human mature-Factor D-specific Antibody VL Sequences (CDRs and FR regions, Kabat and Chothia)

| Antibody | LC FR3 | LC CDR3 |
|---|---|---|
| 6G6 | GVPDRFSGSGSGTDFTLRISRVEAEDLGVYYC (SEQ ID NO: 53) | FQGSHVPPT (SEQ ID NO: 54) |
| 14A11 | GVPDRFSGSGSGTDFTLRISRVEAEDLGIYYC (SEQ ID NO: 56) | FQGSHVPPT (SEQ ID NO: 54) |
| 27B3 | GVPDRFSGSGSGTDFTLKISRVEAEDLGVYYC (SEQ ID NO: 59) | FQGSHVPPT (SEQ ID NO: 54) |
| 58F5 | GVPDRFSGSGSGTDFTLKISRVEADDLGVYYC (SEQ ID NO: 61) | FQGSHVPPT (SEQ ID NO: 54) |
| 49G3 | GVPDRFSGSGSGTDFTLKISRVEAEDLGVYYC (SEQ ID NO: 59) | FQGSHVPPT (SEQ ID NO: 54) |
| 10G1 | GVPDRFSGSGSGTDFTLKISRVEAEDLGVYYC (SEQ ID NO: 59) | FQGSHVPPT (SEQ ID NO: 54) |

| Antibody | LC FR4 |
|---|---|
| 6G6 | FGGGTKLEIKR (SEQ ID NO: 55) |
| 14A11 | FGGGTKLEIKR (SEQ ID NO: 55) |
| 27B3 | FGGGTKLEIKR (SEQ ID NO: 55) |
| 58F5 | FGGGTKLEIKR (SEQ ID NO: 55) |
| 49G3 | FGGGTKLEIKR (SEQ ID NO: 55) |
| 10G1 | FGGGTKLEIKR (SEQ ID NO: 55) |

TABLE 9

Consensus Sequences for anti-human mature-Factor D-specific HC CDRs:

| Antibody | Region | Sequence |
|---|---|---|
| 6G6 | HC-CDR1 | TSGMGVS (SEQ ID NO: 25) |
| 14A11 | HC-CDR1 | TSGMGVS (SEQ ID NO: 25) |
| 27B3 | HC-CDR1 | ISGMGVS (SEQ ID NO: 33) |
| 58F5 | HC-CDR1 | TSIMGVS (SEQ ID NO: 38) |
| 49G3 | HC-CDR1 | SSGMGVS (SEQ ID NO: 43) |
| 10G1 | HC-CDR1 | SSGMGVS (SEQ ID NO: 43) |
| Consensus | HC-CDR1 | XSXMGVS (SEQ ID NO: 65) Wherein X at position 1 is T, I or S; X at position 3 is G or I |
| 6G6 | HC-CDR2 | HIYWDDEKHYHPSLKS (SEQ ID NO: 27) |
| 14A11 | HC-CDR2 | HIYWDDEKHYHPSLKS (SEQ ID NO: 27) |

TABLE 9-continued

Consensus Sequences for anti-human mature-Factor D-specific HC CDRs:

| Antibody | Region | Sequence |
|---|---|---|
| 27B3 | HC-CDR2 | HIYWDDEKHYNPSLKR (SEQ ID NO: 34) |
| 58F5 | HC-CDR2 | HIYWDDEKHYNPSLKS (SEQ ID NO: 39) |
| 49G3 | HC-CDR2 | HIYWDDEKHYNPSLKS (SEQ ID NO: 39) |
| 10G1 | HC-CDR2 | HIYWDDEKHYNPSLKS (SEQ ID NO: 39) |
| Consensus | HC-CDR2 | HIYWDDEKHYXPSLKX (SEQ ID NO: 66) Wherein X at position 11 is H or N; X at position 16 is S or R |
| 6G6 | HC-CDR3 | RYYGYRSFMDY (SEQ ID NO: 29) |
| 14A11 | HC-CDR3 | RYYGYRSFMDY (SEQ ID NO: 29) |
| 27B3 | HC-CDR3 | RYYGYGSIMDY (SEQ ID NO: 36) |
| 58F5 | HC-CDR3 | RYYGYNYVMHY (SEQ ID NO: 41) |
| 49G3 | HC-CDR3 | RYYGYNYVMHY (SEQ ID NO: 41) |
| 10G1 | HC-CDR3 | RYYGYNSIMHY (SEQ ID NO: 47) |
| Consensus | HC-CDR3 | RYYGYXXXMXY (SEQ ID NO: 67) Wherein X at position 6 is R, G or N; X at position 7 is S or Y; X at position 8 is F, I or V; X at position 10 is D or H |

TABLE 10

Consensus Sequences for mature-Factor D-specific LC CDRs:

| Antibody | Region | Sequence |
|---|---|---|
| 6G6 | LC-CDR1 | RSNQSIVHSNGNTYFE (SEQ ID NO: 50) |
| 14A11 | LC-CDR1 | RSNQSIVHSNGNTYFE (SEQ ID NO: 50) |
| 27B3 | LC-CDR1 | RSSQSIVHSNGNTYFE (SEQ ID NO: 58) |
| 58F5 | LC-CDR1 | RSSQSIVHSNGNTYLE (SEQ ID NO: 60) |
| 49G3 | LC-CDR1 | RSSQSILHSNGNTYFE (SEQ ID NO: 62) |
| 10G1 | LC-CDR1 | RSSESIVHSNGNTYLE (SEQ ID NO: 63) |
| Consensus | LC-CDR1 | RSXXSIXHSNGNTYXE (SEQ ID NO: 68) Wherein: X at position 3 is N or S; X at position 4 is Q or E; X at position 7 is V or L; X at position 15 is F or L |
| 6G6 | LC-CDR2 | KVSNRFS (SEQ ID NO: 52) |
| 14A11 | LC-CDR2 | KVSNRFS (SEQ ID NO: 52) |
| 27B3 | LC-CDR2 | KVSNRFS (SEQ ID NO: 52) |
| 58F5 | LC-CDR2 | KVSNRFS (SEQ ID NO: 52) |
| 49G3 | LC-CDR2 | KVSNRFS (SEQ ID NO: 52) |
| 10G1 | LC-CDR2 | KVYNRFS (SEQ ID NO: 64) |
| Consensus | LC-CDR2 | KVXNRFS (SEQ ID NO: 69) Wherein X at position 3 is S or Y |
| 6G6 | LC-CDR3 | FQGSHVPPT (SEQ ID NO: 54) |
| 14A11 | LC-CDR3 | FQGSHVPPT (SEQ ID NO: 54) |
| 27B3 | LC-CDR3 | FQGSHVPPT (SEQ ID NO: 54) |
| 58F5 | LC-CDR3 | FQGSHVPPT (SEQ ID NO: 54) |
| 49G3 | LC-CDR3 | FQGSHVPPT (SEQ ID NO: 54) |
| 10G1 | LC-CDR3 | FQGSHVPPT (SEQ ID NO: 54) |
| Consensus | LC-CDR3 | FQGSHVPPT (SEQ ID NO: 54) |

SEQ ID NO: 70: human IgG4 constant region:
ASTKGPSVFPLAPCSRSTSESTAALGCLVKDYFPEPVTVSWNSGALTSGVHTF
PAVLQSSGLYSLSSVVTVPSSSLGTKTYTCNVDHKPSNTKVDKRVESKYGPPCPSCP
APEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK SEQ ID NO: 71: human IgG4 constant region with S228P mutation
ASTKGPSVFPLAPCSRSTSESTAALGCLVKDYFPEPVTVSWNSGALTSGVHTF
PAVLQSSGLYSLSSVVTVPSSSLGTKTYTCNVDHKPSNTKVDKRVESKYGPPCPPCP
APEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK SEQ ID NO: 245: human IgG4 constant region with S228P mutation and also a mutation that promotes FcRn interactions at low pH
ASTKGPSVFPLAPCSRSTSESTAALGCLVKDYFPEPVTVSWNSGALTSGVHTF
PAVLQSSGLYSLSSVVTVPSSSLGTKTYTCNVDHKPSNTKVDKRVESKYGPPCPPCP
APEFLGGPSVFLFPPKPKDTLMISRTPEVTCVVVDVSQEDPEVQFNWYVDGVEVHN AKTKPREEQFNSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNYKTTPPVLD
SDGSFFLYSRLTVDKSRWQEGNVFSCSVLHEALHSHYTQKSLSLSLGK
SEQ ID NO: 72: human IgK constant region TVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC SEQ ID NO: 218: mouse IgG2a constant region:
AKTTAPSVYPLAPVCGDTTGSSVTLGCLVKGYFPEPVTLTWNSGSLSSGVHT
FPAVLQSDLYTLSSSVTVTSSTWPSQSITCNVAHPASSTKVDKKIEPRGPTIKPCPPCK
CPAPNLLGGPSVFIFPPKIKDVLMISLSPIVTCVVVDVSEDDPDVQISWFVNNVEVHT
AQTQTHREDYNSTLRVVSALPIQHQDWMSGKEFKCKVNNKDLPAPIERTISKPKGSV
RAPQVYVLPPPEEEMTKKQVTLTCMVTDFMPEDIYVEWTNNGKTELNYKNTEPVL
DSDGSYFMYSKLR VEKKNWVERNSYSCSVVHEGLHNHHTTKSFSRTPGK SEQ ID NO: 219: mouse IgK constant region:
ADAAPTVSIFPPSSEQLTSGGASVVCFLNNFYPKDINVKWKIDGSERQNGVLN
SWTDQDSKDSTYSMSSTLTLTKDEYERHNSYTCEATHKTSTSPIVKSFNRNEC DNA encoding mouse anti-human mature-Factor D-specific Antibody
mAb heavy and light chains:
SEQ ID NO: 73: nucleic acid encoding 6G6 HC variable region
CAGATTACTCTGAAAGAGTCTGGCCCTGGGATATTGCAGTCCTCCCAGAC
CCTCAGTCTGACTTGTTCTTTCTCTGGGATTTCACTGACTACTTCTGGTATGGGTG
TGAGCTGGATTCGTCAGCCTTCAGGAAAGGGTCTGGAATGGCTGGCACACATTT
ATTGGGATGATGAGAAACACTATCATCCATCCCTGAAGAGCCGGCTCACAATCT
CCAAGGATGCCTCCAGAAACCAGGTTTTCTTCAGGATCCTTAGTGTGGACACTGC
AGATACTGCCACATACTACTGTGCTCTCCGTTACTACGGTTATAGGTCTTTTATG
GACTACTGGGGTCAAGGAACCTCAGTCACCGTCTCCTCA SEQ ID NO: 74: nucleic acid encoding 14A11 HC variable region
CAGATTACTCTGAAAGAGTCTGGCCCTGGGATATTGCAGTCCTCCCAGAC
CCTCAGTCTGACTTGTTCTTTCTCTGGGGTTTCACTGACTACTTCTGGTATGGGTG
TGAGCTGGATTCGTCAGCCTTCAGGAAAGGGTCTGGAATGGCTGGCACACATTT
ATTGGGATGATGAGAAACACTATCATCCATCCCTGAAGAGCCGGCTCACAATCT
CCAAGGATGCCTCCAGAAACCAGGTTTTCTTCAGGATCCTTAGTGTGGACACTGC
AGATACTGCCACATATTACTGTGCTCTCCGTTACTACGGTTATAGGTCTTTTATGG
ACTATTGGGGTCAAGGAACCTCAGTCACCGTCTCCTCA SEQ ID NO: 75: nucleic acid encoding 27B3 HC variable region
CAGGTTACTCTGAAAGAGTCTGGCCCTGGGATATTGCAGTCCTCCCAGAC
CCTCAGTCTGACTTGTTCTTTCTCTGGGATTTCACTGAATATTTCCGGTATGGGTG
TGAGCTGGATTCGTCAGCCTTCAGGAAAGGGTCTGGAGTGGCTGGCACACATTT
ACTGGGATGATGAAAAACACTATAATCCATCCCTGAAGAGACGGCTCACTATCT
CCAAGGATGCCTCCAGAAACCAGGTTTTCTTCAGGATCAGTAGTGTGGACTCTGC
AGATACTGCCACATACTACTGTGCGCTCCGTTACTACGGTTATGGTTCTATTATG
GACTATTGGGGTCATGGAACCTCAGTCACCGTCTCCTCA SEQ ID NO: 76: nucleic acid encoding 58F5 HC variable region
CAGGTTACTCTGAAAGAGTCTGGCCCTGGGATATTGCAGTCCTCCCAGAC
CCTCAGTCTGACTTGTTCTTTCTCTGGGATTTCATTGAATACTTCTATTATGGGTG
TGAGCTGGATTCGTCAGCCTTCAGGAAAGGGTCTGGAGTGGCTGGCACACATTT
ACTGGGATGATGAGAAACACTATAACCCATCCCTGAAGAGCGACTCACAATCT
CCAAGGATGCCTCCAGAAACCAGGTATTCCTCAAGATCATTAGTGTGGACACTG
CAGATACTGCCACATACTACTGTGCTCTCCGTTACTACGGTTATAACTATGTTAT
GCACTACTGGGGTCAAGGAACCTCAGTCACCGTCTCCTCA SEQ ID NO: 77: nucleic acid encoding 49G3 HC variable region
CAGGTTACTCTGAAAGAGTCTGGCCCTGGGATATTGCAGTCCTCCCAGAC
CCTCAGTCTGACTTGTTCTTTCTCTGGGATTTCACTGAGTTCTTCTGGTATGGGTG
TGAGCTGGATTCGTCAGCCTTCAGGAAAGGGTCTGGAGTGGCTGGCACACATTT
ACTGGGATGATGAGAAACACTATAACCCATCCCTGAAGAGCCGGCTCACAATCT
CCAAGGATGCCTCCAGAAACCAGATATTCCTCAAGATCATTAGTGTGGACACTG
CAGATACTGCCACATATTATTGTGCTCTCCGTTACTACGGTTATAACTATGTTATG
CACTACTGGGGTCAAGGAACCTCAGTCACCGTCTCCTCA SEQ ID NO: 78: nucleic acid encoding 10G1 HC variable region
CAGGTTACTCTGAAAGAGTCTGGCCCTGGGATATTGCAGTCCTCCCAGAC
CCTCAGTCTGACTTGTTCTTTCTCTGGGGTTTCACTGAGTTCTTCTGGTATGGGTG
TGAGCTGGATTCGTCAGCCTTCAGGAAAGGGTCTGGAGTGGCTGGCACACATTT
ACTGGGATGATGAGAAACACTATAACCCATCCCTGAAGAGCCGGCTCACAATCT
CCAAGGGTGCCTCCAGAAACCAGGTCTTCCTCAAGATCATTAGTGTGGACACTG
CAGATACTGCCACATACTACTGTGCTCTCCGTTACTACGGTTATAACTCTATTAT
GCACTACTGGGGTCAAGGAGCCTCAGTCACCGTCTCCTCA SEQ ID NO: 79: nucleic acid encoding 6G6 LC variable region
GATGTTTTGATGACCCAATCTCCACTCTCCCTGCCTGTCAGTCTTGGAGAT
CAAGCCTCCATCTTTTGCAGATCTAATCAGAGCATTGTACATAGTAATGGAAACA
CCTATTTCGAATGGTACCTGCAGAAACCAGGCCAGTCTCCAAAGCTCCTGATCTA

```
                            -continued
CAAAGTTTCCAACCGATTTTCTGGGGTCCCAGACAGGTTCAGTGGCAGTGGATC
AGGGACAGATTTCACACTCAGGATCAGCAGAGTGGAGGCTGAGGATCTGGGAGT
TTATTACTGCTTTCAAGGTTCACATGTTCCTCCGACGTTCGGTGGAGGCACCAAG
CTGGAAATCAAACGG SEQ ID NO: 80: nucleic acid encoding 14A11 LC variable region
GATGTTTTGATGACCCAATCTCCACTCTCCCTGCCTGTCAGTCTTGGAGAT
CAAGCCTCCATCTTTTGCAGATCTAATCAGAGCATTGTTCATAGTAATGGAAACA
CCTATTTCGAATGGTACCTGCAGAAACCAGGCCAGTCTCCAAAGCTCCTGATCTA
CAAAGTTTCCAACCGATTTTCTGGGGTCCCAGACAGGTTCAGTGGCAGTGGATC
AGGGACAGATTTCACACTCAGGATCAGCAGAGTGGAGGCTGAGGATCTGGGAAT
TTATTACTGCTTTCAAGGTTCACATGTTCCTCCGACGTTCGGTGGAGGCACCAAG
CTGGAAATCAAACGG SEQ ID NO: 81: nucleic acid encoding 27B3 LC variable region
GATGTTTTGATGACCCAAACTCCACTCTCCCTGCCTGTCAGTCTTGGAGAT
CAAGCCTCCATCTCTTGCAGATCTAGTCAGAGCATTGTTCATAGTAATGGAAATA
CCTATTTTGAATGGTACCTCCAGAAACCAGGCCAGTCTCCAAAGCTCCTGATCTA
CAAGGTTTCCAACCGATTTTCTGGGGTCCCAGACAGGTTCAGTGGCAGTGGATC
AGGGACAGATTTCACACTCAAGATCAGCAGAGTGGAGGCTGAGGATCTGGGAGT
TTATTACTGCTTTCAAGGTTCACATGTTCCTCCGACGTTCGGTGGAGGCACCAAG
CTGGAGATCAAACGG SEQ ID NO: 82: nucleic acid encoding 58F5 LC variable region
GATGTTTTGATGACCCAAACTCCACTCTCCCTGCCTGTCAGTCTTGGAGAT
CAAGCCTCCATCTCTTGCAGATCTAGTCAGAGCATTGTACATAGTAATGGAAAC
ACCTATTTAGAATGGTACCTGCAGAAACCAGGCCAGTCTCCAAAGCTCCTGATCT
ACAAAGTTTCCAACCGATTTTCTGGGTCCCAGACAGATTCAGTGGCAGTGGAT
CAGGGACAGATTTCACACTCAAGATCAGCAGAGTGGAGGCTGATGATCTGGGAG
TTTATTACTGCTTTCAAGGTTCACATGTTCCTCCGACGTTCGGTGGAGGCACCAA
GCTGGAAATCAAACGG SEQ ID NO: 83: nucleic acid encoding 49G3 LC variable region
GATGTTTTGATGACCCAAACTCCACTCTCCCTGCCTGTCAGTCTTGGAGAT
CAAGCCTCCATCTCTTGCAGATCTAGTCAGAGCATTCTACATAGTAATGGAAACA
CCTATTTTGAATGGTACCTGCAGAAACCAGGCCAGTCTCCAAAGCTCCTGATCTA
CAAAGTTTCCAACCGATTTTCTGGGGTCCCAGACAGGTTCAGTGGCAGTGGATC
AGGGACAGATTTCACACTCAAGATCAGCAGAGTGGAGGCTGAGGATCTGGGAGT
TTATTACTGCTTTCAAGGTTCACATGTTCCTCCGACGTTCGGTGGAGGCACCAAG
CTGGAAATCAAACGG SEQ ID NO: 84: nucleic acid encoding 10G1 LC variable region
GATGTTTTGATGACCCAAACTCCACTCTCCCTGCCTGTCAGTCTTGGAGAT
CAAGCCTCCATCTCTTGCAGATCTAGTGAGAGCATTGTACATAGTAATGGAAAC
ACCTATTTAGAATGGTACCTGCAGAAACCAGGCCAGTCTCCAAAGCTCCTGATCT
ACAAAGTTTACAACCGATTTTCTGGGGTCCCAGACAGGTTCAGTGGCAGTGGAT
CAGGGACAGATTTCACACTCAAGATCAGCAGAGTGGAGGCTGAGGATCTGGGA
GTTTATTACTGCTTTCAAGGTTCACATGTTCCTCCGACGTTCGGTGGAGGCACCA
AGCTGGAGATCAAACGG
```

Example 3

This Example describes the functional characterization of recombinant purified anti-human mature factor D-specific antibodies in several in vitro assays.

Background/Rationale:

This Example describes the functional characterization of recombinant anti-human mature factor D-specific monoclonal antibodies that were generated as described in Examples 1 and 2 for binding to human mature Factor D and binding to human pro-Factor D.

Methods:

Sandwich ELISA Assay

Purified, recombinant anti-human mature-Factor D-specific antibodies 6G6, 14A11, 10G1, 49G3, 27B3 and 58F5 (human IgG4 Fc) that were generated as described in Examples 1 and 2 were tested in a sandwich ELISA format as detection antibodies. Recombinant human pro-factor D protein (SEQ ID NO:2), referred to as "pro" and recombinant human mature-factor D protein (SEQ ID NO:3), referred to as "mature" were captured by plate-bound goat anti-human CFD polyclonal AF1824 (R&D systems). Purified recombinant antibodies 6G6, 14A11, 10G1, 49G3, 27B3 and 58F5 as well as a control human IgG4 were added to the washed plate and incubated. An HRP-tagged anti-mouse secondary antibody followed by TMB substrate was used to develop the assay.

Figure 8:
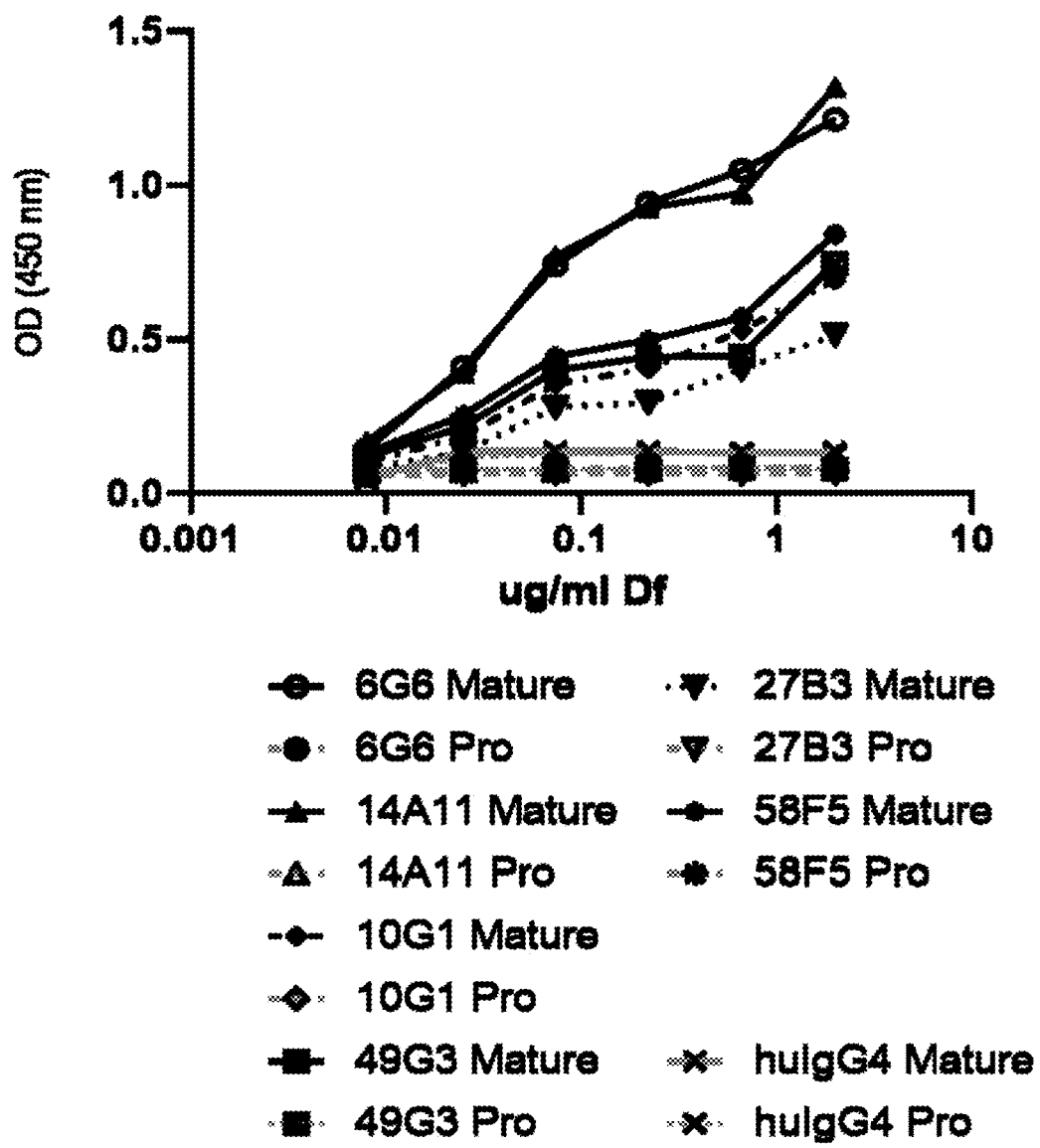
FIG. 8 graphically illustrates the detection (or lack thereof) of recombinant human pro-Factor D or mature-Factor D with numerous candidate anti-human mature-Factor-D-specific antibodies.

Results:

FIG. 8 graphically illustrates the detection of recombinant human pro-Factor D or mature-Factor D with numerous candidate anti-human mature-Factor-D-specific antibodies. As shown in FIG. 8, all the purified antibodies tested, namely 6G6, 14A11, 10G1, 49G3, 27B3 and 58F5, were found to be specific for the mature form of Factor D as compared to pro-Factor D in an ELISA assay format.

Affinity Assay

Affinities of candidate antibodies to human mature-Factor-D versus human pro-Factor D were determined as follows.

Association and dissociation constants were determined by Octet Fortebio. 20 nM recombinant human IgG4 candidate antibodies 6G6, 14A11, 10G1, 49G3, 27B3 and 58F5 were loaded onto anti-human sensors and allowed to associate and dissociate over 5 minute time periods with recombinant human mature-Factor-D (111 nM) or recombinant human pro-Factor D (111 nM). The results are shown below in TABLE 11.

TABLE 11

Affinities of Candidate Antibodies to human mature-factor D versus human pro-factor D

| Candidate antibody | KD (M) mature-Factor D | KD (M) pro-Factor D |
|---|---|---|
| 6G6 | 1.43E−08 | NC |
| 14A11 | 9.77E−09 | NC |
| 10G1 | 7.31E−10 | NC |
| 49G3 | 2.30E−09 | NC |
| 58F5 | <1.0E−12 | NC |
| 27B3 | 2.41E−08 | NC |
| blank | NC | NC |

NC = instrument software could not calculate

Based on the results described in this Example, the antibodies 6G6 and 14A11 were chosen for further analysis and development due to their superior sensitivity and specificity for mature human factor D versus human pro-factor D.

Conclusion:

As described in Example 1-3, the inventors have generated mature-Factor D-specific monoclonal antibodies that specifically bind to mature Factor D and do not bind to Pro-Factor D. As further described in Examples 10-12, the level of mature Factor D correlates with alternative pathway activity, therefore, mature Factor D-specific monoclonal antibodies may be used to measure the level of mature Factor D as a surrogate endpoint in a diagnostic assay to assess the level of alternative pathway activation in a mammalian subject. As further described herein in Example 12, the mature-Factor D-specific monoclonal antibodies may be used as a pharmacodynamic (PD) measurement of MASP-3 inhibition in a subject treated with a MASP-3 inhibitor, which may be used to determine efficacious dosing of a MASP-3 inhibitor.

Example 4

This Example describes the generation of monoclonal antibodies raised against mature human factor D and selected for the ability to detect both mature- and pro-Factor D proteins (i.e., antibodies that bind to an epitope of Factor D that is common to both mature and pro-Factor D proteins).

Background/Rationale:

This Example describes the generation of anti-human factor D antibodies capable of binding both the pro and mature form of human Factor D. The antibodies described in this Example bind to both pro-factor D and mature factor D and are useful as coating antibodies in an ELISA assay to assess the status of Factor D in a biological sample.

Methods:

Immunization with the Mature Factor D Antigen

C57BL/6, MASP-1/3 knockout mice were immunized with recombinant human mature Factor D-His tagged protein. The mice were immunized two times, subcutaneously, with 50 µL of adjuvant-emulsions of protein (50-100 µg total protein per injection). Serum samples from the immunized mice were prepared from tail bleeds and tested by ELISA for the presence of antigen-specific antibodies capable of binding to plate-immobilized recombinant human pro-factor D (SEQ ID NO:2) and recombinant human mature Factor D (SEQ ID NO:3), both strep-tagged, as follows.

Recombinant human Pro-CFD-Strep tagged or recombinant human mature CFD-Strep tagged were immobilized on Maxisorp™ ELISA plates at 1 µg/mL in PBS, 100 µL/well, overnight at 4° C. Plate wells were washed three times with 300 µL PBS containing 0.05% Tween 20 (PBST), blocked for 1 hour at room temperature with 250 µL PBS containing 1% BSA and washed again. Serum from representative mouse #1189 was diluted in PBST and allowed to bind for 1 hour at room temperature, then washed three times in PBST. An HRP-labeled goat anti-mouse IgG Fc antibody was then applied (100 µL/well), allowed to bind for 1 hour at room temperature, and then washed three times with PBST. TMB substrate (ThermoFisher) (100 µL/well) was then applied and incubated for 5 minutes at room temperature. The reaction was then stopped with 1N $H_2SO_4$ (50 µL/well). The plate was read for optical density at 450 nM with a Biotek™ ELISA plate reader. The results from the serum from a representative mouse (mouse #1189) are shown in FIG. 9.

Figure 9:
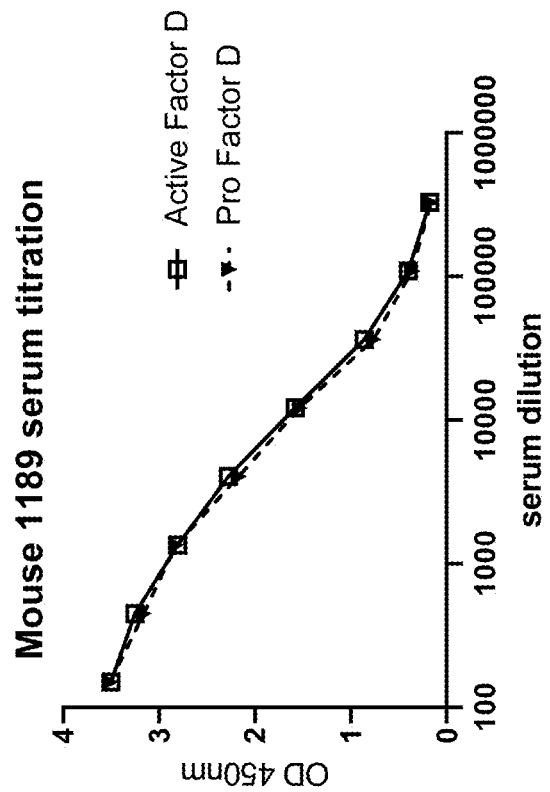
FIG. 9 graphically illustrates a titration of the serum of a representative mouse #1189 after immunization with human mature Factor D in the presence of recombinant mature Factor D or recombinant pro-Factor D.

Results:

FIG. 9 graphically illustrates a titration of the serum of a representative mouse #1189 after immunization with human mature Factor D in the presence of recombinant mature Factor D or recombinant pro-Factor D. As shown in FIG. 9, the serum from representative mouse #1189 contains antibodies capable of binding to both mature Factor D and pro-Factor D. Based on these results, mouse #1189 was selected for hybridoma fusion which was carried out as follows.

A final injection of 50 µg total protein in 50 µL was delivered subcutaneously to mouse #1189 four days prior to hybridoma fusion. Three days prior to the fusion, mouse #1189 was treated subcutaneously with 50 µg of an anti-CD40 agonizing antibody in PBS (R&D Systems, Minneapolis, MN) to increase B cells numbers (see Rycyzyn et al., Hybridoma 27:25-30, 2008). The mouse was sacrificed, and the spleen cells were harvested and fused to a selected murine myeloma cell line P3/NSI/1-AG4-1 (NS-1) (ATCC No. TIB18) using 50% polyethylene glycol or 50% polyethylene glycol plus 10% DMSO. The fusions generated hybridoma cells which were plated in 96 well Nunc tissue culture treated plates containing HAT (hypoxanthine, aminopterin and thymidine) medium to inhibit proliferation of non-fused cells, myeloma hybrids and spleen hybrids. Hybridoma wells were fed by replacement of 80% of media with fresh medium containing HAT supplement.

After hybridoma selection, the culture supernatants were assayed for binding to recombinant human pro-factor D and mature factor D as follows.

Hybridoma Screening

Hybridoma supernatants were first screened for binding to immobilized recombinant human mature Factor D-Streptavidin. 54 hybridomas were identified and were then tested for their ability to bind to recombinant human pro-Factor D-Strep when captured by a polyclonal goat anti-human factor D antibody AF1824 (R&D Systems) as follows. Hybridoma supernatants were diluted two-fold in PBS, 0.05% Tween 20 (PBST). Supernatant from NS-1 myeloma cell line (NS-1 sup) was included as a control. ELISA plates were coated with polyclonal anti-human factor D antibody AF1824. Out of 54 hybridomas tested, the supernatants from 5 hybridomas (3C5, 30H2, 11H1, 12H10 and 7H2) showed equal binding affinity to recombinant human pro-factor D and recombinant human mature Factor D and were selected for DNA cloning and recombinant antibody production, as further described in Example 5.

Example 5

This Example describes the cloning and sequence analysis of anti-human Factor D antibodies that bind to both pro-Factor D and mature-Factor D.

Background/Rationale:

This Example describes the cloning and sequence analysis of antibodies produced by the hybridomas selected for the ability to detect both mature- and pro-Factor D proteins (i.e., clones 3C5, 30H2, 11H1, 12H10 and 7H2 that bind to an epitope of Factor D that is common to both mature and pro-Factor D proteins) that were generated as described in Example 4.

Methods:

Cloning and Purification of Recombinant Antibodies:

Hybridoma clones 3C5, 30H2, 11H1, 12H10 and 7H2 were generated and selected for the ability to detect both mature- and pro-Factor D proteins as described in Example 4. These hybridomas were subcloned by serial dilution methods. The heavy chain and light chain variable regions were cloned using RT-PCR and were sequenced. Antibody-encoding sequences were amplified from total RNA with isotype-specific reverse primers using the SMARTer™ RACE 5'/3' kit (Takara Bio). After verifying the sequences, the variable (V) regions were re-amplified with designed cloning primers and cloned into expression vectors carrying either the human IgG4 heavy chain (SEQ ID NO:71) and kappa light chain (SEQ ID NO:72) constant regions or the mouse IgG2a (SEQ ID NO:218) and kappa light chain (SEQ ID NO:219) constant regions using the In-Fusion HD™ cloning kit (Clontech). The expression constructs were co-transfected transiently into Expi293 cells (Life Technologies), and after 5 days of culture, secreted recombinant antibodies were purified from supernatants by protein A chromatography.

The sequences of the heavy chain variable regions and light chain variable regions are shown in FIGS. 10A and 10B, respectively ("SIN"="SEQ ID NO:" in FIG. 10A and FIG. 10B), and are included below. The complementarity determining regions (CDRs) and framework regions (FRs) of each are provided in TABLES 12-13 below.

Anti-Human Factor D (C-Term) Antibody Heavy Chain Variable Regions

FIG. 10A shows an amino acid alignment of the heavy chain variable region (VH) sequences for the anti-human Factor D clones: 3C5_VH (SEQ ID NO:85), 30H2_VH (SEQ ID NO:85), 11H1_VH (SEQ ID NO:86), 12H10_VH (SEQ ID NO:87), and 7H2_VH (SEQ ID NO:88).

Presented below is the heavy chain variable region (VH) sequence for each anti-human factor-D antibody. The Kabat CDRs are underlined.

3C5_VH:
SEQ ID NO: 85
EVKLVESGGGLVQPGGSLKLSCATSGFTFSDYGMAWVRQAPGKGPEWVA
FISNLAYSFYYVDIVMGRFTISRENAKNTLYLEMSSLRSEDTAMYYCAR
VGLYGNFFMDYWGQGTSVTVSS

30H2_VH:
SEQ ID NO: 85
EVKLVESGGGLVQPGGSLKLSCATSGFTFSDYGMAWVRQAPGKGPEWVA
FISNLAYSFYYVDIVMGRFTISRENAKNTLYLEMSSLRSEDTAMYYCAR
VGLYGNFFMDYWGQGTSVTVSS

11H1_VH:
SEQ ID NO: 86
EVQLVESGGGLVQPKGSLKLSCAASGFSFNTYAMNWVRQAPGKGLEWVA
RIRSKSNNYATHYADSVKDRFTISRDDSESMLYLQMNNLKTEDTAMYYC
VRQGYYWYFDVWGTGTTVTVSS

12H10_VH:
SEQ ID NO: 87
EVQLVESGGGLVQPKGSLKLSCAASGFSFNTYAMNWVRQAPGKGLEWVA
RIRSKSNNYATYYADSVKDRFTISRDDSESMLYLQMNNLKTEDTAMYYC
VRHGYYWYFDVWGTGTTVTVSS

7H2_VH:
SEQ ID NO: 88
EVQVVESGGGLVRPKGSLKLSCAASGFSFNTYAMNWVRQAPGKGLEWVA
RIRSKSNNYATYYADSVKDRFTISRDDSESMLSLQMNNLKTEDTAMYYC
VRQGYYWYFDVWGTGTTVTVSS

TABLE 12 anti-human Factor D (C-term) Antibody VH Sequences (CDRs and FR regions, Kabat)

| Antibody | HC FR1 | HC CDR1 |
|---|---|---|
| 3C5 | EVKLVESGGGLVQPG GSLKLSCATSGFTFS (SEQ ID NO: 94) | DYGMA (SEQ ID NO: 95) |
| 30H2 | EVKLVESGGGLVQPG GSLKLSCATSGFTFS (SEQ ID NO: 94) | DYGMA (SEQ ID NO: 95) |
| 11H1 | EVQLVESGGGLVQPK GSLKLSCAASGFSFN (SEQ ID NO: 100) | TYAMN (SEQ ID NO: 101) |
| 12H10 | EVQLVESGGGLVQPK GSLKLSCAASGFSFN (SEQ ID NO: 100) | TYAMN (SEQ ID NO: 101) |
| 7H2 | EVQVVESGGGLVRPK GSLKLSCAASGFSFN (SEQ ID NO: 109) | TYAMN (SEQ ID NO: 101) |

| Antibody | HC FR2 | HC CDR2 |
|---|---|---|
| 3C5 | WVRQAPGKGPEWVA (SEQ ID NO: 96) | FISNLAYSFYYVDIVMG (SEQ ID NO: 97) |
| 30H2 | WVRQAPGKGPEWVA (SEQ ID NO: 96) | FISNLAYSFYYVDIVMG (SEQ ID NO: 97) |
| 11H1 | WVRQAPGKGLEWVA (SEQ ID NO: 102) | RIRSKSNNYATHYADSVKD (SEQ ID NO: 103) |
| 12H10 | WVRQAPGKGLEWVA (SEQ ID NO: 102) | RIRSKSNNYATYYADSVKD (SEQ ID NO: 107) |
| 7H2 | WVRQAPGKGLEWVA (SEQ ID NO: 102) | RIRSKSNNYATYYADSVKD (SEQ ID NO: 107) |

| Antibody | HC FR3 | HC CDR3 |
|---|---|---|
| 3C5 | RFTISRENAKNTLYLE MSSLRSEDTAMYYCAR (SEQ ID NO: 98) | VGLYGNFFMDY (SEQ ID NO: 99) |
| 30H2 | RFTISRENAKNTLYLE MSSLRSEDTAMYYCAR (SEQ ID NO: 98) | VGLYGNFFMDY (SEQ ID NO: 99) |
| 11H1 | RFTISRDDSESMLYLQ MNNLKTEDTAMYYCVR (SEQ ID NO: 104) | QGYYWYFDV (SEQ ID NO: 105) |
| 12H10 | RFTISRDDSESMLYLQ MNNLKTEDTAMYYCVR (SEQ ID NO: 104) | HGYYWYFDV (SEQ ID NO: 108) |
| 7H2 | RFTISRDDSESMLSLQ MNNLKTEDTAMYYCVR (SEQ ID NO: 246) | QGYYWYFDV (SEQ ID NO: 105) |

TABLE 12-continued anti-human Factor D (C-term) Antibody VH Sequences (CDRs and FR regions, Kabat)

| Antibody | HC FR4 |
|---|---|
| 3C5 | WGQGTSVTVSS (SEQ ID NO: 30) |
| 30H2 | WGQGTSVTVSS (SEQ ID NO: 30) |
| 11H1 | WGTGTTVTVSS (SEQ ID NO: 106) |
| 12H10 | WGTGTTVTVSS (SEQ ID NO: 106) |
| 7H2 | WGTGTTVTVSS (SEQ ID NO: 106) |

Anti-Human Factor D Antibody Light Chain Variable Regions:

FIG. 10B shows an amino acid alignment of the light chain variable region (VL) sequences for the anti-human Factor D clones: 3C5_VL (SEQ ID NO:89), 30H2_VL (SEQ ID NO:90), 11H1_VL (SEQ ID NO:91), 12H10_VL (SEQ ID NO:92) and 7H2_VL (SEQ ID NO:93).

Presented below are the light chain variable region (VL) sequences for the anti-human Factor D antibodies. The Kabat CDRs are underlined. These regions are the same whether numbered by the Kabat or Chothia system.

3C5_VL:
SEQ ID NO: 89
DIQMNQSPSSLSASLGDTITITCHASQNINVWLSWYQQKPGNIPELLIYKASNLHTGVPSRFSGNRSGTSFTLTISSLQPEDIGTYFCQQGQSYPLTFGAGTKLELRR

30H2_VL:
SEQ ID NO: 90
DIQMNQSPSSLSASLGDTITITCHASQNINVWLSWYQQKPGNIPELLIYKASNLHTGVPSRFSGNRSGTSFTLTISSLQPEDIGTYFCQQGQSYPLTFGAGTKLEIKR

11H1_VL:
SEQ ID NO: 91
DVLMTQTPLSLPVSLGDQASISCRSSQSIVHSNGNTYLEWYLQKPGQSPKLLIYTVSNRFSGVPDRFSGSGSGTDFTLKISRVEAEDLGVYYCFQGSHVPWTFGGGTKLEIKR

12H10_VL:
SEQ ID NO: 92
DVLMTQTPLSLPVSLGDQASISCRSSQSIVHSDGNTYLEWYLQKPGQSPKLLIYRVSNRFSGVPDRFSGSGSGTDFTLKISRVEAEDLGVYYCFQGSHVPYTFGGGTKLEIKR

7H2_VL:
SEQ ID NO: 93
DVLMTQTPLSLPVSLGDQASISCRSSQSIVHSNGNTYLEWYLQKPGQSPKLLIYTVSNRFSGVPDRFRGSGSGTDFTLKISRVEAEDLGVYYCFQGSHVPWTFGGGTKLEIKR

TABLE 13 anti-human Factor D (C-term) Antibody VL Sequences (CDRs and FR regions, Kabat and Chothia)

| Antibody | LC FR1 | LC CDR1 |
|---|---|---|
| 3C5 | DIQMNQSPSSLSASLGDTITITC (SEQ ID NO: 110) | HASQNINVWLS (SEQ ID NO: 111) |
| 30H2 | DIQMNQSPSSLSASLGDTITITC (SEQ ID NO: 110) | HASQNINVWLS (SEQ ID NO: 111) |
| 11H1 | DVLMTQTPLSLPVSLGDQASISC (SEQ ID NO: 118) | RSSQSIVHSNGNTYLE (SEQ ID NO: 60) |
| 12H10 | DVLMTQTPLSLPVSLGDQASISC (SEQ ID NO: 118) | RSSQSIVHSDGNTYLE (SEQ ID NO: 123) |
| 7H2 | DVLMTQTPLSLPVSLGDQASISC (SEQ ID NO: 118) | RSSQSIVHSNGNTYLE (SEQ ID NO: 60) |
| Antibody | LC FR2 | LC CDR2 |
| 3C5 | WYQQKPGNIPELLIY (SEQ ID NO: 112) | KASNLHT (SEQ ID NO: 113) |
| 30H2 | WYQQKPGNIPELLIY (SEQ ID NO: 112) | KASNLHT (SEQ ID NO: 113) |
| 11H1 | WYLQKPGQSPKLLIY (SEQ ID NO: 51) | TVSNRFS (SEQ ID NO: 119) |
| 12H10 | WYLQKPGQSPKLLIY (SEQ ID NO: 51) | RVSNRFS (SEQ ID NO: 124) |
| 7H2 | WYLQKPGQSPKLLIY (SEQ ID NO: 51) | TVSNRFS (SEQ ID NO: 119) |
| Antibody | LC FR3 | LC CDR3 |
| 3C5 | GVPSRFSGNRSGTSFT LTISSLQPEDIGTYFC (SEQ ID NO: 114) | QQGQSYPLT (SEQ ID NO: 115) |
| 30H2 | GVPSRFSGNRSGTSFT LTISSLQPEDIGTYFC (SEQ ID NO: 114) | QQGQSYPLT (SEQ ID NO: 115) |
| 11H1 | GVPDRFSGSGSGTDFT LKISRVEAEDLGVYYC (SEQ ID NO: 120) | FQGSHVPWT (SEQ ID NO: 121) |
| 12H10 | GVPDRFSGSGSGTDFT LKISRVEAEDLGVYYC (SEQ ID NO: 120) | FQGSHVPYT (SEQ ID NO: 125) |
| 7H2 | GVPDRFRGSGSGTDFT LKISRVEAEDLGVYYC (SEQ ID NO: 126) | FQGSHVPWT (SEQ ID NO: 121) |
| Antibody | LC FR4 | |
| 3C5 | FGAGTKLELRR (SEQ ID NO: 116) | |
| 30H2 | FGAGTKLEIKR (SEQ ID NO: 117) | |
| 11H1 | FGGGTKLEIKR (SEQ ID NO: 122) | |
| 12H10 | FGGGTKLEIKR (SEQ ID NO: 122) | |
| 7H2 | FGGGTKLEIKR (SEQ ID NO: 122) | |

DNA encoding mouse anti-human Factor D antibodies (that bind to both pro- and mature-Factor D) heavy and light chains:

SEQ ID NO: 127: 3C5_VH
GAGGTGAAGCTGGTGGAGTCTGGGGGAGGCTTAGTGCAGCCTGGAGGGT
CCCTGAAACTCTCCTGTGCAACCTCTGGATTCACTTTCAGTGACTACGGAATGGC
GTGGGTTCGACAGGCTCCAGGGAAGGGGCCTGAGTGGGTAGCATTCATTAGTAA
TTTGGCATATAGTTTCTACTATGTAGACATTGTGATGGGCCGATTCACCATCTCT
AGAGAGAATGCCAAGAACACCCTGTACCTGGAAATGAGCAGTCTGAGGTCTGAG
GACACGGCCATGTATTACTGTGCAAGAGTGGGGCTCTATGGTAACTTTTTTATGG
ACTACTGGGGTCAAGGAACCTCAGTCACCGTCTCCTCA

SEQ ID NO: 127: 30H2_VH
GAGGTGAAGCTGGTGGAGTCTGGGGGAGGCTTAGTGCAGCCTGGAGGGT
CCCTGAAACTCTCCTGTGCAACCTCTGGATTCACTTTCAGTGACTACGGAATGGC
GTGGGTTCGACAGGCTCCAGGGAAGGGGCCTGAGTGGGTAGCATTCATTAGTAA
TTTGGCATATAGTTTCTACTATGTAGACATTGTGATGGGCCGATTCACCATCTCT
AGAGAGAATGCCAAGAACACCCTGTACCTGGAAATGAGCAGTCTGAGGTCTGAG
GACACGGCCATGTATTACTGTGCAAGAGTGGGGCTCTATGGTAACTTTTTTATGG
ACTACTGGGGTCAAGGAACCTCAGTCACCGTCTCCTCA

SEQ ID NO: 128: 11H1_VH
GAGGTGCAGCTTGTTGAGTCTGGTGGAGGATTGGTGCAGCCTAAAGGGTC
ATTGAAACTCTCATGTGCAGCCTCTGGATTCAGCTTCAATACCTACGCCATGAAC
TGGGTCCGCCAGGCTCCAGGAAAGGGTTTGGAATGGGTTGCTCGCATAAGAAGT
AAAAGTAATAATTATGCAACACATTATGCCGATTCAGTGAAAGACAGATTCACC
ATCTCCAGAGATGATTCAGAAAGCATGCTCTATCTGCAAATGAACAACTTGAAA
ACTGAGGACACAGCCATGTATTACTGTGTGAGACAGGGTTACTACTGGTACTTC
GATGTCTGGGGCACAGGGACCACGGTCACCGTCTCCTCA

SEQ ID NO: 129: 12H10_VH
GAGGTGCAGCTTGTTGAGTCTGGTGGAGGATTGGTGCAGCCTAAAGGGTC
ATTGAAACTCTCATGTGCAGCCTCTGGATTCAGCTTCAATACCTACGCCATGAAC
TGGGTCCGCCAGGCTCCAGGAAAGGGTTTGGAATGGGTTGCTCGCATAAGAAGT
AAAAGTAATAATTATGCAACATATTATGCCGATTCAGTGAAAGACAGATTCACC
ATCTCCAGAGATGATTCAGAAAGCATGCTCTATCTGCAAATGAACAACTTGAAA
ACTGAGGACACAGCCATGTATTACTGTGTGAGACATGGTTACTACTGGTACTTCG
ATGTCTGGGGCACAGGGACCACGGTCACCGTCTCCTCA

SEQ ID NO: 130: 7H2_VH
GAGGTGCAGGTTGTTGAGTCTGGTGGAGGATTGGTGCGGCCTAAAGGGTC
ATTGAAACTCTCATGTGCAGCCTCTGGATTCAGCTTCAATACCTACGCCATGAAC
TGGGTCCGCCAGGCTCCAGGAAAGGGTTTGGAATGGGTTGCTCGCATAAGAAGT
AAAAGTAATAATTATGCAACATATTATGCCGATTCAGTGAAAGACAGATTCACC
ATCTCCAGAGATGATTCAGAAAGCATGCTCTCTCTGCAAATGAACAACTTGAAA
ACTGAGGACACAGCCATGTATTACTGTGTGAGACAGGGTTACTACTGGTACTTC
GATGTCTGGGGCACAGGGACCACGGTCACCGTCTCCTCA

SEQ ID NO: 131: 3C5_VL
GACATCCAGATGAACCAGTCTCCATCCAGTCTGTCTGCATCCCTTGGAGA
CACAATTACCATCACTTGCCATGCCAGTCAGAACATTAATGTTTGGTTAAGCTGG
TACCAGCAGAAACCAGGAAATATTCCTGAACTTTTGATCTATAAGGCTTCCAACT
TGCACACAGGCGTCCCTTCTAGGTTTAGTGGCAATAGATCTGGAACAAGTTTCAC
ATTAACCATCAGCAGCCTGCAGCCTGAAGACATTGGCACTTACTTCTGTCAACAG
GGTCAAAGTTATCCGCTCACGTTCGGTGCTGGGACCAAGCTGGAGCTGAGACGG

SEQ ID NO: 132: 30H2_VL
GACATCCAGATGAACCAGTCTCCATCCAGTCTGTCTGCATCCCTTGGAGA
CACAATTACCATCACTTGCCATGCCAGTCAGAACATTAATGTTTGGTTAAGCTGG
TACCAGCAGAAACCAGGAAATATTCCTGAACTTTTGATCTATAAGGCTTCCAACT
TGCACACAGGCGTCCCTTCTAGGTTTAGTGGCAATAGATCTGGAACAAGTTTCAC
ATTAACCATCAGCAGCCTGCAGCCTGAAGACATTGGCACTTACTTCTGTCAACAG
GGTCAAAGTTATCCGCTCACGTTCGGTGCGGGGACCAAGCTGGAAATAAAACGG

SEQ ID NO: 133: 11H1_VL
GATGTTTTGATGACCCAAACTCCACTCTCCCTGCCTGTCAGTCTTGGAGAT
CAAGCCTCCATCTCTTGCAGATCTAGTCAGAGCATTGTACATAGTAATGGAAAC
ACCTATTTAGAATGGTACCTGCAGAAACCAGGCCAGTCTCCAAAGCTCCTGATCT
ACACAGTTTCCAACCGATTTTCTGGGGTCCCAGACAGGTTCAGTGGCAGTGGATC
AGGGACAGATTTCACACTCAAGATCAGCAGAGTGGAGGCTGAGGATCTGGGAGT
TTATTACTGCTTTCAAGGTTCACATGTTCCGTGGACGTTCGGTGGAGGCACCAAG
CTGGAAATCAAACGG

SEQ ID NO: 134: 12H10_VL
GATGTTTTGATGACCCAAACTCCACTCTCCCTGCCTGTCAGTCTTGGAGAT
CAAGCCTCCATCTCTTGCAGATCTAGTCAGAGCATTGTACATAGTGATGAAAC
ACCTATTTAGAATGGTACCTGCAGAAACCAGGCCAGTCTCCAAAGCTCCTGATCT
ACACAGTTTCCAACCGATTTTCTGGGGTCCCAGACAGGTTCAGTGGCAGTGGAT
CAGGGACAGATTTCACACTCAAGATCAGCAGAGTGGAGGCTGAGGATCTGGGA
GTTTATTACTGCTTTCAAGGTTCACATGTTCCGTACACGTTCGGAGGAGGCACCA
AGCTGGAAATCAAACGG

-continued

```
SEQ ID NO: 135: 7H2_VL
GATGTTTTGATGACCCAAACTCCACTCTCCCTGCCTGTCAGTCTTGGAGAT
CAAGCCTCCATCTCTTGCAGATCTAGTCAGAGCATTGTACATAGTAATGGAAAC
ACCTATTTAGAATGGTACCTGCAGAAACCAGGCCAGTCTCCAAAGCTCCTGATCT
ACACAGTTTCCAACCGATTTTCTGGGGTCCCAGACAGGTTCCGTGGCAGTGGATC
AGGGACAGATTTCACACTCAAGATCAGCAGAGTGGAGGCTGAGGATCTGGGAGT
TTATTACTGCTTTCAAGGTTCACATGTTCCGTGGACGTTCGGTGGAGGCACCAAG
CTGGAAATCAAACGG
```

Binding Titers of Anti-Human Factor D Antibodies

Recombinant purified monoclonal antibody IgG2a Fc clones 3C5, 30H2, 11H1, 12H10 and 7H2 were analyzed in a binding assay for the ability to bind to human mature Factor D and human pro-Factor D as follows:

The candidate antibodies were titrated starting at 3 µg/mL antibody binding to 1 µg/mL plate-immobilized recombinant human mature Factor D-His or recombinant human Pro-Factor D-His proteins. Bound antibodies were detected by a labeled goat polyclonal antibody specific for mouse IgG Fc (Jackson ImmunoResearch). The results of representative antibodies 3C5 and 12H10 are shown in FIGS. 11A and 11B, respectively.

Figures 11A, 11B:
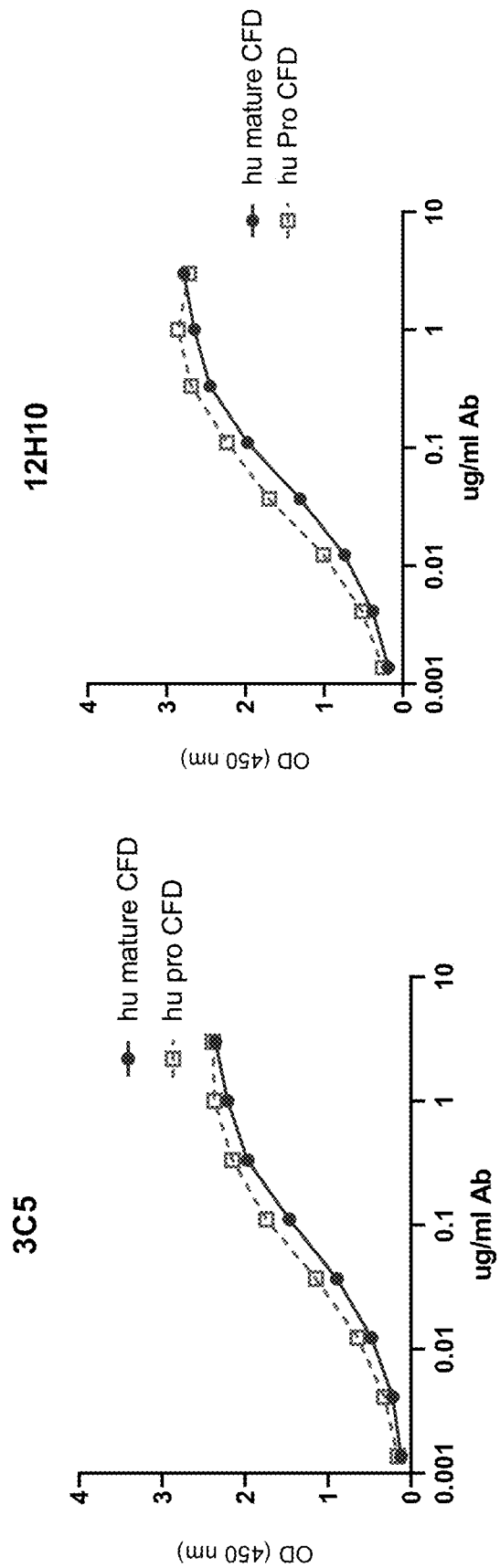
FIG. 11A graphically illustrates the binding of recombinant human pro-Factor D or mature-Factor D with candidate anti-human Factor D antibody 3C5, demonstrating that antibody 3C5 binds to both human pro-Factor D and mature-Factor D, as described in Example 5.
FIG. 11B graphically illustrates the binding of recombinant human pro-Factor D or mature-Factor D with candidate anti-human Factor D antibody 12H10, demonstrating that antibody 12H10 binds to both human pro-Factor D and mature-Factor D, as described in Example 5.

FIG. 11A graphically illustrates the binding of recombinant human pro-Factor D or mature-Factor D with candidate anti-human Factor D antibody 3C5, demonstrating that antibody 3C5 binds to both human pro-Factor D and mature-Factor D.

FIG. 11B graphically illustrates the binding of recombinant human pro-Factor D or mature-Factor D with candidate anti-human Factor D antibody 12H10, demonstrating that antibody 12H10 binds to both human pro-Factor D and mature-Factor D.

Example 6

This Example describes the development of an ELISA assay capable of detecting the presence and amount of mature-Factor D in human and cynomolgus monkey serum.
Background/Rationale:

Purified, recombinant antibodies were generated against a unique N-terminal epitope "ILGGREA" (SEQ ID NO:5) present on both mature human Factor D and mature cynomolgus monkey Factor D as described in Examples 1-3 herein. As described in Examples 4 and 5 herein, purified recombinant antibodies were also generated against mature Factor D which were selected for the ability to detect both pro-Factor D and mature Factor D (i.e., bind to an epitope common to the mature and pro forms of Factor D) are were determined to be suitable for use in an immunoassay. This Example describes the analysis of several representative anti-Factor D antibodies (3C5, 12H10 and others) as coating antibodies in combination with a representative anti-human mature factor D-specific antibody 14A11 in an ELISA assay.
Methods:
1. Testing the Use of Anti-Human Factor D Antibodies 3C5, 11H1, 12H10 and 30H2 for Use as Coating Antibodies in an ELISA Assay with Detection by Anti-Human Mature Factor D-Specific mAb 14A11

Human IgG4 Fc recombinant purified anti-Factor D antibodies (3C5, 11H1, 12H10 and 30H2) were coated onto ELISA plates and allowed to capture recombinant human and cynomolgus mature and pro-Factor D (huMat CFD, cy Mat CFD, huProCFD and cyPro CFD). Also captured was Factor D-depleted human serum (CFD Dpl serum) and a sample of pooled normal cynomolgus plasma (NCP). Captured Factor D was detected with a mouse IgG2a Fc version of anti-human mature Factor D-specific mAb 14A11. An HRP-labeled F(ab')2 fragment donkey anti-mouse IgG H&L antibody (Jackson ImmunoResearch) was used to signal the detection antibody, followed by development with TMB substrate (ThermoFisher).

Figure 12B:
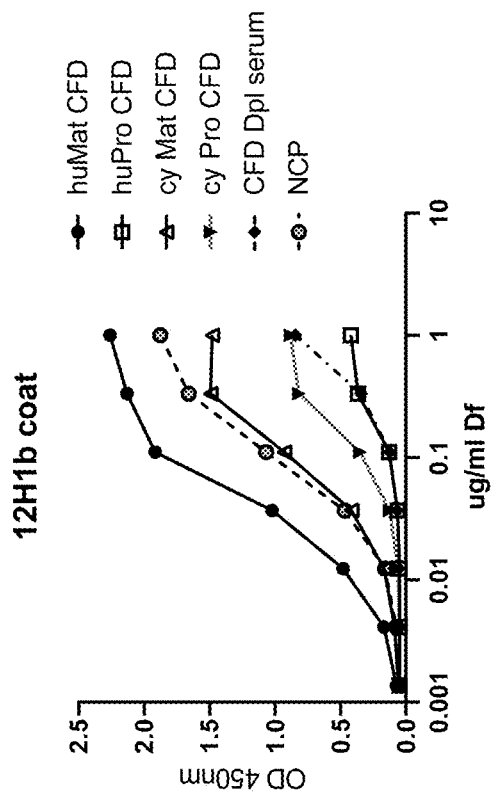
FIG. 12B graphically illustrates the results of an ELISA assay in which the recombinant anti-Factor D antibody 12H10 was coated onto the ELISA plate and allowed to capture recombinant human and cynomolgus mature and pro-Factor D (huMat CFD, cy Mat CFD, huProCFD and cyPro CFD). Also captured was Factor D-depleted human serum (CFD Dpl serum) and a sample of pooled normal cynomolgus plasma (NCP). Detection of captured Factor D was done with a mouse IgG2a Fc version of anti-human mature Factor D-specific mAb 14A11, as described in Example 6.
Figure 12A:
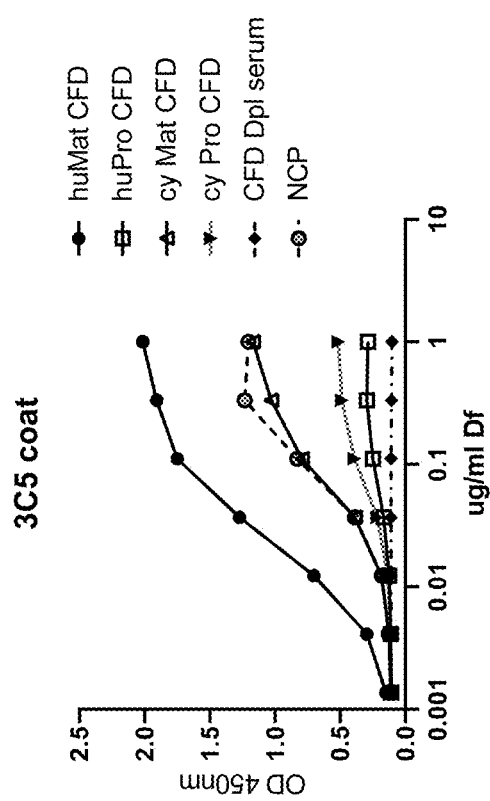
FIG. 12A graphically illustrates the results of an ELISA assay in which the recombinant anti-Factor D antibody 3C5 was coated onto the ELISA plate and allowed to capture recombinant human and cynomolgus mature and pro-Factor D (huMat CFD, cy Mat CFD, huProCFD and cyPro CFD). Also captured was Factor D-depleted human serum (CFD Dpl serum) and a sample of pooled normal cynomolgus plasma (NCP). Detection of captured Factor D was done with a mouse IgG2a Fc version of anti-human mature Factor D-specific mAb 14A11, as described in Example 6.

The results of the ELISA assay with representative antibodies 3C5 and 12H10 are shown in FIGS. 12A and 12B, respectively.
Results:

FIG. 12A graphically illustrates the results of an ELISA assay in which the recombinant anti-Factor D antibody 3C5 was coated onto the ELISA plate and allowed to capture recombinant human and cynomolgus mature and pro-Factor D (huMat CFD, cy Mat CFD, huProCFD and cyPro CFD). Also captured was Factor D-depleted human serum (CFD Dpl serum) and a sample of pooled normal cynomolgus plasma (NCP). Captured Factor D was detected with a mouse IgG2a Fc version of anti-human mature Factor D-specific mAb 14A11.

FIG. 12B graphically illustrates the results of an ELISA assay in which the recombinant anti-Factor D antibody 12H10 was coated onto the ELISA plate and allowed to capture recombinant human and cynomolgus mature and pro-Factor D (huMat CFD, cy Mat CFD, huProCFD and cyPro CFD). Also captured was Factor D-depleted human serum (CFD Dpl serum) and a sample of pooled normal cynomolgus plasma (NCP). Capture Factor D was detected with a mouse IgG2a Fc version of anti-human mature Factor D-specific mAb 14A11.

As shown in FIGS. 12A and 12B, both anti-Factor D antibodies 3C5 and 12H10 are suitable for use as coating antibodies in combination with the anti-human mature-Factor D-specific antibody 14A11 in an ELISA assay for detecting mature Factor D in human and cynomolgus plasma.

2. ELISA Assay to Detect Mature Factor D with a Combination of Coating Antibody 3C5 (Anti-Human/Cyno Factor D) and Detection Antibody 14A11 (Anti-Human/Cyno Mature-Factor D-Specific)
Methods:

Human IgG4 Fc recombinant purified antibody 3C5 was coated onto an ELISA plate and was tested with the following samples (3-fold serial dilutions):

1: Cynomolgus recombinant mature Factor D (cy Mat CFD, 1 µg/mL to 1.4 pg/mL)

2: Human recombinant mature Factor D (hu Mat CFD 1 µg/mL to 1.4 pg/mL)

3: Cynomolgus recombinant Pro-Factor D (cy Pro CFD 1 µg/mL to 1.4 pg/mL)

4: Human recombinant Pro-Factor D (hu Pro CFD 1 µg/mL to 1.4 pg/mL)

5: Purified (from human plasma) human Factor D (CFD) (1 µg/mL to 1.4 pg/mL)

6: Human Factor D-depleted serum (CFD-Dpl serum, 50% to 0.07%)

7: Normal human serum (NHS, 50% to 0.07%)

8: Serum from a human 3MC patient (3MC, 25% to 0.03%)

Captured Factor D was detected with a mouse IgG2a Fc version of anti-human mature Factor D-specific mAb 14A11. An HRP-labeled F(ab')2 fragment donkey anti-mouse IgG H&L antibody (Jackson ImmunoResearch) was used to signal the detection antibody, followed by development with TMB substrate (ThermoFisher).

Micro-titer ELISA plates (Maxisorb, Nunc), were coated with antibody clone 3C5 at a concentration of 3 µg/mL using coating buffer (PBS: 1.06 mM potassium phosphate monobasic $KH_2PO_4$, 155 mM sodium chloride NaCl, 8.97 mM sodium phosphate dibasic $NaZHPO_4$-$7H_2O$, pH7.4 (ThermoFisher). The plate was incubated overnight at 4° C. The next day, the plate was washed 3 times with PBS buffer with 0.05% and Tween20 (PBST). Residual protein binding sites were blocked by adding 250 µL of 1% bovine serum albumen (BSA) in PBST (PBST-BSA) to each well in the plate and incubated at room temperature for 1 hour. The plates were then washed three times with PBST buffer. 3-fold Serial dilutions of samples #1-6 in a concentration range as shown above were added to the plates and incubated for one hour at room temperature. Wells were then washed three times. 100 µL of antibody clone 14A11 (diluted to 3 µg/mL in PBST-BSA) was then added to each well and incubated for one hour at room temperature. The plates were washed three times. 100 µL of Horseradish Peroxidase labeled F(ab')2 Fragment Donkey anti-Mouse IgG H&L antibody (Jackson ImmunoResearch), diluted 1:30,000, was added to each well and incubated for one hour at room temperature. Wells were then washed three times. 100 µL of room temperature TMB substrate solution (ThermoFisher) was then added and incubated at room temperature for 5 minutes. 50 µL of 1N $H_2SO_4$ was added to stop the reaction. The absorbance was measured at 450 nm using Biotek Synergy HT ELISA micro-titre plate reader.

Figure 13:
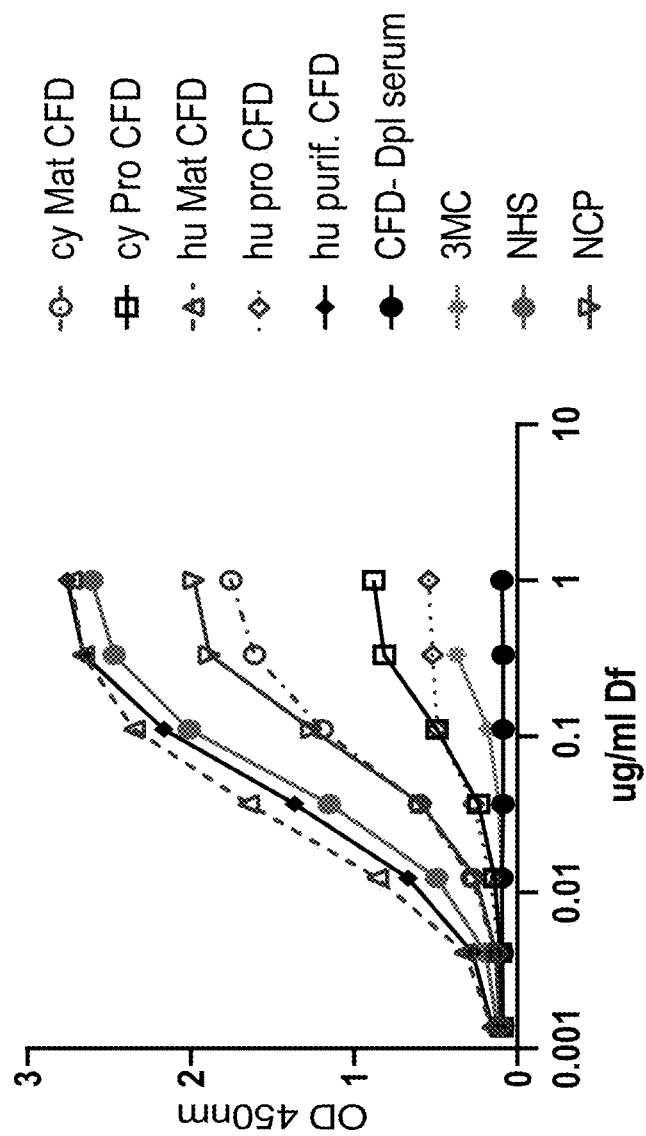
FIG. 13 graphically illustrates the detection of human and cynomolgus monkey mature Factor D and Pro-Factor D with a combination of capture antibody 3C5 (anti-human/cyno Factor D) and detection antibody 14A11 (anti-human/cyno mature-Factor D-specific) in an ELISA assay, as described in Example 6.

Results:

FIG. 13 graphically illustrates the detection of human and cynomolgus monkey mature Factor D and Pro-Factor D with a combination of capture antibody 3C5 (anti-human/cyno Factor D) and detection antibody 14A11 (anti-human/cyno mature-Factor D-specific) in an ELISA assay. As shown in FIG. 13, binding of recombinant human mature factor D (hu Mat CFD), Normal Human Serum (NHS) and purified human complement factor D (hu purif. CFD, Complement Technologies) far exceed binding of recombinant human and cynomolgus pro factor D (hu pro CFD, cy Pro CFD), as well as the plasma from a patient with 3MC syndrome (3MC). Human factor D depleted serum (CFD-Dpl serum) is non-binding. Recombinant cynomolgus mature factor D (cy Mat CFD) and normal cynomolgus plasma (NCP) give less robust readouts than their human corollaries.

Example 7

This Example describes the generation of monoclonal antibodies that specifically bind to human Pro-Factor D Background/Rationale:

This Example describes the generation of anti-human Pro-Factor D-specific antibodies. The antibodies described in this Example specifically bind to human Pro-Factor D and do not bind to human mature Factor D.

Methods:

1. Construction of the Pro-Factor D Antigen

As shown in FIGS. 2 and 3, the pro-peptide of human Factor D is "APPRGR" (SEQ ID NO:4), corresponding to residues 20-25 of human full-length Factor D. A synthetic peptide-KLH conjugate was generated comprising the amino acids 20-25 of human complement Factor D "APPRGR" (SEQ ID NO:4), with the addition of a C-terminal Cysteine to allow for conjugation to KLH by Sulfo-SMCC linkage chemistry.

1. Immunization with the Pro-Factor D Antigen

BALB/c mice were immunized with the synthetic peptide-KLH conjugate comprising the amino acids 20-25 of human complement Factor D "APPRGR" (SEQ ID NO:4), with the addition of a C-terminal Cysteine to allow for conjugation to KLH by Sulfo-SMCC linkage chemistry. The mice were immunized four times, subcutaneously, with 100 to 200 µL of adjuvant emulsions of peptide conjugate (50-100 µg total protein per injection.)

Serum samples from the immunized mice were prepared from retro-orbital bleeds and tested by ELISA assay for the presence of antigen-specific antibodies capable of binding to plate-immobilized recombinant human Pro-Factor D (SEQ ID NO:2) and recombinant human mature Factor D (SEQ ID NO:3) as follows.

Recombinant human Pro-CFD-His or recombinant human mature CFD-His were immobilized on Maxisorp™ ELISA plates at 1 µg/mL in PBS, 100 µL/well, incubated overnight at 4° ° C. Plate wells were then washed three times with 300 µL PBS containing 0.05% Tween 20 (PBST), blocked for 1 hour at room temperature with 250 µL PBS containing 1% BSA and washed again. Serum from mouse #2, taken after the third boost, was diluted in PBST and allowed to bind for 1 hour at room temperature, then washed three times in PBST. An HRP-labeled goat anti-mouse IgG Fc antibody (Jackson ImmunoResearch) was then applied (100 µL/well), allowed to bind for 1 hour at room temperature, and then washed three times with PBST. TMB substrate (Thermo Fisher) (100 µL/well) was then applied and incubated for 5 minutes at room temperature. The reaction was then stopped with 1N $H_2SO_4$ (50 µL/well). The plate was read for optical density at 450 nM with a Biotek™ ELISA plate reader.

Figure 14:
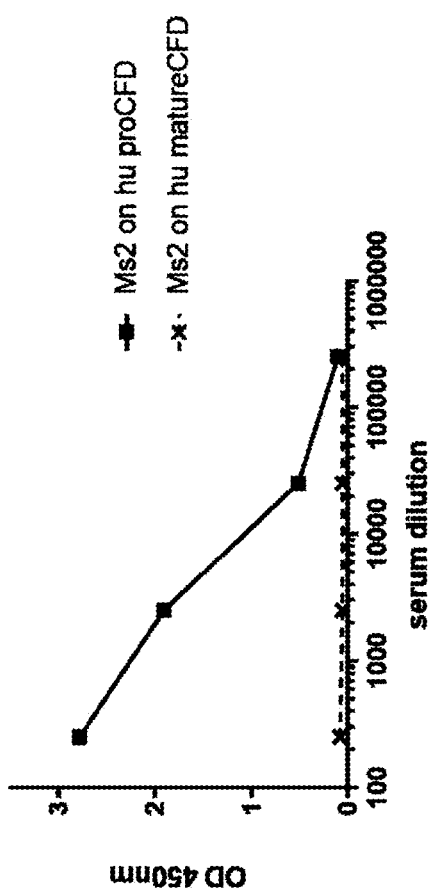
FIG. 14 graphically illustrates a titration of the serum of a representative mouse #2 after immunization with a synthetic peptide corresponding to amino acid residues 26-32 of human complement factor D: "ILGGREA" (SEQ ID NO:5) in the presence of recombinant mature Factor D or recombinant pro-Factor D.

FIG. 14 graphically illustrates a titration of the serum of a representative mouse #2 (Ms2) after immunization with a synthetic peptide comprising "APPRGR" (SEQ ID NO:4) corresponding to amino acid residues 20-25 of human complement factor D in the presence of recombinant mature Factor D (hu mature CFD) or recombinant pro-Factor D (hu proCFD). As shown in FIG. 14, the serum from representative mouse #2 contains antibodies capable of selectively binding to pro-Factor D as compared to mature Factor D.

The mice showing the most favorable binding to pro-Factor D and the least favorable binding to mature-Factor D (i.e., mouse #2) were selected for hybridoma fusion. Three days prior to the fusion, mice were treated subcutaneously with 50 µg of an anti-CD40 agonist mAb in PBS (R&D Systems, Minneapolis, MN) to increase B cells numbers (see Rycyzyn et al., *Hybridoma* 27:25-30, 2008). The mice were sacrificed, and the spleen cells were harvested and fused to a selected murine myeloma cell line P3/NSI/1-AG4-1 (NS-1) (ATCC No. TIB18) using 50% polyethylene glycol or 50% polyethylene glycol plus 10% DMSO. The fusions generated hybridoma cells which were plated in 96 well Nunc tissue culture treated plates containing HAT (hypoxanthine, aminopterin and thymidine) medium to inhibit proliferation of non-fused cells, myeloma hybrids and spleen hybrids. Hybridoma wells were fed by replacement of 80% of media with fresh medium containing HAT supplement. After hybridoma selection, the culture supernatants were assayed for binding to recombinant human Pro-Factor D and mature Factor D as described below.

2. Hybridoma Screening

Hybridoma supernatants were first screening for binding to immobilized recombinant human pro-Factor D. Hybridomas testing positive by ELISA for binding to immobilized recombinant human pro-Factor D-His (n=6) (1F9, 2A4, 13A10, 18F5, 20A1, 21H1) were then tested for binding to recombinant human mature Factor D.

The specificity of anti-human pro-CFD hybridomas were further analyzed as follows. Hybridoma supernatants (18F5, 1F9, 2A4, 20A1, 13A10, 21H1) were tested for their ability to detect recombinant pro-Factor D or mature Factor D when captured by a polyclonal goat anti-human factor D antibody AF1824 (R&D Systems) as follows. ELISA plates were coated with polyclonal anti-human factor D antibody AF1824 (R&D Systems). Hybridoma supernatants were diluted two-fold in PBS, 0.05% Tween 20 (PBST). Control samples included: Control supernatant from a hybridoma known to bind to human MASP3 (aM3 35C1) was similarly diluted. Control samples also included: PBST, 1 µg/ml of Mouse IgG (Jackson Immunoresearch 015-000-003), and 1 µg/ml mouse monoclonal anti-human CFD (R&D Systems MAB1824). Hybridoma supernatants and control samples were allowed to bind to captured pro or mature Factor D for one hour at room temperature. After washing three times with PBST, 100 µL/well of HRP-goat anti-mouse IgG Fc gamma secondary antibody (Jackson ImmunoResearch) diluted in PBST was added and incubated for 1 hour at room temperature. After washing three times with PBST, TMB substrate (ThermoFisher), 100 µL/well, was added. After 4 minutes the reaction was stopped with 50 µL/well of 1N $H_2SO_4$, then read at 450 nm on a Biotek™ ELISA plate reader.

Figure 15:
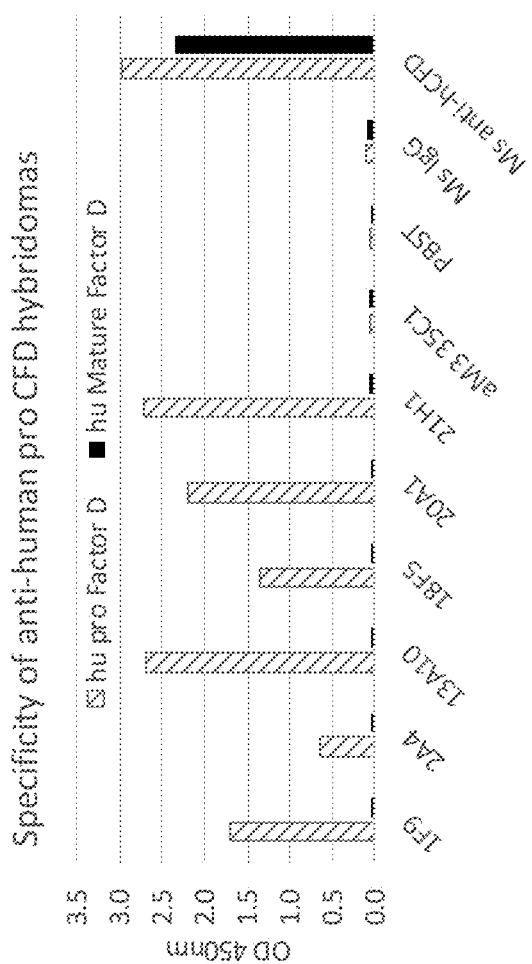
FIG. 15 graphically illustrates the results of a capture ELISA assay in which hybridoma supernatants were screened for binding to human Pro-Factor D or human mature-Factor D when captured by a polyclonal anti-Factor D antibody AF1824 (R&D Systems), as described in Example 7.

FIG. 15 graphically illustrates the results of a capture ELISA assay in which hybridoma supernatants were screened for binding to human pro-Factor D or human mature-Factor D when captured by a polyclonal anti-Factor D antibody AF1824 (R&D Systems).

As shown in FIG. 15, out of 6 hybridomas tested, the supernatants from all 6 hybridomas (18F5, 1F9, 2A4, 20A1, 13A10, 21H1) showed preferential binding to recombinant human pro-Factor D as compared to recombinant human mature-Factor D.

Hybridomas 18F5, 1F9, 2A4, 20A1, 13A10, 21H1 were selected for DNA cloning and recombinant antibody production.

Example 8

This Example describes the cloning and sequence analysis of anti-human pro-Factor D-specific monoclonal antibodies.
Background/Rationale:

This Example describes the cloning and sequence analysis of antibodies produced by the hybridomas showing preferential binding to the pro form of Factor D (i.e., 18F5, 1F9, 2A4, 20A1, 13A10, 21H1) described in Example 7.
Methods:

1. Cloning and Purification of Recombinant Antibodies

Positive hybridomas 18F5, 1F9, 2A4, 20A1, 13A10, 21H1 were generated and identified as described in Example 7. These hybridomas were subcloned by serial dilution methods.

The heavy chain and light chain variable regions were cloned from the hybridomas 18F5, 1F9, 2A4, 20A1, 13A10, 21H1 using RT-PCR and were sequenced. Antibody-encoding sequences were amplified from total RNA with isotype-specific reverse primers using the SMARTer™ RACE 5'/3' kit (Takara Bio). After verifying the sequences, the variable (V) regions were re-amplified with designed cloning primers and cloned into expression vectors carrying either the human IgG4 heavy chain (SEQ ID NO:71) and kappa light chain (SEQ ID NO:72) constant regions or the mouse IgG2a (SEQ ID NO:218) and kappa light chain (SEQ ID NO:219) constant regions using the In-Fusion HD™ cloning kit (Clontech). The expression constructs were co-transfected transiently into Expi293 cells (Life Technologies), and after 5 days of culture, secreted recombinant antibodies were purified from supernatants by protein A chromatography.

The sequences of the heavy chain variable regions and light chain variable regions are shown in FIGS. 16A and 16B, respectively ("SIN"="SEQ ID NO:" in FIG. 16A and FIG. 16B), and are included below. The complementarity regions (CDRs) and framework regions (FRs) of each are provided in TABLES 13-16 below.

Anti-Human Pro-Factor D-Specific Antibody Heavy Chain Variable Region (VH) Sequences FIG. 16A shows an amino acid alignment of the heavy chain variable region (VH) sequences for the anti-human pro-Factor D-specific clones: 18F5_VH (SEQ ID NO:136), 1F9_VH (SEQ ID NO:137), 2A4_VH (SEQ ID NO:138), 20A1_VH (SEQ ID NO:139), 13A10_VH (SEQ ID NO:140) and 21H1_VH (SEQ ID NO:141).

Presented below is the heavy chain variable region (VH) sequence for each anti-human Pro-Factor-D-specific antibody. The Kabat CDRs are underlined.

```
18F5_VH:
                                  SEQ ID NO: 136
EVKLEESGGGLVQPGGSMKLSCVASGFTFGNYWMSWVRQSPEKGLEWVA
EIRLKSDNYATHYAESVKGKFTISRDDSKSRLYLQMNSLRGEDTGLYYC
TNAWFASWGQGTLVTVSA

1F9_VH:
                                  SEQ ID NO: 137
EVKLEESGGGLVQPGGSMKLSCVASGFTFGSYWMSWVRQSPEKGLEWVA
EIRLKSDNYAAHYAESVKGKFTISRDDSKSRLYLQMNSLRGEDTGIYYC
TNAWFASWGQGTLVTVSA

2A4_VH:
                                  SEQ ID NO: 138
EVKLEESGGGLVQPGGSMKLSCVASGFTFSTYWMSWVRQSPEKGLEWVA
EIRLKSDNYATHYTESVKGKFTISRDDSKSRLYLQMNSLRVEDTGIYYC
TNAWFAYWGQGTLVTVSA

20A1_VH:
                                  SEQ ID NO: 139
EVKLEESGGGLVQPGGSMKLSCIASGFTFSTYWMSWVRQSPEKGLEWVA
EIRLKSENYATYYAESVKGKFIISRDDSKSRLYLQMNSLRAEDTGIYYC
TNAWFANWGQGTLVTVSA

13A10_VH:
                                  SEQ ID NO: 140
DVQLQESGPGLVKPSQSLSLTCTVTGYSITSDYAWNWIRQFPGNKLEWM
GYISYIGGIGYNPSLKSRISITRDTSKNQFFLHLNSVTTGDTATYYCAR
NGAMDFWGQGISVTVSS

21H1_VH:
                                  SEQ ID NO: 141
DVQLQESGPGLVKPSQSLSLTCTVTGYSITSDYAWNWIRQFPGNKLEWM
GYISYSGSTGYSPSLKSRISITRDTSKNQFFLHLNSVTTGDTATYYCAR
NGAMDYWGQGISVTVSS
```

TABLE 14 anti-human pro-Factor D-specific Antibody VH Sequences (CDRs and FR regions, Kabat)

| Antibody | HC FR1 | HC CDR1 |
|---|---|---|
| 18F5 | EVKLEESGGGLVQPG GSMKLSCVASGFTFG (SEQ ID NO: 148) | NYWMS (SEQ ID NO: 149) |
| 1F9 | EVKLEESGGGLVQPG GSMKLSCVASGFTFG (SEQ ID NO: 148) | SYWMS (SEQ ID NO: 155) |
| 2A4 | EVKLEESGGGLVQPG GSMKLSCVASGFTFS (SEQ ID NO: 247) | TYWMS (SEQ ID NO: 158) |
| 20A1 | EVKLEESGGGLVQPG GSMKLSCIASGFTFS (SEQ ID NO: 162) | TYWMS (SEQ ID NO: 158) |
| 13A10 | DVQLQESGPGLVKPS QSLSLTCTVTGYSIT (SEQ ID NO: 166) | SDYAWN (SEQ ID NO: 167) |
| 21H1 | DVQLQESGPGLVKPS QSLSLTCTVTGYSIT (SEQ ID NO: 166) | SDYAWN (SEQ ID NO: 167) |

| Antibody | HC FR2 | HC CDR2 |
|---|---|---|
| 18F5 | WVRQSPEKGLEWVA (SEQ ID NO: 150) | EIRLKSDNYATHYAESVKG (SEQ ID NO: 151) |
| 1F9 | WVRQSPEKGLEWVA (SEQ ID NO: 150) | EIRLKSDNYAAHYAESVKG (SEQ ID NO: 156) |
| 2A4 | WVRQSPEKGLEWVA (SEQ ID NO: 150) | EIRLKSDNYATHYTESVKG (SEQ ID NO: 159) |
| 20A1 | WVRQSPEKGLEWVA (SEQ ID NO: 150) | EIRLKSENYATYYAESVKG (SEQ ID NO: 163) |
| 13A10 | WIRQFPGNKLEWMG (SEQ ID NO: 168) | YISYIGGIGYNPSLKS (SEQ ID NO: 169) |
| 21H1 | WIRQFPGNKLEWMG (SEQ ID NO: 168) | YISYSGSTGYSPSLKS (SEQ ID NO: 173) |

| Antibody | HC FR3 | HC CDR3 |
|---|---|---|
| 18F5 | KFTISRDDSKSRLYLQ MNSLRGEDTGLYYCTN (SEQ ID NO: 152) | AWFAS (SEQ ID NO: 153) |
| 1F9 | KFTISRDDSKSRLYLQ MNSLRGEDTGIYYCTN (SEQ ID NO: 157) | AWFAS (SEQ ID NO: 153) |
| 2A4 | KFTISRDDSKSRLYLQ MNSLRVEDTGIYYCTN (SEQ ID NO: 160) | AWFAY (SEQ ID NO: 161) |
| 20A1 | KFIISRDDSKSRLYLQ MNSLRAEDTGIYYCTN (SEQ ID NO: 164) | AWFAN (SEQ ID NO: 165) |
| 13A10 | RISITRDTSKNQFFLH LNSVTTGDTATYYCAR (SEQ ID NO: 170) | NGAMDF (SEQ ID NO: 171) |
| 21H1 | RISITRDTSKNQFFLH LNSVTTGDTATYYCAR (SEQ ID NO: 170) | NGAMDY (SEQ ID NO: 174) |

| Antibody | HC FR4 |
|---|---|
| 18F5 | WGQGTLVTVSA (SEQ ID NO: 154) |
| 1F9 | WGQGTLVTVSA (SEQ ID NO: 154) |
| 2A4 | WGQGTL VTVSA (SEQ ID NO: 154) |
| 20A1 | WGQGTL VTVSA (SEQ ID NO: 154) |
| 13A10 | WGQGISVTVSS (SEQ ID NO: 172) |
| 21H1 | WGQGISVTVSS (SEQ ID NO: 172) |

Anti-Human Pro-Factor D-Specific Antibody Light Chain Variable Region (VL) Sequences FIG. 16B shows an amino acid alignment of the light chain variable region (VL) sequences for the anti-human mature-Factor D-specific clones: 18F5_VL (SEQ ID NO:142), 1F9_VL (SEQ ID NO:143), 2A4_VL (SEQ ID NO:144), 20A1_VL (SEQ ID NO:145), 13A10_VL (SEQ ID NO:146), and 21H1_VL (SEQ ID NO:147).

Presented below is the light chain variable region (VL) sequence for each anti-human pro-factor-D-specific antibody. The Kabat CDRs are underlined. These regions are the same whether numbered by the Kabat or Chothia system.

18F5_VL:
SEQ ID NO: 142
DIVMSQSPSSLAVSVGEKVTMSCMSSQSLLYSKDQKNYLAWYQQKPGQS
PKLLIYWASTRESGVPDRFTGSGSGTDFTLTISSVKAEDLAVYYCLQYY
TYPYTFGGGTKLEIKR

1F9_VL:
SEQ ID NO: 143
DIVMSQSPSSLTVSVGEKVTMSCMSSQSLLYSKDQKNYLAWYQQKPGQS
PTLLIYWASTRESGVPDRFTGSGSGTDFTLTISSVKAEDLAVYYCLQYY
TYPYTFGGGTKLEIKR

2A4_VL:
SEQ ID NO: 144
DIVMSQSPSSLAVSVGEKFTMSCKSSQSLLYSRDQKNYLAWYQQQPGQS
PKLLIYWASTRESGVPDRFTGSGSGTDFTLTISSVKTEDLAVYYCLQYY
SYPYTFGGGTKLEIKR

20A1_VL:
SEQ ID NO: 145
DIVMSQSPSSLVVSVGEKVTMSCKSSQNLLYSRDQKNYLAWYQQKPGQS
PNLLIYWASTRESGVPDRFTGSGSGTDFSLTISSVKAEDLAVYYCLQYY
SYPYTFGGGTKLEMKR

13A10_VL:
SEQ ID NO: 146
DIVLTQSPASLAVSLGQRATISCKASQSVDYDGDSYMNWYQQKPGQPPK
LLIYDASNLESGIPARFSGSGSGTDFTLNIHPVEEEDAATYYCQQSNEA
PWTFGGGTKLEIKR

21H1_VL:
SEQ ID NO: 147
DIVLTQSPASLAVSLGQRATISCKASQSVDYDGDSYMNWYQQKPGQPPK
LLIYDASTLESGIPARFSGSGSGTDFTLNIHPVEEEDAATYYCQQNYEA
PWTFGGGTKLEIKR

TABLE 15 anti-human pro-Factor D-specific Antibody VL Sequences (CDRs and FR regions, Kabat and Chothia)

| Antibody | LC FR1 | LC CDR1 |
|---|---|---|
| 18F5 | DIVMSQSPSSLAVSVGEKVTMSC (SEQ ID NO: 175) | MSSQSLLYSKDQKNYLA (SEQ ID NO: 176) |
| 1F9 | DIVMSQSPSSLTVSVGEKVTMSC (SEQ ID NO: 181) | MSSQSLLYSKDQKNYLA (SEQ ID NO: 176) |
| 2A4 | DIVMSQSPSSLAVSVGEKFTMSC (SEQ ID NO: 183) | KSSQSLLYSRDQKNYLA (SEQ ID NO: 184) |
| 20A1 | DIVMSQSPSSLVVSVGEKVTMSC (SEQ ID NO: 188) | KSSQNLLYSRDQKNYLA (SEQ ID NO: 189) |
| 13A10 | DIVLTQSPASLAVSLGQRATISC (SEQ ID NO: 193) | KASQSVDYDGDSYMN (SEQ ID NO: 194) |
| 21H1 | DIVLTQSPASLAVSLGQRATISC (SEQ ID NO: 193) | KASQSVDYDGDSYMN (SEQ ID NO: 194) |

| Antibody | LC FR2 | LC CDR2 |
|---|---|---|
| 18F5 | WYQQKPGQSPKLLIY (SEQ ID NO: 177) | WASTRES (SEQ ID NO: 178) |
| 1F9 | WYQQKPGQSPTLLIY (SEQ ID NO: 182) | WASTRES (SEQ ID NO: 178) |
| 2A4 | WYQQQPGQSPKLLIY (SEQ ID NO: 185) | WASTRES (SEQ ID NO: 178) |
| 20A1 | WYQQKPGQSPNLLIY (SEQ ID NO: 190) | WASTRES (SEQ ID NO: 178) |
| 13A10 | WYQQKPGQPPKLLIY (SEQ ID NO: 195) | DASNLES (SEQ ID NO: 196) |
| 21H1 | WYQQKPGQPPKLLIY (SEQ ID NO: 195) | DASTLES (SEQ ID NO: 199) |

| Antibody | LC FR3 | LC CDR3 |
|---|---|---|
| 18F5 | GVPDRFTGSGSGTDFTLTISSVKAEDLAVYYC (SEQ ID NO: 179) | LQYYTYPYT (SEQ ID NO: 180) |
| 1F9 | GVPDRFTGSGSGTDFTLTISSVKAEDLAVYYC (SEQ ID NO: 179) | LQYYTYPYT (SEQ ID NO: 180) |
| 2A4 | GVPDRFTGSGSGTDFTLTISSVKTEDLAVYYC (SEQ ID NO: 186) | LQYYSYPYT (SEQ ID NO: 187) |
| 20A1 | GVPDRFTGSGSGTDFSLTISSVKAEDLAVYYC (SEQ ID NO: 191) | LQYYSYPYT (SEQ ID NO: 187) |
| 13A10 | GIPARFSGSGSGTDFTLNIHPVEEEDAATYYC (SEQ ID NO: 197) | QQSNEAPWT (SEQ ID NO: 198) |
| 21H1 | GIPARFSGSGSGTDFTLNIHPVEEEDAATYYC (SEQ ID NO: 197) | QQNYEAPWT (SEQ ID NO: 200) |

| Antibody | LC FR4 |
|---|---|
| 18F5 | FGGGTKLEIKR (SEQ ID NO: 55) |
| 1F9 | FGGGTKLEIKR (SEQ ID NO: 55) |
| 2A4 | FGGGTKLEIKR (SEQ ID NO: 55) |
| 20A1 | FGGGTKLEMKR (SEQ ID NO: 192) |
| 13A10 | FGGGTKLEIKR (SEQ ID NO: 55) |
| 21H1 | FGGGTKLEIKR (SEQ ID NO: 55) |

TABLE 16

Consensus Sequences for anti-human pro-Factor D-specific HC CDRs:

| Antibody | Region | Sequence |
|---|---|---|
| 18F5 | HC-CDR1 | NYWMS (SEQ ID NO: 149) |
| 1F9 | HC-CDR1 | SYWMS (SEQ ID NO: 155) |
| 2A4 | HC-CDR1 | TYWMS (SEQ ID NO: 158) |
| 20A1 | HC-CDR1 | TYWMS (SEQ ID NO: 158) |
| Consensus | HC-CDR1 | XYWMS (SEQ ID NO: 201) Wherein: X at position 1 is N, S or T |
| 18F5 | HC-CDR2 | EIRLKSDNYATHYAESVKG (SEQ ID NO: 151) |
| 1F9 | HC-CDR2 | EIRLKSDNYAAHYAESVKG (SEQ ID NO: 156) |
| 2A4 | HC-CDR2 | EIRLKSDNYATHYTESVKG (SEQ ID NO: 159) |
| 20A1 | HC-CDR2 | EIRLKSENYATYYAESVKG (SEQ ID NO: 163) |
| Consensus | HC-CDR2 | EIRLKSXNYAXXYXESVKG (SEQ ID NO: 202) Wherein: X at position 7 is D or E; X at position 11 is T or A; X at position 12 is H or Y; X at position 14 is A or T |
| 18F5 | HC-CDR3 | AWFAS (SEQ ID NO: 153) |
| 1F9 | HC-CDR3 | AWFAS (SEQ ID NO: 153) |
| 2A4 | HC-CDR3 | AWFAY (SEQ ID NO: 161) |
| 20A1 | HC-CDR3 | AWFAN (SEQ ID NO: 165) |
| Consensus | HC-CDR3 | AWFAX (SEQ ID NO: 203) Wherein X at position 5 is S, Y or N |

TABLE 17

Consensus Sequences for pro-Factor D-specific LC CDRs:

| Antibody | Region | Sequence |
|---|---|---|
| 18F5 | LC-CDR1 | MSSQSLLYSKDQKNYLA (SEQ ID NO: 176) |
| 1F9 | LC-CDR1 | MSSQSLLYSKDQKNYLA (SEQ ID NO: 176) |

TABLE 17-continued

Consensus Sequences for pro-Factor D-specific LC CDRs:

| Antibody | Region | Sequence |
|---|---|---|
| 2A4 | LC-CDR1 | KSSQSLLYSRDQKNYLA (SEQ ID NO: 184) |
| 20A1 | LC-CDR1 | KSSQNLLYSRDQKNYLA (SEQ ID NO: 189) |
| Consensus | LC-CDR1 | XSSQXLLYSXDQKNYLA (SEQ ID NO: 204) Wherein: X at position 1 is M or K; X at position 5 is S or N; X at position 10 is K or R |
| 18F5 | LC-CDR2 | WASTRES (SEQ ID NO: 178) |
| 1F9 | LC-CDR2 | WASTRES (SEQ ID NO: 178) |
| 2A4 | LC-CDR2 | WASTRES (SEQ ID NO: 178) |
| 20A1 | LC-CDR2 | WASTRES (SEQ ID NO: 178) |
| Consensus | LC-CDR2 | WASTRES (SEQ ID NO: 178) |
| 18F5 | LC-CDR3 | LQYYTYPYT (SEQ ID NO: 180) |
| 1F9 | LC-CDR3 | LQYYTYPYT (SEQ ID NO: 180) |
| 2A4 | LC-CDR3 | LQYYSYPYT (SEQ ID NO: 187) |
| 20A1 | LC-CDR3 | LQYYSYPYT (SEQ ID NO: 187) |
| Consensus | LC-CDR3 | LQYYXYPYT (SEQ ID NO: 205) Wherein X at position 5 is T or S |

Nucleic Acid Sequences Encoding Pro-Factor D-Specific Monoclonal Antibodies:

18F5_VH:

SEQ ID NO: 206

```
GAAGTGAAGCTTGAGGAGTCTGGAGGAGGCCTGGTGCAACCTGGAGGAT
CCATGAAACTCTCCTGTGTAGCCTCTGGATTTACTTTCGGTAACTACTGGATGTC
TTGGGTCCGCCAGTCTCCAGAGAAGGGGCTTGAGTGGGTTGCTGAAATTAGATT
GAAATCTGATAATTATGCAACACATTATGCGGAGTCTGTGAAAGGGAAGTTCAC
CATCTCAAGAGATGATTCCAAAAGTCGTCTCTACCTGCAAATGAACAGCTTAAG
AGGTGAAGACACTGGACTTTATTACTGTACGAATGCCTGGTTTGCTTCCTGGGGC
CAAGGGACTCTGGTCACTGTCTCTGCA
```

1F9_VH:

SEQ ID NO: 207

```
GAAGTGAAGCTTGAGGAGTCTGGAGGAGGCTTGGTGCAACCTGGAGGAT
CCATGAAACTCTCCTGTGTTGCCTCTGGATTTACTTTCGGTAGCTACTGGATGTCT
TGGGTCCGCCAGTCTCCAGAGAAGGGGCTTGAGTGGGTTGCTGAAATTAGATTG
AAATCTGATAATTATGCAGCACATTATGCGGAGTCTGTGAAAGGGAAGTTCACC
ATCTCAAGAGATGATTCCAAAAGTCGTCTCTACCTGCAAATGAACAGCTTAAGA
GGCGAAGACACTGGAATTTATTACTGTACGAATGCCTGGTTTGCTTCCTGGGGCC
AAGGGACTCTGGTCACTGTTTCTGCA
```

2A4_VH:

SEQ ID NO: 208

```
GAAGTGAAGCTTGAGGAGTCTGGAGGAGGCTTGGTGCAACCTGGAGGAT
CCATGAAACTCTCCTGTGTTGCCTCTGGATTTACTTTCAGCACTTATTGGATGTCT
TGGGTCCGCCAGTCTCCAGAGAAGGGGCTTGAGTGGGTTGCTGAAATTAGATTG
AAATCTGATAATTATGCAACACATTATACGGAGTCTGTGAAAGGGAAGTTCACC
ATCTCAAGAGATGATTCCAAAAGTCGTCTCTACCTGCAAATGAACAGTTTAAGA
GTTGAAGACACTGGAATTTATTATTGTACGAATGCCTGGTTTGCTTACTGGGGCC
AAGGGACTCTGGTCACTGTCTCTGCA
```

20A1_VH:

SEQ ID NO: 209

```
GAAGTGAAGCTTGAGGAGTCTGGAGGAGGCTTGGTGCAACCTGGAGGAT
CCATGAAACTCTCCTGTATTGCCTCTGGATTTACTTTCAGTACCTACTGGATGTCT
TGGGTCCGCCAGTCTCCAGAGAAGGGGCTTGAGTGGGTTGCTGAAATTAGATTG
AAATCTGAAAATTATGCAACATATTATGCGGAGTCTGTGAAAGGGAAGTTCATC
ATCTCAAGAGATGATTCCAAAAGTCGTCTCTACCTGCAAATGAACAGCTTAAGA
GCTGAAGACACTGGAATTTATTACTGTACGAATGCCTGGTTTGCTAACTGGGGCC
AAGGGACTCTGGTCACTGTCTCTGCA
```

13A10_VH:

SEQ ID NO: 210

```
GATGTGCAGCTTCAGGAGTCGGGACCTGGCCTGGTGAAACCTTCTCAGTC
TCTGTCCCTCACCTGCACTGTCACTGGCTACTCAATCACCAGTGATTATGCCTGG
AACTGGATCCGGCAGTTTCCAGGAAACAAACTGGAGTGGATGGGCTACATAAGC
TACATTGGTGGCATTGGCTACAACCCATCTCTCAAAAGTCGAATCTCTATCACTC
GAGACACATCCAAGAACCAGTTCTTCCTGCACTTGAATTCTGTGACTACTGGGGA
CACAGCCACATATTACTGTGCAAGAAACGGGGCTATGGACTTCTGGGGTCAAGG
AATCTCAGTCACCGTCTCCTCA
```

-continued

21H1_VH:
SEQ ID NO: 211
GATGTGCAGCTTCAGGAGTCGGGACCTGGCCTGGTGAAACCTTCTCAGTC
TCTGTCCCTCACCTGCACTGTCACTGGCTACTCAATCACCAGTGATTATGCCTGG
AACTGGATCCGGCAGTTTCCAGGAAACAAACTGGAGTGGATGGGCTACATAAGT
TACAGTGGTAGCACTGGCTATAGCCCATCTCTCAAAAGTCGAATCTCTATCACTC
GAGACACATCCAAGAACCAGTTCTTCCTGCACTTGAATTCTGTGACTACTGGAGA
CACAGCCACATATTACTGTGCACGAAACGGGGCTATGGACTACTGGGGTCAAGG
AATCTCAGTCACCGTCTCCTCA

18F5_VK:
SEQ ID NO: 212
GACATTGTGATGTCACAGTCTCCATCCTCCCTAGCTGTGTCAGTTGGAGA
GAAGGTTACTATGAGCTGCATGTCCAGTCAGAGCCTTTTATATAGTAAAGATCAA
AAGAACTACTTGGCCTGGTACCAACAGAAACCAGGGCAGTCTCCTAAACTGCTG
ATTTACTGGGCATCCACTAGGGAATCTGGGGTCCCTGATCGCTTCACAGGCAGTG
GATCTGGGACAGATTTCACTCTCACCATCAGCAGTGTGAAGGCTGAAGACCTGG
CAGTTTATTACTGTCTGCAATATTATACCTATCCGTACACGTTCGGAGGGGGGAC
CAAGCTGGAAATAAAACGG

1F9_VK:
SEQ ID NO: 213
GACATTGTGATGTCACAGTCTCCATCCTCCCTAACTGTGTCAGTTGGAGA
GAAGGTTACTATGAGCTGCATGTCCAGTCAGAGCCTTTTATATAGTAAAGATCAA
AAGAACTACTTGGCCTGGTACCAACAGAAACCAGGGCAGTCTCCTACACTGCTG
ATTTACTGGGCATCCACTAGGGAATCTGGGGTCCCTGATCGCTTCACAGGCAGTG
GATCTGGGACAGATTTCACTCTCACCATCAGCAGTGTGAAGGCTGAAGACCTGG
CAGTTTATTACTGTCTGCAATATTATACCTATCCGTACACGTTCGGAGGGGGGAC
CAAGCTGGAAATAAAACGG

2A4_VK:
SEQ ID NO: 214
GACATTGTGATGTCACAGTCTCCATCCTCCCTAGCTGTGTCAGTTGGAGA
GAAGTTTACTATGAGCTGCAAGTCCAGTCAGAGCCTTTTATATAGTCGCGATCAA
AAGAACTACTTGGCCTGGTACCAGCAGCAACCAGGGCAGTCTCCTAAACTTCTG
ATTTACTGGGCATCCACTAGGGAGTCTGGGGTCCCTGATCGCTTCACAGGCAGTG
GATCTGGGACAGATTTCACTCTCACCATCAGCAGTGTGAAGACTGAAGACCTGG
CAGTTTATTACTGTCTCCAATATTATAGCTATCCGTACACTTTCGGAGGGGGGAC
CAAGCTGGAAATAAAACGG

20A1_VK:
SEQ ID NO: 215
GACATTGTGATGTCACAGTCTCCATCCTCCCTAGTTGTGTCAGTTGGAGAG
AAGGTTACTATGAGCTGTAAGTCCAGTCAGAACCTTTTATATAGTAGGGATCAA
AAGAACTACTTGGCCTGGTACCAGCAGAAACCAGGGCAGTCTCCTAACTTGCTG
ATTTACTGGGCATCCACTAGGGAATCTGGGGTCCCTGATCGCTTCACAGGCAGTG
GATCTGGGACAGATTTCTCTCTCACCATCAGCAGTGTGAAGGCTGAAGACCTGG
CAGTTTATTACTGTCTCCAATATTATAGCTATCCGTACACGTTCGGAGGGGGGAC
CAAGCTGGAAATGAAACGG

13A10_VK:
SEQ ID NO: 216
GACATTGTGCTGACCCAATCTCCAGCTTCTTTGGCTGTGTCTCTAGGGCAG
AGGGCCACCATCTCCTGCAAGGCCAGCCAAAGTGTTGATTATGATGGTGATAGT
TATATGAACTGGTACCAACAGAAACCAGGACAGCCACCCAAACTCCTCATCTAT
GATGCATCCAATCTAGAATCTGGGATCCCAGCCAGGTTTAGTGGCAGTGGGTCT
GGGACAGACTTCACCCTCAACATCCATCCTGTGGAGGAGGAGGATGCTGCAACC
TATTACTGTCAGCAAAGTAATGAGGCTCCGTGGACGTTCGGTGGAGGCACCAAG
CTGGAAATCAAACGG

21H1_VK:
SEQ ID NO: 217
GACATTGTGCTGACCCAATCTCCAGCTTCTTTGGCTGTGTCTCTAGGGCAG
AGGGCCACCATCTCCTGCAAGGCCAGCCAAAGTGTTGATTATGATGGTGATAGT
TATATGAACTGGTACCAACAGAAACCAGGACAGCCACCCAAACTCCTCATTTAT
GATGCTTCCACTCTAGAATCTGGGATCCCAGCCAGGTTTAGTGGCAGTGGGTCTG
GGACAGACTTCACCCTCAACATCCATCCTGTGGAGGAGGAGGATGCTGCAACCT
ATTACTGTCAGCAAAATTATGAGGCTCCGTGGACGTTCGGTGGAGGCACCAAGC
TGGAAATCAAACGG

Example 9

This Example describes the functional characterization of recombinant purified anti-human pro-Factor D-specific antibodies in several in vitro assays.

Background/Rationale:

This Example describes the functional characterization of recombinant anti-human pro-Factor D-specific monoclonal antibodies that were generated as described in Examples 7 and 8 for binding to human pro-Factor D and binding to human mature-Factor D.

Methods:

1. Purified Recombinant Antibodies: Binding to Immobilized Pro-Factor D and Mature Factor D Monoclonal anti-human pro-CFD antibodies 18F5, 1F9, 2A4, 20A1, 13A10, and 21H1 were made recombinantly on a human IgG4 framework as described in Example 8. These antibodies showed preferential binding by ELISA as hybridoma supernatants on immobilized recombinant human pro-Factor D (as described in Example 7) and were re-tested as recombinant antibodies for their ability to bind to immobilized recombinant human mature Factor D or recombinant human pro-Factor D as described below.

Purified, recombinant antibodies 18F5, 1F9, 2A4, 20A1, 13A10, and 21H1 were serially diluted in PBST from 3 µg/ml in 3-fold dilutions on ELISA plates coated with 1 µg/ml recombinant human pro-Factor D and mature-Factor D and blocked with PBS, 1% BSA. Control purified antibodies were likewise diluted and included: Rat monoclonal anti-mouse CFD (R&D Systems MAB5430), Monoclonal mouse anti-human CFD (R&D MAB18241, Rat IgG (Jackson ImmunoResearch 012-000-003) and Mouse IgG (Jackson ImmunoResearch 015-000-003). After a 1 hour incubation, the plates were washed and an HRP-tagged anti-mouse, rat or human secondary antibody (Southern Biotech 9230-05) was added and incubated for an hour, followed by a wash, then TMB substrate (ThermoFisher). The reaction was stopped with addition of 1N $H_2SO_4$, and read at 450 nm on a Biotek™ ELISA plate reader.
Results:

FIG. 17A graphically illustrates the detection of recombinant human pro-Factor D with numerous candidate anti-human pro Factor-D-specific antibodies. As shown in FIG. 17A, all the purified antibodies tested, namely, 18F5, 1F9, 2A4, 20A1, 13A10, and 21H1 were capable of detecting the pro form of Factor D.

FIG. 17B graphically illustrates the detection of recombinant human mature-Factor D with numerous candidate anti-human pro Factor-D-specific antibodies. As shown in FIG. 17B, none of the purified antibodies tested, namely, 18F5, 1F9, 2A4, 20A1, 13A10, or 21H1, were capable of detecting the mature form of Factor D. Control samples included rat IgG and mouse IgG, which bind neither human pro or mature Factor D. Two forms of commercial anti-Factor D antibodies were tested, namely MAB5430 and MAB18241. Both of these commercial antibodies lack specificity for either pro or mature human Factor D.
2. Further Analysis of Purified Recombinant Anti-Pro-Factor D-Specific Antibody 21H1: Specificity and Sensitivity
A. Detection of Recombinant Human Pro-Factor D and Mature Factor D
Methods:

Purified, recombinant anti-pro Factor D-specific antibody 21H1 (human IgG4 Fc) was tested in a sandwich ELISA format as the coating/capturing antibody. After overnight incubation, blocking and washing, recombinant human pro-Factor D and mature-Factor D were diluted to 2 µg/mL normal human plasma, then subsequently in PBST-BSA. A control of no additional Factor D was treated similarly. Assay wells were incubated for 1 hour at room temperature, then washed three times with PBST. Captured molecules were detected with 0.1 µg/mL biotin-labeled, affinity purified, goat polyclonal antibody raised to human mature Factor D (R&D BAF1824) in PBST-BSA. After incubation and washing HRP-tagged Streptavidin was added, incubated, and washed, followed by TMB substrate (ThermoFisher). The results are shown in FIG. 18.
Results:

FIG. 18 graphically illustrates the detection of recombinant pro-Factor D and mature (active) Factor D in an ELISA assay with recombinant anti-pro-Factor D antibody 21H1 as the coating antibody and goat polyclonal anti-Factor D antibody BAF1824 (R&D Systems) as the detection antibody. As shown in FIG. 18, there is greater signaling in the presence of mature Factor D than for buffer and matrix (No Factor D). mAb 21H1 continues to detect pro-Factor D out to the lowest concentration tested (0.46 ng/ml), while the matrix or mature Factor D signaling is at background levels at 10 ng/ml. These results demonstrate that the specificity of the assay is due to the anti-pro Factor D-specific antibody, 21H1.
B. Analysis for the Presence of Human Pro-Factor D in Human Serum
Methods:

Purified, recombinant anti-pro-Factor D-specific antibody 21H1 (human IgG4 Fc) was tested in a sandwich ELISA format as the coating/capturing antibody. After overnight incubation of 1 µg/ml 21H1 antibody, plates were blocked and washed, and recombinant human pro-Factor D (Pro-CFD) was diluted to 1 µg/ml in 50% Normal Human Plasma (NHP), 50% Normal Human Serum (NHS) or 50% Factor D Depleted Serum (Df-Dpl serum), then subsequently in PBST-BSA. Controls of no additional Factor D in sera were treated similarly (unspiked). Assay wells were incubated for 1 hour at room temperature then washed three times with PBST. Captured molecules were detected with 0.1 µg/ml biotin-labeled, affinity purified, goat polyclonal antibody raised to human mature Factor D (R&D BAF1824) in PBST-BSA. After incubation and washing, HRP-tagged Streptavidin was added, incubated, and washed, followed by TMB substrate. The results are shown in FIG. 19.
Results:

FIG. 19 graphically illustrates the amount of pro-Factor D present in normal human plasma (NHP), normal human serum (NHS) or Factor-D-depleted serum (Df-Dpl serum) as determined in an ELISA assay with anti-Pro-Factor D antibody 21H1 as the coating antibody and goat polyclonal anti-Factor D antibody AF1824 (R&D Systems) as the detection antibody. As shown in FIG. 19, positive signaling results from the spiking of recombinant pro-Factor D into diluent, normal human plasma, normal human serum, or factor D-depleted serum. Very low to no signaling occurs with unspiked normal human plasma, normal human serum, or factor D-depleted serum.
C. Analysis for the presence of human pro-Factor D in Test Serum Samples
Methods:

Purified, recombinant anti-pro-Factor D-specific antibody 21H1 (human IgG4 Fc) was tested in a sandwich ELISA format as the coating/capturing antibody with Normal Human Serum (NHS, Complement Technologies), C1q-Depleted Serum (C1q-Dpl, Complement Technologies A399), Factor D-Depleted Serum (Df-Dpl, Complement Technologies FactorD-Dpl) and 3MC-syndrome patient serum (Patient 3, deficient in MASP-3 activity, kindly provided by Dr. Wilhelm Schwaeble). After overnight incubation of 1 µg/mL 21H1 antibody in PBS, blocking and washing, sera were diluted 1:10 in PBST-BSA, then subsequently 2-fold in PBST-BSA. Assay wells were incubated for 1 hour at room temperature, then washed three times with PBST. Captured molecules were detected with 0.1 µg/mL biotin-labeled, affinity purified, goat polyclonal antibody raised to human mature Factor D (R&D BAF1824) in PBST-BSA. After incubation and washing, HRP-tagged Streptavidin was added, incubated, and washed, followed by TMB substrate (ThermoFisher).
Results:

FIG. 20 graphically illustrates the amount of pro-Factor D present in Normal Human Serum (NHS), C1q-Depleted Serum (C1q-Dpl), Factor D-Depleted Serum (Df-Dpl) and 3MC-syndrome patient serum as determined in an ELISA assay with anti-pro-Factor D antibody 21H1 as the coating antibody and goat polyclonal anti-Factor D antibody AF1824 (R&D Systems) as the detection antibody. While Normal Human Serum and human serum depleted of Factor D or C1q have very low signaling when diluted 10-fold and beyond, serum from a 3MC syndrome patient results in strong detection of pro-Factor D.

Conclusion:

As described in Examples 7-9, the inventors have generated Pro-Factor D-specific monoclonal antibodies that specifically bind to Pro-Factor D and do not bind to mature Factor D. As further described in Examples 10-12, the level of Pro-Factor D correlates with alternative pathway activity, therefore, Pro-Factor D-specific monoclonal antibodies may be used to measure the level of Pro-Factor D as a surrogate endpoint in a diagnostic assay to assess the level of alternative pathway activation in a mammalian subject. As further described herein in Example 12, the Pro-Factor D-specific monoclonal antibodies may be used as a pharmacodynamic (PD) measurement of MASP-3 inhibition in a subject treated with a MASP-3 inhibitor, which may be used to determine efficacious dosing of a MASP-3 inhibitor.

Example 10

This Example describes the generation of humanized antibodies that bind to MASP-3 and inhibit the maturation of pro-Factor D to factor D and thereby inhibit the Alternative Pathway.

Background/Rationale:

As shown in FIG. 1 and described herein, it has been determined that MASP-3 is required for the conversion of pro-Factor D to Factor D, therefore MASP-3 is a key regulator of the alternative pathway of complement (APC). Numerous high-affinity anti-MASP-3 inhibitory monoclonal antibodies have been generated as described in WO2018/026722, hereby incorporated herein by reference. As further described in WO2018/026722, several representative MASP-3 inhibitory antibodies (e.g., 4D5, 10D12 and 13B1) were humanized. Representative humanized MASP-3 inhibitory antibodies are described below.

Presented below is the heavy chain variable region (VH) and light chain variable region (VL) sequence for representative humanized MASP-3 inhibitory antibodies. The Kabat CDRs are underlined.

h4D5-14-1-NA_VH
(SEQ ID NO: 220)
QVQLVQSGAEVKKPGASVKVSCKASGYTFTTDDINWVRQAPGQGLEWIG
WIYPRDDRTKYNDKFKDKATLTVDTSSNTAYMELSSLRSEDTAVYYCSS
LEDTYWGQGTLVTVSS h4D5-14-1-NA_VL
(SEQ ID NO: 221)
DIVMTQSPDSLAVSLGERATINCKSSQSLLASRTRKNYLAWYQQKPGQP
PKLLIYWASTRESGVPDRFSGSGSGTDFTLTISSLQAEDVAVYYCKQSY
NLYTFGQGTKVEIKR h4D5-19-1-NA_VH
(SEQ ID NO: 222)
QVQLVQSGAEVKKPGASVKVSCKASGYTFTTDDINWVRQAPGQGLEWIG
WIYPRDDRTKYNDKFKDRATLTVDTSSNTAYMELSSLRSEDTAVYYCSS
LEDTYWGQGTLVTVSS h4D5-19-1-NA_VL
(SEQ ID NO: 221)
DIVMTQSPDSLAVSLGERATINCKSSQSLLASRTRKNYLAWYQQKPGQP
PKLLIYWASTRESGVPDRFSGSGSGTDFTLTISSLQAEDVAVYYCKQSY
NLYTFGQGTKVEIKR h10D12-45-21-GA_VH
(SEQ ID NO: 223)
QIQLVQSGSELKKPGASVKVSCKASGYIFTSYGMSWVRQAPGKGLKWMG
WINTYSGVPTYADDFKGRFVFSLDTSVRTPYLQISSLKAEDTAVYFCAR
GGEAMDYWGQGTLVTVSS h10D12-45-21-GA_VL
(SEQ ID NO: 224)
DVLMTQTPLSLSVTPGQPASISCKSSQSLLDSDAKTYLNWLLQRPGQSP
KRLIYLVSKLDSGVPDRFSGSGSGTDFTLKISRVEAEDVGVYYCWQGTH
FPWTFGQGTKVEIKR h10D12-49-21-GA_VH
(SEQ ID NO: 225)
QIQLVQSGSELKKPGASVKVSCKASGYIFTSYGMSWVRQAPGKGLKWMG
WINTYSGVPTYADDFKGRFVFSLDTSVRTPYLQISSLKAEDTATYFCAR
GGEAMDYWGQGTLVTVSS h10D12-49-21-GA_VL
(SEQ ID NO: 224)
DVLMTQTPLSLSVTPGQPASISCKSSQSLLDSDAKTYLNWLLQRPGQSP
KRLIYLVSKLDSGVPDRFSGSGSGTDFTLKISRVEAEDVGVYYCWQGTH
FPWTFGQGTKVEIKR h13B1-9-1-NA_VH
(SEQ ID NO: 226)
QVQLVQSGAEVKKPGASVKVSCKASGYTFTGKWIEWVRQAPGQGLEWIG
EILPGTGSTNYAQKFQGRATFTADSSTSTAYMELSSLRSEDTAVYYCLR
SEDVWGQGTLVTVSS h13B1-9-1-NA_VL
(SEQ ID NO: 227)
DIVMTQSPDSLAVSLGERATINCKSSQSLLASRTRKNYLAWYQQKPGQP
PKLLIYWASTRESGVPDRFSGSGSGTDFTLTISSLQAEDVAVYYCKQSY
NIPTFGQGTKVEIKR h13B1-10-1-NA_VH
(SEQ ID NO: 228)
QVQLVQSGAEVKKPGASVKVSCKASGYTFTGKWIEWVRQAPGQGLEWIG
EILPGTGSTNYNEKFKGRATFTADSSTSTAYMELSSLRSEDTAVYYCLR
SEDVWGQGTLVTVSS h13B1-10-1-NA_VL
(SEQ ID NO: 227)
DIVMTQSPDSLAVSLGERATINCKSSQSLLASRTRKNYLAWYQQKPGQP
PKLLIYWASTRESGVPDRFSGSGSGTDFTLTISSLQAEDVAVYYCKQSY
NIPTFGQGTKVEIKR

TABLE 18 anti-human MASP-3-specific mAb HC CDRs:

| Antibody | Region | Sequence |
| --- | --- | --- |
| h4D5-14-1 NA | HC-CDR1 | TDDIN (SEQ ID NO: 229) |
| h4D5-19-1 NA | HC-CDR1 | TDDIN (SEQ ID NO: 229) |
| h10D12-45-21-GA | HC-CDR1 | SYGMS (SEQ ID NO: 230) |
| h10D12-49-21-GA | HC-CDR1 | SYGMS (SEQ ID NO: 230) |
| h13B1-9-1-NA | HC-CDR1 | GKWIE (SEQ ID NO: 231) |
| h13B1-10-1-NA | HC-CDR1 | GKWIE (SEQ ID NO: 231) |
| h4D5-14-1 NA | HC-CDR2 | WIYPRDDRTKYNDKFKD (SEQ ID NO: 232) |
| h4D5-19-1 NA | HC-CDR2 | WIYPRDDRTKYNDKFKD (SEQ ID NO: 232) |

TABLE 18-continued anti-human MASP-3-specific mAb HC CDRs:

| Antibody | Region | Sequence |
|---|---|---|
| h10D12-45-21-GA | HC-CDR2 | WINTYSGVPTYADDFKG (SEQ ID NO: 233) |
| h10D12-49-21-GA | HC-CDR2 | WINTYSGVPTYADDFKG (SEQ ID NO: 233) |
| h13B1-9-1-NA | HC-CDR2 | EILPGTGSTNYAQKFQG (SEQ ID NO: 234) |
| h13B1-10-1-NA | HC-CDR2 | EILPGTGSTNYNEKFKG (SEQ ID NO: 235) |
| h4D5-14-1 NA | HC-CDR3 | LEDTY (SEQ ID NO: 236) |
| h4D5-19-1 NA | HC-CDR3 | LEDTY (SEQ ID NO: 236) |
| h10D12-45-21-GA | HC-CDR3 | GGEAMDY (SEQ ID NO: 237) |
| h10D12-49-21-GA | HC-CDR3 | GGEAMDY (SEQ ID NO: 237) |
| h13B1-9-1-NA | HC-CDR3 | SEDV (SEQ ID NO: 238) |
| h13B1-10-1-NA | HC-CDR3 | SEDV (SEQ ID NO: 238) |

TABLE 19 anti-human MASP-3-specific mAbs LC CDRs:

| Antibody | Region | Sequence |
|---|---|---|
| h4D5-14-1 NA | LC-CDR1 | KSSQSLLASRTRKNYLA (SEQ ID NO: 239) |
| h4D5-19-1 NA | LC-CDR1 | KSSQSLLASRTRKNYLA (SEQ ID NO: 239) |
| h10D12-45-21-GA | LC-CDR1 | KSSQSLLDSDAKTYLN (SEQ ID NO: 240) |
| h10D12-49-21-GA | LC-CDR1 | KSSQSLLDSDAKTYLN (SEQ ID NO: 240) |
| h13B1-9-1-NA | LC-CDR1 | KSSQSLLASRTRKNYLA (SEQ ID NO: 239) |
| h13B1-10-1-NA | LC-CDR1 | KSSQSLLASRTRKNYLA (SEQ ID NO: 239) |
| h4D5-14-1 NA | LC-CDR2 | WASTRES (SEQ ID NO: 178) |
| h4D5-19-1 NA | LC-CDR2 | WASTRES (SEQ ID NO: 178) |
| h10D12-45-21-GA | LC-CDR2 | LVSKLDS (SEQ ID NO: 241) |
| h10D12-49-21-GA | LC-CDR2 | LVSKLDS (SEQ ID NO: 241) |
| h13B1-9-1-NA | LC-CDR2 | WASTRES (SEQ ID NO: 178) |
| h13B1-10-1-NA | LC-CDR2 | WASTRES (SEQ ID NO: 178) |
| h4D5-14-1 NA | LC-CDR3 | KQSYNLYT (SEQ ID NO: 242) |
| h4D5-19-1 NA | LC-CDR3 | KQSYNLYT (SEQ ID NO: 242) |
| h10D12-45-21-GA | LC-CDR3 | WQGTHFPWT (SEQ ID NO: 243) |
| h10D12-49-21-GA | LC-CDR3 | WQGTHFPWT (SEQ ID NO: 243) |
| h13B1-9-1-NA | LC-CDR3 | KQSYNIPT (SEQ ID NO: 244) |
| h13B1-10-1-NA | LC-CDR3 | KQSYNIPT (SEQ ID NO: 244) |

TABLE 20

Representative humanized high afinity MASP-3 inhibitory antibodies

| MASP-3 Antibody Reference No. | Heavy Chain Variable Region aa (SEQ ID NO) | Light Chain Variable Region aa (SEQ ID NO) | Heavy Chain: CDR1; CDR2; CDR3 (SEQ ID NOs) | Light Chain: CDR1; CDR2; CDR3 (SEQ ID NOs) |
|---|---|---|---|---|
| h4D5-14-1-NA | 220 | 221 | 229, 232, 236 | 239, 178, 242 |
| h4D5-19-1-NA | 222 | 221 | 229, 232, 236 | 239, 178, 242 |
| h10D12-45-21-GA | 223 | 224 | 230, 233, 237 | 240, 241, 243 |
| h10D12-49-21-GA | 225 | 224 | 230, 233, 237 | 240, 241, 243 |
| h13B1-9-1-NA | 226 | 227 | 231, 234, 238 | 239, 178, 244 |
| h13B1-10-1-NA | 228 | 227 | 231, 235, 238 | 239, 178, 244 |

In some embodiments, the variable light chain and heavy chain fragments of the MASP-3 inhibitory antibodies were isolated in a full-length IgG4 format as follows: In some embodiments, the chimeric mAbs were fused to the human IgG4 constant region (SEQ ID NO:70). In some embodiments, the chimeric mAbs were fused to the human IgG4 constant region which contains the stabilizing S228P amino acid substation (SEQ ID NO:71). In some embodiments, the chimeric mAbs were fused to the human IgG4 constant region which contains the S228P amino acid substitution and also a mutation that promotes FcRn interactions at low pH (SEQ ID NO:245).

As further described in WO2018/026722, high affinity MASP-3 inhibitory antibodies 13B1, 10D12 and 4D5 completely inhibit the alternative pathway in mammalian subjects such as rodents and non-primates at molar concentrations less than the concentration of the MASP-3 target (e.g., at a molar ratio of from about 1:1 to about 2.5:1 (MASP-3 target to mAb) (see in Examples 11-21). As described in Example 11, a single dose administration of a high affinity MASP-3 inhibitory antibody, mAb 13B1, to mice led to near-complete ablation of systemic alternative pathway complement activity for at least 14 days. As further described in Example 12, in a study conducted in a well-established animal model associated with PNH it was demonstrated that mAb 13B1 significantly improved the survival of PNH-like red blood cells and protected PNH-like red blood cells significantly better than did C5 inhibition. As described in Example 13, it was further demonstrated that mAb 13B1 reduced the incidence and severity of disease in a mouse model of arthritis. As further described in WO2018/026722, representative high affinity MASP-3 inhibitory mAbs 13B1, 10D12 and 4D5 are highly effective at blocking the alternative pathway in primates. Single dose administration of mAb 13B1, 10D12 or 4D5 to cynomolgus monkeys resulted in sustained ablation of systemic alternative pathway activity lasting for approximately 16 days. The extent of alternative pathway ablation in cynomolgus monkeys treated with high affinity MASP-3 inhibitory antibodies was comparable to that achieved by factor D blockade in vitro and in vivo, indicating complete blockade of factor D conversion by the MASP-3 inhibitory antibodies. Therefore, high affinity MASP-3 inhibitory mAbs have therapeutic utility in the treatment of patients suffering from diseases or disorders related to alternative pathway hyperactivity, such as, for example, wherein the disease or disorder related to alternative pathway hyperactivity (also referred to as alternative-pathway disease or disorder) is selected from the group consisting of: paroxysmal nocturnal hemoglobinuria (PNH), age-related macular degeneration (AMD, including wet and dry AMD), ischemia-reperfusion injury, arthritis, disseminated intravascular coagulation, thrombotic microangiopathy (including hemolytic uremic syndrome (HUS), atypical hemolytic uremic syndrome (aHUS), thrombotic thrombocytopenia purpura (TTP) or transplant-associated TMA), asthma, dense deposit disease, pauci-immune necrotizing crescentic glomerulonephritis, traumatic brain injury, aspiration pneumonia, endophthalmitis, neuromyelitis optica, Behcet's disease, multiple sclerosis, Guillain Barre Syndrome, Alzheimer's disease, Amylotrophic lateral sclerosis (ALS), lupus nephritis, systemic lupus erythematosus (SLE), Diabetic retinopathy, Uveitis, Chronic obstructive pulmonary disease (COPD), C3 glomerulopathy, transplant rejection, Graft-versus-host disease (GVHD), hemodialysis, sepsis, Systemic inflammatory response syndrome (SIRS), Acute Respiratory Distress Syndrome (ARDS), ANCA vasculitis, Anti-phospholipid syndrome, Atherosclerosis, IgA Nephropathy and Myasthenia Gravis.

Example 11

Analysis of Factor D in Cynomolgus Monkey Samples before and after Treatment with a representative MASP-3 inhibitory antibody (13B1) in an immunoassay using mature Factor D-specific antibody 14A11 as a detection antibody.
Background/Rationale:
As described in Example 10, numerous high affinity MASP-3 inhibitory antibodies have been generated that are capable of inhibiting steady-state (resting) pro-factor D maturation in vivo. This Example describes an analysis of the status of Factor D (i.e., the amount of mature Factor-D) in cynomolgus monkeys after treatment with a representative high affinity MASP-3 inhibitory mAb 13B1, which is known to be capable of inhibiting APC activity in a non-human primate.
Methods:
In this study, 9 cynomolgus monkeys (3 animals per mAb condition) were given a single 5 mg/kg intravenous dose with one of three representative high affinity MASP-3 inhibitory antibodies: 4D5, 10D12, or 13B1 (IgG4 constant region). Plasma (EDTA) and serum samples were collected at regular intervals over a period of three weeks or longer. Plasma samples from a single dose of 13B1 in cynomolgus monkey were tested for the amount of mature Factor D as follows. ELISA plates were coated overnight with 3 μg/mL of anti-human/cyno Factor D mAb 3C5 (human IgG4) which binds to both human pro-Factor D and mature-Factor D. The plates were washed, blocked, and loaded with 20-fold dilutions of study samples and incubated at room temperature for 1 hour. After washing, a 3 μg/mL solution of mature Factor D-specific antibody 14A11 was added and incubated for 1 hour. After washing, an HRP-labeled secondary antibody (HRP-labeled F(ab')2 Fragment Donkey anti-Mouse IgG H&L antibody (Jackson ImmunoResearch)) was used to signal the detection antibody, followed by development with TMB (ThermoFisher). Samples were interpolated from a 4-parameter logistics curve of cynomolgus recombinant mature Factor D dilutions. The results are shown in FIG. 21A and FIG. 21B.
Results:
FIG. 21A graphically illustrates the amount of mature Factor D in a cynomolgus monkey over a time period after treatment with representative anti-MASP-3 inhibitory mAb 13B1. As shown in FIG. 21A, the level of mature Factor D drops to a low level within 24 hours after administration of the MASP-3 mAb and remains low for about 500 hours post treatment.
FIG. 21B graphically illustrates the standard curve as determined from a 4-parameter logistics curve of cynomolgus recombinant mature Factor D dilutions. The sample readouts were interpolated from this standard curve, and graphed as ug/ml of cynomolgus mature factor D.
The results in this Example demonstrate that an immunoassay utilizing an antibody specific for mature Factor D may be used to monitor the serum level of mature Factor D after treatment with a MASP-3 inhibitory antibody that inhibits the conversion of pro-Factor D to mature Factor D.

Example 12

Analysis of the pharmacology of representative anti-MASP-3 mAb (13B1) in cynomolgus monkeys as part of a single-dose pharmacokinetic (PK) and pharmacodynamic (PD) study.
Background/Rationale:
As demonstrated in Example 11, an immunoassay utilizing an antibody specific for mature Factor D may be used to monitor the serum level of mature Factor D after treatment with a MASP-3 inhibitory antibody that inhibits the conversion of pro-Factor D to mature Factor D. This Example describes the use of an immunoassay utilizing an antibody specific for mature Factor D to quantitate the plasma concentration of mature Factor D in a single-dose pharmacokinetic (PK) and pharmacodynamic (PD) study in female cynomolgus monkeys.
Methods:
The pharmacology of anti-MASP-3 mAb 13B1 in monkeys was explored as part of a single-dose pharmacokinetic (PK) and pharmacodynamic (PD) study in female cynomolgus monkeys. mAb 13B1 was administered by subcutaneous (SC) injection at 0.5 mg/kg, 1.5 mg/kg, or 5 mg/kg; or by intravenous (IV) bolus injection at 5 mg/kg or 100 mg/kg. Each study group contained 3 monkeys. Serial blood samples were collected for the assessment of PK and PD from pre-dose out to 1344 hours (8 weeks) post-dose.
The effect of mAb 13B1 on alternative pathway activity was assessed by the quantitation of mature Factor D in an ELISA assay and also by using an ex vivo Factor Ba activity assay. The concentration of Factor Ba produced upon stimulation was calculated by the subtraction of Factor Ba concentration in unstimulated samples from the Factor Ba concentration in stimulated samples. A decrease in mature (i.e., active) Factor D plasma concentration and a decrease in stimulated Factor Ba concentration are indicative of mAb13B1 PD activity Mature Factor D plasma concentration data and stimulated Factor Ba concentration were summarized by timepoint and dose group using mean, median, standard deviation and coefficient of variation (CV %).
Serum samples were stimulated with zymosan to activate the alternative pathway. The extent of alternative pathway activation by zymosan was determined by the quantitation of Factor Ba as follows. For determining generation of the fluid phase marker Ba, the APC was induced in ex vivo assays by incubating zymosan (1 mg/mL final) in serum (5% final, diluted in GVB+Mg/EGTA) prepared from anti-MASP-3 mAb-treated cynomolgus monkeys. The mixtures were incubated at 37°C for 40 minutes, and the APC activity was measured by ELISA-based detection of the complement endpoints. Ba was detected in the reaction supernatants using commercially available ELISA kits (Quidel). Absorbance values of all tests were normalized by setting pretreatment values as 100% activity, and a pre-treatment sample incubated, but not exposed to zymosan, to 0%.

Mature Factor D ELISA assay: ELISA plates were coated overnight with 3 µg/mL of anti-human/cyno Factor D mAb 3C5 (human IgG4) which binds to both human pro-Factor D and mature-Factor D. The plates were washed, blocked, and loaded with 20-fold dilutions of study samples and incubated at room temperature for 1 hour. After washing, a 3 µg/mL solution of mature Factor D-specific antibody 14A11 was added and incubated for 1 hour. After washing, an HRP-labeled secondary antibody (Jackson ImmunoResearch) was added to develop the assay.

Results:

FIG. 22A graphically illustrates the concentration of mature Factor D in monkeys over a time period of 56 days (1344 hours) after s.c. or i.v. administration of anti-MASP-3 mAb 13B1, as determined in an ELISA assay with mature Factor D-specific antibody 14A11 utilized as a detection antibody. As shown in FIG. 22A, administration of mAb 13B1 in monkeys was associated with a dose-dependent decrease in mature Factor D concentration.

FIG. 22B graphically illustrates the ex vivo alternative pathway activity (% baseline) over a time period of 56 days (1344 hours) after administration anti-MASP-3 mAb 13B1, as determined in a Factor Ba assay. As shown in FIG. 22B, following administration of mAb 13B1, ex vivo alternative pathway activity was inhibited in a dose-dependent manner. With increasing dose, the extent and duration of the inhibition of ex vivo activity increased. Following s.c. or i.v. administration of 5 mg/kg mAb 13B1, ex vivo activity decreased to approximately 10% of pre-dose levels for approximately 2 weeks. At the highest dose levels evaluated, ex vivo activity was inhibited for the duration of the sampling period.

FIG. 23 graphically illustrates the relationship of anti-MASP-3 mAb 13B1 effects on ex vivo alternative pathway activity and mature Factor D concentration following a single intravenous bolus or subcutaneous administration in monkeys. As shown in FIG. 23, the effect of mAb 13B1 on mature Factor D concentration was linearly related to the effect of mAb 13B1 on ex vivo alternative pathway activity.

The relationship between mAb 13B1 concentration and PD effect on mature CFD concentration in the monkey study was explored graphically and fit using a sigmoidal concentration-response model. Due to the lag between mAb13B1 serum concentration and decrease in mature CFD concentration, data collected prior to 72 hours post-dose were excluded from the analysis. A plot of the observed data and PD model fit is presented in FIG. 24.

FIG. 24 graphically illustrates the relationship between anti-MASP-3 mAb13B1 serum concentration and pharmacodynamic effect of mature Factor D concentration following a single administration to monkeys.

Summary of Results:

As expected for MASP-3 inhibition, APC inhibition in mice and non-human primates is associated with a decrease in the activation of systemic CFD. Post-dose concentration measurements of plasma CFD, by enzyme-linked immunosorbent assays (ELISAs) that specifically detect the either the zymogen form (inactive proenzyme) or the mature form, demonstrate that anti-MASP-3 mAb13B1 blocks the maturation of CFD to the active form without a measurable change in the level of total CFD. A single 5 mg/kg dose of mAb13B1 administered s.c. can maintain ≥90% alternative pathway blockade for approximately 2 weeks in nonhuman primates.

Following administration of anti-MASP-3 mAb13B1 in monkeys, ex vivo alternative pathway activity was inhibited in a dose-dependent manner. With increasing dose, the extent and duration of the inhibition of ex vivo activity increased. Following s.c. or i.v. administration of 5 mg/kg mAb13B1, ex vivo activity decreased to approximately 10% of pre-dose levels for approximately 2 weeks. Administration of mAb13B1 in monkeys was also associated with a dose-dependent decrease in mature CFD concentration. The effect of mAb13B1 on mature CFD concentration was generally linearly related to the effect of mAb13B1 on ex vivo alternative pathway activity. These data indicate that mAb13B1 inhibits MASP-3 activity after a single administration in monkeys, and that the inhibition of MASP-3 leads to a decrease in alternative pathway activity. The decrease in mature Factor D plasma concentration and stimulated Factor Ba concentration demonstrated the mAb13B1 dose-dependent inhibition of the alternative pathway in monkeys.

Example 13

Phase 1 Clinical Trial to assess safety, tolerability, pharmacokinetic (PK) and pharmacodynamics (PD) of mAb13B1

Background/Rationale:

As described herein, mAb13B1 is a humanized monoclonal antibody that binds to the serine protease domain of MASP-3 and inhibits its activity. This Example describes a Phase 1 first in human study that will be carried out to assess safety, tolerability, pharmacokinetic (PK) and pharmacodynamics (PD) of mAb13B1. The PD analysis in this study comprises the use of immunoassays disclosed herein to assess the extent of alternative pathway complement (APC) inhibition in the subjects treated with mAb13B1 by capturing and detecting mature Factor D in the test sample, wherein mature Factor D is either captured or detected with a mature Factor D-specific monoclonal antibody or fragment thereof that specifically binds to an epitope in "ILGGREA" (SEQ ID NO:5) present in mature Factor D, but does not bind to Pro-Factor D; and/or capturing and detecting Pro-Factor D in the test sample, wherein Pro-Factor D is either captured or detected with a Pro-Factor D-specific monoclonal antibody or fragment thereof that specifically binds to an epitope on the activation ("Pro") peptide "APPRGR" (SEQ ID NO:4) present in Pro-Factor D, but does not bind to mature Factor D.

Methods:

The Phase 1 first-in-human study of mAb13B1 will consist of a single ascending-dose study of IV and SC administration of mAb13B1 and a multiple ascending-dose study of SC administration of mAb13B1. In both parts of the study, healthy subjects will be enrolled to assess safety, tolerability, pharmacokinetics (PK), pharmacodynamics (PD), and immunogenicity. The aim of single ascending-dose study will be to establish a dose range and schedule that is well tolerated and provides ≥90% inhibition of MASP-3 activity for approximately 30 days (measured by reduction in mature CFD plasma concentration in an immunoassay as disclosed herein). The multiple ascending-dose portion of the study is designed to determine a dose level and frequency of SC dosing that will sustain ≥90% inhibition of MASP-3. Nonclinical toxicity studies of mAb13B1 indicate that there is an adequate safety margin to conduct initial human testing at the proposed doses in healthy subjects, and it is predicted that dose levels explored in the Phase 1 study will provide efficacy in diseases characterized by APC overactivity for a period of time that would be convenient for patients.

As described herein, mAb13B1 is a humanized monoclonal antibody (mAb) that binds to the serine protease domain of MASP-3 and inhibits its activity. By inhibiting MASP-3, mAb13B1 blocks the proteolytic activation of CFD and thereby disrupts the APC and its associated amplification of complement activity. mAb13B1 comprises a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT). mAb13B1 comprises a humanized variable region of murine origin fused to IgG4 constant region of human origin set forth as SEQ ID NO:245. mAb13B1 is secreted as a disulfide-linked glycosylated tetramer consisting of 2 identical 219-amino-acid kappa light chains and 2 identical 440-amino-acid heavy chains.

The Drug Product used in this Phase 1 trial contains mAb13B1 at a concentration of 110 mg/mL, 20 mM histidine, 100 mg/mL sucrose, and 0.035% polysorbate 80 at a pH of 6.0.

Dosage Determination

As described in Example 12, the relationship between mAb13B1 concentration and PD effect on mature CFD concentration in the 2 single-dose studies in monkeys was explored graphically and fit using a sigmoidal concentration-response model. Due to the lag between mAb 13B1 serum concentration and decrease in mature CFD concentration, data collected prior to 72 hours post-dose were excluded from the analysis. The plot of the observed data and PD model fit is shown in FIG. 24.

The mAb13B1 PK and PD model parameters were then scaled to predict mAb13B1 PK and PD effect in humans across a wide dose range. The PK model parameters were scaled to human using allometric coefficients typically used for monoclonal antibodies (Deng R. et al., MAbs, 3(1):61-6, 2011; Dong J. et al., Clin Pharmacokinet 50(2): 131-42, 2011). Based on the in vitro potency and binding affinity data, the PD model parameters were assumed to be the same in humans as in monkeys. The mAb13B1 exposure-response relationship model was used to estimate the mAb13B1 concentration associated with a 10%, 50%, and 90% decrease in mature CFD concentrations. Using the mAb13B1 PK model, mAb13B1 serum concentration over time profiles were simulated across a range of IV and SC dose levels in humans. The predicted mAb13B1 exposure values and PD effect across the range of IV and SC dose levels in humans are presented in TABLE 21.

TABLE 21

Predicted mAb13B1 Exposure and Pharmacodynamic Effect Following a Single Subcutaneous or Intravenous Administration in Healthy Volunteers

| Cohort | Dose and Route (mg/kg) | Predicted Pharmacokinetics mAb13B1 Exposure | | Predicted Pharmacodynamics Reduction in Mature CFD | |
|---|---|---|---|---|---|
| | | $C_{max}$ (μg/mL) | $AUC_{(0-168\ h)}$ (μg*h/mL) | $E_{max}$ (%) | Duration > 90% |
| 1 | 0.1 IV$^a$ | 2.07 | 90.3 | ~10 | 0 |
| 2 | 0.3 IV$^a$ | 6.24 | 323 | ~50 | 0 |
| 3 | 1 IV$^a$ | 20.9 | 1420 | ~90 | 0 |
| 4 | 3 IV$^a$ | 62.8 | 5140 | >90 | ~1 week |
| 5 | 3 SC | 31.0 | 4160 | >90 | ~1 week |
| 6 | 5 SC | 53.5 | 7310 | >90 | ~2 weeks |
| 7 | 8 SC | 87.6 | 12100 | >90 | ~4 weeks |
| 8 | 8 IV$^a$ | 168 | 14800 | >90 | ~4 weeks |

$AUC_{(0-168\ h)}$ = Area under the concentration curve over time from 0 to 168 hours postdose;
$C_{max}$ = Maximum observed concentration;
$E_{max}$ = Maximum pharmacodynamic effect;
IV = Intravenous;
CFD = complementfactor D;
SC = subcutaneous
$^a$30-minute infusion The predicted mAb13B1 pharmacokinetic (PK) profile and pharmacodynamic (PD) activity suggest that a single IV administration of 0.1 mg/kg in humans would be associated with a maximum 10% decrease in mature CFD plasma concentration. Similarly, a single SC or IV administration of 8 mg/kg is predicted to be associated with a >90% decrease in mature CFD levels for approximately 4 weeks.

Summary of Results

A total of 80 healthy subjects were administered mAb13B1 intravenously (IV) at dosages of 0.1 mg/kg, 0.3 mg/kg, 1 mg/kg, or 3 mg/kg or subcutaneously (SC) at dosages of 3 mg/kg or 5 mg/kg. At all doses tested, mAb13B1 was well tolerated, with no apparent safety signals.

FIG. 25A graphically illustrates the concentration of mAb13B1 in plasma of subjects over a time period of up to 84 days after IV administration of mAb13B1, as determined by ELISA. As shown in FIG. 25A, increased dosing resulted in higher levels of mAb13B1 and a longer period of time during which mAb13B1 was detected in plasma samples.

FIG. 25B graphically illustrates the levels of mature Factor D in subjects over a time period of 84 days after IV administration of anti-MASP-3 mAb 13B1, as determined in an ELISA assay with mature Factor D-specific antibody 14A11 used as a detection antibody. As shown in FIG. 25B, administration of mAb 13B1 was associated with a dose-dependent decrease in mature Factor D concentration as well as a dose-dependent increase in the duration of the effect. At dosages of 3 mg/kg, IV administration resulted in a decrease in mature CFD levels below detectable levels (i.e., a decrease of approximately 90% or more) that persisted for up to four weeks. It was also determined that the single lowest subcutaneous dose of mAb 13B1 was able to suppress mature Factor D concentration to below detectable levels (i.e., a decrease of approximately 90% or more) for four weeks in most subjects.

These data illustrate that the PK and PD profile across all dosages tested is favorable and supports low-dose, once-monthly (or less frequent) dosing for mAb 13B1. Such dosing may be either intravenous or subcutaneous.

The utility of the pro-Factor D and mature Factor D assays to measure a pharmacodynamic response in normal human volunteers who received a single dose of MASP-3 inhibitory antibody 13B1 has been demonstrated in the ongoing Phase 1 study. At multiple dose levels of Ab 13B1, the pro-Factor D and mature Factor D plasma concentrations consistently show an inverse correlation. Relative to pre-dose, baseline levels, pro-Factor D levels increased as mature Factor D levels decreased following Ab 13B1 administration. Furthermore, the extent of the measured increase of pro-Factor D consistently approximated the decrease in the concentration of mature Factor D. This observation is concordant with the expected outcome of inhibition of MASP-3 and Factor D maturation in humans if the clearance rates of pro-Factor D and mature Factor D do not differ dramatically. In summary, the outcomes of the two assays that measure the two different forms of Factor D are supportive of one another and, when utilized together, may provide additional diagnostic value for characterizing therapeutic MASP-3 inhibition.

Accordingly, in one aspect, the present disclosure provides a pharmaceutical composition comprising a MASP-3 inhibitory antibody in an aqueous solution comprising a buffer system having a pH of 6.0±5%, 20±5% mM histidine, 100±5% mg/mL sucrose, and 0.035%±5%, polysorbate 80, wherein said MASP-3 inhibitory antibody is included at a concentration of 110 mg/mL±5%, and wherein said MASP-3 inhibitory antibody comprises a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT). In one embodiment, the pharmaceutical composition is sterile. In one embodiment, the MASP-3 inhibitory antibody or antigen-binding fragment thereof comprises a heavy chain variable region comprising at least 80%, 85%, 90%, 95%, 98%, 99% or 100% identical to SEQ ID NO:226 or SEQ ID NO:227 and a light chain variable region comprising at least 80%, 85%, 90%, 95%, 98%, 99% or 100% identical to SEQ ID NO:227. In one embodiment, the MASP-3 inhibitory antibody or antigen binding fragment thereof is selected from the group consisting of a human antibody, a humanized antibody, a chimeric antibody, a murine antibody, and an antigen-binding fragment of any of the foregoing. In one embodiment, the MASP-3 inhibitory antibody or antigen-binding fragment thereof is selected from the group consisting of a single chain antibody, an ScFv, a Fab fragment, an Fab' fragment, an F(ab')2 fragment, a univalent antibody lacking a hinge region and a whole antibody. In one embodiment, the MASP-3 inhibitory antibody further comprises an immunoglobulin constant region. In one embodiment, the MASP-3 inhibitory antibody comprises a human IgG4 constant region. In one embodiment, the MASP-3 inhibitory antibody comprises a human IgG4 constant region with an S228P mutation. In one embodiment, the MASP-3 inhibitory antibody comprises a mutation that promotes FcRn interations at low pH, such as, for example, wherein the MASP-3 inhibitory antibody comprises human IgG4 constant region set forth as SEQ ID NO:245. In one embodiment, the pharmaceutical composition is administered to a subject in need thereof at a dosage in the range of 0.1 to 10 mg of MASP-3 inhibitory antibody per kg of body weight (such as from 0.1 mg/kg to 8 mg/kg, from 0.3 mg/kg to 5 mg/kg, from 0.3 mg/kg to 3 mg/kg, from 1 mg/kg to 3 mg/kg, from 1 mg/kg to 5 mg/kg, from 2 mg/kg to 5 mg/kg, 0.1±5% mg/kg, 0.3±5% mg/kg, 1.0±5% mg/kg, 3.0±5% mg/kg, 5.0±5% mg/kg, or 8.0±5% mg/kg). In one embodiment, the pharmaceutical composition is administered to a subject in need thereof at a dosage in the range of 0.5 to 5 mL per 100 kg of body weight (such as from 0.7 mL to 4.5 mL, from 1.0 mL to 3.5 mL, from 1.5 mL to 3.0 mL, from 2 mL to 2.5 mL, 0.5±5% mL, 0.7±5% mL, 1.1±5% mL, 1.4±5% mL, 2.1±5% mL, 2.3±5% mL, 2.8±5% mL, 3.4±5% mL, or 4.5±5% mL).

In another aspect, the present disclosure provides an article of manufacture containing a pharmaceutical composition comprising a MASP-3 inhibitory antibody in a unit dosage form suitable for therapeutic administration to a human subject, such as a unit dosage in the range of from 10 mg to 1000 mg (such as from 50 mg to 800 mg, or from 75 mg to 500, such as from 100 mg to 300 mg, such as 125 to 275 mg, such as 150 to 200 mg, such as 150±5% mg, 155±5% mg, 160±5% mg, 165±5% mg, 170±5% mg, 175±5% mg 180±5% mg, 185±5% mg, or 190±5% mg) of MASP-3 inhibitory antibody. wherein said MASP-3 inhibitory antibody comprises a heavy chain variable region comprising a HC-CDR1 comprising SEQ ID NO:231 (GKWIE); a HC-CDR2 comprising SEQ ID NO:234 (EILPGTGSTNYNEKFKG) or SEQ ID NO:235 (EILPGTGSTNYAQKFQG); and a HC-CDR3 comprising SEQ ID NO:238 (SEDV); and a light chain variable region comprising a LC-CDR1 comprising SEQ ID NO:239, a LC-CDR2 comprising SEQ ID NO:178 (WASTRES); and a LC-CDR3 comprising SEQ ID NO:244 (KQSYNIPT).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated antibody or antigen-binding fragment thereof that specifically binds to an epitope on the activation ("Pro") peptide of human Factor D, wherein the isolated antibody or antigen-binding fragment thereof comprises a binding domain comprising the following six CDRs:
   (i): (a) an HC-CDR1 comprising the amino acid sequence XYWMS (SEQ ID NO:201), wherein X at position 1 is N, S or T; (b) an HC-CDR2 comprising the amino acid sequence EIRLKSXNYAXXYXESVKG (SEQ ID NO:202), wherein: X at position 7 is D or E, X at position 11 is T or A, X at position 12 is H or Y and X at position 14 is A or T; (c) an HC-CDR3 comprising the amino acid sequence AWFAX (SEQ ID NO:203), wherein X at position 5 is S, Y or N; (d) a LC-CDR1 comprising the amino acid sequence XSSQXLLY-SXDQKNYLA (SEQ ID NO:204), wherein X at position 1 is M or K, X at position 5 is S or N, and X at position 10 is K or R; (e) a LC-CDR2 comprising the amino acid sequence WASTRES (SEQ ID NO: 178); and (f) a LC-CDR3 comprising the amino acid sequence LQYYXYPYT (SEQ ID NO:205), wherein X at position 5 is T or S; or
   (ii): (a) a CDR-H1 comprising SEQ ID NO:167, (b) a CDR-H2 comprising SEQ ID NO:169 or SEQ ID NO: 173; (c) a CDR-H3 comprising SEQ ID NO:171 or SEQ ID NO: 174; (d) a CDR-L1 comprising SEQ ID NO: 194, (e) a CDR-L2 comprising SEQ ID NO:196 or SEQ ID NO: 199 and (f) a CDR-L3 comprising SEQ ID NO: 198 or SEQ ID NO:200.

2. The isolated antibody or antigen-binding fragment thereof of claim 1, wherein the isolated antibody or antigen-binding fragment thereof comprises a binding domain comprising the following six CDRs: (a) an HC-CDR1 comprising SEQ ID NO:149 or SEQ ID NO:155, (b) a HC-CDR2 comprising SEQ ID NO:151 or SEQ ID NO:156; (c) an HC-CDR3 comprising SEQ ID NO:153; (d) a LC-CDR1 comprising SEQ ID NO:176, (e) a LC-CDR2 comprising SEQ ID NO:178 and (f) a LC-CDR3 comprising SEQ ID NO:180.

3. The isolated antibody or antigen-binding fragment thereof of claim 1, wherein the isolated antibody or antigen-binding fragment thereof comprises a binding domain comprising the following six CDRs: (a) an HC-CDR1 comprising SEQ ID NO:158, (b) an HC-CDR2 comprising SEQ ID NO:159 or SEQ ID NO:163; (c) an HC-CDR3 comprising SEQ ID NO:161 or SEQ ID NO:165; (d) a LC-CDR-1 comprising SEQ ID NO:184 or SEQ ID NO:189, (e) a LC-CDR2 comprising SEQ ID NO:178 and (f) a LC-CDR3 comprising SEQ ID NO:187.

4. The isolated antibody or antigen-binding fragment thereof of claim 1, wherein the isolated antibody or antigen-binding fragment thereof comprises a binding domain comprising the following six CDRs: (a) a CDR-H1 comprising SEQ ID NO:167, (b) a CDR-H2 comprising SEQ ID NO:169 or SEQ ID NO:173; (c) a CDR-H3 comprising SEQ ID NO:171 or SEQ ID NO:174; (d) a CDR-L1 comprising SEQ ID NO:194, (e) a CDR-L2 comprising SEQ ID NO: 196 or SEQ ID NO:199 and (f) a CDR-L3 comprising SEQ ID NO: 198 or SEQ ID NO:200.

5. A nucleic acid molecule encoding the CDRs of a heavy chain variable region of an antibody, or antigen-binding fragment thereof, that specifically binds human Pro-Factor D as set forth in claim 1.

6. A nucleic acid molecule encoding the CDRs of a light chain variable region of an antibody, or antigen-binding fragment thereof, that specifically binds human pro-Factor D as set forth in claim 1.

7. A cloning vector or expression cassette comprising a nucleic acid molecule encoding the CDRs of a heavy chain variable region of an antibody, or antigen-binding fragment thereof, that specifically binds human Pro-Factor D as set forth in claim 1 and/or a nucleic acid molecule encoding the CDRs of a light chain variable region of an antibody, or antigen-binding fragment thereof, that specifically binds human pro-Factor D as set forth in claim 1.

8. A cell comprising at least one of a nucleic acid molecule encoding the CDRs of a heavy chain variable region of an antibody, or antigen-binding fragment thereof, that specifically binds human Pro-Factor D as set forth in claim 1 and/or a nucleic acid molecule encoding the CDRs of a light chain variable region of an antibody, or antigen-binding fragment thereof, that specifically binds human pro-Factor D as set forth in claim 1.

9. A method of generating an isolated antibody, or antigen-binding fragment thereof, that specifically binds human Pro-Factor D comprising culturing the cell of claim 8 under conditions allowing for expression of the nucleic acid molecules encoding the antibody, or antigen-binding fragment thereof, that specifically binds human Pro-Factor D and isolating said anti-Pro-Factor-D specific antibody, or antigen-binding fragment thereof.

10. A kit for detecting the presence or amount of Pro-Factor D in a test sample, said kit comprising (a) at least one container, and (b) at least one antibody, or antigen-binding fragment thereof, that specifically binds human Pro-Factor D as set forth in claim 1; and wherein the mature Factor D-specific antibody comprises (a) an HC-CDR1 comprising the amino acid sequence XSXMGVS (SEQ ID NO: 65), wherein X at position 1 is T, I, or S and X at position 3 is G or I; (b) an HC-CDR2 comprising the amino acid sequence HIYWDDEKHYXPSLKX (SEQ ID NO: 66), wherein X at position 11 is H or N and X at position 16 is S or R; (c) an HC-CDR3 comprising the amino acid sequence RYYGYXXXMXY (SEQ ID NO: 67), wherein X at position 6 is R, G or N, X at position 7 is S or Y, X at position 8 is F, I or V, and X at position 10 is D or H; (d) a LC-CDR1 comprising the amino acid sequence RSXXSIXHSNGNTYXE (SEQ ID NO: 68), wherein: X at position 3 is N or S, X at position 4 is Q or E, X at position 7 is V or L, and X at position 15 is F or L; (e) a LC-CDR2 comprising the amino acid sequence KVXNRFS (SEQ ID NO:69), wherein: X at position 3 is S or Y; and (f) a LC-CDR3 comprising the amino acid sequence FQGSHVPPT (SEQ ID NO:54).

11. A method of determining the presence or amount of Pro-Factor D in a test sample, the method comprising:
(a) contacting a test sample with an anti-human Pro-Factor D-specific monoclonal antibody or antigen-binding fragment thereof, in an in vitro immunoassay; and
(b) detecting the presence or amount of the antibody or antigen-binding fragment thereof bound to Pro-Factor D, wherein the presence of binding indicates the presence or amount of Pro-Factor D in the sample;
wherein the anti-human Pro-Factor D-specific antibody or antigen binding fragment thereof specifically binds to an epitope in the activation ("Pro") peptide of human Factor D, and wherein the anti-human Pro-Factor D-specific antibody or antigen binding fragment thereof comprises:
(i): (a) an HC-CDR1 comprising the amino acid sequence XYWMS (SEQ ID NO:201), wherein X at position 1 is N, S or T; (b) an HC-CDR2 comprising the amino acid sequence EIRLKSXNYAXXYXESVKG (SEQ ID NO:202), wherein: X at position 7 is D or E, X at position 11 is T or A, X at position 12 is H or Y and X at position 14 is A or T; (c) an HC-CDR3 comprising the amino acid sequence AWFAX (SEQ ID NO:203), wherein X at position 5 is S, Y or N; (d) a LC-CDR1 comprising the amino acid sequence XSSQXLLY-SXDOKNYLA (SEQ ID NO:204), wherein X at position 1 is M or K, X at position 5 is S or N, and X at position 10 is K or R; (e) a LC-CDR2 comprising the amino acid sequence WASTRES (SEQ ID NO: 178); and (f) a LC-CDR3 comprising the amino acid sequence LOYYXYPYT (SEQ ID NO:205), wherein X at position 5 is T or S; or
(ii): (a) a CDR-H1 comprising SEQ ID NO:167, (b) a CDR-H2 comprising SEQ ID NO:169 or SEQ ID NO: 173; (c) a CDR-H3 comprising SEQ ID NO: 171 or SEQ ID NO: 174; (d) a CDR-L1 comprising SEQ ID NO: 194, (e) a CDR-L2 comprising SEQ ID NO:196 or SEQ ID NO: 199 and (f) a CDR-L3 comprising SEQ ID NO: 198 or SEQ ID NO:200.

12. The method of claim 11, wherein the antibody or antigen-binding fragment thereof specifically binds human Pro-Factor D (SEQ ID NO:2) and does not bind to human mature Factor D (SEQ ID NO:3).

13. The method of claim 11, wherein the anti-human Pro-Factor D-specific antibody or antigen-binding fragment thereof is immobilized on a substrate.

14. The method of claim 11, wherein the immunoassay is an ELISA assay.

15. The method of claim 11, wherein said anti-human Pro-Factor D-specific antibody or antigen-binding fragment thereof is labeled with a detectable moiety and step (b) comprises detecting the presence or amount of said detectable moiety.

16. The method of claim 11, wherein the test sample is a biological sample obtained from a mammalian subject.

17. The method of claim 16, wherein the mammalian subject is suffering from, or at risk for developing an alternative pathway disease or disorder.

18. The method of claim 11, wherein the anti-human Pro-Factor D-specific antibody or antigen-binding fragment thereof comprises a binding domain comprising HC-CDR-1, HC-CDR-2 and HC-CDR-3 in a heavy chain variable region selected from the group consisting of SEQ ID NO:s 136-139 and comprising LC-CDR-1, LC-CDR2 and LC-CDR3 in a light chain variable region selected from the group consisting of SEQ ID NO:s 142-145, wherein the CDRs are numbered according to the Kabat numbering system.

19. The method of claim 11, wherein the anti-human Pro-Factor D-specific antibody or antigen-binding fragment thereof comprises a binding domain comprising the following six CDRs: (a) a CDR-H1 comprising SEQ ID NO:167, (b) a CDR-H2 comprising SEQ ID NO:169 or SEQ ID NO:173; (c) a CDR-H3 comprising SEQ ID NO:171 or SEQ ID NO:174; (d) a CDR-L1 comprising SEQ ID NO:194, (e) a CDR-L2 comprising SEQ ID NO:196 or SEQ ID NO:199 and (f) a CDR-L3 comprising SEQ ID NO:198 or SEQ ID NO:200.

20. A method of assessing the extent of alternative pathway complement (APC) activation in a test sample comprising:
(a) providing a test sample;
(b) performing an immunoassay comprising at least one of:
(i) capturing and detecting mature Factor D in the test sample, wherein mature Factor D is either captured or detected with a mature Factor D-specific monoclonal antibody or antigen-binding fragment thereof that specifically binds to an epitope in "ILGGREA" (SEQ ID NO:5) present in mature Factor D, but does not bind to Pro-Factor D; and capturing and detecting Pro-Factor D in the test sample, wherein Pro-Factor D is either captured or detected with a Pro-Factor D-specific monoclonal antibody or antigen-binding fragment thereof that specifically binds to an epitope on the activation ("Pro") peptide "APPRGR" (SEQ ID NO:4) present in Pro-Factor D, but does not bind to mature Factor D; and/or (ii) capturing and detecting Pro-Factor D in the test sample, wherein Pro-Factor D is either captured or detected with a Pro-Factor D-specific monoclonal antibody or antigen-binding fragment thereof that specifically binds to an epitope on the activation ("Pro") peptide "APPRGR" (SEQ ID NO:4) present in Pro-Factor D, but does not bind to mature Factor D; and (c) comparing the level of mature Factor D detected in accordance with (b)(i) with a predetermined level or control sample and/or comparing the level of Pro-Factor D detected in accordance with (b)(ii) with a predetermined level or control sample, wherein the level of mature Factor D and/or Pro-Factor D detected in the test sample is indicative of the extent of alternative pathway complement activation; wherein the Pro-Factor D-specific monoclonal antibody or antigen-binding fragment thereof comprises:

(i): an HC-CDR1 comprising the amino acid sequence XYWMS (SEQ ID NO:201), wherein X at position 1 is N, S or T; an HC-CDR2 comprising the amino acid sequence EIRLKSXNYAXXYXESVKG (SEQ ID NO:202), wherein: X at position 7 is D or E, X at position 11 is T or A, X at position 12 is H or Y and X at position 14 is A or T; an HC-CDR3 comprising the amino acid sequence AWFAX (SEQ ID NO:203), wherein X at position 5 is S, Y or N; a LC-CDR1 comprising the amino acid sequence XSSQXLLY-SXDOKNYLA (SEQ ID NO:204), wherein X at position 1 is M or K, X at position 5 is S or N, and X at position 10 is K or R; a LC-CDR2 comprising the amino acid sequence WASTRES (SEQ ID NO:178); and a LC-CDR3 comprising the amino acid sequence LQYYXYPYT (SEQ ID NO:205), wherein X at position 5 is T or S; or (ii): a CDR-H1 comprising SEQ ID NO: 167, a CDR-H2 comprising SEQ ID NO: 169 or SEQ ID NO:173; a CDR-H3 comprising SEQ ID NO:171 or SEQ ID NO:174; a CDR-L1 comprising SEQ ID NO: 194, a CDR-L2 comprising SEQ ID NO: 196 or SEQ ID NO: 199 and a CDR-L3 comprising SEQ ID NO: 198 or SEQ ID NO:200.

21. The method of claim 20, wherein step (b)(ii) comprises capturing Pro-Factor D with a Pro-Factor D-specific monoclonal antibody or antigen-binding fragment thereof that specifically binds to an epitope on the activation ("Pro") peptide "APPRGR" (SEQ ID NO:4) present in Pro-Factor D, but does not bind to mature Factor D and detecting with an antibody or antigen-binding fragment thereof that binds to an epitope shared by both human mature Factor D and human Pro-Factor D; wherein the antibody or antigen binding fragment thereof that binds to an epitope shared by both human mature Factor D and human Pro-Factor D comprises:

(a) HC-CDR1-3 of SEQ ID NOs: 95, 97, and 99; and LC-CDR1-3 of SEQ ID NOs: 111, 113, and 115;
(b) HC-CDR1-3 of SEQ ID NOs: 101, 103, and 105; and LC-CDR1-3 of SEQ ID NOs: 60, 119, and 121;
(c) HC-CDR1-3 of SEQ ID NOs: 101, 107, and 108; and LC-CDR1-3 of SEQ ID NOs: 123, 124, and 125; or
(d) HC-CDR1-3 of SEQ ID NOs: 101, 107, and 105; and LC-CDR1-3 of SEQ ID NOs: 60, 126, and 121.

22. The method of claim 20, wherein step (b)(ii) comprises capturing Pro-Factor D with an anti-Factor D antibody or antigen-binding fragment thereof that binds to an epitope shared by both human mature Factor D and human Pro-Factor D and detecting with a monoclonal antibody or antigen-binding fragment thereof that specifically binds to an epitope on the activation ("Pro") peptide "APPRGR" (SEQ ID NO:4) present in Pro-Factor D, but does not bind to mature Factor D; wherein the antibody or antigen binding fragment thereof that binds to an epitope shared by both human mature Factor D and human Pro-Factor D comprises:

(a) HC-CDR1-3 of SEQ ID NOs: 95, 97, and 99; and LC-CDR1-3 of SEQ ID NOs: 111, 113, and 115;
(b) HC-CDR1-3 of SEQ ID NOs: 101, 103, and 105; and LC-CDR1-3 of SEQ ID NOs: 60, 119, and 121;
(c) HC-CDR1-3 of SEQ ID NOs: 101, 107, and 108; and LC-CDR1-3 of SEQ ID NOs: 123, 124, and 125; or
(d) HC-CDR1-3 of SEQ ID NOs: 101, 107, and 105; and LC-CDR1-3 of SEQ ID NOs: 60, 126, and 121.

23. The method of claim 20, wherein the test sample is a biological sample obtained from a mammalian subject.

24. The method of claim 23, wherein the biological sample comprises whole blood, serum, plasma, urine, or cerebrospinal fluid.

25. The method of claim 20, wherein the control sample is a sample taken from the subject prior to treatment with a MASP-3 inhibitory agent, or a sample taken at an earlier point in time during a course of treatment with a MASP-3 inhibitory agent.

26. The method of claim 25, wherein the MASP-3 inhibitory agent is a MASP-3 inhibitory antibody or antigen-binding fragment thereof.

27. A method for monitoring the efficacy of treatment with a MASP-3 inhibitory antibody, or antigen-binding fragment thereof, in a mammalian subject, the method comprising:

(a) administering a dose of a MASP-3 inhibitory antibody, or antigen-binding fragment thereof, to a mammalian subject at a first point in time;
(b) assessing a first concentration of Pro-Factor D in a biological sample obtained from the subject after step (a);
(c) treating the subject with the MASP-3 inhibitory antibody, or antigen-binding fragment thereof, at a second point in time;
(d) assessing a second concentration of Pro-Factor D in a biological sample obtained from the subject after step (c); and
(e) comparing the level of Pro-Factor D assessed in step (b) with the level of Pro-Factor D assessed in step (d) to determine the efficacy of the MASP-3 inhibitory antibody or antigen-binding fragment thereof in the mammalian subject;
wherein the immunoassay comprises (i) a first monoclonal antibody, or antigen-binding fragment thereof, that specifically binds to an epitope in the pro peptide of human Factor D, wherein the epitope comprises or consists of the amino acids APPRGR (SEQ ID NO:4) and does not bind to human mature Factor D; and (ii) a second antibody, or antigen-binding fragment thereof, that binds to an epitope shared by both human mature Factor D and human Pro-Factor D, wherein the first and second antibody or antigen-binding fragments thereof function together in the immunoassay to specifically detect or quantitate the amount of Pro-Factor D protein (SEQ ID NO:2) and not mature-Factor D protein (SEQ ID NO:3) that may be present in the biological sample, and wherein the first antibody or antigen-binding fragment thereof comprises:

(i): an HC-CDR1 comprising the amino acid sequence XYWMS (SEQ ID NO:201), wherein X at position 1 is N, S or T; an HC-CDR2 comprising the amino acid sequence EIRLKSXNYAXXYXESVKG (SEQ ID NO:202), wherein: X at position 7 is D or E, X at position 11 is T or A, X at position 12 is H or Y and X at position 14 is A or T; an HC-CDR3 comprising the amino acid sequence AWFAX (SEQ ID NO:203), wherein X at position 5 is S, Y or N; a LC-CDR1 comprising the amino acid sequence XSSQXLLY-SXDOKNYLA (SEQ ID NO:204), wherein X at position 1 is M or K, X at position 5 is S or N, and X at position 10 is K or R; a LC-CDR2 comprising the amino acid sequence WASTRES (SEQ ID NO:178); and a LC-CDR3 comprising the amino acid sequence LOYYXYPYT (SEQ ID NO:205), wherein X at position 5 is T or S; or (ii): a CDR-H1 comprising SEQ ID NO:167, a CDR-H2 comprising SEQ ID NO: 169 or SEQ ID NO:173; a CDR-H3 comprising SEQ ID NO:171 or SEQ ID NO:174; a CDR-L1 comprising SEQ ID NO:194, a CDR-L2 comprising SEQ ID NO: 196 or SEQ ID NO: 199 and a CDR-L3 comprising SEQ ID NO: 198 or SEQ ID NO:200; and wherein the second antibody or antigen binding fragment comprises:

(a) HC-CDR1-3 of SEQ ID NOs: 95, 97, and 99; and LC-CDR1-3 of SEQ ID NOs: 111, 113, and 115;

(b) HC-CDR1-3 of SEQ ID NOs: 101, 103, and 105; and LC-CDR1-3 of SEQ ID NOs: 60, 119, and 121;

(c) HC-CDR1-3 of SEQ ID NOs: 101, 107, and 108; and LC-CDR1-3 of SEQ ID NOs: 123, 124, and 125; or (d) HC-CDR1-3 of SEQ ID NOs: 101, 107, 105; and LC-CDR1-3 of SEQ ID NOs: 60, 126, and 121.

28. The method of claim 27, wherein the method further comprises adjusting the dose of the MASP-3 inhibitory antibody or antigen-binding fragment thereof.

29. The method of claim 28, wherein the dose of MASP-3 inhibitory antibody or antigen-binding fragment thereof administered to the subject is increased if the level of mature Factor D is higher than the control or reference standard.

30. The method of claim 28, wherein the dose of MASP-3 inhibitory antibody or antigen-binding fragment thereof administered to the subject is increased if the level of Pro-Factor D is lower than the control or reference standard.

31. The method of claim 27, wherein steps (b) and (d) further comprise assessing the concentration of mature Factor D in the biological samples.

32. The method of claim 31, further comprising (i) a third monoclonal antibody, or antigen-binding fragment thereof, that specifically binds to an epitope in the N-terminal region of human mature Factor D, wherein the epitope comprises or consists of the amino acids ILGGREA (SEQ ID NO:5) and does not bind to human Pro-Factor D; and (ii) a second antibody, or antigen-binding fragment thereof, that binds to an epitope shared by both human mature Factor D and human Pro-Factor D, wherein the third and second antibody or antigen-binding fragments thereof function together to specifically detect or quantitate the amount of mature Factor D protein (SEQ ID NO:3) and not Pro-Factor D protein (SEQ ID NO:2) that may be present in the biological sample; wherein the third antibody or antigen binding fragment thereof comprises (a) an HC-CDR1 comprising the amino acid sequence XSXMGVS (SEQ ID NO: 65), wherein X at position 1 is T, I, or S and X at position 3 is G or I; (b) an HC-CDR2 comprising the amino acid sequence HIYWD-DEKHYXPSLKX (SEQ ID NO: 66), wherein X at position 11 is H or N and X at position 16 is S or R; (c) an HC-CDR3 comprising the amino acid sequence RYYGYXXXMXY (SEQ ID NO: 67), wherein X at position 6 is R, G or N, X at position 7 is S or Y, X at position 8 is F, I or V, and X at position 10 is D or H; (d) a LC-CDR1 comprising the amino acid sequence RSXXSIXHSNGNTYXE (SEQ ID NO: 68), wherein: X at position 3 is N or S, X at position 4 is Q or E, X at position 7 is V or L, and X at position 15 is F or L; (e) a LC-CDR2 comprising the amino acid sequence KVXNRFS (SEQ ID NO: 69), wherein: X at position 3 is S or Y; and (f) a LC-CDR3 comprising the amino acid sequence FQGSHVPPT (SEQ ID NO: 54).

33. The method of claim 27 wherein the MASP-3 inhibitory antibody or antigen-binding fragment thereof is a monoclonal antibody or antigen-binding fragment thereof.

\* \* \* \* \*

SEQUENCE LISTING

```
<160> NUMBER OF SEQ ID NOS: 247

<210> SEQ ID NO 1
<211> LENGTH: 253
<212> TYPE: PRT
<213> ORGANISM: Homo sapiens

<400> SEQUENCE: 1
```

-continued

```
Met His Ser Trp Glu Arg Leu Ala Val Leu Val Leu Leu Gly Ala Ala
1               5                   10                  15

Ala Cys Ala Ala Pro Pro Arg Gly Arg Ile Leu Gly Gly Arg Glu Ala
            20                  25                  30

Glu Ala His Ala Arg Pro Tyr Met Ala Ser Val Gln Leu Asn Gly Ala
        35                  40                  45

His Leu Cys Gly Gly Val Leu Val Ala Glu Gln Trp Val Leu Ser Ala
    50                  55                  60

Ala His Cys Leu Glu Asp Ala Ala Asp Gly Lys Val Gln Val Leu Leu
65                  70                  75                  80

Gly Ala His Ser Leu Ser Gln Pro Glu Pro Ser Lys Arg Leu Tyr Asp
                85                  90                  95

Val Leu Arg Ala Val Pro His Pro Asp Ser Gln Pro Asp Thr Ile Asp
            100                 105                 110

His Asp Leu Leu Leu Leu Gln Leu Ser Glu Lys Ala Thr Leu Gly Pro
        115                 120                 125

Ala Val Arg Pro Leu Pro Trp Gln Arg Val Asp Arg Asp Val Ala Pro
    130                 135                 140

Gly Thr Leu Cys Asp Val Ala Gly Trp Gly Ile Val Asn His Ala Gly
145                 150                 155                 160

Arg Arg Pro Asp Ser Leu Gln His Val Leu Leu Pro Val Leu Asp Arg
                165                 170                 175

Ala Thr Cys Asn Arg Arg Thr His His Asp Gly Ala Ile Thr Glu Arg
            180                 185                 190

Leu Met Cys Ala Glu Ser Asn Arg Arg Asp Ser Cys Lys Gly Asp Ser
        195                 200                 205

Gly Gly Pro Leu Val Cys Gly Gly Val Leu Glu Gly Val Val Thr Ser
    210                 215                 220

Gly Ser Arg Val Cys Gly Asn Arg Lys Lys Pro Gly Ile Tyr Thr Arg
225                 230                 235                 240

Val Ala Ser Tyr Ala Ala Trp Ile Asp Ser Val Leu Ala
                245                 250

<210> SEQ ID NO 2
<211> LENGTH: 234
<212> TYPE: PRT
<213> ORGANISM: Homo sapiens

<400> SEQUENCE: 2

Ala Pro Pro Arg Gly Arg Ile Leu Gly Gly Arg Glu Ala Glu Ala His
1               5                   10                  15

Ala Arg Pro Tyr Met Ala Ser Val Gln Leu Asn Gly Ala His Leu Cys
            20                  25                  30

Gly Gly Val Leu Val Ala Glu Gln Trp Val Leu Ser Ala Ala His Cys
        35                  40                  45

Leu Glu Asp Ala Ala Asp Gly Lys Val Gln Val Leu Leu Gly Ala His
    50                  55                  60

Ser Leu Ser Gln Pro Glu Pro Ser Lys Arg Leu Tyr Asp Val Leu Arg
65                  70                  75                  80

Ala Val Pro His Pro Asp Ser Gln Pro Asp Thr Ile Asp His Asp Leu
                85                  90                  95

Leu Leu Leu Gln Leu Ser Glu Lys Ala Thr Leu Gly Pro Ala Val Arg
            100                 105                 110

Pro Leu Pro Trp Gln Arg Val Asp Arg Asp Val Ala Pro Gly Thr Leu
```

```
                115                 120                 125
Cys Asp Val Ala Gly Trp Gly Ile Val Asn His Ala Gly Arg Arg Pro
130                 135                 140

Asp Ser Leu Gln His Val Leu Leu Pro Val Leu Asp Arg Ala Thr Cys
145                 150                 155                 160

Asn Arg Arg Thr His His Asp Gly Ala Ile Thr Glu Arg Leu Met Cys
                165                 170                 175

Ala Glu Ser Asn Arg Arg Asp Ser Cys Lys Gly Asp Ser Gly Gly Pro
            180                 185                 190

Leu Val Cys Gly Gly Val Leu Glu Gly Val Val Thr Ser Gly Ser Arg
        195                 200                 205

Val Cys Gly Asn Arg Lys Lys Pro Gly Ile Tyr Thr Arg Val Ala Ser
210                 215                 220

Tyr Ala Ala Trp Ile Asp Ser Val Leu Ala
225                 230

<210> SEQ ID NO 3
<211> LENGTH: 228
<212> TYPE: PRT
<213> ORGANISM: Homo sapiens

<400> SEQUENCE: 3

Ile Leu Gly Gly Arg Glu Ala Glu Ala His Ala Arg Pro Tyr Met Ala
1               5                   10                  15

Ser Val Gln Leu Asn Gly Ala His Leu Cys Gly Gly Val Leu Val Ala
                20                  25                  30

Glu Gln Trp Val Leu Ser Ala Ala His Cys Leu Glu Asp Ala Ala Asp
            35                  40                  45

Gly Lys Val Gln Val Leu Leu Gly Ala His Ser Leu Ser Gln Pro Glu
        50                  55                  60

Pro Ser Lys Arg Leu Tyr Asp Val Leu Arg Ala Val Pro His Pro Asp
65                  70                  75                  80

Ser Gln Pro Asp Thr Ile Asp His Asp Leu Leu Leu Leu Gln Leu Ser
                85                  90                  95

Glu Lys Ala Thr Leu Gly Pro Ala Val Arg Pro Leu Pro Trp Gln Arg
            100                 105                 110

Val Asp Arg Asp Val Ala Pro Gly Thr Leu Cys Asp Val Ala Gly Trp
        115                 120                 125

Gly Ile Val Asn His Ala Gly Arg Arg Pro Asp Ser Leu Gln His Val
    130                 135                 140

Leu Leu Pro Val Leu Asp Arg Ala Thr Cys Asn Arg Arg Thr His His
145                 150                 155                 160

Asp Gly Ala Ile Thr Glu Arg Leu Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
        195                 200                 205

Lys Pro Gly Ile Tyr Thr Arg Val Ala Ser Tyr Ala Ala Trp Ile Asp
    210                 215                 220

Ser Val Leu Ala
225

<210> SEQ ID NO 4
<211> LENGTH: 6
```

<212> TYPE: PRT
<213> ORGANISM: Artificial Sequence
<220> FEATURE:
<223> OTHER INFORMATION: Synthetic

<400> SEQUENCE: 4

```
Ala Pro Pro Arg Gly Arg
1               5
```

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

```
Ile Leu Gly Gly Arg Glu Ala
1               5
```

<210> SEQ ID NO 6
<211> LENGTH: 29
<212> TYPE: PRT
<213> ORGANISM: Artificial Sequence
<220> FEATURE:
<223> OTHER INFORMATION: Synthetic

<400> SEQUENCE: 6

```
Ile Leu Gly Gly Arg Glu Ala Gly Pro Gly Pro Gly Ala Lys Phe Val
1               5                   10                  15

Ala Ala Ala Trp Thr Leu Lys Ala Ala Lys Lys Cys
            20                  25
```

<210> SEQ ID NO 7
<211> LENGTH: 728
<212> TYPE: PRT
<213> ORGANISM: Homo sapiens

<400> SEQUENCE: 7

```
Met Arg Trp Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
                20                  25                  30

Ser Pro Gly Tyr Pro Asp Ser Tyr Pro Ser Asp Ser Glu Val Thr Trp
            35                  40                  45

Asn Ile Thr Val Pro Asp Gly Phe Arg Ile Lys Leu Tyr Phe Met His
        50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175
```

```
Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
            195                 200                 205

Ser Ser Glu Cys Leu Tyr Thr Ile Glu Leu Glu Glu Gly Phe Met Val
210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
            275                 280                 285

Gly Trp Arg Leu Ser Tyr Arg Ala Ala Gly Asn Glu Cys Pro Glu Leu
            290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
            355                 360                 365

Ala Pro Gly Glu Leu Glu His Gly Leu Ile Thr Phe Ser Thr Arg Asn
            370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Glu Cys Gly Gln Pro Ser Arg Ser Leu Pro Ser Leu Val Lys
            435                 440                 445

Arg Ile Ile Gly Gly Arg Asn Ala Glu Pro Gly Leu Phe Pro Trp Gln
450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Ala Ser Trp Ile Leu Thr Ala Ala
                485                 490                 495

His Val Leu Arg Ser Gln Arg Arg Asp Thr Thr Val Ile Pro Val Ser
            500                 505                 510

Lys Glu His Val Thr Val Tyr Leu Gly Leu His Asp Val Arg Asp Lys
            515                 520                 525

Ser Gly Ala Val Asn Ser Ser Ala Ala Arg Val Val Leu His Pro Asp
            530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Val Cys Leu Pro Arg
                565                 570                 575

Leu Glu Pro Glu Gly Pro Ala Pro His Met Leu Gly Leu Val Ala Gly
            580                 585                 590
```

Trp Gly Ile Ser Asn Pro Asn Val Thr Val Asp Glu Ile Ser Ser
            595                 600                 605

Gly Thr Arg Thr Leu Ser Asp Val Leu Gln Tyr Val Lys Leu Pro Val
610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Glu Gly Gly
                645                 650                 655

Lys Asp Thr Cys Leu Gly Asp Ser Gly Gly Ala Phe Val Ile Phe Asp
                660                 665                 670

Asp Leu Ser Gln Arg Trp Val Val Gln Gly Leu Val Ser Trp Gly Gly
            675                 680                 685

Pro Glu Glu Cys Gly Ser Lys Gln Val Tyr Gly Val Tyr Thr Lys Val
690                 695                 700

Ser Asn Tyr Val Asp Trp Val Trp Glu Gln Met Gly Leu Pro Gln Ser
705                 710                 715                 720

Val Val Glu Pro Gln Val Glu Arg
                725

<210> SEQ ID NO 8
<211> LENGTH: 253
<212> TYPE: PRT
<213> ORGANISM: Macaca fascicularis

<400> SEQUENCE: 8

Met His Ser Trp Glu His Leu Ala Val Leu Val Leu Leu Gly Val Ala
1               5                   10                  15

Ala Cys Ala Ala Gln Pro Arg Gly Arg Ile Leu Gly Gly Arg Glu Ala
            20                  25                  30

Glu Ala His Ala Arg Pro Tyr Met Ala Ser Val Gln Val Asn Gly Glu
        35                  40                  45

His Leu Cys Gly Gly Val Leu Val Ala Glu Gln Trp Val Leu Ser Ala
    50                  55                  60

Ala His Cys Leu Glu Asp Ala Ala Asp Gly Lys Val Gln Val Leu Leu
65                  70                  75                  80

Gly Ala His Ser Leu Ser Gln Pro Glu Pro Ser Lys Arg Leu Tyr Asp
                85                  90                  95

Val Leu Arg Ala Val Pro His Pro Asp Ser Arg Pro Asp Thr Ile Asp
            100                 105                 110

His Asp Leu Leu Leu Leu Gln Leu Ser Glu Lys Ala Thr Leu Gly Pro
        115                 120                 125

Ala Val Arg Pro Leu Pro Trp Gln Arg Val Asp Arg Asp Val Glu Pro
    130                 135                 140

Gly Thr Leu Cys Asp Val Ala Gly Trp Gly Ile Val Ser His Ala Gly
145                 150                 155                 160

Arg Arg Pro Asp Arg Leu Gln His Val Leu Leu Pro Val Leu Asp Arg
                165                 170                 175

Ala Thr Cys Asn Arg Arg Thr His His Asp Gly Ala Ile Thr Gln Arg
            180                 185                 190

Met Met Cys Ala Glu Ser Asn Arg Arg Asp Ser Cys Lys Gly Asp Ser
        195                 200                 205

Gly Gly Pro Leu Val Cys Gly Gly Val Leu Glu Gly Val Val Thr Ser
    210                 215                 220

Gly Ser Arg Val Cys Gly Asn Arg Lys Lys Pro Gly Ile Tyr Thr Arg
225                 230                 235                 240

```
Val Ala Ser Tyr Ala Ala Trp Ile Asp Ser Val Leu Ala
            245                 250

<210> SEQ ID NO 9
<211> LENGTH: 261
<212> TYPE: PRT
<213> ORGANISM: Canis lupus

<400> SEQUENCE: 9

Met Ala Pro Arg Leu Gly Pro Val Pro Leu Val Pro Val Leu Leu Leu
1               5                   10                  15

Gly Ala Ala Leu Cys Ala Ala Gln Pro Arg Gly Arg Ile Leu Gly Gly
                20                  25                  30

Ser Glu Ala Glu Ser His Ala Arg Pro Tyr Met Ala Ser Val Gln Val
        35                  40                  45

Asp Gly Lys His Val Cys Gly Gly Phe Leu Val Ser Glu Arg Trp Val
    50                  55                  60

Leu Ser Ala His Cys Leu Glu Asp Val Ala Asp Gly Lys Val Arg
65                  70                  75                  80

Val Leu Leu Gly Ala His Ser Leu Ser Gln Pro Glu Pro Ser Lys Arg
                85                  90                  95

Trp Tyr Asp Val Leu Arg Ala Val Pro His Pro Asp Ser Arg Arg Asp
            100                 105                 110

Thr Ile Glu His Asp Leu Leu Leu Gln Leu Ser Glu Asp Ala Glu
        115                 120                 125

Leu Gly Pro Ala Val Gln Pro Leu Arg Trp Gln Arg Glu Asp Arg Asp
    130                 135                 140

Val Ala Ala Gly Thr Arg Cys Asp Val Ala Gly Trp Gly Val Val Ser
145                 150                 155                 160

His Thr Gly Arg Arg Pro Asp Arg Leu Gln His Leu Ile Leu Pro Val
                165                 170                 175

Leu Asp Arg Ala Thr Cys Asn Leu Arg Thr Tyr His Asp Gly Thr Ile
            180                 185                 190

Thr Glu Arg Met Met Cys Ala Glu Ser Asn Arg Arg Asp Ser Cys Lys
        195                 200                 205

Gly Asp Ser Gly Gly Pro Leu Val Cys Gly Gly Val Ala Glu Ala Val
    210                 215                 220

Val Thr Ser Gly Ser Arg Val Cys Gly Asn Arg Lys Lys Pro Gly Ile
225                 230                 235                 240

Tyr Thr Arg Val Ala Ser Tyr Ala Ala Trp Ile Asp Gly Val Met Ala
                245                 250                 255

Gly Gly Ala Ala Ala
            260

<210> SEQ ID NO 10
<211> LENGTH: 263
<212> TYPE: PRT
<213> ORGANISM: Rattus rattus

<400> SEQUENCE: 10

Met His Ser Ser Val Tyr Leu Val Ala Leu Val Val Leu Glu Ala Ala
1               5                   10                  15

Val Cys Val Ala Gln Pro Arg Gly Arg Ile Leu Gly Gly Gln Glu Ala
                20                  25                  30

Met Ala His Ala Arg Pro Tyr Met Ala Ser Val Gln Val Asn Gly Thr
        35                  40                  45
```

```
His Val Cys Gly Gly Thr Leu Val Asp Glu Gln Trp Val Leu Ser Ala
        50                  55                  60

Ala His Cys Met Asp Gly Val Thr Lys Asp Glu Val Val Gln Val Leu
65                  70                  75                  80

Leu Gly Ala His Ser Leu Ser Ser Pro Glu Pro Tyr Lys His Leu Tyr
                85                  90                  95

Asp Val Gln Ser Val Val Leu His Pro Gly Ser Arg Pro Asp Ser Val
            100                 105                 110

Glu Asp Asp Leu Met Leu Phe Lys Leu Ser His Asn Ala Ser Leu Gly
        115                 120                 125

Pro His Val Arg Pro Leu Pro Leu Gln Arg Glu Asp Arg Glu Val Lys
    130                 135                 140

Pro Gly Thr Leu Cys Asp Val Ala Gly Trp Gly Val Val Thr His Ala
145                 150                 155                 160

Gly Arg Arg Pro Asp Val Leu Gln Gln Leu Thr Val Ser Ile Met Asp
                165                 170                 175

Arg Asn Thr Cys Asn Leu Arg Thr Tyr His Asp Gly Ala Ile Thr Lys
            180                 185                 190

Asn Met Met Cys Ala Glu Ser Asn Arg Arg Asp Thr Cys Arg Gly Asp
        195                 200                 205

Ser Gly Gly Pro Leu Val Cys Gly Asp Ala Val Glu Ala Val Val Thr
    210                 215                 220

Trp Gly Ser Arg Val Cys Gly Asn Arg Arg Lys Pro Gly Val Phe Thr
225                 230                 235                 240

Arg Val Ala Thr Tyr Val Pro Trp Ile Glu Asn Val Leu Ser Gly Asn
                245                 250                 255

Val Ser Val Asn Val Thr Ala
            260

<210> SEQ ID NO 11
<211> LENGTH: 259
<212> TYPE: PRT
<213> ORGANISM: Mus musculus

<400> SEQUENCE: 11

Met His Ser Ser Val Tyr Phe Val Ala Leu Val Ile Leu Gly Ala Ala
1               5                   10                  15

Val Cys Ala Ala Gln Pro Arg Gly Arg Ile Leu Gly Gly Gln Glu Ala
            20                  25                  30

Ala Ala His Ala Arg Pro Tyr Met Ala Ser Val Gln Val Asn Gly Thr
        35                  40                  45

His Val Cys Gly Gly Thr Leu Leu Asp Glu Gln Trp Val Leu Ser Ala
    50                  55                  60

Ala His Cys Met Asp Gly Val Thr Asp Asp Ser Val Gln Val Leu
65                  70                  75                  80

Leu Gly Ala His Ser Leu Ser Ala Pro Glu Pro Tyr Lys Arg Trp Tyr
                85                  90                  95

Asp Val Gln Ser Val Val Pro His Pro Gly Ser Arg Pro Asp Ser Leu
            100                 105                 110

Glu Asp Asp Leu Ile Leu Phe Lys Leu Ser Gln Asn Ala Ser Leu Gly
        115                 120                 125

Pro His Val Arg Pro Leu Pro Leu Gln Tyr Glu Asp Lys Glu Val Glu
    130                 135                 140

Pro Gly Thr Leu Cys Asp Val Ala Gly Trp Gly Val Val Thr His Ala
```

```
                145             150             155             160
Gly Arg Arg Pro Asp Val Leu His Gln Leu Arg Val Ser Ile Met Asn
                165             170             175
Arg Thr Thr Cys Asn Leu Arg Thr Tyr His Asp Gly Val Val Thr Ile
                180             185             190
Asn Met Met Cys Ala Glu Ser Asn Arg Arg Asp Thr Cys Arg Gly Asp
                195             200             205
Ser Gly Ser Pro Leu Val Cys Gly Asp Ala Val Glu Gly Val Val Thr
                210             215             220
Trp Gly Ser Arg Val Cys Gly Asn Gly Lys Lys Pro Gly Val Tyr Thr
225             230             235             240
Arg Val Ser Ser Tyr Arg Met Trp Ile Glu Asn Ile Thr Asn Gly Asn
                245             250             255
Met Thr Ser

<210> SEQ ID NO 12
<211> LENGTH: 121
<212> TYPE: PRT
<213> ORGANISM: Artificial Sequence
<220> FEATURE:
<223> OTHER INFORMATION: Synthetic

<400> SEQUENCE: 12

Gln Ile Thr Leu Lys Glu Ser Gly Pro Gly Ile Leu Gln Ser Ser Gln
1               5                   10                  15
Thr Leu Ser Leu Thr Cys Ser Phe Ser Gly Ile Ser Leu Thr Thr Ser
                20                  25                  30
Gly Met Gly Val Ser Trp Ile Arg Gln Pro Ser Gly Lys Gly Leu Glu
            35                  40                  45
Trp Leu Ala His Ile Tyr Trp Asp Asp Glu Lys His Tyr His Pro Ser
    50                  55                  60
Leu Lys Ser Arg Leu Thr Ile Ser Lys Asp Ala Ser Arg Asn Gln Val
65                  70                  75                  80
Phe Phe Arg Ile Leu Ser Val Asp Thr Ala Asp Thr Ala Thr Tyr Tyr
                85                  90                  95
Cys Ala Leu Arg Tyr Tyr Gly Tyr Arg Ser Phe Met Asp Tyr Trp Gly
                100                 105                 110
Gln Gly Thr Ser Val Thr Val Ser Ser
            115                 120

<210> SEQ ID NO 13
<211> LENGTH: 121
<212> TYPE: PRT
<213> ORGANISM: Artificial Sequence
<220> FEATURE:
<223> OTHER INFORMATION: Synthetic

<400> SEQUENCE: 13

Gln Ile Thr Leu Lys Glu Ser Gly Pro Gly Ile Leu Gln Ser Ser Gln
1               5                   10                  15
Thr Leu Ser Leu Thr Cys Ser Phe Ser Gly Val Ser Leu Thr Thr Ser
                20                  25                  30
Gly Met Gly Val Ser Trp Ile Arg Gln Pro Ser Gly Lys Gly Leu Glu
            35                  40                  45
Trp Leu Ala His Ile Tyr Trp Asp Asp Glu Lys His Tyr His Pro Ser
    50                  55                  60
Leu Lys Ser Arg Leu Thr Ile Ser Lys Asp Ala Ser Arg Asn Gln Val
```

```
                65                  70                  75                  80
Phe Phe Arg Ile Leu Ser Val Asp Thr Ala Asp Thr Ala Thr Tyr Tyr
                    85                  90                  95
Cys Ala Leu Arg Tyr Tyr Gly Tyr Arg Ser Phe Met Asp Tyr Trp Gly
                    100                 105                 110
Gln Gly Thr Ser Val Thr Val Ser Ser
                    115                 120

<210> SEQ ID NO 14
<211> LENGTH: 121
<212> TYPE: PRT
<213> ORGANISM: Artificial Sequence
<220> FEATURE:
<223> OTHER INFORMATION: Synthetic

<400> SEQUENCE: 14

Gln Val Thr Leu Lys Glu Ser Gly Pro Gly Ile Leu Gln Ser Ser Gln
1               5                   10                  15
Thr Leu Ser Leu Thr Cys Ser Phe Ser Gly Ile Ser Leu Asn Ile Ser
                    20                  25                  30
Gly Met Gly Val Ser Trp Ile Arg Gln Pro Ser Gly Lys Gly Leu Glu
                    35                  40                  45
Trp Leu Ala His Ile Tyr Trp Asp Asp Glu Lys His Tyr Asn Pro Ser
        50                  55                  60
Leu Lys Arg Arg Leu Thr Ile Ser Lys Asp Ala Ser Arg Asn Gln Val
65                  70                  75                  80
Phe Phe Arg Ile Ser Ser Val Asp Ser Ala Asp Thr Ala Thr Tyr Tyr
                    85                  90                  95
Cys Ala Leu Arg Tyr Tyr Gly Tyr Gly Ser Ile Met Asp Tyr Trp Gly
                    100                 105                 110
His Gly Thr Ser Val Thr Val Ser Ser
                    115                 120

<210> SEQ ID NO 15
<211> LENGTH: 121
<212> TYPE: PRT
<213> ORGANISM: Artificial Sequence
<220> FEATURE:
<223> OTHER INFORMATION: Synthetic

<400> SEQUENCE: 15

Gln Val Thr Leu Lys Glu Ser Gly Pro Gly Ile Leu Gln Ser Ser Gln
1               5                   10                  15
Thr Leu Ser Leu Thr Cys Ser Phe Ser Gly Ile Ser Leu Asn Thr Ser
                    20                  25                  30
Ile Met Gly Val Ser Trp Ile Arg Gln Pro Ser Gly Lys Gly Leu Glu
                    35                  40                  45
Trp Leu Ala His Ile Tyr Trp Asp Asp Glu Lys His Tyr Asn Pro Ser
        50                  55                  60
Leu Lys Ser Arg Leu Thr Ile Ser Lys Asp Ala Ser Arg Asn Gln Val
65                  70                  75                  80
Phe Leu Lys Ile Ile Ser Val Asp Thr Ala Asp Thr Ala Thr Tyr Tyr
                    85                  90                  95
Cys Ala Leu Arg Tyr Tyr Gly Tyr Asn Tyr Val Met His Tyr Trp Gly
                    100                 105                 110
Gln Gly Thr Ser Val Thr Val Ser Ser
                    115                 120
```

<210> SEQ ID NO 16
<211> LENGTH: 121
<212> TYPE: PRT
<213> ORGANISM: Artificial Sequence
<220> FEATURE:
<223> OTHER INFORMATION: Synthetic

<400> SEQUENCE: 16

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Ile Ser Leu Ser Ser Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Glu Lys His Tyr Asn Pro Ser
    50                  55                  60

Leu Lys Ser Arg Leu Thr Ile Ser Lys Asp Ala Ser Arg Asn Gln Ile
65                  70                  75                  80

Phe Leu Lys Ile Ile Ser Val Asp Thr Ala Asp Ala Thr Tyr Tyr
                85                  90                  95

Cys Ala Leu Arg Tyr Tyr Gly Tyr Asn Tyr Val Met His Tyr Trp Gly
            100                 105                 110

Gln Gly Thr Ser Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: Synthetic

<400> SEQUENCE: 17

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Val Ser Leu Ser Ser Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Glu Lys His Tyr Asn Pro Ser
    50                  55                  60

Leu Lys Ser Arg Leu Thr Ile Ser Lys Gly Ala Ser Arg Asn Gln Val
65                  70                  75                  80

Phe Leu Lys Ile Ile Ser Val Asp Thr Ala Asp Ala Thr Tyr Tyr
                85                  90                  95

Cys Ala Leu Arg Tyr Tyr Gly Tyr Asn Ser Ile Met His Tyr Trp Gly
            100                 105                 110

Gln Gly Ala Ser Val Thr Val Ser Ser
        115                 120

<210> SEQ ID NO 18
<211> LENGTH: 113
<212> TYPE: PRT
<213> ORGANISM: Artificial Sequence
<220> FEATURE:
<223> OTHER INFORMATION: Synthetic

<400> SEQUENCE: 18

Asp Val Leu Met Thr Gln Ser Pro Leu Ser Leu Pro Val Ser Leu Gly

```
              1               5                  10                 15
Asp Gln Ala Ser Ile Phe Cys Arg Ser Asn Gln Ser Ile Val His Ser
                        20                  25                 30

Asn Gly Asn Thr Tyr Phe Glu Trp Tyr Leu Gln Lys Pro Gly Gln Ser
                   35                  40                  45

Pro Lys Leu Leu Ile Tyr Lys Val Ser Asn Arg Phe Ser Gly Val Pro
               50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                    85                  90                  95

Ser His Val Pro Pro Thr Phe Gly Gly Gly Thr Lys Leu Glu Ile Lys
                   100                 105                 110

Arg

<210> SEQ ID NO 19
<211> LENGTH: 113
<212> TYPE: PRT
<213> ORGANISM: Artificial Sequence
<220> FEATURE:
<223> OTHER INFORMATION: Synthetic

<400> SEQUENCE: 19

Asp Val Leu Met Thr Gln Ser Pro Leu Ser Leu Pro Val Ser Leu Gly
1               5                  10                  15

Asp Gln Ala Ser Ile Phe Cys Arg Ser Asn Gln Ser Ile Val His Ser
                    20                  25                 30

Asn Gly Asn Thr Tyr Phe Glu Trp Tyr Leu Gln Lys Pro Gly Gln Ser
                   35                  40                  45

Pro Lys Leu Leu Ile Tyr Lys Val Ser Asn Arg Phe Ser Gly Val Pro
               50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Ile Tyr Tyr Cys Phe Gln Gly
                    85                  90                  95

Ser His Val Pro Pro Thr Phe Gly Gly Gly Thr Lys Leu Glu Ile Lys
                   100                 105                 110

Arg

<210> SEQ ID NO 20
<211> LENGTH: 113
<212> TYPE: PRT
<213> ORGANISM: Artificial Sequence
<220> FEATURE:
<223> OTHER INFORMATION: Synthetic

<400> SEQUENCE: 20

Asp Val Leu Met Thr Gln Thr Pro Leu Ser Leu Pro Val Ser Leu Gly
1               5                  10                  15

Asp Gln Ala Ser Ile Ser Cys Arg Ser Ser Gln Ser Ile Val His Ser
                    20                  25                 30

Asn Gly Asn Thr Tyr Phe Glu Trp Tyr Leu Gln Lys Pro Gly Gln Ser
                   35                  40                  45

Pro Lys Leu Leu Ile Tyr Lys Val Ser Asn Arg Phe Ser Gly Val Pro
               50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 21
<211> LENGTH: 113
<212> TYPE: PRT
<213> ORGANISM: Artificial Sequence
<220> FEATURE:
<223> OTHER INFORMATION: Synthetic

<400> SEQUENCE: 21

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 22
<211> LENGTH: 113
<212> TYPE: PRT
<213> ORGANISM: Artificial Sequence
<220> FEATURE:
<223> OTHER INFORMATION: Synthetic

<400> SEQUENCE: 22

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asn Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 23
<211> LENGTH: 113
<212> TYPE: PRT

```
<213> ORGANISM: Artificial Sequence
<220> FEATURE:
<223> OTHER INFORMATION: Synthetic

<400> SEQUENCE: 23

Asp Val Leu Met Thr Gln Thr Pro Leu Ser Leu Pro Val Ser Leu Gly
1               5                   10                  15

Asp Gln Ala Ser Ile Ser Cys Arg Ser Ser Glu Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Tyr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 24
<211> LENGTH: 30
<212> TYPE: PRT
<213> ORGANISM: Artificial Sequence
<220> FEATURE:
<223> OTHER INFORMATION: Synthetic

<400> SEQUENCE: 24

Gln Ile Thr Leu Lys Glu Ser Gly Pro Gly Ile Leu Gln Ser Ser Gln
1               5                   10                  15

Thr Leu Ser Leu Thr Cys Ser Phe Ser Gly Ile Ser Leu Thr
            20                  25                  30

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Thr Ser Gly Met Gly Val Ser
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Trp Ile Arg Gln Pro Ser Gly Lys Gly Leu Glu Trp Leu Ala
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Synthetic
```

```
<400> SEQUENCE: 27

His Ile Tyr Trp Asp Asp Glu Lys His Tyr His Pro Ser Leu Lys Ser
1               5                   10                  15

<210> SEQ ID NO 28
<211> LENGTH: 32
<212> TYPE: PRT
<213> ORGANISM: Artificial Sequence
<220> FEATURE:
<223> OTHER INFORMATION: Synthetic

<400> SEQUENCE: 28

Arg Leu Thr Ile Ser Lys Asp Ala Ser Arg Asn Gln Val Phe Phe Arg
1               5                   10                  15

Ile Leu Ser Val Asp Thr Ala Asp Thr Ala Thr Tyr Tyr Cys Ala Leu
                20                  25                  30

<210> SEQ ID NO 29
<211> LENGTH: 11
<212> TYPE: PRT
<213> ORGANISM: Artificial Sequence
<220> FEATURE:
<223> OTHER INFORMATION: Synthetic

<400> SEQUENCE: 29

Arg Tyr Tyr Gly Tyr Arg Ser Phe Met Asp Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic

<400> SEQUENCE: 30

Trp Gly Gln Gly Thr Ser Val Thr Val Ser Ser
1               5                   10

<210> SEQ ID NO 31
<211> LENGTH: 30
<212> TYPE: PRT
<213> ORGANISM: Artificial Sequence
<220> FEATURE:
<223> OTHER INFORMATION: Synthetic

<400> SEQUENCE: 31

Gln Ile Thr Leu Lys Glu Ser Gly Pro Gly Ile Leu Gln Ser Ser Gln
1               5                   10                  15

Thr Leu Ser Leu Thr Cys Ser Phe Ser Gly Val Ser Leu Thr
                20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Synthetic

<400> SEQUENCE: 32

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Ile Ser Leu Asn
                20                  25                  30
```

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Ile Ser Gly Met Gly Val Ser
1               5

<210> SEQ ID NO 34
<211> LENGTH: 16
<212> TYPE: PRT
<213> ORGANISM: Artificial Sequence
<220> FEATURE:
<223> OTHER INFORMATION: Synthetic

<400> SEQUENCE: 34

His Ile Tyr Trp Asp Asp Glu Lys His Tyr Asn Pro Ser Leu Lys Arg
1               5                   10                  15

<210> SEQ ID NO 35
<211> LENGTH: 32
<212> TYPE: PRT
<213> ORGANISM: Artificial Sequence
<220> FEATURE:
<223> OTHER INFORMATION: Synthetic

<400> SEQUENCE: 35

Arg Leu Thr Ile Ser Lys Asp Ala Ser Arg Asn Gln Val Phe Phe Arg
1               5                   10                  15

Ile Ser Ser Val Asp Ser Ala Asp Thr Ala Thr Tyr Tyr Cys Ala Leu
                20                  25                  30

<210> SEQ ID NO 36
<211> LENGTH: 11
<212> TYPE: PRT
<213> ORGANISM: Artificial Sequence
<220> FEATURE:
<223> OTHER INFORMATION: Synthetic

<400> SEQUENCE: 36

Arg Tyr Tyr Gly Tyr Gly Ser Ile Met Asp Tyr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic

<400> SEQUENCE: 37

Trp Gly His Gly Thr Ser Val Thr Val Ser Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Thr Ser Ile Met Gly Val Ser

```
<210> SEQ ID NO 39
<211> LENGTH: 16
<212> TYPE: PRT
<213> ORGANISM: Artificial Sequence
<220> FEATURE:
<223> OTHER INFORMATION: Synthetic

<400> SEQUENCE: 39

His Ile Tyr Trp Asp Asp Glu Lys His Tyr Asn Pro Ser Leu Lys Ser
1               5                   10                  15

<210> SEQ ID NO 40
<211> LENGTH: 32
<212> TYPE: PRT
<213> ORGANISM: Artificial Sequence
<220> FEATURE:
<223> OTHER INFORMATION: Synthetic

<400> SEQUENCE: 40

Arg Leu Thr Ile Ser Lys Asp Ala Ser Arg Asn Gln Val Phe Leu Lys
1               5                   10                  15

Ile Ile Ser Val Asp Thr Ala Asp Thr Ala Thr Tyr Tyr Cys Ala Leu
            20                  25                  30

<210> SEQ ID NO 41
<211> LENGTH: 11
<212> TYPE: PRT
<213> ORGANISM: Artificial Sequence
<220> FEATURE:
<223> OTHER INFORMATION: Synthetic

<400> SEQUENCE: 41

Arg Tyr Tyr Gly Tyr Asn Tyr Val Met His Tyr
1               5                   10

<210> SEQ ID NO 42
<211> LENGTH: 30
<212> TYPE: PRT
<213> ORGANISM: Artificial Sequence
<220> FEATURE:
<223> OTHER INFORMATION: Synthetic

<400> SEQUENCE: 42

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Ile Ser Leu Ser
            20                  25                  30

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Ser Ser Gly Met Gly Val Ser
1               5

<210> SEQ ID NO 44
<211> LENGTH: 32
<212> TYPE: PRT
<213> ORGANISM: Artificial Sequence
<220> FEATURE:
```

<223> OTHER INFORMATION: Synthetic

<400> SEQUENCE: 44

Arg Leu Thr Ile Ser Lys Asp Ala Ser Arg Asn Gln Ile Phe Leu Lys
1               5                   10                  15

Ile Ile Ser Val Asp Thr Ala Asp Thr Ala Thr Tyr Tyr Cys Ala Leu
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Synthetic

<400> SEQUENCE: 45

Gln Val Thr Leu Lys Glu Ser Gly Pro Gly Ile Leu Gln Ser Ser Gln
1               5                   10                  15

Thr Leu Ser Leu Thr Cys Ser Phe Ser Gly Val Ser Leu Ser
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Synthetic

<400> SEQUENCE: 46

Arg Leu Thr Ile Ser Lys Gly Ala Ser Arg Asn Gln Val Phe Leu Lys
1               5                   10                  15

Ile Ile Ser Val Asp Thr Ala Asp Thr Ala Thr Tyr Tyr Cys Ala Leu
            20                  25                  30

<210> SEQ ID NO 47
<211> LENGTH: 11
<212> TYPE: PRT
<213> ORGANISM: Artificial Sequence
<220> FEATURE:
<223> OTHER INFORMATION: Synthetic

<400> SEQUENCE: 47

Arg Tyr Tyr Gly Tyr Asn Ser Ile Met His Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic

<400> SEQUENCE: 48

Trp Gly Gln Gly Ala Ser Val Thr Val Ser Ser
1               5                   10

<210> SEQ ID NO 49
<211> LENGTH: 23
<212> TYPE: PRT
<213> ORGANISM: Artificial Sequence
<220> FEATURE:
<223> OTHER INFORMATION: Synthetic

<400> SEQUENCE: 49

Asp Val Leu Met Thr Gln Ser Pro Leu Ser Leu Pro Val Ser Leu Gly

```
                1               5                  10                  15
Asp Gln Ala Ser Ile Phe Cys
                20

<210> SEQ ID NO 50
<211> LENGTH: 16
<212> TYPE: PRT
<213> ORGANISM: Artificial Sequence
<220> FEATURE:
<223> OTHER INFORMATION: Synthetic

<400> SEQUENCE: 50

Arg Ser Asn Gln Ser Ile Val His Ser Asn Gly Asn Thr Tyr Phe Glu
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

Trp Tyr Leu Gln Lys Pro Gly Gln Ser Pro Lys Leu Leu Ile Tyr
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Synthetic

<400> SEQUENCE: 52

Lys Val Ser Asn Arg Phe Ser
1               5

<210> SEQ ID NO 53
<211> LENGTH: 32
<212> TYPE: PRT
<213> ORGANISM: Artificial Sequence
<220> FEATURE:
<223> OTHER INFORMATION: Synthetic

<400> SEQUENCE: 53

Gly Val Pro Asp Arg Phe Ser Gly Ser Gly Ser Gly Thr Asp Phe Thr
1               5                   10                  15

Leu Arg Ile Ser Arg Val Glu Ala Glu Asp Leu Gly Val Tyr Tyr Cys
                20                  25                  30

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Phe Gln Gly Ser His Val Pro Pro Thr
1               5

<210> SEQ ID NO 55
<211> LENGTH: 11
<212> TYPE: PRT
<213> ORGANISM: Artificial Sequence
<220> FEATURE:
```

<223> OTHER INFORMATION: Synthetic

<400> SEQUENCE: 55

Phe Gly Gly Gly Thr Lys Leu Glu Ile Lys Arg
1               5                   10

<210> SEQ ID NO 56
<211> LENGTH: 32
<212> TYPE: PRT
<213> ORGANISM: Artificial Sequence
<220> FEATURE:
<223> OTHER INFORMATION: Synthetic

<400> SEQUENCE: 56

Gly Val Pro Asp Arg Phe Ser Gly Ser Gly Ser Gly Thr Asp Phe Thr
1               5                   10                  15

Leu Arg Ile Ser Arg Val Glu Ala Glu Asp Leu Gly Ile Tyr Tyr Cys
            20                  25                  30

<210> SEQ ID NO 57
<211> LENGTH: 23
<212> TYPE: PRT
<213> ORGANISM: Artificial Sequence
<220> FEATURE:
<223> OTHER INFORMATION: Synthetic

<400> SEQUENCE: 57

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 58
<211> LENGTH: 16
<212> TYPE: PRT
<213> ORGANISM: Artificial Sequence
<220> FEATURE:
<223> OTHER INFORMATION: Synthetic

<400> SEQUENCE: 58

Arg Ser Ser Gln Ser Ile Val His Ser Asn Gly Asn Thr Tyr Phe Glu
1               5                   10                  15

<210> SEQ ID NO 59
<211> LENGTH: 32
<212> TYPE: PRT
<213> ORGANISM: Artificial Sequence
<220> FEATURE:
<223> OTHER INFORMATION: Synthetic

<400> SEQUENCE: 59

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 60
<211> LENGTH: 16
<212> TYPE: PRT
<213> ORGANISM: Artificial Sequence
<220> FEATURE:
<223> OTHER INFORMATION: Synthetic

<400> SEQUENCE: 60

Arg Ser Ser Gln Ser Ile Val His Ser Asn Gly Asn Thr Tyr Leu Glu

<210> SEQ ID NO 61
<211> LENGTH: 32
<212> TYPE: PRT
<213> ORGANISM: Artificial Sequence
<220> FEATURE:
<223> OTHER INFORMATION: Synthetic

<400> SEQUENCE: 61

Gly Val Pro Asp Arg Phe Ser Gly Ser Gly Ser Gly Thr Asp Phe Thr
1               5                   10                  15

Leu Lys Ile Ser Arg Val Glu Ala Asp Asp Leu Gly Val Tyr Tyr Cys
            20                  25                  30

<210> SEQ ID NO 62
<211> LENGTH: 16
<212> TYPE: PRT
<213> ORGANISM: Artificial Sequence
<220> FEATURE:
<223> OTHER INFORMATION: Synthetic

<400> SEQUENCE: 62

Arg Ser Ser Gln Ser Ile Leu His Ser Asn Gly Asn Thr Tyr Phe Glu
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Synthetic

<400> SEQUENCE: 63

Arg Ser Ser Glu Ser Ile Val His Ser Asn Gly Asn Thr Tyr Leu Glu
1               5                   10                  15

<210> SEQ ID NO 64
<211> LENGTH: 7
<212> TYPE: PRT
<213> ORGANISM: Artificial Sequence
<220> FEATURE:
<223> OTHER INFORMATION: Synthetic

<400> SEQUENCE: 64

Lys Val Tyr Asn Arg Phe Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Wherein Xaa at position 1 is T or I or S
<220> FEATURE:
<221> NAME/KEY: VARIANT
<222> LOCATION: (3)..(3)
<223> OTHER INFORMATION: Wherein Xaa at position 3 is G or I

<400> SEQUENCE: 65

Xaa Ser Xaa Met Gly Val Ser
1               5

```
<210> SEQ ID NO 66
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (11)..(11)
<223> OTHER INFORMATION: Wherein Xaa at position 11 is H or N
<220> FEATURE:
<221> NAME/KEY: VARIANT
<222> LOCATION: (16)..(16)
<223> OTHER INFORMATION: Wherein Xaa at position 16 is S or R

<400> SEQUENCE: 66

His Ile Tyr Trp Asp Asp Glu Lys His Tyr Xaa Pro Ser Leu Lys Xaa
1               5                   10                  15

<210> SEQ ID NO 67
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (6)..(6)
<223> OTHER INFORMATION: Wherein Xaa at position 6 is R or G or N
<220> FEATURE:
<221> NAME/KEY: VARIANT
<222> LOCATION: (7)..(7)
<223> OTHER INFORMATION: Wherein Xaa at position 7 is S or Y
<220> FEATURE:
<221> NAME/KEY: VARIANT
<222> LOCATION: (8)..(8)
<223> OTHER INFORMATION: Wherein Xaa at position 8 is F or I or V
<220> FEATURE:
<221> NAME/KEY: VARIANT
<222> LOCATION: (10)..(10)
<223> OTHER INFORMATION: Wherein Xaa at position 10 is D or H

<400> SEQUENCE: 67

Arg Tyr Tyr Gly Tyr Xaa Xaa Xaa Met Xaa Tyr
1               5                   10

<210> SEQ ID NO 68
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: Wherein Xaa at position 3 is N or S
<220> FEATURE:
<221> NAME/KEY: VARIANT
<222> LOCATION: (4)..(4)
<223> OTHER INFORMATION: Wherein Xaa at position 4 is Q or E
<220> FEATURE:
<221> NAME/KEY: VARIANT
<222> LOCATION: (7)..(7)
<223> OTHER INFORMATION: Wherein Xaa at position 7 is V or L
<220> FEATURE:
<221> NAME/KEY: VARIANT
<222> LOCATION: (15)..(15)
<223> OTHER INFORMATION: Wherein Xaa at position 15 is F or L

<400> SEQUENCE: 68

Arg Ser Xaa Xaa Ser Ile Xaa His Ser Asn Gly Asn Thr Tyr Xaa Glu
1               5                   10                  15
```

```
<210> SEQ ID NO 69
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (3)..(3)
<223> OTHER INFORMATION: Wherein Xaa at position 3 is S or Y

<400> SEQUENCE: 69

Lys Val Xaa Asn Arg Phe Ser
1               5

<210> SEQ ID NO 70
<211> LENGTH: 327
<212> TYPE: PRT
<213> ORGANISM: Homo sapiens

<400> SEQUENCE: 70

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
```

```
                    290                 295                 300
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 71
<211> LENGTH: 327
<212> TYPE: PRT
<213> ORGANISM: Homo sapiens

<400> SEQUENCE: 71

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 72
<211> LENGTH: 106
<212> TYPE: PRT
<213> ORGANISM: Homo sapiens

<400> SEQUENCE: 72

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 73
<211> LENGTH: 363
<212> TYPE: DNA
<213> ORGANISM: Artificial Sequence
<220> FEATURE:
<223> OTHER INFORMATION: Synthetic

<400> SEQUENCE: 73

| | | | | | |
|---|---|---|---|---|---|
| cagattactc | tgaaagagtc | tggccctggg | atattgcagt | cctcccagac | cctcagtctg | 60 |
| acttgttctt | tctctgggat | tcactgact | acttctggta | tgggtgtgag | ctggattcgt | 120 |
| cagccttcag | gaaagggtct | ggaatggctg | gcacacattt | attgggatga | tgagaaacac | 180 |
| tatcatccat | ccctgaagag | ccggctcaca | atctccaagg | atgcctccag | aaaccaggtt | 240 |
| ttcttcagga | tccttagtgt | ggacactgca | gatactgcca | catactactg | tgctctccgt | 300 |
| tactacggtt | ataggtcttt | tatggactac | tggggtcaag | gaacctcagt | caccgtctcc | 360 |
| tca | | | | | | 363 |

<210> SEQ ID NO 74
<211> LENGTH: 363
<212> TYPE: DNA
<213> ORGANISM: Artificial Sequence
<220> FEATURE:
<223> OTHER INFORMATION: Synthetic

<400> SEQUENCE: 74

| | | | | | |
|---|---|---|---|---|---|
| cagattactc | tgaaagagtc | tggccctggg | atattgcagt | cctcccagac | cctcagtctg | 60 |
| acttgttctt | tctctggggt | ttcactgact | acttctggta | tgggtgtgag | ctggattcgt | 120 |
| cagccttcag | gaaagggtct | ggaatggctg | gcacacattt | attgggatga | tgagaaacac | 180 |
| tatcatccat | ccctgaagag | ccggctcaca | atctccaagg | atgcctccag | aaaccaggtt | 240 |
| ttcttcagga | tccttagtgt | ggacactgca | gatactgcca | catattactg | tgctctccgt | 300 |
| tactacggtt | ataggtcttt | tatggactat | tggggtcaag | gaacctcagt | caccgtctcc | 360 |
| tca | | | | | | 363 |

<210> SEQ ID NO 75

```
<211> LENGTH: 363
<212> TYPE: DNA
<213> ORGANISM: Artificial Sequence
<220> FEATURE:
<223> OTHER INFORMATION: Synthetic

<400> SEQUENCE: 75
caggttactc tgaaagagtc tggccctggg atattgcagt cctcccagac cctcagtctg      60
acttgttctt tctctgggat ttcactgaat atttccggta tgggtgtgag ctggattcgt     120
cagccttcag gaaagggtct ggagtggctg gcacacattt actgggatga tgaaaaacac     180
tataatccat ccctgaagag acggctcact atctccaagg atgcctccag aaaccaggtt     240
ttcttcagga tcagtagtgt ggactctgca gatactgcca catactactg tgcgctccgt     300
tactacggtt atggttctat tatggactat tggggtcatg gaacctcagt caccgtctcc     360
tca                                                                   363

<210> SEQ ID NO 76
<211> LENGTH: 363
<212> TYPE: DNA
<213> ORGANISM: Artificial Sequence
<220> FEATURE:
<223> OTHER INFORMATION: Synthetic

<400> SEQUENCE: 76
caggttactc tgaaagagtc tggccctggg atattgcagt cctcccagac cctcagtctg      60
acttgttctt tctctgggat ttcattgaat acttctatta tgggtgtgag ctggattcgt     120
cagccttcag gaaagggtct ggagtggctg gcacacattt actgggatga tgagaaacac     180
tataacccat ccctgaagag ccgactcaca atctccaagg atgcctccag aaaccaggta     240
ttcctcaaga tcattagtgt ggacactgca gatactgcca catactactg tgctctccgt     300
tactacggtt ataactatgt tatgcactac tggggtcaag gaacctcagt caccgtctcc     360
tca                                                                   363

<210> SEQ ID NO 77
<211> LENGTH: 363
<212> TYPE: DNA
<213> ORGANISM: Artificial Sequence
<220> FEATURE:
<223> OTHER INFORMATION: Synthetic

<400> SEQUENCE: 77
caggttactc tgaaagagtc tggccctggg atattgcagt cctcccagac cctcagtctg      60
acttgttctt tctctgggat ttcactgagt tcttctggta tgggtgtgag ctggattcgt     120
cagccttcag gaaagggtct ggagtggctg gcacacattt actgggatga tgagaaacac     180
tataacccat ccctgaagag ccggctcaca atctccaagg atgcctccag aaaccagata     240
ttcctcaaga tcattagtgt ggacactgca gatactgcca catattattg tgctctccgt     300
tactacggtt ataactatgt tatgcactac tggggtcaag gaacctcagt caccgtctcc     360
tca                                                                   363

<210> SEQ ID NO 78
<211> LENGTH: 363
<212> TYPE: DNA
<213> ORGANISM: Artificial Sequence
<220> FEATURE:
<223> OTHER INFORMATION: Synthetic

<400> SEQUENCE: 78
```

| | |
|---|---|
| caggttactc tgaaagagtc tggccctggg atattgcagt cctcccagac cctcagtctg | 60 |
| acttgttctt tctctggggt ttcactgagt tcttctggta tgggtgtgag ctggattcgt | 120 |
| cagccttcag gaaagggtct ggagtggctg gcacacattt actgggatga tgagaaacac | 180 |
| tataacccat ccctgaagag ccggctcaca atctccaagg gtgcctccag aaaccaggtc | 240 |
| ttcctcaaga tcattagtgt ggacactgca gatactgcca catactactg tgctctccgt | 300 |
| tactacggtt ataactctat tatgcactac tggggtcaag agcctcagt caccgtctcc | 360 |
| tca | 363 |

<210> SEQ ID NO 79
<211> LENGTH: 339
<212> TYPE: DNA
<213> ORGANISM: Artificial Sequence
<220> FEATURE:
<223> OTHER INFORMATION: Synthetic

<400> SEQUENCE: 79

| | |
|---|---|
| gatgttttga tgacccaatc tccactctcc ctgcctgtca gtcttggaga tcaagcctcc | 60 |
| atcttttgca gatctaatca gagcattgta catagtaatg gaaacaccta tttcgaatgg | 120 |
| tacctgcaga aaccaggcca gtctccaaag ctcctgatct acaaagtttc caaccgattt | 180 |
| tctggggtcc cagacaggtt cagtggcagt ggatcaggga cagatttcac actcaggatc | 240 |
| agcagagtgg aggctgagga tctgggagtt tattactgct ttcaaggttc acatgttcct | 300 |
| ccgacgttcg gtggaggcac caagctggaa atcaaacgg | 339 |

<210> SEQ ID NO 80
<211> LENGTH: 339
<212> TYPE: DNA
<213> ORGANISM: Artificial Sequence
<220> FEATURE:
<223> OTHER INFORMATION: Synthetic

<400> SEQUENCE: 80

| | |
|---|---|
| gatgttttga tgacccaatc tccactctcc ctgcctgtca gtcttggaga tcaagcctcc | 60 |
| atcttttgca gatctaatca gagcattgtt catagtaatg gaaacaccta tttcgaatgg | 120 |
| tacctgcaga aaccaggcca gtctccaaag ctcctgatct acaaagtttc caaccgattt | 180 |
| tctggggtcc cagacaggtt cagtggcagt ggatcaggga cagatttcac actcaggatc | 240 |
| agcagagtgg aggctgagga tctgggaatt tattactgct ttcaaggttc acatgttcct | 300 |
| ccgacgttcg gtggaggcac caagctggaa atcaaacgg | 339 |

<210> SEQ ID NO 81
<211> LENGTH: 339
<212> TYPE: DNA
<213> ORGANISM: Artificial Sequence
<220> FEATURE:
<223> OTHER INFORMATION: Synthetic

<400> SEQUENCE: 81

| | |
|---|---|
| gatgttttga tgacccaaac tccactctcc ctgcctgtca gtcttggaga tcaagcctcc | 60 |
| atctcttgca gatctagtca gagcattgtt catagtaatg gaaataccta ttttgaatgg | 120 |
| tacctccaga aaccaggcca gtctccaaag ctcctgatct acaaggtttc caaccgattt | 180 |
| tctggggtcc cagacaggtt cagtggcagt ggatcaggga cagatttcac actcaagatc | 240 |
| agcagagtgg aggctgagga tctgggagtt tattactgct ttcaaggttc acatgttcct | 300 |

```
ccgacgttcg gtggaggcac caagctggag atcaaacgg              339
```

<210> SEQ ID NO 82
<211> LENGTH: 339
<212> TYPE: DNA
<213> ORGANISM: Artificial Sequence
<220> FEATURE:
<223> OTHER INFORMATION: Synthetic

<400> SEQUENCE: 82

```
gatgttttga tgacccaaac tccactctcc ctgcctgtca gtcttggaga tcaagcctcc    60
atctcttgca gatctagtca gagcattgta catagtaatg aaacaccta tttagaatgg   120
tacctgcaga aaccaggcca gtctccaaag ctcctgatct acaaagtttc caaccgattt   180
tctggggtcc cagacagatt cagtggcagt ggatcaggga cagatttcac actcaagatc   240
agcagagtgg aggctgatga tctgggagtt tattactgct ttcaaggttc acatgttcct   300
ccgacgttcg gtggaggcac caagctggaa atcaaacgg                         339
```

<210> SEQ ID NO 83
<211> LENGTH: 339
<212> TYPE: DNA
<213> ORGANISM: Artificial Sequence
<220> FEATURE:
<223> OTHER INFORMATION: Synthetic

<400> SEQUENCE: 83

```
gatgttttga tgacccaaac tccactctcc ctgcctgtca gtcttggaga tcaagcctcc    60
atctcttgca gatctagtca gagcattcta catagtaatg aaacaccta ttttgaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcct   300
ccgacgttcg gtggaggcac caagctggaa atcaaacgg                         339
```

<210> SEQ ID NO 84
<211> LENGTH: 339
<212> TYPE: DNA
<213> ORGANISM: Artificial Sequence
<220> FEATURE:
<223> OTHER INFORMATION: Synthetic

<400> SEQUENCE: 84

```
gatgttttga tgacccaaac tccactctcc ctgcctgtca gtcttggaga tcaagcctcc    60
atctcttgca gatctagtga gagcattgta catagtaatg aaacaccta tttagaatgg   120
tacctgcaga aaccaggcca gtctccaaag ctcctgatct acaaagttta caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcct   300
ccgacgttcg gtggaggcac caagctggag atcaaacgg                         339
```

<210> SEQ ID NO 85
<211> LENGTH: 120
<212> TYPE: PRT
<213> ORGANISM: Artificial Sequence
<220> FEATURE:
<223> OTHER INFORMATION: Synthetic

<400> SEQUENCE: 85

Glu Val Lys Leu Val Glu Ser Gly Gly Gly Leu Val Gln Pro Gly Gly

```
                1               5                   10                  15
            Ser Leu Lys Leu Ser Cys Ala Thr Ser Gly Phe Thr Phe Ser Asp Tyr
                           20                  25                  30

Gly Met Ala Trp Val Arg Gln Ala Pro Gly Lys Gly Pro Glu Trp Val
                           35                  40                  45

Ala Phe Ile Ser Asn Leu Ala Tyr Ser Phe Tyr Tyr Val Asp Ile Val
                       50                  55                  60

Met Gly Arg Phe Thr Ile Ser Arg Glu Asn Ala Lys Asn Thr Leu Tyr
            65                  70                  75                  80

Leu Glu Met Ser Ser Leu Arg Ser Glu Asp Thr Ala Met Tyr Tyr Cys
                           85                  90                  95

Ala Arg Val Gly Leu Tyr Gly Asn Phe Phe Met Asp Tyr Trp Gly Gln
                           100                 105                 110

Gly Thr Ser Val Thr Val Ser Ser
                           115                 120
```

<210> SEQ ID NO 86
<211> LENGTH: 120
<212> TYPE: PRT
<213> ORGANISM: Artificial Sequence
<220> FEATURE:
<223> OTHER INFORMATION: Synthetic

<400> SEQUENCE: 86

```
            Glu Val Gln Leu Val Glu Ser Gly Gly Gly Leu Val Gln Pro Lys Gly
            1               5                   10                  15

Ser Leu Lys Leu Ser Cys Ala Ala Ser Gly Phe Ser Phe Asn Thr Tyr
                           20                  25                  30

Ala Met Asn Trp Val Arg Gln Ala Pro Gly Lys Gly Leu Glu Trp Val
                           35                  40                  45

Ala Arg Ile Arg Ser Lys Ser Asn Asn Tyr Ala Thr His Tyr Ala Asp
                       50                  55                  60

Ser Val Lys Asp Arg Phe Thr Ile Ser Arg Asp Asp Ser Glu Ser Met
            65                  70                  75                  80

Leu Tyr Leu Gln Met Asn Asn Leu Lys Thr Glu Asp Thr Ala Met Tyr
                           85                  90                  95

Tyr Cys Val Arg Gln Gly Tyr Tyr Trp Tyr Phe Asp Val Trp Gly Thr
                           100                 105                 110

Gly Thr Thr Val Thr Val Ser Ser
                           115                 120
```

<210> SEQ ID NO 87
<211> LENGTH: 120
<212> TYPE: PRT
<213> ORGANISM: Artificial Sequence
<220> FEATURE:
<223> OTHER INFORMATION: Synthetic

<400> SEQUENCE: 87

```
            Glu Val Gln Leu Val Glu Ser Gly Gly Gly Leu Val Gln Pro Lys Gly
            1               5                   10                  15

Ser Leu Lys Leu Ser Cys Ala Ala Ser Gly Phe Ser Phe Asn Thr Tyr
                           20                  25                  30

Ala Met Asn Trp Val Arg Gln Ala Pro Gly Lys Gly Leu Glu Trp Val
                           35                  40                  45

Ala Arg Ile Arg Ser Lys Ser Asn Asn Tyr Ala Thr Tyr Tyr Ala Asp
                       50                  55                  60
```

```
Ser Val Lys Asp Arg Phe Thr Ile Ser Arg Asp Asp Ser Glu Ser Met
 65                  70                  75                  80

Leu Tyr Leu Gln Met Asn Asn Leu Lys Thr Glu Asp Thr Ala Met Tyr
                 85                  90                  95

Tyr Cys Val Arg His Gly Tyr Tyr Trp Tyr Phe Asp Val Trp Gly Thr
                100                 105                 110

Gly Thr Thr Val Thr Val Ser Ser
            115                 120
```

<210> SEQ ID NO 88
<211> LENGTH: 120
<212> TYPE: PRT
<213> ORGANISM: Artificial Sequence
<220> FEATURE:
<223> OTHER INFORMATION: Synthetic

<400> SEQUENCE: 88

```
Glu Val Gln Val Val Glu Ser Gly Gly Gly Leu Val Arg Pro Lys Gly
 1               5                  10                  15

Ser Leu Lys Leu Ser Cys Ala Ala Ser Gly Phe Ser Phe Asn Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Ser Asn Asn Tyr Ala Thr Tyr Tyr Ala Asp
 50                  55                  60

Ser Val Lys Asp Arg Phe Thr Ile Ser Arg Asp Asp Ser Glu Ser Met
 65                  70                  75                  80

Leu Ser Leu Gln Met Asn Asn Leu Lys Thr Glu Asp Thr Ala Met Tyr
                 85                  90                  95

Tyr Cys Val Arg Gln Gly Tyr Tyr Trp Tyr Phe Asp Val Trp Gly Thr
                100                 105                 110

Gly Thr Thr Val Thr Val Ser Ser
            115                 120
```

<210> SEQ ID NO 89
<211> LENGTH: 108
<212> TYPE: PRT
<213> ORGANISM: Artificial Sequence
<220> FEATURE:
<223> OTHER INFORMATION: Synthetic

<400> SEQUENCE: 89

```
Asp Ile Gln Met Asn Gln Ser Pro Ser Ser Leu Ser Ala Ser Leu Gly
 1               5                  10                  15

Asp Thr Ile Thr Ile Thr Cys His Ala Ser Gln Asn Ile Asn Val Trp
                20                  25                  30

Leu Ser Trp Tyr Gln Gln Lys Pro Gly Asn Ile Pro Glu Leu Leu Ile
                35                  40                  45

Tyr Lys Ala Ser Asn Leu His Thr Gly Val Pro Ser Arg Phe Ser Gly
 50                  55                  60

Asn Arg Ser Gly Thr Ser Phe Thr Leu Thr Ile Ser Ser Leu Gln Pro
 65                  70                  75                  80

Glu Asp Ile Gly Thr Tyr Phe Cys Gln Gln Gly Gln Ser Tyr Pro Leu
                 85                  90                  95

Thr Phe Gly Ala Gly Thr Lys Leu Glu Leu Arg Arg
                100                 105
```

<210> SEQ ID NO 90

```
<211> LENGTH: 108
<212> TYPE: PRT
<213> ORGANISM: Artificial Sequence
<220> FEATURE:
<223> OTHER INFORMATION: Synthetic

<400> SEQUENCE: 90

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Glu Leu Leu Ile
        35                  40                  45

Tyr Lys Ala Ser Asn Leu His Thr Gly Val Pro Ser Arg Phe Ser Gly
    50                  55                  60

Asn Arg Ser Gly Thr Ser Phe Thr Leu Thr Ile Ser Ser Leu Gln Pro
65                  70                  75                  80

Glu Asp Ile Gly Thr Tyr Phe Cys Gln Gln Gly Gln Ser Tyr Pro Leu
                85                  90                  95

Thr Phe Gly Ala Gly Thr Lys Leu Glu Ile Lys Arg
            100                 105

<210> SEQ ID NO 91
<211> LENGTH: 113
<212> TYPE: PRT
<213> ORGANISM: Artificial Sequence
<220> FEATURE:
<223> OTHER INFORMATION: Synthetic

<400> SEQUENCE: 91

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg

<210> SEQ ID NO 92
<211> LENGTH: 113
<212> TYPE: PRT
<213> ORGANISM: Artificial Sequence
<220> FEATURE:
<223> OTHER INFORMATION: Synthetic

<400> SEQUENCE: 92

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
```

```
                35                  40                  45
Pro Lys Leu Leu Ile Tyr Arg Val Ser Asn Arg Phe Ser Gly Val Pro
     50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                 85                  90                  95
Ser His Val Pro Tyr Thr Phe Gly Gly Gly Thr Lys Leu Glu Ile Lys
                100                 105                 110
Arg

<210> SEQ ID NO 93
<211> LENGTH: 113
<212> TYPE: PRT
<213> ORGANISM: Artificial Sequence
<220> FEATURE:
<223> OTHER INFORMATION: Synthetic

<400> SEQUENCE: 93

Asp Val Leu Met Thr Gln Thr Pro Leu Ser Leu Pro Val Ser Leu Gly
  1               5                  10                  15
Asp Gln Ala Ser Ile Ser Cys Arg Ser Ser Gln Ser Ile Val His Ser
                 20                  25                  30
Asn Gly Asn Thr Tyr Leu Glu Trp Tyr Leu Gln Lys Pro Gly Gln Ser
             35                  40                  45
Pro Lys Leu Leu Ile Tyr Thr Val Ser Asn Arg Phe Ser Gly Val Pro
     50                  55                  60
Asp Arg Phe Arg Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                 85                  90                  95
Ser His Val Pro Trp Thr Phe Gly Gly Gly Thr Lys Leu Glu Ile Lys
                100                 105                 110
Arg

<210> SEQ ID NO 94
<211> LENGTH: 30
<212> TYPE: PRT
<213> ORGANISM: Artificial Sequence
<220> FEATURE:
<223> OTHER INFORMATION: Synthetic

<400> SEQUENCE: 94

Glu Val Lys Leu Val Glu Ser Gly Gly Gly Leu Val Gln Pro Gly Gly
  1               5                  10                  15
Ser Leu Lys Leu Ser Cys Ala Thr Ser Gly Phe Thr Phe Ser
                 20                  25                  30

<210> SEQ ID NO 95
<211> LENGTH: 5
<212> TYPE: PRT
<213> ORGANISM: Artificial Sequence
<220> FEATURE:
<223> OTHER INFORMATION: Synthetic

<400> SEQUENCE: 95

Asp Tyr Gly Met Ala
  1               5
```

```
<210> SEQ ID NO 96
<211> LENGTH: 14
<212> TYPE: PRT
<213> ORGANISM: Artificial Sequence
<220> FEATURE:
<223> OTHER INFORMATION: Synthetic

<400> SEQUENCE: 96

Trp Val Arg Gln Ala Pro Gly Lys Gly Pro Glu Trp Val Ala
1               5                   10

<210> SEQ ID NO 97
<211> LENGTH: 17
<212> TYPE: PRT
<213> ORGANISM: Artificial Sequence
<220> FEATURE:
<223> OTHER INFORMATION: Synthetic

<400> SEQUENCE: 97

Phe Ile Ser Asn Leu Ala Tyr Ser Phe Tyr Tyr Val Asp Ile Val Met
1               5                   10                  15

Gly

<210> SEQ ID NO 98
<211> LENGTH: 32
<212> TYPE: PRT
<213> ORGANISM: Artificial Sequence
<220> FEATURE:
<223> OTHER INFORMATION: Synthetic

<400> SEQUENCE: 98

Arg Phe Thr Ile Ser Arg Glu Asn Ala Lys Asn Thr Leu Tyr Leu Glu
1               5                   10                  15

Met Ser Ser Leu Arg Ser Glu Asp Thr Ala Met Tyr Tyr Cys Ala Arg
            20                  25                  30

<210> SEQ ID NO 99
<211> LENGTH: 11
<212> TYPE: PRT
<213> ORGANISM: Artificial Sequence
<220> FEATURE:
<223> OTHER INFORMATION: Synthetic

<400> SEQUENCE: 99

Val Gly Leu Tyr Gly Asn Phe Phe Met Asp Tyr
1               5                   10

<210> SEQ ID NO 100
<211> LENGTH: 30
<212> TYPE: PRT
<213> ORGANISM: Artificial Sequence
<220> FEATURE:
<223> OTHER INFORMATION: Synthetic

<400> SEQUENCE: 100

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Ser Phe Asn
            20                  25                  30

<210> SEQ ID NO 101
<211> LENGTH: 5
<212> TYPE: PRT
<213> ORGANISM: Artificial Sequence
<220> FEATURE:
<223> OTHER INFORMATION: Synthetic
```

```
<400> SEQUENCE: 101

Thr Tyr Ala Met Asn
1               5

<210> SEQ ID NO 102
<211> LENGTH: 14
<212> TYPE: PRT
<213> ORGANISM: Artificial Sequence
<220> FEATURE:
<223> OTHER INFORMATION: Synthetic

<400> SEQUENCE: 102

Trp Val Arg Gln Ala Pro Gly Lys Gly Leu Glu Trp Val Ala
1               5                   10

<210> SEQ ID NO 103
<211> LENGTH: 19
<212> TYPE: PRT
<213> ORGANISM: Artificial Sequence
<220> FEATURE:
<223> OTHER INFORMATION: Synthetic

<400> SEQUENCE: 103

Arg Ile Arg Ser Lys Ser Asn Asn Tyr Ala Thr His Tyr Ala Asp Ser
1               5                   10                  15

Val Lys Asp

<210> SEQ ID NO 104
<211> LENGTH: 32
<212> TYPE: PRT
<213> ORGANISM: Artificial Sequence
<220> FEATURE:
<223> OTHER INFORMATION: Synthetic

<400> SEQUENCE: 104

Arg Phe Thr Ile Ser Arg Asp Asp Ser Glu Ser Met Leu Tyr Leu Gln
1               5                   10                  15

Met Asn Asn Leu Lys Thr Glu Asp Thr Ala Met Tyr Tyr Cys Val Arg
                20                  25                  30

<210> SEQ ID NO 105
<211> LENGTH: 9
<212> TYPE: PRT
<213> ORGANISM: Artificial Sequence
<220> FEATURE:
<223> OTHER INFORMATION: Synthetic

<400> SEQUENCE: 105

Gln Gly Tyr Tyr Trp Tyr Phe Asp Val
1               5

<210> SEQ ID NO 106
<211> LENGTH: 11
<212> TYPE: PRT
<213> ORGANISM: Artificial Sequence
<220> FEATURE:
<223> OTHER INFORMATION: Synthetic

<400> SEQUENCE: 106

Trp Gly Thr Gly Thr Thr Val Thr Val Ser Ser
1               5                   10

<210> SEQ ID NO 107
<211> LENGTH: 19
```

```
<212> TYPE: PRT
<213> ORGANISM: Artificial Sequence
<220> FEATURE:
<223> OTHER INFORMATION: Synthetic

<400> SEQUENCE: 107

Arg Ile Arg Ser Lys Ser Asn Asn Tyr Ala Thr Tyr Tyr Ala Asp Ser
1               5                   10                  15

Val Lys Asp

<210> SEQ ID NO 108
<211> LENGTH: 9
<212> TYPE: PRT
<213> ORGANISM: Artificial Sequence
<220> FEATURE:
<223> OTHER INFORMATION: Synthetic

<400> SEQUENCE: 108

His Gly Tyr Tyr Trp Tyr Phe Asp Val
1               5

<210> SEQ ID NO 109
<211> LENGTH: 30
<212> TYPE: PRT
<213> ORGANISM: Artificial Sequence
<220> FEATURE:
<223> OTHER INFORMATION: Synthetic

<400> SEQUENCE: 109

Glu Val Gln Val Val Glu Ser Gly Gly Gly Leu Val Arg Pro Lys Gly
1               5                   10                  15

Ser Leu Lys Leu Ser Cys Ala Ala Ser Gly Phe Ser Phe Asn
            20                  25                  30

<210> SEQ ID NO 110
<211> LENGTH: 23
<212> TYPE: PRT
<213> ORGANISM: Artificial Sequence
<220> FEATURE:
<223> OTHER INFORMATION: Synthetic

<400> SEQUENCE: 110

Asp Ile Gln Met Asn Gln Ser Pro Ser Ser Leu Ser Ala Ser Leu Gly
1               5                   10                  15

Asp Thr Ile Thr Ile Thr Cys
            20

<210> SEQ ID NO 111
<211> LENGTH: 11
<212> TYPE: PRT
<213> ORGANISM: Artificial Sequence
<220> FEATURE:
<223> OTHER INFORMATION: Synthetic

<400> SEQUENCE: 111

His Ala Ser Gln Asn Ile Asn Val Trp Leu Ser
1               5                   10

<210> SEQ ID NO 112
<211> LENGTH: 15
<212> TYPE: PRT
<213> ORGANISM: Artificial Sequence
<220> FEATURE:
<223> OTHER INFORMATION: Synthetic

<400> SEQUENCE: 112
```

Trp Tyr Gln Gln Lys Pro Gly Asn Ile Pro Glu Leu Leu Ile Tyr
1               5                   10                  15

<210> SEQ ID NO 113
<211> LENGTH: 7
<212> TYPE: PRT
<213> ORGANISM: Artificial Sequence
<220> FEATURE:
<223> OTHER INFORMATION: Synthetic

<400> SEQUENCE: 113

Lys Ala Ser Asn Leu His Thr
1               5

<210> SEQ ID NO 114
<211> LENGTH: 32
<212> TYPE: PRT
<213> ORGANISM: Artificial Sequence
<220> FEATURE:
<223> OTHER INFORMATION: Synthetic

<400> SEQUENCE: 114

Gly Val Pro Ser Arg Phe Ser Gly Asn Arg Ser Gly Thr Ser Phe Thr
1               5                   10                  15

Leu Thr Ile Ser Ser Leu Gln Pro Glu Asp Ile Gly Thr Tyr Phe Cys
                20                  25                  30

<210> SEQ ID NO 115
<211> LENGTH: 9
<212> TYPE: PRT
<213> ORGANISM: Artificial Sequence
<220> FEATURE:
<223> OTHER INFORMATION: Synthetic

<400> SEQUENCE: 115

Gln Gln Gly Gln Ser Tyr Pro Leu Thr
1               5

<210> SEQ ID NO 116
<211> LENGTH: 11
<212> TYPE: PRT
<213> ORGANISM: Artificial Sequence
<220> FEATURE:
<223> OTHER INFORMATION: Synthetic

<400> SEQUENCE: 116

Phe Gly Ala Gly Thr Lys Leu Glu Leu Arg Arg
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic

<400> SEQUENCE: 117

Phe Gly Ala Gly Thr Lys Leu Glu Ile Lys Arg
1               5                   10

<210> SEQ ID NO 118
<211> LENGTH: 23
<212> TYPE: PRT
<213> ORGANISM: Artificial Sequence
<220> FEATURE:
<223> OTHER INFORMATION: Synthetic

<400> SEQUENCE: 118

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 119
<211> LENGTH: 7
<212> TYPE: PRT
<213> ORGANISM: Artificial Sequence
<220> FEATURE:
<223> OTHER INFORMATION: Synthetic

<400> SEQUENCE: 119

Thr Val Ser Asn Arg Phe Ser
1               5

<210> SEQ ID NO 120
<211> LENGTH: 32
<212> TYPE: PRT
<213> ORGANISM: Artificial Sequence
<220> FEATURE:
<223> OTHER INFORMATION: Synthetic

<400> SEQUENCE: 120

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 121
<211> LENGTH: 9
<212> TYPE: PRT
<213> ORGANISM: Artificial Sequence
<220> FEATURE:
<223> OTHER INFORMATION: Synthetic

<400> SEQUENCE: 121

Phe Gln Gly Ser His Val Pro Trp Thr
1               5

<210> SEQ ID NO 122
<211> LENGTH: 11
<212> TYPE: PRT
<213> ORGANISM: Artificial Sequence
<220> FEATURE:
<223> OTHER INFORMATION: Synthetic

<400> SEQUENCE: 122

Phe Gly Gly Gly Thr Lys Leu Glu Ile Lys Arg
1               5                   10

<210> SEQ ID NO 123
<211> LENGTH: 16
<212> TYPE: PRT
<213> ORGANISM: Artificial Sequence
<220> FEATURE:
<223> OTHER INFORMATION: Synthetic

<400> SEQUENCE: 123

Arg Ser Ser Gln Ser Ile Val His Ser Asp Gly Asn Thr Tyr Leu Glu
1               5                   10                  15

<210> SEQ ID NO 124

```
<211> LENGTH: 7
<212> TYPE: PRT
<213> ORGANISM: Artificial Sequence
<220> FEATURE:
<223> OTHER INFORMATION: Synthetic

<400> SEQUENCE: 124

Arg Val Ser Asn Arg Phe Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic

<400> SEQUENCE: 125

Phe Gln Gly Ser His Val Pro Tyr Thr
1               5

<210> SEQ ID NO 126
<211> LENGTH: 32
<212> TYPE: PRT
<213> ORGANISM: Artificial Sequence
<220> FEATURE:
<223> OTHER INFORMATION: Synthetic

<400> SEQUENCE: 126

Gly Val Pro Asp Arg Phe Arg Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 127
<211> LENGTH: 360
<212> TYPE: DNA
<213> ORGANISM: Artificial Sequence
<220> FEATURE:
<223> OTHER INFORMATION: Synthetic

<400> SEQUENCE: 127
gaggtgaagc tggtggagtc tgggggaggc ttagtgcagc ctggagggtc cctgaaactc      60
tcctgtgcaa cctctggatt cactttcagt gactacggaa tggcgtgggt tcgacaggct    120
ccagggaagg ggcctgagtg ggtagcattc attagtaatt tggcatatag tttctactat    180
gtagacattg tgatgggccg attcaccatc tctagagaga tgccaagaac acccctgtac    240
ctggaaatga gcagtctgag gtctgaggac acggccatgt attactgtgc aagagtgggg    300
ctctatggta acttttttat ggactactgg ggtcaaggaa cctcagtcac cgtctcctca    360

<210> SEQ ID NO 128
<211> LENGTH: 360
<212> TYPE: DNA
<213> ORGANISM: Artificial Sequence
<220> FEATURE:
<223> OTHER INFORMATION: Synthetic

<400> SEQUENCE: 128
gaggtgcagc ttgttgagtc tgtggagga ttggtgcagc ctaaagggtc attgaaactc       60
tcatgtgcag cctctggatt cagcttcaat acctacgcca tgaactgggt ccgccaggct    120
ccaggaaagg gtttggaatg ggttgctcgc ataagaagta aaagtaataa ttatgcaaca    180
cattatgccg attcagtgaa agacagattc accatctcca gagatgattc agaaagcatg    240
```

```
ctctatctgc aaatgaacaa cttgaaaact gaggacacag ccatgtatta ctgtgtgaga    300
cagggttact actggtactt cgatgtctgg ggcacaggga ccacggtcac cgtctcctca    360
```

<210> SEQ ID NO 129
<211> LENGTH: 360
<212> TYPE: DNA
<213> ORGANISM: Artificial Sequence
<220> FEATURE:
<223> OTHER INFORMATION: Synthetic

<400> SEQUENCE: 129

```
gaggtgcagc ttgttgagtc tggtggagga ttggtgcagc ctaaagggtc attgaaactc     60
tcatgtgcag cctctggatt cagcttcaat acctacgcca tgaactgggt ccgccaggct    120
ccaggaaagg gtttggaatg ggttgctcgc ataagaagta aaagtaataa ttatgcaaca    180
tattatgccg attcagtgaa agacagattc accatctcca gagatgattc agaaagcatg    240
ctctatctgc aaatgaacaa cttgaaaact gaggacacag ccatgtatta ctgtgtgaga    300
catggttact actggtactt cgatgtctgg ggcacaggga ccacggtcac cgtctcctca    360
```

<210> SEQ ID NO 130
<211> LENGTH: 360
<212> TYPE: DNA
<213> ORGANISM: Artificial Sequence
<220> FEATURE:
<223> OTHER INFORMATION: Synthetic

<400> SEQUENCE: 130

```
gaggtgcagg ttgttgagtc tggtggagga ttggtgcggc ctaaagggtc attgaaactc     60
tcatgtgcag cctctggatt cagcttcaat acctacgcca tgaactgggt ccgccaggct    120
ccaggaaagg gtttggaatg ggttgctcgc ataagaagta aaagtaataa ttatgcaaca    180
tattatgccg attcagtgaa agacagattc accatctcca gagatgattc agaaagcatg    240
ctctctctgc aaatgaacaa cttgaaaact gaggacacag ccatgtatta ctgtgtgaga    300
cagggttact actggtactt cgatgtctgg ggcacaggga ccacggtcac cgtctcctca    360
```

<210> SEQ ID NO 131
<211> LENGTH: 324
<212> TYPE: DNA
<213> ORGANISM: Artificial Sequence
<220> FEATURE:
<223> OTHER INFORMATION: Synthetic

<400> SEQUENCE: 131

```
gacatccaga tgaaccagtc tccatccagt ctgtctgcat cccttggaga cacaattacc     60
atcacttgcc atgccagtca gaacattaat gtttggttaa ctggtaccag cagaaaccca    120
ggaaatattc ctgaactttt gatctataag gcttccaact tgcacacagg cgtcccttct    180
aggtttagtg gcaatagatc tggaacaagt ttcacattaa ccatcagcag cctgcagcct    240
gaagacattg gcacttactt ctgtcaacag ggtcaaagtt atccgctcac gttcggtgct    300
gggaccaagc tggagctgag acgg                                          324
```

<210> SEQ ID NO 132
<211> LENGTH: 324
<212> TYPE: DNA
<213> ORGANISM: Artificial Sequence
<220> FEATURE:
<223> OTHER INFORMATION: Synthetic

<400> SEQUENCE: 132

```
gacatccaga tgaaccagtc tccatccagt ctgtctgcat cccttggaga cacaattacc    60
atcacttgcc atgccagtca gaacattaat gtttggttaa gctggtacca gcagaaacca   120
ggaaatattc ctgaactttt gatctataag gcttccaact tgcacacagg cgtcccttct   180
aggtttagtg gcaatagatc tggaacaagt ttcacattaa ccatcagcag cctgcagcct   240
gaagacattg gcacttactt ctgtcaacag ggtcaaagtt atccgctcac gttcggtgcg   300
gggaccaagc tggaaataaa acgg                                           324
```

<210> SEQ ID NO 133
<211> LENGTH: 339
<212> TYPE: DNA
<213> ORGANISM: Artificial Sequence
<220> FEATURE:
<223> OTHER INFORMATION: Synthetic

<400> SEQUENCE: 133

```
gatgttttga tgacccaaac tccactctcc ctgcctgtca gtcttggaga tcaagcctcc    60
atctcttgca gatctagtca gagcattgta catagtaatg gaaacaccta tttagaatgg   120
tacctgcaga aaccaggcca gtctccaaag ctcctgatct acacagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttccg   300
tggacgttcg gtggaggcac caagctggaa atcaaacgg                           339
```

<210> SEQ ID NO 134
<211> LENGTH: 339
<212> TYPE: DNA
<213> ORGANISM: Artificial Sequence
<220> FEATURE:
<223> OTHER INFORMATION: Synthetic

<400> SEQUENCE: 134

```
gatgttttga tgacccaaac tccactctcc ctgcctgtca gtcttggaga tcaagcctcc    60
atctcttgca gatctagtca gagcattgta catagtgatg gaaacaccta tttagaatgg   120
tacctgcaga aaccaggcca gtctccaaag ctcctgatct acagagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttccg   300
tacacgttcg gaggaggcac caagctggaa atcaaacgg                           339
```

<210> SEQ ID NO 135
<211> LENGTH: 339
<212> TYPE: DNA
<213> ORGANISM: Artificial Sequence
<220> FEATURE:
<223> OTHER INFORMATION: Synthetic

<400> SEQUENCE: 135

```
gatgttttga tgacccaaac tccactctcc ctgcctgtca gtcttggaga tcaagcctcc    60
atctcttgca gatctagtca gagcattgta catagtaatg gaaacaccta tttagaatgg   120
tacctgcaga aaccaggcca gtctccaaag ctcctgatct acacagtttc caaccgattt   180
tctggggtcc cagacaggtt ccgtggcagt ggatcaggga cagatttcac actcaagatc   240
agcagagtgg aggctgagga tctgggagtt tattactgct ttcaaggttc acatgttccg   300
tggacgttcg gtggaggcac caagctggaa atcaaacgg                           339
```

<210> SEQ ID NO 136
<211> LENGTH: 116
<212> TYPE: PRT
<213> ORGANISM: Artificial Sequence
<220> FEATURE:
<223> OTHER INFORMATION: Synthetic

<400> SEQUENCE: 136

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Gly Asn Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Gly Glu Asp Thr Gly Leu Tyr
                85                  90                  95

Tyr Cys Thr Asn Ala Trp Phe Ala Ser Trp Gly Gln Gly Thr Leu Val
            100                 105                 110

Thr Val Ser Ala
        115

<210> SEQ ID NO 137
<211> LENGTH: 116
<212> TYPE: PRT
<213> ORGANISM: Artificial Sequence
<220> FEATURE:
<223> OTHER INFORMATION: Synthetic

<400> SEQUENCE: 137

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Gly Ser Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Asp Asn Tyr Ala Ala His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Gly Glu Asp Thr Gly Ile Tyr
                85                  90                  95

Tyr Cys Thr Asn Ala Trp Phe Ala Ser Trp Gly Gln Gly Thr Leu Val
            100                 105                 110

Thr Val Ser Ala
        115

<210> SEQ ID NO 138
<211> LENGTH: 116
<212> TYPE: PRT
<213> ORGANISM: Artificial Sequence
<220> FEATURE:
<223> OTHER INFORMATION: Synthetic

<400> SEQUENCE: 138

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Thr Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Thr Glu
50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Val Glu Asp Thr Gly Ile Tyr
                85                  90                  95

Tyr Cys Thr Asn Ala Trp Phe Ala Tyr Trp Gly Gln Gly Thr Leu Val
            100                 105                 110

Thr Val Ser Ala
        115
```

<210> SEQ ID NO 139
<211> LENGTH: 116
<212> TYPE: PRT
<213> ORGANISM: Artificial Sequence
<220> FEATURE:
<223> OTHER INFORMATION: Synthetic

<400> SEQUENCE: 139

```
Glu Val Lys Leu Glu Glu Ser Gly Gly Gly Leu Val Gln Pro Gly Gly
1               5                   10                  15

Ser Met Lys Leu Ser Cys Ile Ala Ser Gly Phe Thr Phe Ser Thr Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Glu Asn Tyr Ala Thr Tyr Tyr Ala Glu
50                  55                  60

Ser Val Lys Gly Lys Phe Ile Ile Ser Arg Asp Asp Ser Lys Ser Arg
65                  70                  75                  80

Leu Tyr Leu Gln Met Asn Ser Leu Arg Ala Glu Asp Thr Gly Ile Tyr
                85                  90                  95

Tyr Cys Thr Asn Ala Trp Phe Ala Asn Trp Gly Gln Gly Thr Leu Val
            100                 105                 110

Thr Val Ser Ala
        115
```

<210> SEQ ID NO 140
<211> LENGTH: 115
<212> TYPE: PRT
<213> ORGANISM: Artificial Sequence
<220> FEATURE:
<223> OTHER INFORMATION: Synthetic

<400> SEQUENCE: 140

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ile Gly Gly Ile Gly Tyr Asn Pro Ser Leu
50                  55                  60
```

```
Lys Ser Arg Ile Ser Ile Thr Arg Asp Thr Ser Lys Asn Gln Phe Phe
 65                  70                  75                  80

Leu His Leu Asn Ser Val Thr Thr Gly Asp Thr Ala Thr Tyr Tyr Cys
                 85                  90                  95

Ala Arg Asn Gly Ala Met Asp Phe Trp Gly Gln Gly Ile Ser Val Thr
            100                 105                 110

Val Ser Ser
        115

<210> SEQ ID NO 141
<211> LENGTH: 115
<212> TYPE: PRT
<213> ORGANISM: Artificial Sequence
<220> FEATURE:
<223> OTHER INFORMATION: Synthetic

<400> SEQUENCE: 141

Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Ser Thr Gly Tyr Ser Pro Ser Leu
 50                  55                  60

Lys Ser Arg Ile Ser Ile Thr Arg Asp Thr Ser Lys Asn Gln Phe Phe
 65                  70                  75                  80

Leu His Leu Asn Ser Val Thr Thr Gly Asp Thr Ala Thr Tyr Tyr Cys
                 85                  90                  95

Ala Arg Asn Gly Ala Met Asp Tyr Trp Gly Gln Gly Ile Ser Val Thr
            100                 105                 110

Val Ser Ser
        115

<210> SEQ ID NO 142
<211> LENGTH: 114
<212> TYPE: PRT
<213> ORGANISM: Artificial Sequence
<220> FEATURE:
<223> OTHER INFORMATION: Synthetic

<400> SEQUENCE: 142

Asp Ile Val Met Ser Gln Ser Pro Ser Ser Leu Ala Val Ser Val Gly
 1               5                  10                  15

Glu Lys Val Thr Met Ser Cys Met Ser Ser Gln Ser Leu Leu Tyr Ser
                20                  25                  30

Lys Asp Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Leu Gln
                 85                  90                  95

Tyr Tyr Thr Tyr Pro Tyr Thr Phe Gly Gly Gly Thr Lys Leu Glu Ile
            100                 105                 110

Lys Arg
```

<210> SEQ ID NO 143
<211> LENGTH: 114
<212> TYPE: PRT
<213> ORGANISM: Artificial Sequence
<220> FEATURE:
<223> OTHER INFORMATION: Synthetic

<400> SEQUENCE: 143

Asp Ile Val Met Ser Gln Ser Pro Ser Ser Leu Thr Val Ser Val Gly
1               5                   10                  15

Glu Lys Val Thr Met Ser Cys Met Ser Ser Gln Ser Leu Leu Tyr Ser
                20                  25                  30

Lys Asp Gln Lys Asn Tyr Leu Ala Trp Tyr Gln Gln Lys Pro Gly Gln
            35                  40                  45

Ser Pro Thr Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Leu Gln
                85                  90                  95

Tyr Tyr Thr Tyr Pro Tyr Thr Phe Gly Gly Gly Thr Lys Leu Glu Ile
                100                 105                 110

Lys Arg

<210> SEQ ID NO 144
<211> LENGTH: 114
<212> TYPE: PRT
<213> ORGANISM: Artificial Sequence
<220> FEATURE:
<223> OTHER INFORMATION: Synthetic

<400> SEQUENCE: 144

Asp Ile Val Met Ser Gln Ser Pro Ser Ser Leu Ala Val Ser Val Gly
1               5                   10                  15

Glu Lys Phe Thr Met Ser Cys Lys Ser Ser Gln Ser Leu Leu Tyr Ser
                20                  25                  30

Arg Asp Gln Lys Asn Tyr Leu Ala Trp Tyr Gln Gln Gln Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Thr Glu Asp Leu Ala Val Tyr Tyr Cys Leu Gln
                85                  90                  95

Tyr Tyr Ser Tyr Pro Tyr Thr Phe Gly Gly Gly Thr Lys Leu Glu Ile
                100                 105                 110

Lys Arg

<210> SEQ ID NO 145
<211> LENGTH: 114
<212> TYPE: PRT
<213> ORGANISM: Artificial Sequence
<220> FEATURE:
<223> OTHER INFORMATION: Synthetic

<400> SEQUENCE: 145

Asp Ile Val Met Ser Gln Ser Pro Ser Ser Leu Val Val Ser Val Gly
1               5                   10                  15

```
Glu Lys Val Thr Met Ser Cys Lys Ser Gln Asn Leu Leu Tyr Ser
            20                  25                  30

Arg Asp Gln Lys Asn Tyr Leu Ala Trp Tyr Gln Gln Lys Pro Gly Gln
        35                  40                  45

Ser Pro Asn Leu Leu Ile Tyr Trp Ala Ser Thr Arg Glu Ser Gly Val
 50                  55                  60

Pro Asp Arg Phe Thr Gly Ser Gly Ser Gly Thr Asp Phe Ser Leu Thr
65                  70                  75                  80

Ile Ser Ser Val Lys Ala Glu Asp Leu Ala Val Tyr Tyr Cys Leu Gln
                85                  90                  95

Tyr Tyr Ser Tyr Pro Tyr Thr Phe Gly Gly Gly Thr Lys Leu Glu Met
            100                 105                 110

Lys Arg

<210> SEQ ID NO 146
<211> LENGTH: 112
<212> TYPE: PRT
<213> ORGANISM: Artificial Sequence
<220> FEATURE:
<223> OTHER INFORMATION: Synthetic

<400> SEQUENCE: 146

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Asp Ala Ser Asn Leu Glu Ser Gly Ile Pro Ala
 50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Ala Pro Trp Thr Phe Gly Gly Gly Thr Lys Leu Glu Ile Lys Arg
            100                 105                 110

<210> SEQ ID NO 147
<211> LENGTH: 110
<212> TYPE: PRT
<213> ORGANISM: Artificial Sequence
<220> FEATURE:
<223> OTHER INFORMATION: Synthetic

<400> SEQUENCE: 147

Asp Ile Val Leu Thr Gln Ser Pro Ala Ser Leu Ala Val Ser Leu Gly
1               5                   10                  15

Gln Thr Ile Ser Cys Lys Ala Ser Gln Ser Val Asp Tyr Asp Gly Asp
            20                  25                  30

Ser Tyr Met Asn Trp Tyr Gln Gln Lys Pro Gly Gln Pro Pro Lys Leu
        35                  40                  45

Leu Ile Tyr Asp Ala Ser Thr Leu Glu Ser Gly Ile Pro Ala Arg Phe
 50                  55                  60

Ser Gly Ser Gly Ser Gly Thr Asp Phe Thr Leu Asn Ile His Pro Val
65                  70                  75                  80

Glu Glu Glu Asp Ala Ala Thr Tyr Tyr Cys Gln Gln Asn Tyr Glu Ala
                85                  90                  95
```

Pro Trp Thr Phe Gly Gly Gly Thr Lys Leu Glu Ile Lys Arg
            100                 105                 110

<210> SEQ ID NO 148
<211> LENGTH: 30
<212> TYPE: PRT
<213> ORGANISM: Artificial Sequence
<220> FEATURE:
<223> OTHER INFORMATION: Synthetic

<400> SEQUENCE: 148

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Gly
            20                  25                  30

<210> SEQ ID NO 149
<211> LENGTH: 5
<212> TYPE: PRT
<213> ORGANISM: Artificial Sequence
<220> FEATURE:
<223> OTHER INFORMATION: Synthetic

<400> SEQUENCE: 149

Asn Tyr Trp Met Ser
1               5

<210> SEQ ID NO 150
<211> LENGTH: 14
<212> TYPE: PRT
<213> ORGANISM: Artificial Sequence
<220> FEATURE:
<223> OTHER INFORMATION: Synthetic

<400> SEQUENCE: 150

Trp Val Arg Gln Ser Pro Glu Lys Gly Leu Glu Trp Val Ala
1               5                   10

<210> SEQ ID NO 151
<211> LENGTH: 19
<212> TYPE: PRT
<213> ORGANISM: Artificial Sequence
<220> FEATURE:
<223> OTHER INFORMATION: Synthetic

<400> SEQUENCE: 151

Glu Ile Arg Leu Lys Ser Asp Asn Tyr Ala Thr His Tyr Ala Glu Ser
1               5                   10                  15

Val Lys Gly

<210> SEQ ID NO 152
<211> LENGTH: 32
<212> TYPE: PRT
<213> ORGANISM: Artificial Sequence
<220> FEATURE:
<223> OTHER INFORMATION: Synthetic

<400> SEQUENCE: 152

Lys Phe Thr Ile Ser Arg Asp Asp Ser Lys Ser Arg Leu Tyr Leu Gln
1               5                   10                  15

Met Asn Ser Leu Arg Gly Glu Asp Thr Gly Leu Tyr Tyr Cys Thr Asn
            20                  25                  30

<210> SEQ ID NO 153

```
<211> LENGTH: 5
<212> TYPE: PRT
<213> ORGANISM: Artificial Sequence
<220> FEATURE:
<223> OTHER INFORMATION: Synthetic

<400> SEQUENCE: 153

Ala Trp Phe Ala Ser
1               5

<210> SEQ ID NO 154
<211> LENGTH: 11
<212> TYPE: PRT
<213> ORGANISM: Artificial Sequence
<220> FEATURE:
<223> OTHER INFORMATION: Synthetic

<400> SEQUENCE: 154

Trp Gly Gln Gly Thr Leu Val Thr Val Ser Ala
1               5                   10

<210> SEQ ID NO 155
<211> LENGTH: 5
<212> TYPE: PRT
<213> ORGANISM: Artificial Sequence
<220> FEATURE:
<223> OTHER INFORMATION: Synthetic

<400> SEQUENCE: 155

Ser Tyr Trp Met Ser
1               5

<210> SEQ ID NO 156
<211> LENGTH: 19
<212> TYPE: PRT
<213> ORGANISM: Artificial Sequence
<220> FEATURE:
<223> OTHER INFORMATION: Synthetic

<400> SEQUENCE: 156

Glu Ile Arg Leu Lys Ser Asp Asn Tyr Ala Ala His Tyr Ala Glu Ser
1               5                   10                  15

Val Lys Gly

<210> SEQ ID NO 157
<211> LENGTH: 32
<212> TYPE: PRT
<213> ORGANISM: Artificial Sequence
<220> FEATURE:
<223> OTHER INFORMATION: Synthetic

<400> SEQUENCE: 157

Lys Phe Thr Ile Ser Arg Asp Asp Ser Lys Ser Arg Leu Tyr Leu Gln
1               5                   10                  15

Met Asn Ser Leu Arg Gly Glu Asp Thr Gly Ile Tyr Tyr Cys Thr Asn
                20                  25                  30

<210> SEQ ID NO 158
<211> LENGTH: 5
<212> TYPE: PRT
<213> ORGANISM: Artificial Sequence
<220> FEATURE:
<223> OTHER INFORMATION: Synthetic

<400> SEQUENCE: 158

Thr Tyr Trp Met Ser
```

<210> SEQ ID NO 159
<211> LENGTH: 19
<212> TYPE: PRT
<213> ORGANISM: Artificial Sequence
<220> FEATURE:
<223> OTHER INFORMATION: Synthetic

<400> SEQUENCE: 159

Glu Ile Arg Leu Lys Ser Asp Asn Tyr Ala Thr His Tyr Thr Glu Ser
1               5                   10                  15

Val Lys Gly

<210> SEQ ID NO 160
<211> LENGTH: 32
<212> TYPE: PRT
<213> ORGANISM: Artificial Sequence
<220> FEATURE:
<223> OTHER INFORMATION: Synthetic

<400> SEQUENCE: 160

Lys Phe Thr Ile Ser Arg Asp Asp Ser Lys Ser Arg Leu Tyr Leu Gln
1               5                   10                  15

Met Asn Ser Leu Arg Val Glu Asp Thr Gly Ile Tyr Tyr Cys Thr Asn
            20                  25                  30

<210> SEQ ID NO 161
<211> LENGTH: 5
<212> TYPE: PRT
<213> ORGANISM: Artificial Sequence
<220> FEATURE:
<223> OTHER INFORMATION: Synthetic

<400> SEQUENCE: 161

Ala Trp Phe Ala Tyr
1               5

<210> SEQ ID NO 162
<211> LENGTH: 30
<212> TYPE: PRT
<213> ORGANISM: Artificial Sequence
<220> FEATURE:
<223> OTHER INFORMATION: Synthetic

<400> SEQUENCE: 162

Glu Val Lys Leu Glu Glu Ser Gly Gly Gly Leu Val Gln Pro Gly Gly
1               5                   10                  15

Ser Met Lys Leu Ser Cys Ile Ala Ser Gly Phe Thr Phe Ser
            20                  25                  30

<210> SEQ ID NO 163
<211> LENGTH: 19
<212> TYPE: PRT
<213> ORGANISM: Artificial Sequence
<220> FEATURE:
<223> OTHER INFORMATION: Synthetic

<400> SEQUENCE: 163

Glu Ile Arg Leu Lys Ser Glu Asn Tyr Ala Thr Tyr Tyr Ala Glu Ser
1               5                   10                  15

Val Lys Gly

<210> SEQ ID NO 164

<211> LENGTH: 32
<212> TYPE: PRT
<213> ORGANISM: Artificial Sequence
<220> FEATURE:
<223> OTHER INFORMATION: Synthetic

<400> SEQUENCE: 164

```
Lys Phe Ile Ile Ser Arg Asp Asp Ser Lys Ser Arg Leu Tyr Leu Gln
1               5                   10                  15
Met Asn Ser Leu Arg Ala Glu Asp Thr Gly Ile Tyr Tyr Cys Thr Asn
            20                  25                  30
```

<210> SEQ ID NO 165
<211> LENGTH: 5
<212> TYPE: PRT
<213> ORGANISM: Artificial Sequence
<220> FEATURE:
<223> OTHER INFORMATION: Synthetic

<400> SEQUENCE: 165

```
Ala Trp Phe Ala Asn
1               5
```

<210> SEQ ID NO 166
<211> LENGTH: 30
<212> TYPE: PRT
<213> ORGANISM: Artificial Sequence
<220> FEATURE:
<223> OTHER INFORMATION: Synthetic

<400> SEQUENCE: 166

```
Asp Val Gln Leu Gln Glu Ser Gly Pro Gly Leu Val Lys Pro Ser Gln
1               5                   10                  15
Ser Leu Ser Leu Thr Cys Thr Val Thr Gly Tyr Ser Ile Thr
            20                  25                  30
```

<210> SEQ ID NO 167
<211> LENGTH: 6
<212> TYPE: PRT
<213> ORGANISM: Artificial Sequence
<220> FEATURE:
<223> OTHER INFORMATION: Synthetic

<400> SEQUENCE: 167

```
Ser Asp Tyr Ala Trp Asn
1               5
```

<210> SEQ ID NO 168
<211> LENGTH: 14
<212> TYPE: PRT
<213> ORGANISM: Artificial Sequence
<220> FEATURE:
<223> OTHER INFORMATION: Synthetic

<400> SEQUENCE: 168

```
Trp Ile Arg Gln Phe Pro Gly Asn Lys Leu Glu Trp Met Gly
1               5                   10
```

<210> SEQ ID NO 169
<211> LENGTH: 16
<212> TYPE: PRT
<213> ORGANISM: Artificial Sequence
<220> FEATURE:
<223> OTHER INFORMATION: Synthetic

<400> SEQUENCE: 169

```
Tyr Ile Ser Tyr Ile Gly Gly Ile Gly Tyr Asn Pro Ser Leu Lys Ser
1               5                   10                  15
```

<210> SEQ ID NO 170
<211> LENGTH: 32
<212> TYPE: PRT
<213> ORGANISM: Artificial Sequence
<220> FEATURE:
<223> OTHER INFORMATION: Synthetic

<400> SEQUENCE: 170

```
Arg Ile Ser Ile Thr Arg Asp Thr Ser Lys Asn Gln Phe Phe Leu His
1               5                   10                  15

Leu Asn Ser Val Thr Thr Gly Asp Thr Ala Thr Tyr Tyr Cys Ala Arg
            20                  25                  30
```

<210> SEQ ID NO 171
<211> LENGTH: 6
<212> TYPE: PRT
<213> ORGANISM: Artificial Sequence
<220> FEATURE:
<223> OTHER INFORMATION: Synthetic

<400> SEQUENCE: 171

```
Asn Gly Ala Met Asp Phe
1               5
```

<210> SEQ ID NO 172
<211> LENGTH: 11
<212> TYPE: PRT
<213> ORGANISM: Artificial Sequence
<220> FEATURE:
<223> OTHER INFORMATION: Synthetic

<400> SEQUENCE: 172

```
Trp Gly Gln Gly Ile Ser Val Thr Val Ser Ser
1               5                   10
```

<210> SEQ ID NO 173
<211> LENGTH: 16
<212> TYPE: PRT
<213> ORGANISM: Artificial Sequence
<220> FEATURE:
<223> OTHER INFORMATION: Synthetic

<400> SEQUENCE: 173

```
Tyr Ile Ser Tyr Ser Gly Ser Thr Gly Tyr Ser Pro Ser Leu Lys Ser
1               5                   10                  15
```

<210> SEQ ID NO 174
<211> LENGTH: 6
<212> TYPE: PRT
<213> ORGANISM: Artificial Sequence
<220> FEATURE:
<223> OTHER INFORMATION: Synthetic

<400> SEQUENCE: 174

```
Asn Gly Ala Met Asp Tyr
1               5
```

<210> SEQ ID NO 175
<211> LENGTH: 23
<212> TYPE: PRT
<213> ORGANISM: Artificial Sequence
<220> FEATURE:
<223> OTHER INFORMATION: Synthetic

```
<400> SEQUENCE: 175

Asp Ile Val Met Ser Gln Ser Pro Ser Ser Leu Ala Val Ser Val Gly
1               5                   10                  15

Glu Lys Val Thr Met Ser Cys
            20

<210> SEQ ID NO 176
<211> LENGTH: 17
<212> TYPE: PRT
<213> ORGANISM: Artificial Sequence
<220> FEATURE:
<223> OTHER INFORMATION: Synthetic

<400> SEQUENCE: 176

Met Ser Ser Gln Ser Leu Leu Tyr Ser Lys Asp Gln Lys Asn Tyr Leu
1               5                   10                  15

Ala

<210> SEQ ID NO 177
<211> LENGTH: 15
<212> TYPE: PRT
<213> ORGANISM: Artificial Sequence
<220> FEATURE:
<223> OTHER INFORMATION: Synthetic

<400> SEQUENCE: 177

Trp Tyr Gln Gln Lys Pro Gly Gln Ser Pro Lys Leu Leu Ile Tyr
1               5                   10                  15

<210> SEQ ID NO 178
<211> LENGTH: 7
<212> TYPE: PRT
<213> ORGANISM: Artificial Sequence
<220> FEATURE:
<223> OTHER INFORMATION: Synthetic

<400> SEQUENCE: 178

Trp Ala Ser Thr Arg Glu Ser
1               5

<210> SEQ ID NO 179
<211> LENGTH: 32
<212> TYPE: PRT
<213> ORGANISM: Artificial Sequence
<220> FEATURE:
<223> OTHER INFORMATION: Synthetic

<400> SEQUENCE: 179

Gly Val Pro Asp Arg Phe Thr Gly Ser Gly Ser Gly Thr Asp Phe Thr
1               5                   10                  15

Leu Thr Ile Ser Ser Val Lys Ala Glu Asp Leu Ala Val Tyr Tyr Cys
            20                  25                  30

<210> SEQ ID NO 180
<211> LENGTH: 9
<212> TYPE: PRT
<213> ORGANISM: Artificial Sequence
<220> FEATURE:
<223> OTHER INFORMATION: Synthetic

<400> SEQUENCE: 180

Leu Gln Tyr Tyr Thr Tyr Pro Tyr Thr
1               5
```

```
<210> SEQ ID NO 181
<211> LENGTH: 23
<212> TYPE: PRT
<213> ORGANISM: Artificial Sequence
<220> FEATURE:
<223> OTHER INFORMATION: Synthetic

<400> SEQUENCE: 181

Asp Ile Val Met Ser Gln Ser Pro Ser Ser Leu Thr Val Ser Val Gly
1               5                   10                  15

Glu Lys Val Thr Met Ser Cys
            20

<210> SEQ ID NO 182
<211> LENGTH: 15
<212> TYPE: PRT
<213> ORGANISM: Artificial Sequence
<220> FEATURE:
<223> OTHER INFORMATION: Synthetic

<400> SEQUENCE: 182

Trp Tyr Gln Gln Lys Pro Gly Gln Ser Pro Thr Leu Leu Ile Tyr
1               5                   10                  15

<210> SEQ ID NO 183
<211> LENGTH: 23
<212> TYPE: PRT
<213> ORGANISM: Artificial Sequence
<220> FEATURE:
<223> OTHER INFORMATION: Synthetic

<400> SEQUENCE: 183

Asp Ile Val Met Ser Gln Ser Pro Ser Ser Leu Ala Val Ser Val Gly
1               5                   10                  15

Glu Lys Phe Thr Met Ser Cys
            20

<210> SEQ ID NO 184
<211> LENGTH: 17
<212> TYPE: PRT
<213> ORGANISM: Artificial Sequence
<220> FEATURE:
<223> OTHER INFORMATION: Synthetic

<400> SEQUENCE: 184

Lys Ser Ser Gln Ser Leu Leu Tyr Ser Arg Asp Gln Lys Asn Tyr Leu
1               5                   10                  15

Ala

<210> SEQ ID NO 185
<211> LENGTH: 15
<212> TYPE: PRT
<213> ORGANISM: Artificial Sequence
<220> FEATURE:
<223> OTHER INFORMATION: Synthetic

<400> SEQUENCE: 185

Trp Tyr Gln Gln Gln Pro Gly Gln Ser Pro Lys Leu Leu Ile Tyr
1               5                   10                  15

<210> SEQ ID NO 186
<211> LENGTH: 32
<212> TYPE: PRT
<213> ORGANISM: Artificial Sequence
<220> FEATURE:
<223> OTHER INFORMATION: Synthetic
```

<400> SEQUENCE: 186

Gly Val Pro Asp Arg Phe Thr Gly Ser Gly Ser Gly Thr Asp Phe Thr
1               5                   10                  15

Leu Thr Ile Ser Ser Val Lys Thr Glu Asp Leu Ala Val Tyr Tyr Cys
            20                  25                  30

<210> SEQ ID NO 187
<211> LENGTH: 9
<212> TYPE: PRT
<213> ORGANISM: Artificial Sequence
<220> FEATURE:
<223> OTHER INFORMATION: Synthetic

<400> SEQUENCE: 187

Leu Gln Tyr Tyr Ser Tyr Pro Tyr Thr
1               5

<210> SEQ ID NO 188
<211> LENGTH: 23
<212> TYPE: PRT
<213> ORGANISM: Artificial Sequence
<220> FEATURE:
<223> OTHER INFORMATION: Synthetic

<400> SEQUENCE: 188

Asp Ile Val Met Ser Gln Ser Pro Ser Ser Leu Val Val Ser Val Gly
1               5                   10                  15

Glu Lys Val Thr Met Ser Cys
            20

<210> SEQ ID NO 189
<211> LENGTH: 17
<212> TYPE: PRT
<213> ORGANISM: Artificial Sequence
<220> FEATURE:
<223> OTHER INFORMATION: Synthetic

<400> SEQUENCE: 189

Lys Ser Ser Gln Asn Leu Leu Tyr Ser Arg Asp Gln Lys Asn Tyr Leu
1               5                   10                  15

Ala

<210> SEQ ID NO 190
<211> LENGTH: 15
<212> TYPE: PRT
<213> ORGANISM: Artificial Sequence
<220> FEATURE:
<223> OTHER INFORMATION: Synthetic

<400> SEQUENCE: 190

Trp Tyr Gln Gln Lys Pro Gly Gln Ser Pro Asn Leu Leu Ile Tyr
1               5                   10                  15

<210> SEQ ID NO 191
<211> LENGTH: 32
<212> TYPE: PRT
<213> ORGANISM: Artificial Sequence
<220> FEATURE:
<223> OTHER INFORMATION: Synthetic

<400> SEQUENCE: 191

Gly Val Pro Asp Arg Phe Thr Gly Ser Gly Ser Gly Thr Asp Phe Ser
1               5                   10                  15

Leu Thr Ile Ser Ser Val Lys Ala Glu Asp Leu Ala Val Tyr Tyr Cys
            20                  25                  30

<210> SEQ ID NO 192
<211> LENGTH: 11
<212> TYPE: PRT
<213> ORGANISM: Artificial Sequence
<220> FEATURE:
<223> OTHER INFORMATION: Synthetic

<400> SEQUENCE: 192

Phe Gly Gly Gly Thr Lys Leu Glu Met Lys Arg
1               5                   10

<210> SEQ ID NO 193
<211> LENGTH: 23
<212> TYPE: PRT
<213> ORGANISM: Artificial Sequence
<220> FEATURE:
<223> OTHER INFORMATION: Synthetic

<400> SEQUENCE: 193

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 194
<211> LENGTH: 15
<212> TYPE: PRT
<213> ORGANISM: Artificial Sequence
<220> FEATURE:
<223> OTHER INFORMATION: Synthetic

<400> SEQUENCE: 194

Lys Ala Ser Gln Ser Val Asp Tyr Asp Gly Asp Ser Tyr Met Asn
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Synthetic

<400> SEQUENCE: 195

Trp Tyr Gln Gln Lys Pro Gly Gln Pro Pro Lys Leu Leu Ile Tyr
1               5                   10                  15

<210> SEQ ID NO 196
<211> LENGTH: 7
<212> TYPE: PRT
<213> ORGANISM: Artificial Sequence
<220> FEATURE:
<223> OTHER INFORMATION: Synthetic

<400> SEQUENCE: 196

Asp Ala Ser Asn Leu Glu Ser
1               5

<210> SEQ ID NO 197
<211> LENGTH: 32
<212> TYPE: PRT
<213> ORGANISM: Artificial Sequence
<220> FEATURE:
<223> OTHER INFORMATION: Synthetic

<400> SEQUENCE: 197

Gly Ile Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
                20                  25                  30

<210> SEQ ID NO 198
<211> LENGTH: 9
<212> TYPE: PRT
<213> ORGANISM: Artificial Sequence
<220> FEATURE:
<223> OTHER INFORMATION: Synthetic

<400> SEQUENCE: 198

Gln Gln Ser Asn Glu Ala Pro Trp Thr
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic

<400> SEQUENCE: 199

Asp Ala Ser Thr Leu Glu Ser
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic

<400> SEQUENCE: 200

Gln Gln Asn Tyr Glu Ala Pro Trp Thr
1               5

<210> SEQ ID NO 201
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Wherein Xaa at position 1 is N or S or T

<400> SEQUENCE: 201

Xaa Tyr Trp Met Ser
1               5

<210> SEQ ID NO 202
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (7)..(7)
<223> OTHER INFORMATION: Wherein Xaa at position 7 is D or E
<220> FEATURE:
<221> NAME/KEY: VARIANT
<222> LOCATION: (11)..(11)
<223> OTHER INFORMATION: Wherein Xaa at position 11 is T or A

```
<220> FEATURE:
<221> NAME/KEY: VARIANT
<222> LOCATION: (12)..(12)
<223> OTHER INFORMATION: Wherein Xaa at position 12 is H or Y
<220> FEATURE:
<221> NAME/KEY: VARIANT
<222> LOCATION: (14)..(14)
<223> OTHER INFORMATION: Wherein Xaa at position 14 is A or T

<400> SEQUENCE: 202

Glu Ile Arg Leu Lys Ser Xaa Asn Tyr Ala Xaa Xaa Tyr Xaa Glu Ser
1               5                   10                  15
Val Lys Gly

<210> SEQ ID NO 203
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (5)..(5)
<223> OTHER INFORMATION: Wherein Xaa at position 5 is S or Y or N

<400> SEQUENCE: 203

Ala Trp Phe Ala Xaa
1               5

<210> SEQ ID NO 204
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: Wherein Xaa at position 1 is M or K
<220> FEATURE:
<221> NAME/KEY: VARIANT
<222> LOCATION: (5)..(5)
<223> OTHER INFORMATION: Wherein Xaa at position 5 is S or N
<220> FEATURE:
<221> NAME/KEY: VARIANT
<222> LOCATION: (10)..(10)
<223> OTHER INFORMATION: Wherein Xaa at position 10 is K or R

<400> SEQUENCE: 204

Xaa Ser Ser Gln Xaa Leu Leu Tyr Ser Xaa Asp Gln Lys Asn Tyr Leu
1               5                   10                  15
Ala

<210> SEQ ID NO 205
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (5)..(5)
<223> OTHER INFORMATION: Wherein Xaa at position 5 is T or S

<400> SEQUENCE: 205

Leu Gln Tyr Tyr Xaa Tyr Pro Tyr Thr
1               5

<210> SEQ ID NO 206
```

```
<211> LENGTH: 348
<212> TYPE: DNA
<213> ORGANISM: Artificial Sequence
<220> FEATURE:
<223> OTHER INFORMATION: Synthetic

<400> SEQUENCE: 206
gaagtgaagc ttgaggagtc tggaggaggc ctggtgcaac ctggaggatc catgaaactc      60
tcctgtgtag cctctggatt tactttcggt aactactgga tgtcttgggt ccgccagtct     120
ccagagaagg ggcttgagtg ggttgctgaa attagattga aatctgataa ttatgcaaca     180
cattatgcgg agtctgtgaa agggaagttc accatctcaa gagatgattc caaaagtcgt     240
ctctacctgc aaatgaacag cttaagaggt gaagacactg gactttatta ctgtacgaat     300
gcctggtttg cttcctgggg ccaagggact ctggtcactg tctctgca                 348

<210> SEQ ID NO 207
<211> LENGTH: 348
<212> TYPE: DNA
<213> ORGANISM: Artificial Sequence
<220> FEATURE:
<223> OTHER INFORMATION: Synthetic

<400> SEQUENCE: 207
gaagtgaagc ttgaggagtc tggaggaggc ttggtgcaac ctggaggatc catgaaactc      60
tcctgtgttg cctctggatt tactttcggt agctactgga tgtcttgggt ccgccagtct     120
ccagagaagg ggcttgagtg ggttgctgaa attagattga aatctgataa ttatgcagca     180
cattatgcgg agtctgtgaa agggaagttc accatctcaa gagatgattc caaaagtcgt     240
ctctacctgc aaatgaacag cttaagaggc gaagacactg gaatttatta ctgtacgaat     300
gcctggtttg cttcctgggg ccaagggact ctggtcactg tttctgca                 348

<210> SEQ ID NO 208
<211> LENGTH: 348
<212> TYPE: DNA
<213> ORGANISM: Artificial Sequence
<220> FEATURE:
<223> OTHER INFORMATION: Synthetic

<400> SEQUENCE: 208
gaagtgaagc ttgaggagtc tggaggaggc ttggtgcaac ctggaggatc catgaaactc      60
tcctgtgttg cctctggatt tactttcagc acttattgga tgtcttgggt ccgccagtct     120
ccagagaagg ggcttgagtg ggttgctgaa attagattga aatctgataa ttatgcaaca     180
cattatacgg agtctgtgaa agggaagttc accatctcaa gagatgattc caaaagtcgt     240
ctctacctgc aaatgaacag tttaagagtt gaagacactg gaatttatta ttgtacgaat     300
gcctggtttg cttactgggg ccaagggact ctggtcactg tctctgca                 348

<210> SEQ ID NO 209
<211> LENGTH: 348
<212> TYPE: DNA
<213> ORGANISM: Artificial Sequence
<220> FEATURE:
<223> OTHER INFORMATION: Synthetic

<400> SEQUENCE: 209
gaagtgaagc ttgaggagtc tggaggaggc ttggtgcaac ctggaggatc catgaaactc      60
tcctgtgtattg cctctggatt tactttcagt acctactgga tgtcttgggt ccgccagtct    120
ccagagaagg ggcttgagtg ggttgctgaa attagattga aatctgaaaa ttatgcaaca    180
```
tattatgcgg agtctgtgaa agggaagttc atcatctcaa gagatgattc caaaagtcgt    240
ctctacctgc aaatgaacag cttaagagct gaagacactg gaatttatta ctgtacgaat    300
gcctggtttg ctaactgggg ccaagggact ctggtcactg tctctgca    348

<210> SEQ ID NO 210
<211> LENGTH: 345
<212> TYPE: DNA
<213> ORGANISM: Artificial Sequence
<220> FEATURE:
<223> OTHER INFORMATION: Synthetic

<400> SEQUENCE: 210
gatgtgcagc ttcaggagtc gggacctggc ctggtgaaac cttctcagtc tctgtccctc     60
acctgcactg tcactggcta ctcaatcacc agtgattatg cctggaactg gatccggcag    120
tttccaggaa acaaactgga gtggatgggc tacataagct acattggtgg cattggctac    180
aacccatctc tcaaaagtcg aatctctatc actcgagaca catccaagaa ccagttcttc    240
ctgcacttga attctgtgac tactggggac acagccacat attactgtgc aagaaacggg    300
gctatggact ctggggtca aggaatctca gtcaccgtct cctca    345

<210> SEQ ID NO 211
<211> LENGTH: 345
<212> TYPE: DNA
<213> ORGANISM: Artificial Sequence
<220> FEATURE:
<223> OTHER INFORMATION: Synthetic

<400> SEQUENCE: 211
gatgtgcagc ttcaggagtc gggacctggc ctggtgaaac cttctcagtc tctgtccctc     60
acctgcactg tcactggcta ctcaatcacc agtgattatg cctggaactg gatccggcag    120
tttccaggaa acaaactgga gtggatgggc tacataagtt acagtggtag cactggctat    180
agcccatctc tcaaaagtcg aatctctatc actcgagaca catccaagaa ccagttcttc    240
ctgcacttga attctgtgac tactggagac acagccacat attactgtgc acgaaacggg    300
gctatggact actggggtca aggaatctca gtcaccgtct cctca    345

<210> SEQ ID NO 212
<211> LENGTH: 342
<212> TYPE: DNA
<213> ORGANISM: Artificial Sequence
<220> FEATURE:
<223> OTHER INFORMATION: Synthetic

<400> SEQUENCE: 212
gacattgtga tgtcacagtc tccatcctcc ctagctgtgt cagttggaga gaaggttact     60
atgagctgca tgtccagtca gagccttta tatagtaaag atcaaaagaa ctacttggcc    120
tggtaccaac agaaaccagg gcagtctcct aaactgctga tttactgggc atccactagg    180
gaatctgggg tccctgatcg cttcacaggc agtggatctg gacagatttc actctcacc    240 atcagcagtg tgaaggctga agacctggca gtttattact gtctgcaata ttatacctat    300
ccgtacacgt tcggagggg gaccaagctg gaaataaaac gg    342

<210> SEQ ID NO 213
<211> LENGTH: 342
<212> TYPE: DNA
<213> ORGANISM: Artificial Sequence
<220> FEATURE:

<223> OTHER INFORMATION: Synthetic

<400> SEQUENCE: 213

| gacattgtga tgtcacagtc tccatcctcc ctaactgtgt cagttggaga gaaggttact | 60 |
| atgagctgca tgtccagtca gagccttttta tatagtaaag atcaaaagaa ctacttggcc | 120 |
| tggtaccaac agaaaccagg gcagtctcct acactgctga tttactgggc atccactagg | 180 |
| gaatctgggg tccctgatcg cttcacaggc agtggatctg ggacagattt cactctcacc | 240 |
| atcagcagtg tgaaggctga agacctggca gtttattact gtctgcaata ttatacctat | 300 |
| ccgtacacgt tcggaggggg gaccaagctg gaaataaaac gg | 342 |

<210> SEQ ID NO 214
<211> LENGTH: 342
<212> TYPE: DNA
<213> ORGANISM: Artificial Sequence
<220> FEATURE:
<223> OTHER INFORMATION: Synthetic

<400> SEQUENCE: 214

| gacattgtga tgtcacagtc tccatcctcc ctagctgtgt cagttggaga gaagtttact | 60 |
| atgagctgca agtccagtca gagccttttta tatagtcgcg atcaaaagaa ctacttggcc | 120 |
| tggtaccagc agcaaccagg gcagtctcct aaacttctga tttactgggc atccactagg | 180 |
| gagtctgggg tccctgatcg cttcacaggc agtggatctg ggacagattt cactctcacc | 240 |
| atcagcagtg tgaagactga agacctggca gtttattact gtctccaata ttatagctat | 300 |
| ccgtacactt tcggaggggg gaccaagctg gaaataaaac gg | 342 |

<210> SEQ ID NO 215
<211> LENGTH: 342
<212> TYPE: DNA
<213> ORGANISM: Artificial Sequence
<220> FEATURE:
<223> OTHER INFORMATION: Synthetic

<400> SEQUENCE: 215

| gacattgtga tgtcacagtc tccatcctcc ctagttgtgt cagttggaga gaaggttact | 60 |
| atgagctgta agtccagtca gaaccttttta tatagtaggg atcaaaagaa ctacttggcc | 120 |
| tggtaccagc agaaaccagg gcagtctcct aacttgctga tttactgggc atccactagg | 180 |
| gaatctgggg tccctgatcg cttcacaggc agtggatctg ggacagattt ctctctcacc | 240 |
| atcagcagtg tgaaggctga agacctggca gtttattact gtctccaata ttatagctat | 300 |
| ccgtacacgt tcggagggg gaccaagctg gaaatgaaac gg | 342 |

<210> SEQ ID NO 216
<211> LENGTH: 336
<212> TYPE: DNA
<213> ORGANISM: Artificial Sequence
<220> FEATURE:
<223> OTHER INFORMATION: Synthetic

<400> SEQUENCE: 216

| gacattgtgc tgacccaatc tccagcttct ttggctgtgt ctctagggca gagggccacc | 60 |
| atctcctgca aggccagcca agtgttgat tatgatggtg atagttatat gaactggtac | 120 |
| caacagaaac caggacagcc acccaaactc ctcatctatg atgcatccaa tctagaatct | 180 |
| gggatcccag ccaggtttag tggcagtggg tctgggacag acttcaccct caacatccat | 240 |
| cctgtggagg aggaggatgc tgcaacctat tactgtcagc aaagtaatga ggctccgtgg | 300 |

```
acgttcggtg gaggcaccaa gctggaaatc aaacgg                               336
```

<210> SEQ ID NO 217
<211> LENGTH: 336
<212> TYPE: DNA
<213> ORGANISM: Artificial Sequence
<220> FEATURE:
<223> OTHER INFORMATION: Synthetic

<400> SEQUENCE: 217

```
gacattgtgc tgacccaatc tccagcttct ttggctgtgt ctctagggca gagggccacc    60
atctcctgca aggccagcca aagtgttgat tatgatggtg atagttatat gaactggtac   120
caacagaaac caggacagcc acccaaactc ctcatttatg atgcttccac tctagaatct   180
gggatcccag ccaggtttag tggcagtggg tctgggacag acttcaccct caacatccat   240
cctgtggagg aggaggatgc tgcaacctat tactgtcagc aaaattatga ggctccgtgg   300
acgttcggtg gaggcaccaa gctggaaatc aaacgg                             336
```

<210> SEQ ID NO 218
<211> LENGTH: 330
<212> TYPE: PRT
<213> ORGANISM: Mus musculus

<400> SEQUENCE: 218

```
Ala Lys Thr Thr Ala Pro Ser Val Tyr Pro Leu Ala Pro Val Cys Gly
  1               5                  10                  15

Asp Thr Thr Gly Ser Ser Val Thr Leu Gly Cys Leu Val Lys Gly Tyr
             20                  25                  30

Phe Pro Glu Pro Val Thr Leu Thr Trp Asn Ser Gly Ser Leu Ser Ser
         35                  40                  45

Gly Val His Thr Phe Pro Ala Val Leu Gln Ser Asp Leu Tyr Thr Leu
     50                  55                  60

Ser Ser Ser Val Thr Val Thr Ser Thr Trp Pro Ser Gln Ser Ile
 65                  70                  75                  80

Thr Cys Asn Val Ala His Pro Ala Ser Ser Thr Lys Val Asp Lys Lys
                 85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
```

```
                      245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
        290                 295                 300

Ser Tyr Ser Cys Ser Val Val His Glu Gly Leu His Asn His Thr
305                 310                 315                 320

Thr Lys Ser Phe Ser Arg Thr Pro Gly Lys
                325                 330

<210> SEQ ID NO 219
<211> LENGTH: 106
<212> TYPE: PRT
<213> ORGANISM: Mus musculus

<400> SEQUENCE: 219

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 220
<211> LENGTH: 114
<212> TYPE: PRT
<213> ORGANISM: Artificial Sequence
<220> FEATURE:
<223> OTHER INFORMATION: Synthetic

<400> SEQUENCE: 220

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Asp
            20                  25                  30

Asp Ile Asn Trp Val Arg Gln Ala Pro Gly Gln Gly Leu Glu Trp Ile
        35                  40                  45

Gly Trp Ile Tyr Pro Arg Asp Asp Arg Thr Lys Tyr Asn Asp Lys Phe
    50                  55                  60

Lys Asp Lys Ala Thr Leu Thr Val Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Ser Ser Leu Glu Asp Thr Tyr Trp Gly Gln Gly Thr Leu Val Thr Val
            100                 105                 110

Ser Ser
```

<210> SEQ ID NO 221
<211> LENGTH: 113
<212> TYPE: PRT
<213> ORGANISM: Artificial Sequence
<220> FEATURE:
<223> OTHER INFORMATION: Synthetic

<400> SEQUENCE: 221

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Tyr Thr Phe Gly Gln Gly Thr Lys Val Glu Ile Lys
            100                 105                 110

Arg

<210> SEQ ID NO 222
<211> LENGTH: 114
<212> TYPE: PRT
<213> ORGANISM: Artificial Sequence
<220> FEATURE:
<223> OTHER INFORMATION: Synthetic

<400> SEQUENCE: 222

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Asp
            20                  25                  30

Asp Ile Asn Trp Val Arg Gln Ala Pro Gly Gln Gly Leu Glu Trp Ile
        35                  40                  45

Gly Trp Ile Tyr Pro Arg Asp Asp Arg Thr Lys Tyr Asn Asp Lys Phe
    50                  55                  60

Lys Asp Arg Ala Thr Leu Thr Val Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Ser Ser Leu Glu Asp Thr Tyr Trp Gly Gln Gly Thr Leu Val Thr Val
            100                 105                 110

Ser Ser

<210> SEQ ID NO 223
<211> LENGTH: 116
<212> TYPE: PRT
<213> ORGANISM: Artificial Sequence
<220> FEATURE:
<223> OTHER INFORMATION: Synthetic

<400> SEQUENCE: 223

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Met Ser Trp Val Arg Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Arg Thr Pro Tyr
65                  70                  75                  80

Leu Gln Ile Ser Ser Leu Lys Ala Glu Asp Thr Ala Val Tyr Phe Cys
                85                  90                  95

Ala Arg Gly Gly Glu Ala Met Asp Tyr Trp Gly Gln Gly Thr Leu Val
            100                 105                 110

Thr Val Ser Ser
            115

<210> SEQ ID NO 224
<211> LENGTH: 113
<212> TYPE: PRT
<213> ORGANISM: Artificial Sequence
<220> FEATURE:
<223> OTHER INFORMATION: Synthetic

<400> SEQUENCE: 224

Asp Val Leu Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Ala Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Val Glu Ile Lys
            100                 105                 110

Arg

<210> SEQ ID NO 225
<211> LENGTH: 116
<212> TYPE: PRT
<213> ORGANISM: Artificial Sequence
<220> FEATURE:
<223> OTHER INFORMATION: Synthetic

<400> SEQUENCE: 225

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Ser Tyr
            20                  25                  30

Gly Met Ser Trp Val Arg Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Arg Thr Pro Tyr
65                  70                  75                  80

-continued

Leu Gln Ile Ser Ser Leu Lys Ala Glu Asp Thr Ala Thr Tyr Phe Cys
            85                  90                  95

Ala Arg Gly Gly Glu Ala Met Asp Tyr Trp Gly Gln Gly Thr Leu Val
            100                 105                 110

Thr Val Ser Ser
        115

<210> SEQ ID NO 226
<211> LENGTH: 113
<212> TYPE: PRT
<213> ORGANISM: Artificial Sequence
<220> FEATURE:
<223> OTHER INFORMATION: Synthetic

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Lys
            20                  25                  30

Trp Ile Glu Trp Val Arg Gln Ala Pro Gly Gln Gly Leu Glu Trp Ile
        35                  40                  45

Gly Glu Ile Leu Pro Gly Thr Gly Ser Thr Asn Tyr Ala Gln Lys Phe
    50                  55                  60

Gln Gly Arg Ala Thr Phe Thr Ala Asp Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Leu Arg Ser Glu Asp Val Trp Gly Gln Gly Thr Leu Val Thr Val Ser
            100                 105                 110

Ser

<210> SEQ ID NO 227
<211> LENGTH: 113
<212> TYPE: PRT
<213> ORGANISM: Artificial Sequence
<220> FEATURE:
<223> OTHER INFORMATION: Synthetic

<400> SEQUENCE: 227

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
            85                  90                  95

Ser Tyr Asn Ile Pro Thr Phe Gly Gln Gly Thr Lys Val Glu Ile Lys
            100                 105                 110

Arg

<210> SEQ ID NO 228
<211> LENGTH: 113
<212> TYPE: PRT

```
<213> ORGANISM: Artificial Sequence
<220> FEATURE:
<223> OTHER INFORMATION: Synthetic

<400> SEQUENCE: 228

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Lys
            20                  25                  30

Trp Ile Glu Trp Val Arg Gln Ala Pro Gly Gln Gly Leu Glu Trp Ile
        35                  40                  45

Gly Glu Ile Leu Pro Gly Thr Gly Ser Thr Asn Tyr Asn Glu Lys Phe
    50                  55                  60

Lys Gly Arg Ala Thr Phe Thr Ala Asp Ser Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Leu Arg Ser Glu Asp Val Trp Gly Gln Gly Thr Leu Val Thr Val Ser
            100                 105                 110

Ser

<210> SEQ ID NO 229
<211> LENGTH: 5
<212> TYPE: PRT
<213> ORGANISM: Artificial Sequence
<220> FEATURE:
<223> OTHER INFORMATION: Synthetic

<400> SEQUENCE: 229

Thr Asp Asp Ile Asn
1               5

<210> SEQ ID NO 230
<211> LENGTH: 5
<212> TYPE: PRT
<213> ORGANISM: Artificial Sequence
<220> FEATURE:
<223> OTHER INFORMATION: Synthetic

<400> SEQUENCE: 230

Ser Tyr Gly Met Ser
1               5

<210> SEQ ID NO 231
<211> LENGTH: 5
<212> TYPE: PRT
<213> ORGANISM: Artificial Sequence
<220> FEATURE:
<223> OTHER INFORMATION: Synthetic

<400> SEQUENCE: 231

Gly Lys Trp Ile Glu
1               5

<210> SEQ ID NO 232
<211> LENGTH: 17
<212> TYPE: PRT
<213> ORGANISM: Artificial Sequence
<220> FEATURE:
<223> OTHER INFORMATION: Synthetic

<400> SEQUENCE: 232

Trp Ile Tyr Pro Arg Asp Asp Arg Thr Lys Tyr Asn Asp Lys Phe Lys
```

```
1               5                   10                  15

Asp

<210> SEQ ID NO 233
<211> LENGTH: 17
<212> TYPE: PRT
<213> ORGANISM: Artificial Sequence
<220> FEATURE:
<223> OTHER INFORMATION: Synthetic

<400> SEQUENCE: 233

Trp Ile Asn Thr Tyr Ser Gly Val Pro Thr Tyr Ala Asp Asp Phe Lys
1               5                   10                  15

Gly

<210> SEQ ID NO 234
<211> LENGTH: 17
<212> TYPE: PRT
<213> ORGANISM: Artificial Sequence
<220> FEATURE:
<223> OTHER INFORMATION: Synthetic

<400> SEQUENCE: 234

Glu Ile Leu Pro Gly Thr Gly Ser Thr Asn Tyr Ala Gln Lys Phe Gln
1               5                   10                  15

Gly

<210> SEQ ID NO 235
<211> LENGTH: 17
<212> TYPE: PRT
<213> ORGANISM: Artificial Sequence
<220> FEATURE:
<223> OTHER INFORMATION: Synthetic

<400> SEQUENCE: 235

Glu Ile Leu Pro Gly Thr Gly Ser Thr Asn Tyr Asn Glu Lys Phe Lys
1               5                   10                  15

Gly

<210> SEQ ID NO 236
<211> LENGTH: 5
<212> TYPE: PRT
<213> ORGANISM: Artificial Sequence
<220> FEATURE:
<223> OTHER INFORMATION: Synthetic

<400> SEQUENCE: 236

Leu Glu Asp Thr Tyr
1               5

<210> SEQ ID NO 237
<211> LENGTH: 7
<212> TYPE: PRT
<213> ORGANISM: Artificial Sequence
<220> FEATURE:
<223> OTHER INFORMATION: Synthetic

<400> SEQUENCE: 237

Gly Gly Glu Ala Met Asp Tyr
1               5

<210> SEQ ID NO 238
<211> LENGTH: 4
<212> TYPE: PRT
```

```
<213> ORGANISM: Artificial Sequence
<220> FEATURE:
<223> OTHER INFORMATION: Synthetic

<400> SEQUENCE: 238

Ser Glu Asp Val
1

<210> SEQ ID NO 239
<211> LENGTH: 17
<212> TYPE: PRT
<213> ORGANISM: Artificial Sequence
<220> FEATURE:
<223> OTHER INFORMATION: Synthetic

<400> SEQUENCE: 239

Lys Ser Ser Gln Ser Leu Leu Ala Ser Arg Thr Arg Lys Asn Tyr Leu
1               5                   10                  15

Ala

<210> SEQ ID NO 240
<211> LENGTH: 16
<212> TYPE: PRT
<213> ORGANISM: Artificial Sequence
<220> FEATURE:
<223> OTHER INFORMATION: Synthetic

<400> SEQUENCE: 240

Lys Ser Ser Gln Ser Leu Leu Asp Ser Asp Ala Lys Thr Tyr Leu Asn
1               5                   10                  15

<210> SEQ ID NO 241
<211> LENGTH: 7
<212> TYPE: PRT
<213> ORGANISM: Artificial Sequence
<220> FEATURE:
<223> OTHER INFORMATION: Synthetic

<400> SEQUENCE: 241

Leu Val Ser Lys Leu Asp Ser
1               5

<210> SEQ ID NO 242
<211> LENGTH: 8
<212> TYPE: PRT
<213> ORGANISM: Artificial Sequence
<220> FEATURE:
<223> OTHER INFORMATION: Synthetic

<400> SEQUENCE: 242

Lys Gln Ser Tyr Asn Leu Tyr Thr
1               5

<210> SEQ ID NO 243
<211> LENGTH: 9
<212> TYPE: PRT
<213> ORGANISM: Artificial Sequence
<220> FEATURE:
<223> OTHER INFORMATION: Synthetic

<400> SEQUENCE: 243

Trp Gln Gly Thr His Phe Pro Trp Thr
1               5

<210> SEQ ID NO 244
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 244

Lys Gln Ser Tyr Asn Ile Pro Thr
1               5

<210> SEQ ID NO 245
<211> LENGTH: 327
<212> TYPE: PRT
<213> ORGANISM: Homo sapiens

<400> SEQUENCE: 245

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Ser His Tyr Thr Gln Lys Ser
305                 310                 315                 320

Leu Ser Leu Ser Leu Gly Lys
```

```
<210> SEQ ID NO 246
<211> LENGTH: 32
<212> TYPE: PRT
<213> ORGANISM: Artificial Sequence
<220> FEATURE:
<223> OTHER INFORMATION: Synthetic

<400> SEQUENCE: 246

Arg Phe Thr Ile Ser Arg Asp Asp Ser Glu Ser Met Leu Ser Leu Gln
1               5                   10                  15

Met Asn Asn Leu Lys Thr Glu Asp Thr Ala Met Tyr Tyr Cys Val Arg
            20                  25                  30

<210> SEQ ID NO 247
<211> LENGTH: 30
<212> TYPE: PRT
<213> ORGANISM: Artificial Sequence
<220> FEATURE:
<223> OTHER INFORMATION: Synthetic

<400> SEQUENCE: 247

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser
            20                  25                  30
```